United States Patent
Clark et al.

(10) Patent No.: US 9,314,468 B2
(45) Date of Patent: Apr. 19, 2016

(54) CHEMOKINE RECEPTOR MODULATORS

(71) Applicant: Altiris Therapeutics, Inc., Atlanta, GA (US)

(72) Inventors: Michael P Clark, Concord, MA (US); Florence F Wagner, Ashland, MA (US); Michael G Natchus, Alpharetta, GA (US); Brandon C Doroh, Duluth, GA (US); Tricia L Johnson, Union City, GA (US); Yesim Altas Tahirovic, Decatur, GA (US); Lawrence Wilson, Atlanta, GA (US); John M Wiseman, Atlanta, GA (US); Jason W Skudlarek, Suwanee, GA (US); Mark A Lockwood, Alpharetta, GA (US)

(73) Assignee: Altiris Therapeutics, Inc., Atlanta, GA (US)

( * ) Notice: Subject to any disclaimer, the term of this patent is extended or adjusted under 35 U.S.C. 154(b) by 161 days.

(21) Appl. No.: 13/677,944

(22) Filed: Nov. 15, 2012

(65) Prior Publication Data

US 2013/0172330 A1    Jul. 4, 2013

Related U.S. Application Data

(63) Continuation of application No. 12/414,352, filed on Mar. 30, 2009, now Pat. No. 8,338,448.

(60) Provisional application No. 61/040,516, filed on Mar. 28, 2008.

(51) Int. Cl.
| | |
|---|---|
| A61K 31/44 | (2006.01) |
| A61K 31/535 | (2006.01) |
| A61K 31/497 | (2006.01) |
| A61K 31/541 | (2006.01) |
| C07D 403/14 | (2006.01) |
| C07D 487/04 | (2006.01) |
| A61K 31/437 | (2006.01) |
| A61K 31/4709 | (2006.01) |
| A61K 31/496 | (2006.01) |
| A61K 31/506 | (2006.01) |
| A61K 31/5377 | (2006.01) |
| A61K 45/06 | (2006.01) |
| C07D 401/12 | (2006.01) |
| C07D 471/04 | (2006.01) |

(52) U.S. Cl.
CPC .............. *A61K 31/541* (2013.01); *A61K 31/437* (2013.01); *A61K 31/4709* (2013.01); *A61K 31/496* (2013.01); *A61K 31/506* (2013.01); *A61K 31/5377* (2013.01); *A61K 45/06* (2013.01); *C07D 401/12* (2013.01); *C07D 403/14* (2013.01); *C07D 471/04* (2013.01); *C07D 487/04* (2013.01)

(58) Field of Classification Search
CPC ............ A61K 31/4745; A61K 31/495; A61K 31/5377

USPC .................. 514/292, 235.2, 253.03
See application file for complete search history.

(56) References Cited

U.S. PATENT DOCUMENTS

| | | | |
|---|---|---|---|
| 5,631,265 A | 5/1997 | Audia et al. | |
| 5,993,817 A | 11/1999 | Yoneda et al. | |
| 6,344,545 B1 | 2/2002 | Allaway et al. | |
| 6,358,915 B1 | 3/2002 | Patierno et al. | |
| 6,429,308 B1 | 8/2002 | Iijima et al. | |
| 6,433,149 B1 | 8/2002 | Blaschuk et al. | |
| 6,475,488 B1 | 11/2002 | Pasqualini et al. | |
| 6,534,626 B1 | 3/2003 | Oravecz et al. | |
| 6,750,348 B1 | 6/2004 | Bridger et al. | |
| 6,835,731 B2 | 12/2004 | Bridger et al. | |
| 2004/0132642 A1 | 7/2004 | Hwang | |
| 2004/0254221 A1 | 12/2004 | Yamamazi et al. | |

(Continued)

FOREIGN PATENT DOCUMENTS

| | | |
|---|---|---|
| EP | 1389460 | 2/2004 |
| EP | 1431290 | 6/2004 |

(Continued)

OTHER PUBLICATIONS

Abdel-Magid, A.F., et al., "Reductive Amination of Aldehydes and Ketones with Sodium Triace-toxyborohydride. Studies on Direct and Indirect Reductive Amination Procedures(1)," *J. Org. Chem.* 61(11):3849-3862 (May 31, 1996).

(Continued)

*Primary Examiner* — Shengjun Wang
(74) *Attorney, Agent, or Firm* — King & Spalding

(57) ABSTRACT

The invention provides compounds of Formula (I)

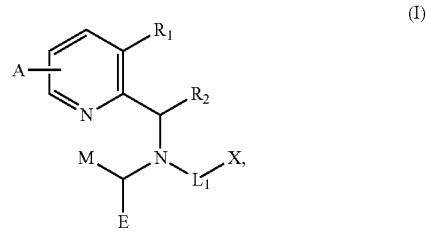

and pharmaceutically acceptable salts, solvates, tautomers, stereoisomers, and/or esters thereof. These compounds, and pharmaceutical composition comprising such compounds are useful treating or preventing HIV infections, and in treating proliferative disorders such as inhibiting the metastasis of various cancers.

8 Claims, No Drawings

(56) References Cited

U.S. PATENT DOCUMENTS

| | | |
|---|---|---|
| 2006/0264451 A1 | 11/2006 | Shim et al. |
| 2007/0054930 A1 | 3/2007 | Shim et al. |
| 2008/0227799 A1 | 9/2008 | Liotta et al. |
| 2008/0261978 A1 | 10/2008 | Clark et al. |
| 2008/0293711 A1 | 11/2008 | Clark et al. |
| 2009/0099194 A1 | 4/2009 | Liotta et al. |

FOREIGN PATENT DOCUMENTS

| | | |
|---|---|---|
| WO | WO 97/00956 | 1/1997 |
| WO | WO 99/47158 | 9/1999 |
| WO | WO 00/56729 | 9/2000 |
| WO | WO 00/56729 | 11/2000 |
| WO | WO 01/38352 | 5/2001 |
| WO | WO 01/56591 | 8/2001 |
| WO | WO 01/85196 | 11/2001 |
| WO | WO 02/094261 | 11/2002 |
| WO | WO 03/029218 | 4/2003 |
| WO | WO 2004/020462 | 3/2004 |
| WO | WO 2004/024178 | 3/2004 |
| WO | WO 2004/093817 | 4/2004 |
| WO | WO 2004/059285 | 7/2004 |
| WO | WO 2004/087068 | 10/2004 |
| WO | WO 2004/091518 | 10/2004 |
| WO | WO 2004/093817 | 11/2004 |
| WO | WO 2004/106493 | 12/2004 |
| WO | WO 2005/048916 | 6/2005 |
| WO | WO 2006/074426 | 7/2006 |
| WO | WO 2006/074428 | 7/2006 |
| WO | WO 2008/008852 | 1/2008 |
| WO | WO 2008/008854 | 1/2008 |
| WO | WO 2008/109154 | 9/2008 |
| WO | WO 2008/112156 | 9/2008 |
| WO | WO 2009/121063 | 10/2009 |

OTHER PUBLICATIONS

Abi-Younes, S., et al., "The stromal cell-derived factor-1 chemokine is a potent platelet agonist highly expressed in atherosclerotic plaques," *Circ. Res.*, 86(2), 131-138 (Feb. 4, 2000).

Alkhatib, G., et al., "CC CKR5: a Rantes, MIP-1alpha, MIP-1beta receptor as a fusion cofactor for macrophage-tropic HIV-1," Science, 272(5270):1955-1958 (Jun. 28, 1996).

Babcock, G., et al., "Ligand-independent Dimerization of CXCR4, a Principal HIV-1 coreceptor," *Journal of Biological Chemistry*,278(5): 3378-3385 (2002).

Blades, M.C., et al., "Stromal cell-derived factor 1 (CXCL12) induces human cell migration into human lymph nodes transplanted into SCID mice," *J. Immunol.* 168(9):4308-4317 (May 1, 2002).

Bleul, C.C., et al., "The lymphocyte chemoattractant SDF-1 is a ligand for LESTR/fusin and blocks HIV-1 entry," *Nature*, 382(6594):829-833 (Aug. 29, 1996).

Braun, C.E., et al., "Guanidine structure and hypoglycemia: some carbocyclic diguanidines," *J. Org. Chem.*, 3(2):146-152 (1938).

Bressler, N.M., and Bressler, S.B., "Preventative ophthalmology. Age-related macular degeneration," *Ophthalmology*, 102(8):1206-1211 (Aug. 1995).

Butcher, E.C., et al. "Lymphocyte trafficking and regional immunity," *Adv. Immunol.*, 72:209-253 (1999).

Campbell, J.J., and Butcher, E.C., "Chemokines in tissue-specific and microenvironment-specific lymphocyte homing," *Curr. Opin. Immunol.*,12(3):336-341 (Jun. 2000).

Chen, W.J., et al. "Recombinant human CXC-chemokine receptor-4 in melanophores are linked to Gi protein: seven transmembrane coreceptors for human immunodeficiency virus entry into cells," *Mol. Pharmacol.*, 53(2):177-181 (Feb. 1998).

Coopman, K. et al., Temporal variation in CB2R levels following T lymphocyte activation: Evidence that cannabinoids modulate CXCL12-induced chemotaxis, *International Immunopharmacology*, 7(2007): 360-371 (2006).

Connor, R.I., et al., "Change in coreceptor use correlates with disease progression in HIV-1-infected individuals," *J. Exp. Med.*, 185(4):621-628 (Feb. 17, 1997).

Crane, I.J., et al., "CXCR4 receptor expression on human retinal pigment epithelial cells from the blood-retina barrier leads to chemokine secretion and migration in response to stromal cell-derived factor 1α," *J. Immunol.*, 165(8):4372-4378 (Oct. 15, 2000).

Davis, C.B., et al. "Signal transduction due to HIV-1 envelope interactions with chemokine receptors CXCR4 or CCR5," *J. Exp. Med.*, 186(10):1793-1798 (Nov. 17, 1997).

Deng, H.K., et al., "Expression cloning of new receptors used by simian and human immunodeficiency viruses," *Nature*, 388(6639):296-300 (Jul. 17, 1997).

Donzella, G.A., et al., "AMD3100, a small molecule inhibitor of HIV-1 entry via the CXCR4 co-receptor," *Nat. Med.*, 4(1):72-77 (Jan. 1998).

Doranz, B.J., et al., "A dual-tropic primary HIV-1 isolate that uses fusin and the beta-chemokine receptors CKR-5, CKR-3, and CKR-2b as fusion cofactors," *Cell*, 85(7):1149-1158 (Jun. 28, 1996).

Dwinell, M.B., et al., "Chemokine receptor expression by human intestinal epithelial cells," *Gastroenterology*, 117(2):359-367 (Aug. 1999).

Eitner, F., et al., "Chemokine receptor (CXCR4) mRNA-expressing leukocytes are increased in human renal allograft rejection," *Transplantation*, 66(11):1551-1557 (Dec. 15, 1998).

Feng, Y., et al., "HIV-1 entry cofactor: functional cDNA cloning of a seven-transmembrane, G protein-coupled receptor," *Science*, 272(5263):872-877 (May 10, 1996).

Förster, R., et al., "CCR7 coordinates the primary immune response by establishing functional microenvironments in secondary lymphoid organs," *Cell*, 99(1):23-33 (Oct. 1, 1999).

Fujii, N., et al., "The therapeutic potential of CXCR4 antagonists in the treatment of HIV," *Expert Opin. Investig. Drugs*, 12(2):185-195 (Feb. 2003).

Gonzalo, J.A., et al., "Critical involvement of the chemotactic axis CXCR4/stromal cell-derived factor-1 alpha in the inflammatory component of allergic airway disease," *J Immunol.*, 165(1),499-508 (Jul. 1, 2000).

Grove, G., "Epidermal cell kinetics in psoriasis," *Int. J. Dermatol.*, 18(2):111-122 (Mar. 1979).

Gupta, S.K., et al., "Chemokine receptors in human endothelial cells. Functional expression of CXCR4 and its transcriptional regulation by inflammatory cytokines," *J. Biol. Chem.*, 273(7):4282-4287 (Feb. 13, 1998).

Harris, E.D., Jr., "Rheumatoid arthritis. Pathophysiology and implications for therapy," *N. Eng. J. Med.*, 322(18):1277-1289 (May 3, 1990).

Hatse, S., et al., "Chemokine receptor inhibition by AMD3100 is strictly confined to CXCR4," *FEBS Lett* 527(1-3):255-262 (Sep. 11, 2002).

Hendrix, C.W., et al., "Safety, pharmacokinetics, and antiviral activity of AMD3100, a selective CXCR4 receptor inhibitor, in HIV-1 infection," *J. Acquir. Immune Defic. Syndr.*, 37(2):1253-1262 (Oct. 1, 2004).

Hereld, D., and Jin, T., Slamming the DOR on chemokine receptor signaling: Heterodimerization silences ligand-occupied CXCR4 and and δ-opiod receptors, *Eur. J. Immunol.*, 38:334-37 (2007).

Homey, B., et al., "Cutting edge: the orphan chemokine receptor G protein-coupled receptor-2 (GPR-2, CCR10) binds the skin-associated chemokine CCL27 (CTACK/ALP/ILC)," *J. Immunol.*, 164(7):3465-3470 (Apr. 1, 2000).

Kang, Y., et al., "A multigenic program mediating breast cancer metastasis to bone," *Cancer Cell*, 3(6):537-549 (Jun. 2003).

Kijowski, J., et al., "The SDF-1-CXCR4 axis stimulates VEGF secretion and activates integrins but does not affect proliferation and survival in lymphohematopoietic cells," *Stem Cells* 19(5):453-466 (2001).

Kumar, A., et al., "CXCR4 Physically Associates with the T Cell Receptor to Signal in T Cells," *Immunity*, 25: 312-224 (2006).

Linton, B.R., et al., "Thermodynamic aspects of dicarboxylate recognition by simple artificial receptors," *J. Org. Chem.*, 66(22):7313-7319 (Nov. 2, 2001).

(56) References Cited

OTHER PUBLICATIONS

Majka, M., et al., "Biological significance of chemokine receptor expression by normal human megakaryoblasts," *Folia. Histochem. Cytobiol.* 39(3):235-244 (2001).

Mićović, V.M., and Mihailović, M.LJ., "The Reduction of Acid Amides with Lithium Aluminum Hydride," *J. Org. Chem.*, 18(9):1190-1200 (1953).

Mellado, M., et al., "Chemokine Signaling and Functional Responses: The Role of Receptor Dimerization and TK Pathway Activation," *Annu. Rev. Immun.*, 19: 397-421 (2001).

Mitra, P., et al., "CXCR4 mRNA expression in colon, esophageal and gastric cancers and hepatitis C infected liver," *Int. J. Oncol.*, 14(5):917-925 (May 1999).

Morales, J., et al., "CTACK, a skin-associated chemokine that preferentially attracts skin-homing memory T cells," *Proc. Natl. Acad. Sci. USA.*, 96(25):14470-14475 (Dec. 7, 1999).

Müller, A., et al., "Involvement of chemokine receptors in breast cancer metastasis," *Nature*, 410(6824):50-56 (Mar. 1, 2001).

Murdoch, C., et al., "Functional expression of chemokine receptor CXCR4 on human epithelial cells," *Immunology*, 98(1):36-41 (Sep. 1998).

Murdock, K.C., et al., "Antitumor agents. 2. Bisguanylhydrazones of anthracene-9,10-dicarboxaldehydes" *J. Med. Chem.* 25(5):505-518 (May 1982).

Nagase, H., et al., "Expression of CXCR4 in eosinophils: functional analyses and cytokine-mediated regulation," *J. Immunol.*, 164(11):5935-5943 (Jun. 1, 2000).

Nanki, T., and Lipsky, P.E., "Cutting edge: stromal cell-derived factor-1 is a costimulator for CD4$^+$T cell activation," *J. Immunol.*, 164(10):5010-5014 (May 15, 2000).

Navenot, J.-M., et al., Kisspeptin-10-Induced Signaling of GPR54 Negatively Regulates Chemotactic Responses Mediated by CXCR4: a Potential Mechanism for the Metastasis Suppressor Activity of Kisspeptins, *Cancer Res.* 65(22): 10450-10456 (2005).

Onuffer, J.J., and Horuk, R., "Chemokines, chemokine receptors and small-molecule antagonists: recent developments," *Trends Pharmacol. Sci.*, 23(10):459-467 (Oct. 2002).

Ottson, N., et al., "Cutting Edge: T Cell Migration Regulated by CXCR4 Chemokine Receptor Signaling to ZAP-70 Tyrosine Kinase," *J Immunol.* 1857-1861 (2001).

Peled, A., et al., "Dependence of human stem cell engraftment and repopulation of NOD/SCID mice on CXCR4," *Science*, 283(5403):845-848 (Feb. 5, 1999).

Pello, O., et al., "Ligand stabilization of CXCR4/δ-opiod receptor heterodimers reveals a mechanism for immune response regulation," *European. J. Immunol.*; 38:537-549 (2008).

Percherancier, Y., et al. Bioluminescence Resonance Energy Transfer Reveals Ligand-induced Conformational Changes in CXCR4 Homo- and Heterodimers, *Journal of Biological Chemistry*, 280(11): 9895-9903 (2004).

Post, D. E., and Van Meir, E. G., "Generation of bidirectional hypoxia/HIF-responsive expression vectors to target gene expression to hypoxic cells," *Gene Ther.*, 8(23):1801-1807 (Dec. 2001).

Rahman, K.M., et al., "Therapeutic intervention of experimental breast cancer bone metastasis by indole-3-carbinol in SCID-human mouse model," *Mol. Cancer Ther.*, 5(11):2747-56 (2006).

Reyes, M.J., et al., "Pyridinium N-(2'-azinyl)aminides: regioselective synthesis of N-(2-pyridyl) substituted polyamines,"*Tetrahedron*, 58(42):8573-8579 (Oct. 14, 2002).

Ross, R., "The pathogenesis of atherosclerosis: a perspective for the 1990s," *Nature*, 362(6423):801-809 (Apr. 29, 1993).

Sanchez, X., et al., "Activation of HIV-1 coreceptor (CXCR4) mediates myelosuppression," *J. Biol. Chem.*, 272(34):27529-27531 (Oct. 31, 1997).

Schols, D., et al., "Bicyclams, a class of potent anti-HIV agents, are targeted at the HIV coreceptor fusin/CXCR-4," *Antiviral Res.*, 35(3):147-156 (Aug. 1997).

Scozzafava, A., et al. "Non-peptidic chemokine receptors antagonists as emerging anti-HIV agents," *J. Enzyme Inhib. Med. Chem.*, 17(2):69-76 (Apr. 2002).

Sierro, F., et al., Disrupted cardiac development but normal hematopoiesis in mice deficient in the second CXCL12/SDF-1 receptor, CXCR7, *PNAS*, 103(37): 14759-14764 (2007).

Sohy, D., et al., "Allosteric Transinhibition by Specific Antagonists in CCR2/CXCR4 Heterodimers," *Journal of Biological Chemistry*, 282(41): 30062-30069 (2007).

Sotsios, Y., et al., "The CXC chemokine stromal cell-derived factor activates a Gi-coupled phosphoinositide 3-kinase in T lymphocytes," *J. Immunol.*, 163(11): 5954-5963 (Dec. 1, 1999).

Staller, P., et al., "Chemokine receptor CXCR4 downregulated by von Hippel-Lindau tumour suppressor pVHL," *Nature*, 425(6955):307-311 (Sep. 18, 2003).

Tamamura, H., et al., "A low-molecular-weight inhibitor against the chemokine receptor CXCR4: a strong anti-HIV peptide T140," *Biochem. Biophys. Res. Commun.*, 253(3): 877-882 (Dec. 30, 1998).

Tamamura, H., et al., "Development of specific CXCR4 inhibitors possessing high selectivity indexes as well as complete stability in serum based on an anti-HIV peptide T140," *Bioorg. Med. Chem. Lett.*, 11(14):1897-1902 (Jul. 23, 2001).

Tamamura, H., et al., "Pharmacophore identification of a specific CXCR4 inhibitor, T140, leads to development of effective anti-HIV agents with very high selectivity indexes," *Bioorg. Med. Chem. Lett.*, 10(23):2633-2637 (Dec. 4, 2000).

Trent, J.O., et al., "Lipid bilayer simulations of CXCR4 with inverse agonists and weak partial agonists," *J. Biol. Chem.*, 278(47):47136-47144 (Nov. 21, 2003) (Epublication Sep. 4, 2003).

Toth, P., et al., "Regulation of CXCR4 Receptor Dimerization by the Chemokine SDF-1 and the HIV-1 Coat Protein gp120: A Fluorescence Resonance Energy Transfer (FRET) Study," *J. Pharm. and Exp. Ther.*, 310(1): 8-17 (2004).

West "Solid state chemistry and its application," *Wilsy*, New York, 1998. pp. 358-365.

Vippagunta "Crystalline solid," *Advanced drug delivery*, 2001, vol. 48, pp. 3-26.

Vlahakis, S.R., et al., "G protein-coupled chemokine receptors induce both survival and apoptotic signaling pathways," *J. Immunol.* 169(10):5546-5554 (Nov. 15, 2002).

Volin, M.V., et al., "Chemokine receptor CXCR4 expression in endothelium," *Biochem Biophys Res Commnun.*, 242(1):46-53 (Jan. 6, 1998).

Ulrich "Crystallization," Chapter 4 *Kirk-Othmer Encyclopedia of Chemical technology*, John Wiley and Sons. 2002.

Xia, M.Q., and Hyman, B.T., "Chemokines/chemokine receptors in the central nervous system and Alzheimer's disease," *J. NeuroVirol.*, 5(1):32-41 (Feb. 1999).

Wald, O., et al., "Involvement of the CXCL12/CXCR4 pathway in the advanced liver disease that is associated with hepatitis C or hepatitis B virus," *Eur. J. Immunol.*, 34(4): 1164-1174 (2004).

Yssel, H., et al., "The role of IgE in asthma," *Clin. Exp. Allergy*; 28(28 Suppl. 5):104-109; discussion 117-118 (Nov. 1998).

Yopp, A., et al., "Sphingosine 1-Phosphate Receptors Regulated Chemokine-Driven Transendothelial Migration of Lymph Node but Not Splenic T Cells," *J. Immunol.*, 2913-2924 (2005).

Zaitseva, M., et al., "Expression and function of CCR5 and CXCR4 on human Langerhans cells and macrophages: implications for HIV primary infection," *Nat. Med.*, 3(12):1369-1375 (Dec. 1997).

Zlotnik, A., and Yoshie, Q., "Chemokines: a new classification system and their role in immunity," *Immunity*, 12(2):121-127 (Feb. 2000).

CHEMOKINE RECEPTOR MODULATORS

REFERENCE TO RELATED APPLICATIONS

This application is a continuation of U.S. patent application Ser. No. 12/414,352, filed Mar. 30, 2009, which claims priority to U.S. Provisional Application No. 61/040,516, filed Mar. 28, 2008, the disclosure of which each is hereby incorporated by reference in its entirety.

FIELD OF THE INVENTION

The invention provides compounds, pharmaceutical compositions and methods of use of certain compounds that are antagonists of the chemokine receptor. The compounds are useful to modulate a medical condition that is mediated by chemokine receptor activity or signaling, such as diseases and disorders associated with reduced hematopoietic stem cell mobilization. The compounds can also be useful in the treatment or prevention of inflammation, the treatment or prevention of human immunodeficiency virus infections (HIV), or the diagnosis, prevention, and treatment of cancer or cancer related pathologies and side effects.

BACKGROUND

Chemokines are considered to be principal mediators in the initiation and maintenance of inflammation. This superfamily of small, secreted cytokines induce, through their interaction with G-protein-coupled receptors, cytoskeletal rearrangements and directional migration of several cell types (Butcher, et al. (1999) *Adv Immunol* 72: 209-253; Campbell and Butcher (2000) *Curr Opin Immunol* 12: 336-341; Zlotnik and Yoshie (2000) *Immunity* 12: 121-127). They have also been found to play an important role in the regulation of endothelial cell function, including proliferation, migration and differentiation during angiogenesis and re-endothelialization after injury (Gupta et al. (1998) *J Biol Chem*, 7:4282-4287).

The chemokine receptor, CXCR4, is known in viral research as a major coreceptor for the entry of T cell linetropic HIV (Feng, et al. (1996) *Science* 272: 872-877; Davis, et al. (1997) *J Exp Med* 186: 1793-1798; Zaitseva, et al. (1997) *Nat Med* 3: 1369-1375; Sanchez, et al. (1997) *J Biol Chem* 272: 27529-27531). T Stromal cell derived factor 1 (SDF-1) is a naturally occurring chemokine that interacts specifically with CXCR4. When SDF-1 binds to CXCR4, CXCR4 activates $G\alpha_1$-protein-mediated signaling (pertussis toxin-sensitive) (Chen, et al. (1998) *Mol Pharmacol* 53: 177-181), including downstream kinase pathways such as Ras/MAP Kinases and phosphatidylinositol 3-kinase ($PI_3K$)/Akt in lymphocyte, megakaryocytes, and hematopoietic stem cells (Bleul, et al. (1996) *Nature* 382: 829-833; Deng, et al. (1997) *Nature* 388: 296-300; Kijowski, et al. (2001) *Stem Cells* 19: 453-466; Majka, et al. (2001) *Folia. Histochem. Cytobiol.* 39: 235-244; Sotsios, et al. (1999) *J. Immunol.* 163: 5954-5963; Vlahakis, et al. (2002) *J. Immunol.* 169: 5546-5554). In mice transplanted with human lymph nodes, SDF-1 induces CXCR4-positive cell migration into the transplanted lymph node (Blades et al. (2002) *J. Immunol.* 168: 4308-4317). These results imply that the interaction between SDF-1 and CXCR4 directs cells to the organ sites with high levels of SDF-1.

Studies have shown that CXCR4 interactions may regulate the migration of metastatic cells. Hypoxia, a reduction in partial oxygen pressure, is a microenvironmental change that occurs in most solid tumors and is a major inducer of tumor angiogenesis and therapeutic resistance. Hypoxia increases CXCR4 levels (Staller, et al. (2003) *Nature* 425: 307-311). Microarray analysis on a sub-population of cells from a bone metastatic model with elevated metastatic activity showed that one of the genes increased in the metastatic phenotype was CXCR4. Furthermore, overexpression of CXCR4 in isolated cells significantly increased the metastatic activity (Kang, et al. (2003) *Cancer Cell* 3: 537-549). In samples collected from various breast cancer patients, Muller et al. (Muller, et al. (2001) *Nature* 410: 50-56) found that CXCR4 expression level is higher in primary tumors relative to normal mammary gland or epithelial cells. These results suggest that the expression of CXCR4 on cancer cell surfaces may direct the cancer cells to sites that express high levels of SDF-I. Consistent with this hypothesis, SDF-1 is highly expressed in the most common destinations of breast cancer metastasis including lymph nodes, lung, liver, and bone marrow. Moreover, CXCR4 antibody treatment has been shown to inhibit metastasis to regional lymph nodes when compared to control isotypes that all metastasized to lymph nodes and lungs (Muller, et al. (2001)).

In addition to regulating migration of cancer cells, CXCR4-SDF-1 interactions may regulate vascularization necessary for metastasis. Blocking either CXCR4/SDF-1 interaction or the $G\alpha_1$ signaling inhibits VEGF-dependent neovascularization. These results indicate that SDF-1/CXCR4 controls signaling systems that are regulators of endothelial cell morphogenesis and angiogenesis. Numerous studies have shown that VEGF and MMPs actively contribute to cancer progression and metastasis.

Cancer is currently the second leading cause of death in developed nations. In 2008, the American Cancer Society estimated that approximately 1.43 million new cases were diagnosed in the U.S. alone, and approximately 565,000 deaths occurred due to cancer (American Cancer Society, Cancer Facts & Figures 2008). Metastasis, the spread and growth of tumor cells to distant organs, is the most devastating attribute of cancer. Most morbidity and mortality associated with certain types of cancer, such as breast cancer, is associated with disease caused by metastatic cells rather than by the primary tumor. Therapy for metastasis currently relies on a combination of early diagnosis and aggressive treatment of the primary tumor.

The establishment and growth of metastases at distant sites is thought to depend on interactions between tumor cells and the host environment. Although a number of mediators have been implicated in the metastasis of cancers such as breast cancer, the precise mechanisms determining the directional migration and invasion of tumor cells into specific organs remain to be established. An incomplete understanding of the molecular and cellular mechanisms underlying metastasis has hindered the development of effective therapies that would eliminate or ameliorate this condition.

Several strategies have been developed to reduce metastatic invasion of malignant cells by regulating adhesion of endothelial cells with antibodies or adhesion molecules (see for example, PCT Publication No. WO 97/00956, U.S. Pat. Nos. 5,993,817; 6,433,149; 6,475,488; and 6,358,915). However, no commercial strategy has provided an effective treatment to prevent metastasis.

As of the end of 2007, an estimated 33 million people worldwide were living with HIV/AIDS, and the Centers for Disease Control and Prevention (CDC) estimate that 1,200,000 U.S. residents are living with HIV infection (UNAIDS/WHO AIDS epidemic update, December 2008; The Henry J. Kaiser Family Foundation HIV/AIDS Policy Fact Sheet, July 2007). Although new infections have decreased in recent years, an estimated 2.6 million new HIV infections occurred worldwide during 2007 and approximately 40,000 new HIV infections occur each year in the United States.

HIV entry within the target cells involves a series of molecular events. The three main steps of virus entry within the cell are: (i) attachment of the virus to the host cells; (ii) interaction of the virus with the co-receptors; (iii) fusion of the virus and host cell membranes. Considering the complexity of the molecular events involved in viral infection, all three of these steps have been considered for the drug design of HIV entry inhibitors. The T-lymphocyte cell surface protein CD4 is the primary receptor involved in the interaction with the viral glycoprotein gp120, but a cellular co-receptor is also needed for the successful entry of the virus within the cell. At least two types of such co-receptors have been identified so far, both of which are chemokine receptors. These chemokine receptors are therefore gateways for HIV entry, determinants of viral tropism and sensitivity.

Compounds targeting CXCR4 have been developed primarily for treatment of HIV because CXCR4 is a major coreceptor for T-tropic HIV infection. For example, U.S. Pat. No. 6,429,308 to Hisamitsu Pharmaceutical Co., Inc. discloses an antisense oligonucleotide to CXCR4 to inhibit the expression of the CXCR4 protein for use as an anti-HIV agent. PCT Publication No. WO 01/56591 to Thomas Jefferson University describes peptide fragments of viral macrophage inflammatory protein II which are described as selectively preventing CXCR4 signal transduction and coreceptor function in mediating entry of HIV-1.

Peptide antagonists of CXCR4 receptors have also been disclosed. Tamamura et al. (Tamamura, et al. (2000) *Bioorg. Med. Chem. Leu.* 10: 2633-2637; Tamamura, et al. (2001) *Bioorg. Med. Chem. Leu.* 11: 1897-1902) reported the identification of a specific peptide-based CXCR4 inhibitor, T140. T140 is a 14-residue peptide that possessed high levels of anti-HIV activity and antagonism of T cell line-tropic HIV-1 entry among all antagonists of CXCR4 (Tamamura, et al. (1998) *Biochem. Biophys. Res. Commun.* 253: 877-882). The compound has been altered to increase its efficacy and bioavailability by, for example, amidating the C-terminal of T-140 and reducing the total positive charges by substituting basic residues with nonbasic polar amino acids to generate TN14003, which is less cytotoxic and more stable in serum compared to T140. The concentration of TN14003 required for 50% protection of HIV-induced cytopathogenicity in MT-4 cells is 0.6 nM in contrast to 410 mM leading to 50% toxicity. U.S. Pat. No. 6,344,545 to Progenics Pharmaceuticals, Inc. describes methods for preventing HIV-1 infection of CD4+ cells with peptide fragments. U.S. Pat. No. 6,534,626 to the U.S. Department of Health & Human Services describes certain peptide chemokine variants for treating HIV infections. PCT Publication No. WO 04/087068 to Emory University describes CXCR4 peptide antagonists, particularly TN14003, and methods of their use to treat metastasis.

Other peptide-based antagonists have also been disclosed. For example, European Patent Publication Nos. 1286684 and 1061944 to the University of British Columbia cover methods of treatment of diseases, including metastasis, using modified peptide CXCR4 antagonists derived from the native SDF-1 ligand. PCT Publication No. WO 04/020462 to Takeda Chemical Industries, Ltd. provides peptide CXCR4 antagonists for treatment and prevention of breast cancer and chronic rheumatoid arthritis. U.S. Patent Application No. 2004/0132642 to the U.S. Dept. of Health & Human Services in part covers methods of inhibiting metastasis or growth of a tumor cell with a polypeptide CXCR4 inhibitor.

Several groups have now also identified chemokines including CXCR4 as a target for treatment of metastatic cancers. For example, PCT Publication Nos. WO 01/38352 to Schering Corporation, WO 04/059285 to Protein Design Labs, Inc., and WO 04/024178 to Burger generally describe methods of treating diseases and specifically inhibiting metastasis by blocking chemokine receptor signaling.

Although advances have been made, inadequate absorption, distribution, metabolism, excretion or toxicity properties of peptide inhibitors have limited their clinical use. Small non-peptide drugs remain a major goal of medicinal chemistry programs in this area.

At the present time, the metal-chelating cyclams and bicyclams represent one of the few reported non-peptide molecules to effectively block CXCR4 (Onuffer and Horuk (2002) *Trends Pharmacol Sci* 23: 459-467.36). One of these non-peptide molecules is AMD3100, which entered clinical trials as an anti-HIV drug that blocks CXCR4-mediated viral entry (Donzella, et al. (1998) *Nat Med* 4: 72-77; Hatse, et al. (2002) *FEBS Lett* 527: 255-262; Fujii, et al. (2003) *Expert Opin Investig Drugs* 12: 185-195; Schols, et al. (1997) *Antiviral Res* 35: 147-156).

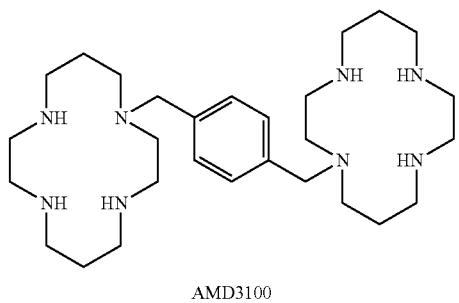 [SMILES: c1cc(CN2CCCNCCNCCCNCC2)ccc1CN1CCCNCCNCCCNCC1]

AMD3100

However, a clinical study showed cardiac-related side effect of AMD3100 which in part caused its withdrawal from clinical development (Scozzafava, et al. (2002) *J Enzyme Inhib Med Chem* 17: 69-7641); Hendrix, et al. (2004) *Journal of Acquired Immune Deficiency Syndromes* 37(2)).

Other nitrogen containing bicyclic molecules have also been developed as CXCR4 antagonists. European Patent Publication No. 1431290 and PCT Publication No. WO 02/094261 to Kureha Chemical Industry Co., Ltd cover CXCR4 inhibitors that are potentially useful in treating various diseases including HIV infection.

U.S. Patent Publication No. 2004/0254221 to Yamamazi, et al. also provides compounds and use thereof to treat various diseases including HIV infections that are CXCR4 antagonists. The compounds are of the general Formula:

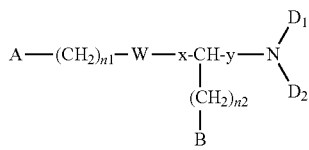

in which A is $A_1$-$G_1$-N($R_1$)—; $A_1$ is hydrogen or an optionally substituted, mono- or polycyclic, heteroaromatic or aromatic ring; $G_1$ is a single bond or —C($R_2$)($R_3$)—; $R_1$, $R_2$, and $R_3$ can be optionally substituted hydrocarbon groups; W is an optionally substituted hydrocarbon or heterocyclic ring; x is —C(=O)NH—; y is —C(=O)—; and $D_1$ is hydrogen atom, alkyl with a polycyclic aromatic ring, or amine.

PCT Publication No. WO 00/56729 and U.S. Pat. No. 6,750,348 to AnorMED describe certain heterocyclic small molecule CXCR4 binding compounds, teaching that these are useful for the protection against HIV infection. The compounds are of the general Formula:

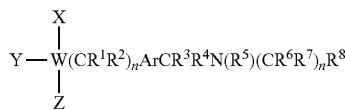

in which W can be a nitrogen or carbon atom; Y is absent or is hydrogen; $R^1$ to $R^7$ can be hydrogen or straight, branched or cyclic $C_{1-6}$ alkyl; $R^8$ is a substituted heterocyclic or aromatic group; Ar is an aromatic or heteroaromatic ring; and X is specified ring structure.

PCT Publication No. WO 2004/091518 to AnorMED also describes certain substituted nitrogen containing compounds that bind to CXCR4 receptors. The compounds are described as having the effect of increasing progenitor cells and/or stem cells, enhancing production of white blood cells, and exhibiting antiviral properties. PCT Publication No. WO 2004/093817 to AnorMED also discloses substituted heterocyclic CXCR4 antagonists which are described as useful to alleviate inflammatory conditions and elevate progenitor cells, as well as white blood cell counts. Similarly, PCT Publication No. WO 2004/106493 to AnorMED describes heterocyclic compounds that bind to CXCR4 and CCR5 receptors consisting of a core nitrogen atom surrounded by three pendant groups, wherein two of the three pendant groups are preferably benzimidazolyl methyl and tetrahydroquinolyl, and the third pendant group contains nitrogen and optionally contains additional rings. The compounds demonstrate protective effects against infections of target cells by a human immunodeficiency virus (HIV).

PCT Patent Application PCT/US06/000604, filed Jan. 9, 2006, describes certain compounds for the treatment of medical disorders mediated by CXCR4. These compounds include two nitrogen linked cyclic substituents off a central aromatic or cyclic alkyl or heteroalkyl.

In light of the fact that chemokine receptors are implicated in metastatic signaling as well as a number of other pathogenic conditions, it is important to identify new effective chemokine receptor modulators.

It is therefore an object of the invention to provide new compounds, methods and compositions that modulate chemokine receptors.

It is another object of the invention to provide compounds, methods and compositions that bind to chemokine receptors and interfere with their binding to their native ligands.

It is also an object of the invention to provide new compounds, methods and compositions for the treatment of viral infection, such as HIV, as well as for treatment of inflammatory and proliferative disorders.

SUMMARY

The present invention provides compounds and compositions that antagonize chemokine receptor signaling. The compounds described herein, are particularly useful for the treatment or prevention of a disorder associated with chemokine receptor binding or activation. These compounds can be used to treat diseases and disorders that are associated with chemokine activation, including diseases and disorders associated with reduced hematopoietic stem cell mobilization. Methods for the treatment of inflammatory, proliferative or infectious diseases and disorders mediated by chemokine signaling are also provided, including the prevention of symptoms associated with certain chemotherapeutics.

The compounds and compositions are particularly useful in disorders associated with the chemokine CXCR4 receptor.

In general embodiments, the compounds, compositions and methods of the invention are of Formula (I)

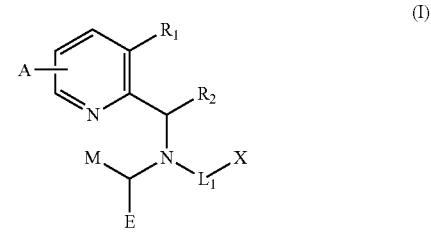

or a pharmaceutically acceptable salt, solvate, tautomer, stereoisomer, and/or ester thereof, wherein:

$R_1$ and $R_2$ are each independently H, optionally substituted alkyl, optionally substituted alkenyl, optionally substituted alkynyl, optionally substituted heteroalkyl including alkoxyalkyl, haloalkyl, $CF_3$, halogen, hydroxy, amino, optionally substituted alkyl or dialkyl amino, optionally substituted alkoxy, hydroxyalkyl, optionally substituted aminoalkyl, optionally substituted carbocyclyl, optionally substituted heterocyclyl, optionally substituted arlakyl, optionally substituted arylakyl, carboxy, acyl, optionally substituted alkoxycarbonyl, or optionally substituted aminocarbonyl; or $R_1$ and $R_2$, taken together with the carbon atoms to which they are shown attached, form a substituted or unsubstituted carbocyclyl or a substituted or unsubstituted heterocyclyl;

M is H or -G-$L_3$-Z;

E is H, —W-J-$L_2$-Y,

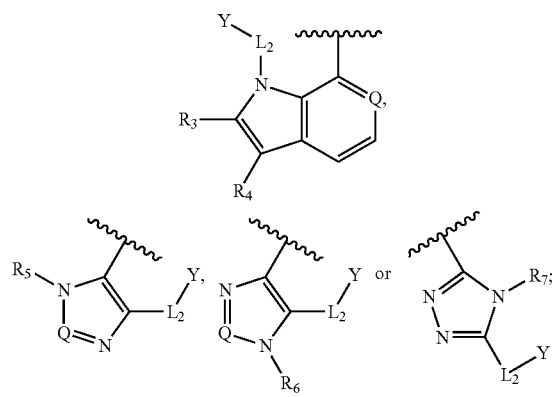

$L_1$, $L_2$, and $L_3$ are each independently selected from the group consisting of a covalent bond, substituted or unsubstituted alkylene, substituted or unsubstituted alkenyl, substituted or unsubstituted alkynyl, substituted or unsubstituted carbocycyl, and substituted or unsubstituted heterocyclyl;

X and Y are independently H, $NR_aR_b$, —$OR_c$, halogen, $CF_3$, optionally substituted alkyl, optionally substituted alkenyl, optionally substituted alkynyl, acyl, carboxy, optionally substituted alkoxycarbonyl, optionally substituted aminocarbonyl, optionally substituted alkyl- or dialkylaminocarbonyl, cyano, optionally substituted heterocyclylacyl, optionally substituted carbocyclylacyl, substituted or unsubstituted carbocyclyl, substituted or unsubstituted heterocyclyl;

Y is selected from the group consisting of H, $NR_aR_b$, $-OR_c$, substituted or unsubstituted carbocyclyl, and substituted or unsubstituted heterocyclyl;

$R_a$ and $R_b$ are each independently selected from the group consisting of H, substituted or unsubstituted alkyl, aldiminyl, substituted or unsubstituted carbocyclyl, substituted or unsubstituted carbocyclylalkyl, substituted or unsubstituted heterocyclylalkyl, and substituted or unsubstituted heterocyclyl; or $R_a$ and $R_b$, together with the nitrogen atom to which they are shown attached form a substituted or unsubstituted heterocyclyl;

$R_c$ is selected from the group consisting of H, substituted or unsubstituted alkyl, substituted or unsubstituted heteroalkyl, substituted or unsubstituted carbocyclyl, substituted or unsubstituted heterocyclyl, substituted or unsubstituted carbocyclylalkyl, substituted or unsubstituted heterocyclylalkyl, J is selected from the group consisting of a covalent bond, alkylene, $-C(O)-NR_d-$, $-C(O)-O-$, $-NR_d-$, and $-C(O)-$;

$R_d$ is selected from the group consisting of H, alkyl, and substituted or substituted arylalkyl;

Q is $CR_e$ or N; $R_e$ is selected from the group consisting of H, alkyl, halo, substituted or unsubstituted amino, cyano, nitro, haloalkyl, hydroxyl, and alkoxyl;

G is selected from the group consisting of a covalent bond, alkylene, $-C(O)-$, $-C(O)-O-$, and $-C(O)-NR_d-$;

W is selected from the group consisting of a covalent bond and a substituted or unsubstituted heterocyclyl;

$R_3$ and $R_4$ are each independently selected from the group consisting of H, substituted or unsubstituted aryl, substituted or unsubstituted heteroaryl, substituted or unsubstituted alkyl, substituted or unsubstituted alkenyl, and substituted or unsubstituted alkynyl; or $R_3$ and $R_4$, taken together with the carbon atoms to which they are shown attached, form a substituted or unsubstituted carbocyclyl or a substituted or unsubstituted heterocyclyl;

$R_5$ and $R_6$ are each independently selected from the group consisting of substituted or unsubstituted aminoalkyl, substituted or unsubstituted carbocyclyl, substituted or unsubstituted carbocyclylalkyl, substituted or unsubstituted heterocyclyl, substituted or unsubstituted heterocyclylalkyl, alkyl, alkenyl, and alkynyl; or -$L_2$-Y and $R_6$, together with the atoms to which they are shown attached form a fused substituted or unsubstituted ring; or E and -$L_1$-X, together with the atoms to which they are shown bonded form a substituted or unsubstituted heterocyclyl;

$R_7$ is selected from the group consisting of H, substituted or unsubstituted alkyl, substituted or unsubstituted aminoalkyl, substituted or unsubstituted carbocyclyl, substituted or unsubstituted heterocyclyl, substituted or unsubstituted carbocyclylalkyl, and substituted or unsubstituted heterocyclylalkyl; or $L_2$-Y and $R_7$ together with the atoms to which they are shown bonded form a fused substituted or unsubstituted ring; and A and B are each independently one or more substituents selected from the group consisting of H, alkyl, halo, substituted or unsubstituted amino, cyano, nitro, haloalkyl, hydroxyl, and alkoxyl;

with the proviso that only one of M, E and $L_1$-X is H.

In certain embodiments, the present invention provides compounds, compositions and methods including the following Formulae:

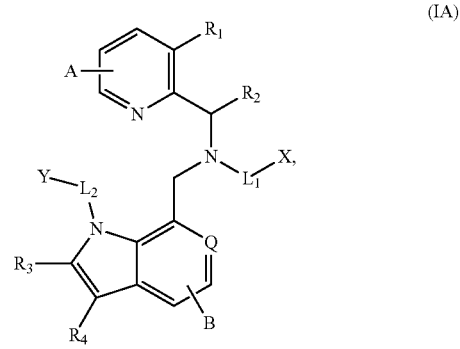

(IA)

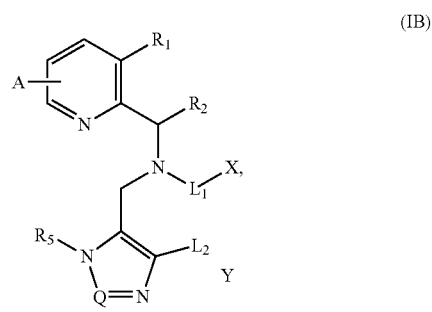

(IB)

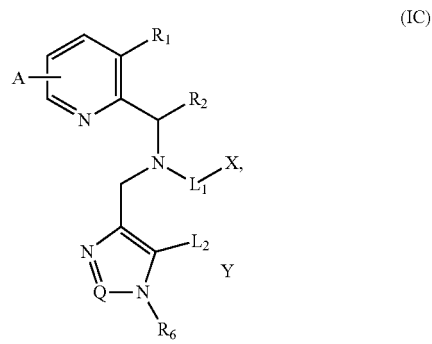

(IC)

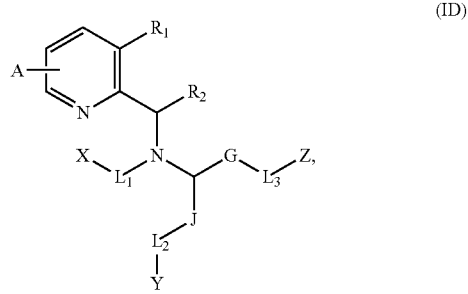

(ID)

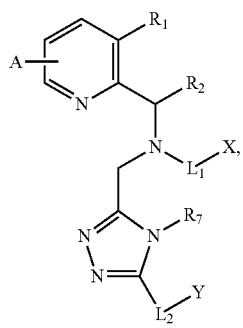
(IE)

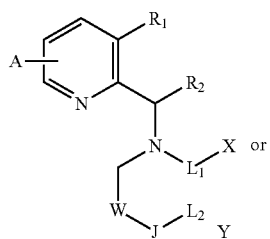
(IF)

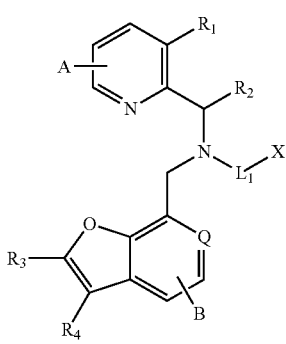
(IG)

or a pharmaceutically acceptable salts, solvates, tautomers, stereoisomers, and/or esters thereof, wherein variables are defined as for Formula I.

In certain more specific embodiments, the present invention provides compounds, compositions and methods including the following Formulae:

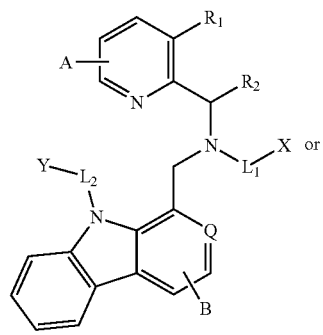
(IA-1)

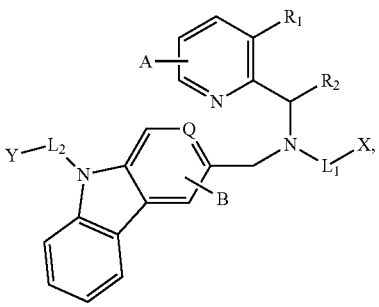
(IA-2)

or a pharmaceutically acceptable salts, solvates, tautomers, stereoisomers, and/or esters thereof, wherein variables are defined as for Formula I. In some embodiments, the present invention is directed to a pharmaceutical composition comprising at least one compound of Formula (I), or a pharmaceutically acceptable salt, solvate, prodrug, tautomer, or ester thereof, and a pharmaceutically acceptable excipient.

In yet another embodiment, the present invention is directed to a pharmaceutical composition comprising at least one compound of Formula (I), or a pharmaceutically acceptable salt, solvate, prodrug, tautomer, or ester thereof, and a pharmaceutically acceptable excipient, and at least one additional pharmaceutically active compound.

In still another embodiment, the present invention is directed to a method of treating a disorder, symptom or disease in a patient in need of such treatment, comprising administering to the patient an effective amount of at least one compound of Formula (I). Typically, the methods of use of the present invention are directed towards treatment or prophylaxis of a disorder, symptom or disease that is modulated by chemokine receptor activity or signaling. Disorders to be treated generally are those in which inhibition of chemokine signaling, particularly that of a CXCR4 receptor, is desirable. In certain embodiments, the compounds are administered to a patient at risk of or suffering from a disorder causing a reduction in lymphocytes or myeloid cells.

DETAILED DESCRIPTION OF THE INVENTION

The compounds, methods, and compositions of the present invention can modulate the effect of chemokine receptors. These compounds can be used to treat diseases and disorders that are associated with CXCR4 activation, including diseases and disorders associated with reduced hematopoietic stem cell mobilization. In addition, methods of treatment of disorders including tumor metastasis or any other disease, particularly hyperproliferative diseases involving chemokine receptors are provided. The compounds can also be used to treat or prevent HIV infection, reduce viral load, or alleviate progression towards, or the symptoms of, AIDS in a host in need thereof.

Compounds described herein have the capacity to interact with chemokine receptors and potentially inhibit receptor signaling. The compounds of the present invention have increased bioavailability and efficacy in inhibiting chemokine receptors.

Although not bound by theory, these compounds may inhibit certain disorders such as metastasis through their capacity to inhibit SDF-1-chemokine receptor interactions, which can decrease cell targeting, and may also reduce VEGF-dependent endothelial cell morphogenesis and angiogenesis. This endothelial cell growth is a key event in metastases of tumors.

DEFINITIONS

The term "organism," "host," or "patient" are used interchangeably to refer to any living entity comprised of at least one cell. A living organism can be as simple as, for example, a single eukaryotic cell or as complex as a mammal, including a human being. In certain embodiments, the organism is a human in need of treatment.

The term "chemokine receptor modulator" means a substance including but not limited to a molecule, polypeptide, polynucleotide, inhibitory polynucleotide, or siRNA, that interferes or inhibits the biological activity of the chemokine receptors including, but not limited to, the binding of a ligand to the receptor. The term "chemokine peptide antagonist" means a polypeptide that specifically binds to a chemokine receptor, particularly polypeptides that are not an antibody. Representative chemokine peptide antagonists include T140 and derivatives of T140. Exemplary derivatives of T140 include, but are not limited to, TN14003, TC14012, and TE14011 as well as those found in Tamamura, H. et al. Org. Biomol. Chem. 1:3656-3662, 2003, which is incorporated by reference herein in its entirety.

The term "therapeutically effective amount" or "effective amount", as used herein, means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, and the particular active ingredient(s) being employed, and like factors within the knowledge and expertise of the attending physician. For example, in reference to cancer or pathologies related to unregulated cell division, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the metastasis of cancer cells, and/or, (4) relieving to some extent (or, preferably, eliminating) one or more symptoms associated with a pathology related to or caused in part by unregulated or aberrant cellular division, including for example, cancer, or angiogenesis. With respect to stem cell mobilization, an effective amount is sufficient to improve stem cell mobilization as measured, for example, by an increase in the presence of and/or activity of blood cell types including those of myeloid (monocytes and macrophages, neutrophils, basophils, eosinophils, erythrocytes, megakaryocytes/platelets, dendritic cells), and/or lymphoid lineages (T-cells, B-cells, NK-cells). Representative dosage ranges and administrative regimes are further described below, however these can be subject to adjustment in individual patients. A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, a "pharmaceutically acceptable carrier" or "pharmaceutically acceptable excipient" refers to a carrier or diluent that does not cause significant irritation to an organism and does not abrogate the biological activity and properties of the administered compound.

An "excipient" refers to an inert substance added to a pharmaceutical composition to further facilitate administration of a compound, such as binders, anti-adherents, coatings, disintegrants, fillers, diluents, flavors, colors, glidants, lubricants, preservatives, sorbitans, and sweeteners. Examples, without limitation, of excipients include calcium carbonate, calcium phosphate, various sugars and types of starch, cellulose derivatives, gelatin, vegetable oils and polyethylene glycols.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to HIV or cancer, these terms can mean that the life expectancy of an individual affected with HIV or cancer will be increased or that one or more of the symptoms of the disease will be reduced.

The term "prodrug" refers to an agent, including nucleic acids and polypeptides, which is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Rocke, ed. (1977). Bioreversible Carriers in Drug in Drug Design, Theory and Application, APhA; H. Bundgaard, 15 ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of P-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3): 183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev, 19(2): 115-130; Fleisher et al. (1985). Design of prodrugs for improved gastrointestinal absorption by intestinal enzyme targeting, Methods Enzymol. 112:360-81; Farquhar D, et al.

(1983). Biologically Reversible Phosphate-Protective Groups, J. Pharm. Sci., 72(3): 24-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci, 11 Supp12:S15-27; Wang, W. et al. (1999) Prodrug approaches to the improved delivery of peptide drugs. Gurr. Pharm. Des., 5(4):265-87.

The term "alkyl", as used herein, unless otherwise specified, includes but is not limited to a saturated straight or branched, primary, secondary, or tertiary hydrocarbon of $C_1$ to $C_{20}$ or $C_1$ to $C_{10}$ and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of halo (e.g., trifluoromethyl), hydroxyl, amino, alkylamino, acylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "alkenyl" refers to an alkyl, as defined herein, in which at least one C—C (single) bond is replaced with a C═C (double) bond. The alkenyl can be branched or straight chain, and can have one, two or more C═C double bonds, which can be conjugated or unconjugated.

The term "alkynyl" refers to an alkyl, as defined herein, in which at least one C—C (single) bond is replaced with a CC (triple) bond. The alkynyl can be branched or straight chain, and can have one, two or more CC triple bonds.

Whenever the terms "$C_1$-$C_5$ alkyl", "$C_2$-$C_5$ alkenyl", "$C_1$-$C_5$ alkoxy", "$C_2$-$C_5$alkenoxy", "$C_2$-$C_5$ alkynyl", and "$C_2$-$C_5$ alkynoxy", "$C_3$-$C_5$" are used, these are considered to include, independently, each member of the group, such that, for example, $C_1$-$C_5$ alkyl includes straight, branched and $C_1$, $C_2$, $C_3$, $C_4$ and $C_5$ alkyl functionalities; $C_2$-$C_5$ alkenyl includes straight and branched $C_2$, $C_3$, $C_4$ and $C_5$ alkenyl functionalities; $C_1$-$C_5$ alkoxy includes straight and branched, $C_1$, $C_2$, $C_3$, $C_4$ and $C_5$ alkoxy functionalities; $C_2$-$C_5$ alkenoxy includes straight and branched $C_2$, $C_3$, $C_4$ and $C_5$ alkenoxy functionalities; $C_2$-$C_5$ alkynyl includes straight and branched $C_1$, $C_2$, $C_3$, $C_4$ and $C_5$ alkynyl functionalities; and $C_2$-$C_5$ alkynoxy includes straight and branched $C_2$, $C_3$, $C_4$ and $C_5$ alkynoxy functionalities, etc.

The term "lower alkyl", as used herein, and unless otherwise specified, includes a $C_1$ to $C_4$ saturated straight or branched alkyl group, optionally including substituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term "alkylene", as used herein, means an organic radical formed from an unsaturated aliphatic hydrocarbon. Typically, an alkylene can be represented by the following Formula: —C(RR')$_n$—, wherein n is an integer of one or more, and R and R' is hydrogen, halo, hydroxyl, amino, cyano (i.e., —CN), nitro, alkoxy, alkylamino, arylamino, sulfate, sulfonic acid, phosphonic acid, phosphate, phosphonate, either unprotected, or protected as necessary, as known to those skilled in the art. Preferably, n is an integer from 1 to 20. More preferably, n is an integer from 1 to 6. The alkylene can be straight, branched, or cyclic. Non-limiting examples of alkylene include —CH$_2$— (methylene), —CH$_2$CH$_2$-(ethylene), —CH$_2$CH$_2$CH$_2$— (propylene), etc.

The term "amino" includes an amine group (i.e., —NH$_2$) as well as an amine group substituted with one or more alkyl groups, substituted alkyl groups (e.g., hydroxyalkyl, alkoxyalkyl, thioalkyl, alkylthioalkyl, etc.), one or two aryl groups, one or two heteroaryl groups, one or two arylalkyl groups, one or two heteroarylalkyl groups, combinations of H, alkyl, aryl, heteroaryl, arylalkyl, and heteroarylalkyl groups. When the amino group has one or more alkyl, aryl, heteroaryl, arylalkyl, or heteroarylalkyl groups, the alkyl, aryl, heteroaryl, arylalkyl, or heteroarylalkyl groups can be unsubstituted or substituted. The terms "alkylamino" or "arylamino" refer to an amino group that has one or two alkyl or aryl substituents, respectively. The terms "arylalkylamino" or "heteroarylalkylamino" refer to an amino group that has one or two arylalkyl or heteroaryl alkyl groups, respectively. In any instance in which the valence of a compound is drawn in error in this application, the valence is to be corrected by including and/or excluding a hydrogen.

The term "amino" can also include amino groups substituted with acyl groups such as —C(O)-alkyl, —C(O)-aryl, —C(O)-heteroaryl, —C(O)—O-alkyl, —C(O)—O-aryl, —C(O)—O-heteroaryl, —C(O)—N(R)-alkyl, —C(O)—N(R)-aryl, —C(O)—N(R)-heteroaryl; sulfonyl groups such as —S(O)$_2$-alkyl, —S(O)$_2$-aryl, —S(O)$_2$-heteroaryl, —S(O)$_2$—O-alkyl, —S(O)$_2$—O-aryl, —S(O)$_2$—O-heteroaryl, —S(O)$_2$—N(R)-alkyl, —S(O)$_2$—N(R)-aryl, —S(O)$_2$—N(R)-heteroaryl, etc. (wherein R is H, alkyl, aryl, heteroaryl). When the substituent on the amino group is an acyl group, the moiety can also be referred to as an "amido" group (i.e., when the acyl group is —C(O)-alkyl, —C(O)-aryl, or —C(O)-heteroaryl), a "urea" moiety (i.e., when the acyl group is —C(O)—N(R)-alkyl, —C(O)—N(R)-aryl, or —C(O)—N(R)-heteroaryl), or a "urethane" moiety (i.e., when the acyl group is —C(O)—O-alkyl, —C(O)—O-aryl, or —C(O)—O-heteroaryl).

Unless stated to the contrary, a substituent is bound to a structure through the last named moiety of the substituent. For example, an "arylalkyl" substituent is bound to a structure through the "alkyl" moiety of the substituent.

The term "aminoalkyl", as used herein, means an amino groups bonded to the parent moiety through an alkyl moiety (i.e., amino-alkyl-), wherein the amino and alkyl portions of the aminoalkyl are each as defined herein. Non-limiting examples of aminoalkyl include H$_2$N—(CH$_2$)$_2$—CH$_2$—, H$_2$N—(CH$_2$)$_3$—CH$_2$—, (CH$_3$)$_2$N—CH$_2$CH$_2$—, CH$_3$—O—CH$_2$CH$_2$NH—CH$_2$—, aryl-NH—(CH$_2$)$_3$—CH$_2$—, heteroaryl-NH—(CH$_2$)$_3$—CH$_2$—, H$_2$N—C(O)—NH—(CH$_2$)$_2$—CH$_2$—, etc. The term aminoalkyl can also refer to nitrogen containing heterocycles attached to an alkylene through the nitrogen atom of the heterocycle, e.g., pyrrolidine-CH$_2$—, piperidine-CH$_2$CH$_2$—, morpholine-CH$_2$CH$_2$—, etc.

The term "amido", "aminoacyl", or "aminocarbonyl", as used herein, means amino-C(O)—, wherein the amino moiety is any amino as defined herein. Non-limiting examples of aminoacyl include phenyl-NH—C(O)—, piperazine-C(O)—, pyrrolidine-C(O)—, (CH$_3$—O—CH$_2$CH$_2$)$_2$N—C(O)—, pyridine-CH$_2$—NH—C(O)—, phenyl-CH$_2$—NH—C(O)—, etc.

The term "aminoacylalkyl", as used herein, means amino-C(O)-alkyl-, wherein the amino-C(O) moiety and alkyl moiety are as defined herein.

The term "arylamino", as used herein, means aryl-amino-, wherein the amino moiety is any amino as defined herein. Non-limiting examples of arylamino include phenyl-NH—, halo substituted phenyl-NH—, etc.

The term "heteroarylamino", as used herein, means heteroaryl-amino-, wherein the amino moiety is any amino as defined herein. Non-limiting examples of arylamino include pyrimidine-NH—, halo substituted pyrimidine-NH—, haloalkyl substituted pyrimidine-NH—, etc.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term "aryl", as used herein, means an aromatic monocyclic or multicyclic ring system comprising about 6 to about 14 carbon atoms, preferably about 6 to about 10 carbon atoms. Non-limiting examples of suitable aryl groups include phenyl, biphenyl, or naphthyl. The term aryl refers to unsubstituted aryl groups or aryl groups substituted with one or more substituents which may be the same or different. The aryl group can be substituted with one or more substituents, including but not limited to substituents selected from the group consisting of hydroxyl, thiol, amino, alkylamino, arylamino, alkoxy, aryloxy, nitro, cyano, sulfonic acid, halo (F, Cl, I, Br), carboxy, ester, acyl, alkyl (i.e., any of the alkyl groups described herein, such as methyl, ethyl, propyl, butyl, etc.), alkenyl (i.e., any of the alkenyl groups described herein, such as vinyl, allyl, 1-propenyl, 1-butenyl, 2-butenyl, etc.), alkynyl (i.e., any of the alkynyl groups described herein, such as 1-ethynyl, 1-propynyl, 2-propynyl, etc.), haloalkyl (i.e., any of the haloalkyl groups described herein), sulfate, sulfonate, sulfonic esters and amides, phosphoric acid, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991.

The term "alkaryl" or "alkylaryl" refers to an alkyl group with an aryl substituent. In one embodiment, the "alk" or "alkyl" portion of the alkaryl is a lower alkyl group. Non-limiting examples of suitable alkylaryl groups include o-tolyl, p-tolyl and xylyl. The bond to the parent moiety is through the aryl.

The term "aralkyl" or "arylalkyl" refers to an aryl group attached to an alkyl group. In one embodiment, the "alk" or "alkyl" portion of the aralkyl is a lower alkyl group. Non-limiting examples of suitable aralkyl groups include benzyl, 2-phenethyl and naphthalenylmethyl. The bond to the parent moiety is through the alkyl. The aryl portion of the arylalkyl group may be substituted or unsubstituted.

The term "alkoxy", as used herein, means alkyl-O—, wherein the alkyl moiety of the alkoxy group is an alkyl group as defined herein.

The term "cycloalkyl" means a non-aromatic mono- or multicyclic fused ring system comprising 3 to 10 ring carbon atoms, preferably 3 to 7 ring carbon atoms, more preferably 3 to 6 ring carbon atoms. The cycloalkyl can be optionally substituted with one or more substituents which may be the same or different. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornenyl, adamantyl and the like. Suitable substituents for cycloalkyls include substituents selected from the group consisting of hydroxyl, thiol, amino, alkylamino, arylamino, alkoxy, aryloxy, nitro, cyano, sulfonic acid, halo (F, Cl, I, Br), carboxy, ester, acyl, alkyl (i.e., any of the alkyl groups described herein, such as methyl, ethyl, propyl, butyl, etc.), alkenyl (i.e., any of the alkenyl groups described herein, such as vinyl, allyl, 1-propenyl, 1-butenyl, 2-butenyl, etc.), alkynyl (i.e., any of the alkynyl groups described herein, such as 1-ethynyl, 1-propynyl, 2-propynyl, etc.), haloalkyl (i.e., any of the haloalkyl groups described herein), sulfate, sulfonate, sulfonic esters and amides, phosphoric acid, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, herein incorporated by reference in its entirety. Substituents can also include fused aromatic rings, e.g.:

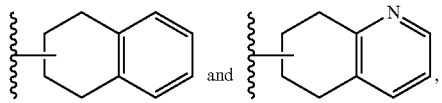

wherein the fused aromatic or heteroaromatic ring can itself be unsubstituted or substituted with one or more substituents as described herein.

The term "halo", as used herein, includes chloro, bromo, iodo, and fluoro.

The term "haloalkyl", as used herein, means an alkyl as defined above wherein one or more hydrogen atoms on the alkyl are replaced by a halo defined above. Non-limiting examples of haloalkyl groups include —$CF_3$, —$CH_2CF_3$, etc.

The term "hydroxyalkyl", as used herein, means an alkyl group having at least one hydroxy substituent. Non-limiting examples of hydroxyalkyl groups include hydroxyethyl, 3-hydroxypropyl, 2-hydroxy propyl, etc.

The term "alkoxyalkyl", as used herein, means alkyl-O-alkyl-, wherein each of the alkyl moieties is as defined herein. The skilled practitioner will recognize that a divalent alkyl group (i.e., an alkyl group bonded to two other moieties) can also be referred to as an "alkylene" group. An alkylene group is an alkyl group in which one of the C—H bonds is replaced with a covalent bond to another moiety. Non-limiting examples of alkoxyalkyl groups include $CH_3$—O—$CH_2CH_2$—, $CH_3$—O—$CH_2CH_2CH_2$—, $CH_3CH_2$—O—$CH_2CH_2$—, $CH_3CH_2$—O—$CH_2CH_2CH_2$—, t-Bu-O—$CH_2CH_2$—, etc.

The term "acyl" refers to a carbonyl group (—C(O)—). For example, arylacyl refers to groups such as phenyl-C(O)—, alkylacyl refers to acetyl, aminoacyl refers to $H_2N$—C(O)— (wherein the N atom can be substituted with aryl, alkyl, heterocyclyl, etc), etc. When the acyl group forms, for example, a ketone, a carboxy group, a carbonate group, a urea group, a thio ester, etc, the non-carbonyl moiety of the such a group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. In one embodiment, aryl groups in the esters comprise a phenyl group. The term "lower acyl" refers to an acyl group in which the non-carbonyl moiety is a lower alkyl.

The term "carboxy", as used herein, means —C(O)OH or an ester thereof.

The term "alkoxycarbonyl", as used herein, means —C(O)—O-alkyl, wherein the alkyl moiety is any alkyl as defined herein.

The term "alkylthioalkyl", as used herein, means alkyl-5-alkyl-, wherein each of the alkyl moieties is as defined herein. Non-limiting examples of alkylthioalkyl groups include $CH_3$—S—$CH_2CH_2$—, $CH_3$—S—$CH_2CH_2CH_2$—, $CH_3CH_2$—S—$CH_2CH_2$—, $CH_3CH_2$—S—$CH_2CH_2CH_2$—, t-Bu-S—$CH_2CH_2$—, etc.

The term "alkylamino", as used herein, means alkylamino-, wherein the amino moiety can be any amino as defined herein.

The term "a 5- to 18-membered saturated heterocyclic ring containing at least one nitrogen atom" means a saturated monocyclic or multicyclic ring system comprising 5 to 18 atoms as the members constituting the ring system wherein the 5 to 18 atoms are chosen from carbon, nitrogen, sulfur, or phosphorous and at least one of the 5 to 18 atoms are nitrogen. The term encompasses a 6-18 membered saturated heterocyclic ring containing one or more, e.g., 2 nitrogen atoms. The multicyclic ring system can be fused or bridged multicyclic rings. The 5- to 18-membered saturated heterocyclic ring can optionally be substituted at any substitutable position (including at a heteroatom) by groups including substituted or unsubstituted alkyl (e.g., hydroxyalkyl, haloalkyl, alkoxyalkyl, etc.), halo, hydroxyl, oxo, amino (as defined herein, e.g., —$NH_2$, amido, sulfonamido, urea moiety, urethane moiety), aminoacyl (as defined herein), aminoalkyl (as defined herein), amino-$S(O)_2$—, alkyl-$S(O)_2$—, arylamino (as defined herein), heteroarylamino (as defined herein), alkylamino (as defined herein), alkoxy, alkoxycarbonyl, aryloxy, nitro, cyano, aryl, heteroaryl, carboxy (as defined herein), sulfonic acid, sulfate, phosphonic acid, phosphate, or phosphonate, either unprotected, or protected as necessary, as known to those skilled in the art. Non-limiting examples of substituted or unsubstituted 5- to 18-membered saturated heterocyclic rings containing at least one nitrogen atom include the following:

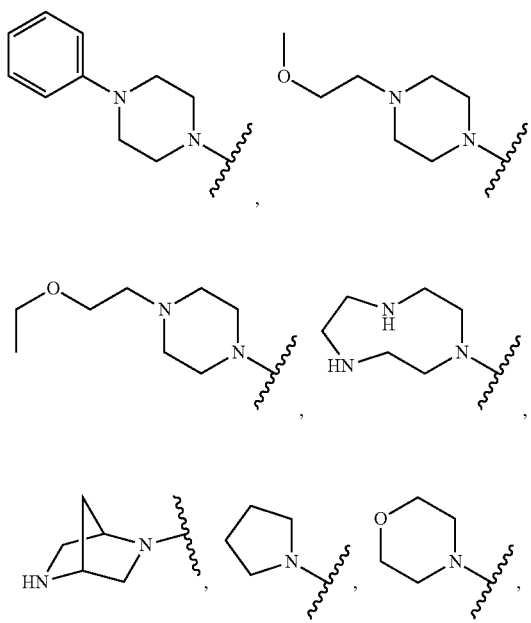

-continued

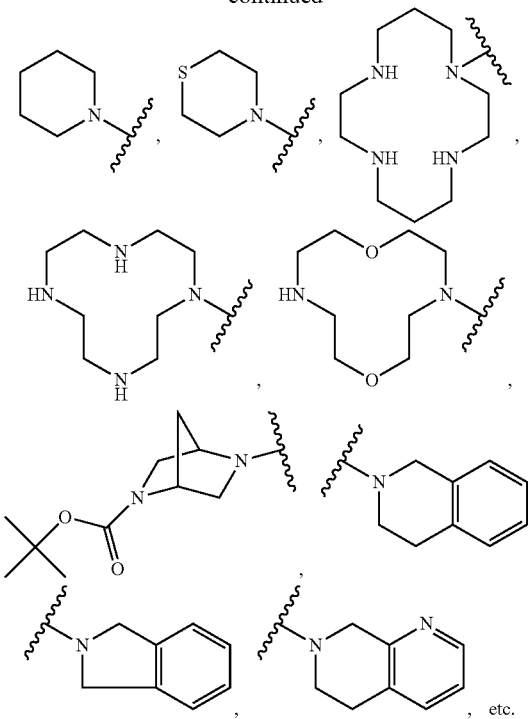

, etc.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

The term "pharmaceutically acceptable salt, solvate, ester or prodrug" is used throughout the specification to describe any pharmaceutically acceptable form (such as an ester, phosphate ester, salt of an ester or a related group, or hydrate) of a compound which, upon administration to a patient, provides the compound described in the specification. Pharmaceutically acceptable salts include those derived from pharmaceutically acceptable inorganic or organic bases and acids such as hydrochloric acid, hydrobromic acid, sulfuric acid, nitric acid, phosphoric acid, methanesulfonic acid, ethanesulfonic acid, p-toluensulfonic acid, salicylic acid, malic acid, maleic acid, succinic acid, tartaric acid, citric acid and the like. Suitable salts include those derived from alkali metals such as potassium and sodium, alkaline earth metals such as calcium and magnesium, among numerous other acids well known in the art, for example as described herein.

The term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The term "heterocyclic" or "heterocyclyl" refers to a cyclic group that may be unsaturated, partially or fully saturated and wherein there is at least one heteroatom, such as oxygen, sulfur, nitrogen, or phosphorus in the ring. Heterocyclic or heterocyclyl groups include heteroaryl groups. Non-limiting examples of non-aromatic heterocyclyls include piperidinyl, piperazinyl, morpholinyl, pyrrolidinyl, morpholino, thiomorpholino, oxiranyl, pyrazolinyl, dioxolanyl, 1,4-dioxanyl, aziridinyl, tetrahydrofuranyl, pyrrolinyl dihydrofuranyl, dioxanyl, tetrahydropyranyl, dihydropyranyl, indolinyl, imidazolyl, tetraazacyclotetradecanyl, dioxadiazacyclododecanyl, diazepanyl, etc., wherein each of the aforementioned heterocyclyls can be unsubstituted or substituted at any substitutable position (including a heteroatom) with one or more substituents (e.g., any of those described herein, including carbonyl groups in the heterocyclic ring).

The term "heteroaryl" or "heteroaromatic", as used herein, refers to an aromatic ring that includes at least one sulfur, oxygen, nitrogen or phosphorus in the aromatic ring. Non-limiting examples of heteroaromatics are furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, tetrazolyl, benzofuranyl, quinolyl, isoquinolyl, benzothienyl, isobenzofuryl, indolyl, isoindolyl, benzimidazolyl, purine, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, 1,2,3-triazole, 1,2,4-triazole, 1,2,3-oxadiazole, thiazine, pyridazine, benzothiophenyl, isopyrrole, thiophene, pyrazine, or pteridinyl wherein said heteroaryl or heterocyclic group can be optionally substituted with one or more substituent. In one embodiment, heterocyclyl and heteroaromatic groups include purine and pyrimidines.

Substituted aromatic or heteroaromatic rings (including aromatic or heteroaromatic portions of functional groups such as arylalkyl or heteroarylalkyl groups) can be substituted with one or more substituents. Non-limiting examples of such substituents selected from the group consisting of hydroxyl, thiol, amino, alkylamino, arylamino, alkoxy, aryloxy, nitro, cyano, sulfonic acid, halo (F, Cl, I, Br), carboxy, ester, acyl, alkyl (i.e., any of the alkyl groups described herein, such as methyl, ethyl, propyl, butyl, etc.), alkenyl (i.e., any of the alkenyl groups described herein, such as vinyl, allyl, 1-propenyl, 1-butenyl, 2-butenyl, etc.), alkynyl (i.e., any of the alkynyl groups described herein, such as 1-ethynyl, 1-propynyl, 2-propynyl, etc.), haloalkyl (i.e., any of the haloalkyl groups described herein), sulfate, sulfonate, sulfonic esters and amides, phosphoric acid, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

Functional oxygen and nitrogen groups (e.g., on a aryl or heteroaryl group) can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl.

The term "heteroarylalkyl", as used herein, means heteroaryl-alkyl-, wherein the heteroaryl and alkyl moieties can be any heteroaryl or alkyl defined herein. Non-limiting examples of heteroarylalkyl include pyridine-methyl- and benzimidazole-methyl-.

The term "heterocyclylalkyl", as used herein, means heterocyclyl-alkyl-, wherein the alkyl moiety may attach to the heterocyclyl ring at any available position, and the heterocyclyl and alkyl moieties can be any heterocyclyl or alkyl defined herein. Non-limiting examples of heteroarylalkyl include pyrrolidine-methyl- and piperidine-methyl.

The term "carbocyclyl" or "carbocyclic" as used herein means a cyclic group in which all of the ring atoms are carbon, which may be unsaturated, partially or fully saturated. Carbocyclic rings can be monocyclic or polycyclic and include aromatic rings (e.g., phenyl, naphthyl, etc.), partially unsaturated non-aromatic rings (dehydronaphthyl, cyclopentenyl, cyclohexenyl, etc.), or fully saturated hydrocarbon rings (cyclopropyl, cyclobutyl, cyclopentyl, cyclohexyl, etc.). The carbocyclic rings can be substituted with any substituents described herein, e.g., those described for substituted aromatic and heteroaromatic rings herein (including carbonyl groups in the ring).

The term "carbocyclylacyl", as used herein, means —C(O)-carbocyclyl, wherein the carbocyclyl moiety is any carbocyclic as defined herein, and include "arylacyl" groups.

The term "arylacyl", as used herein, means —C(O)-aryl, wherein the aryl moiety is any aryl as defined herein.

The term "aldiminyl" as used herein means a group of the Formula —C=N—R, where R is any alkyl, carbocyclyl, or heterocyclyl groups described herein. For example, aldiminyl includes —C=N-alkyl, wherein the alkyl moiety includes any alkyl moiety described herein; —C=N-aryl wherein the aryl moiety includes any described or defined herein; —C=N-cycloalkyl, wherein the cycloalkyl moiety includes any described or defined herein; —C=N-heteroaryl wherein the heteroaryl moiety includes any described or defined herein; —C=N-heterocycloalkyl, wherein the heterocycloalkyl moiety includes any described or defined herein The term "heteorycyclylacyl", as used herein, means —C(O)— heteorycyclyl, wherein the heteorycyclylmoiety is any heteorycyclylas defined herein, and include "heteroarylacyl" groups.

The term "heteroarylacyl", as used herein, means —C(O)-heteroaryl, wherein the heteroaryl moiety is any heteroaryl as defined herein.

The term purine or pyrimidine includes, but is not limited to, adenine, $N_6$-alkylpurines, $N_6$-acylpurines (wherein acyl is C(O)(alkyl, aryl, alkylaryl, or arylalkyl), $N_6$-benzylpurine, $N_6$-halopurine, $N_6$-vinylpurine, $N_6$-acetylenic purine, $N_6$-acyl purine, $N_6$-hydroxyalkyl purine, $N_6$-thioalkyl purine, $N_2$-alkylpurines, $N_2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C_5$_alkylpyrimidines, $C_5$-benzylpyrimidines, $C_5$-halopyrimidines, $C_5$-vinylpyrimidine, $C_5$-acetylenic pyrimidine, $C_5$-acyl pyrimidine, $C_5$-hydroxyalkyl purine, $C_5$-amidopyrimidine, $C_5$-cyanopyrimidine, $C_5$-nitropyrimidine, $C_5$-aminopyrimidine, $N_2$-alkylpurines, $N_2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine.

Compounds of the present invention, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Polymorphic forms of the compounds of the present invention, and of the salts, solvates and/or prodrugs of the compounds of the present invention, are intended to be included in the present invention.

Chemokine Inhibitory Compounds

Compounds of Formula I

In one embodiment, the invention provides compounds of Formula (I), or pharmaceutically acceptable salts, solvates, prodrugs, tautomers, stereoisomers, and esters thereof:

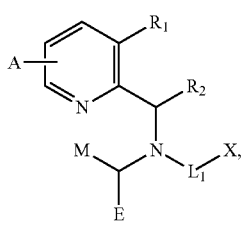

(I)

or a pharmaceutically acceptable salt, solvate, tautomer, stereoisomer, and/or ester thereof, wherein:

$R_1$ and $R_2$ are each independently H, optionally substituted alkyl, optionally substituted alkenyl, optionally substituted alkynyl, optionally substituted heteroalkyl including alkoxyalkyl, haloalkyl, $CF_3$, halogen, hydroxy, amino, optionally substituted alkyl or dialkyl amino, optionally substituted alkoxy, hydroxyalkyl, optionally substituted aminoalkyl, optionally substituted carbocyclyl, optionally substituted heterocyclyl, optionally substituted arlakyl, optionally substituted arylakyl, carboxy, acyl, optionally substituted alkoxycarbonyl, or optionally substituted aminocarbonyl; or $R_1$ and $R_2$, taken together with the carbon atoms to which they are shown attached, form a substituted or unsubstituted carbocyclyl or a substituted or unsubstituted heterocyclyl;

M is H or -G-$L_3$-Z;

E is H, —W-J-$L_2$-Y,

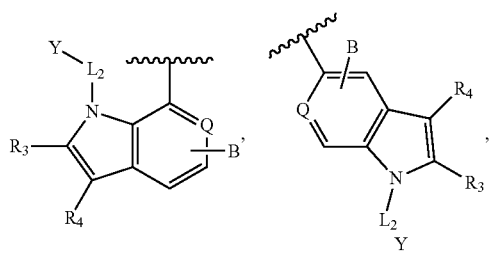

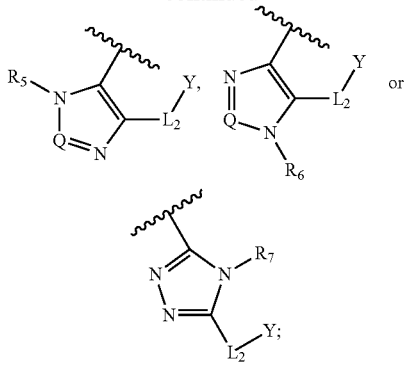

$L_1$, $L_2$, and $L_3$ are each independently selected from the group consisting of a covalent bond, substituted or unsubstituted alkylene, substituted or unsubstituted alkenyl, substituted or unsubstituted alkynyl, substituted or unsubstituted carbocycyl, and substituted or unsubstituted heterocyclyl;

X, Y and Z are independently H, $NR_aR_b$, —$OR_c$, halogen, $CF_3$, optionally substituted alkyl, optionally substituted alkenyl, optionally substituted alkynyl, acyl, carboxy, optionally substituted alkoxycarbonyl, optionally substituted aminocarbonyl, optionally substituted alkyl- or dialkylaminocarbonyl, cyano, optionally substituted heterocyclylacyl, optionally substituted carbocyclylacyl, substituted or unsubstituted carbocyclyl, substituted or unsubstituted heterocyclyl;

$R_a$ and $R_b$ are each independently selected from the group consisting of H, substituted or unsubstituted alkyl, aldiminyl, substituted or unsubstituted carbocyclyl, substituted or unsubstituted carbocyclylalkyl, substituted or unsubstituted heterocyclylalkyl, and substituted or unsubstituted heterocyclyl; or $R_a$ and $R_b$, together with the nitrogen atom to which they are shown attached form a substituted or unsubstituted heterocyclyl;

$R_c$ is selected from the group consisting of H, substituted or unsubstituted alkyl, substituted or unsubstituted heteroalkyl, substituted or unsubstituted carbocyclyl, substituted or unsubstituted heterocyclyl, substituted or unsubstituted carbocyclylalkyl, substituted or unsubstituted heterocyclylalkyl, J is selected from the group consisting of a covalent bond, alkylene, —C(O)—$NR_d$—, —C(O)—O—, —$NR_d$—, and —C(O)—;

$R_d$ is selected from the group consisting of H, alkyl, and substituted or substituted arylalkyl;

Q is $CR_e$ or N;

$R_e$ is selected from the group consisting of H, alkyl, halo, substituted or unsubstituted amino, cyano, nitro, haloalkyl, hydroxyl, and alkoxyl;

G is selected from the group consisting of a covalent bond, alkylene, —C(O)—, —C(O)—O—, and —C(O)—$NR_d$—;

W is selected from the group consisting of a covalent bond and a substituted or unsubstituted heterocyclyl;

$R_3$ and $R_4$ are each independently selected from the group consisting of H, substituted or unsubstituted aryl, substituted or unsubstituted heteroaryl, substituted or unsubstituted alkyl, substituted or unsubstituted alkenyl, and substituted or unsubstituted alkynyl; or $R_3$ and $R_4$, taken together with the carbon atoms to which they are shown attached, form a substituted or unsubstituted carbocyclyl or a substituted or unsubstituted heterocyclyl;

$R_5$ and $R_6$ are each independently selected from the group consisting of substituted or unsubstituted aminoalkyl, substituted or unsubstituted carbocyclyl, substituted or unsubstituted carbocyclylalkyl, substituted or unsubstituted heterocyclyl, substituted or unsubstituted heterocyclylalkyl, alkyl, alkenyl, and alkynyl; or -$L_2$-Y and $R_6$, together with the atoms to which they are shown attached form a fused substituted or unsubstituted ring; or E and -$L_1$X, together with the atoms to which they are shown bonded form a substituted or unsubstituted heterocyclyl;

$R_7$ is selected from the group consisting of H, substituted or unsubstituted alkyl, substituted or unsubstituted aminoalkyl, substituted or unsubstituted carbocyclyl, substituted or unsubstituted heterocyclyl, substituted or unsubstituted carbocyclylalkyl, and substituted or unsubstituted heterocyclylalkyl; or $L_2$Y and $R_7$ together with the atoms to which they are shown bonded form a fused substituted or unsubstituted ring; and A and B are each independently one or more substituents selected from the group consisting of H, alkyl, halo, substituted or unsubstituted amino, cyano, nitro, haloalkyl, hydroxyl, and alkoxyl;

with the proviso that only one of M, E and $L_1$X is H.

In certain embodiments, the compounds of Formula I have sufficient chemical stability for Formulation in a pharmaceutical composition.

In certain embodiments of Formula I, $R_1$ and $R_2$ are each independently H or alkyl; or $R_1$ and $R_2$, taken together with the carbon atoms to which they are shown attached, form a substituted or unsubstituted carbocyclyl or a substituted or unsubstituted heterocyclyl.

In certain embodiments of Formula I, X and Z are each independently selected from the group consisting of H, $NR_aR_b$, and —$OR_c$.

When $R_1$ and $R_2$, taken together with the carbon atoms to which they are shown attached form a substituted or unsubstituted carbocyclyl or a substituted or unsubstituted heterocyclyl, the carbocyclyl groups can include saturated fused rings, such as cyclopentyl, cyclohexyl, cycloheptyl, etc. fused to a pyridyl ring of the parent moiety of Formula (I) or partially or fully unsaturated fused rings. Certain non-limiting examples of such saturated fused rings include:

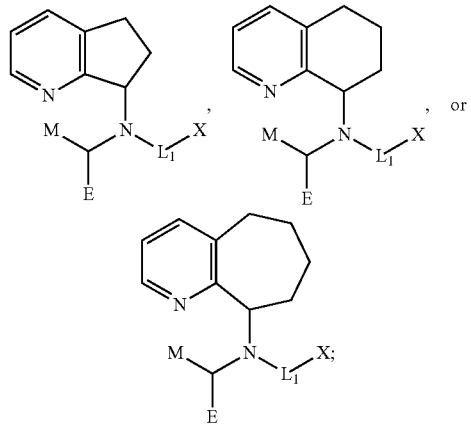

and non-limiting examples of unsaturated fused rings include:

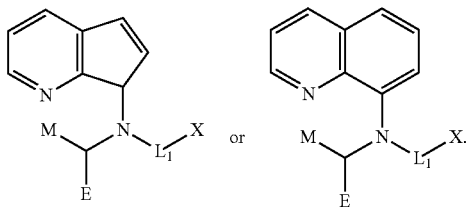

When $R_1$ and $R_2$ combine to form a substituted or unsubstituted heterocyclyl, the substituted or unsubstituted heterocyclyl includes one or more heteroatoms at any suitable stable position(s) in the ring. Non-limiting examples include:

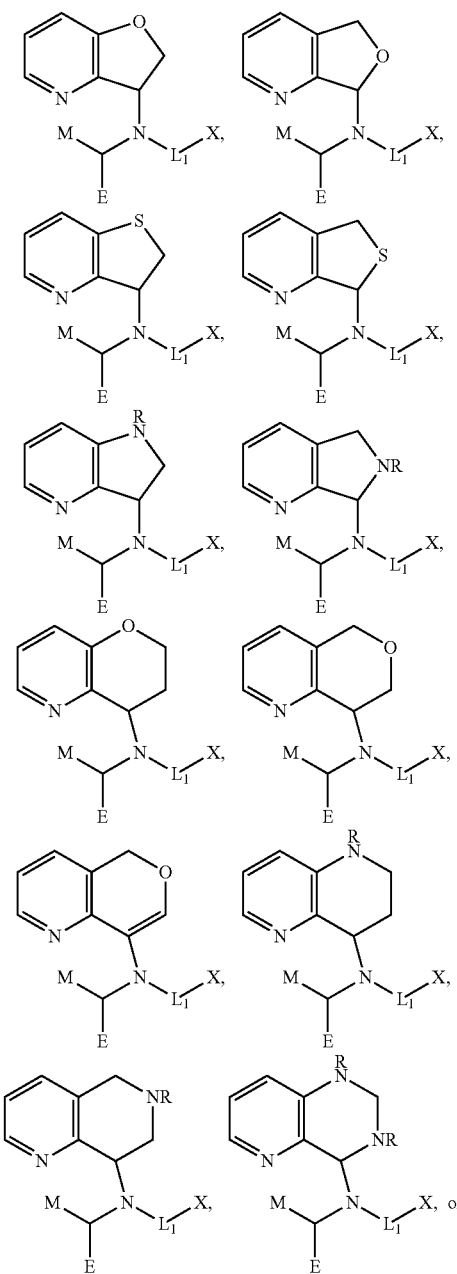

-continued

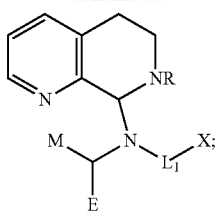

wherein R is any suitable substituent (including H) described herein, and $L_1$, X, E and M are as defined above for Formula (I). In certain embodiments, R is H. In certain other embodiments, R is a substituted alkyl, alkenyl, aralkyl, a residue of an amino acid, or the like.

In some embodiments of Formula (I), the group

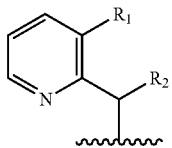

is selected from:

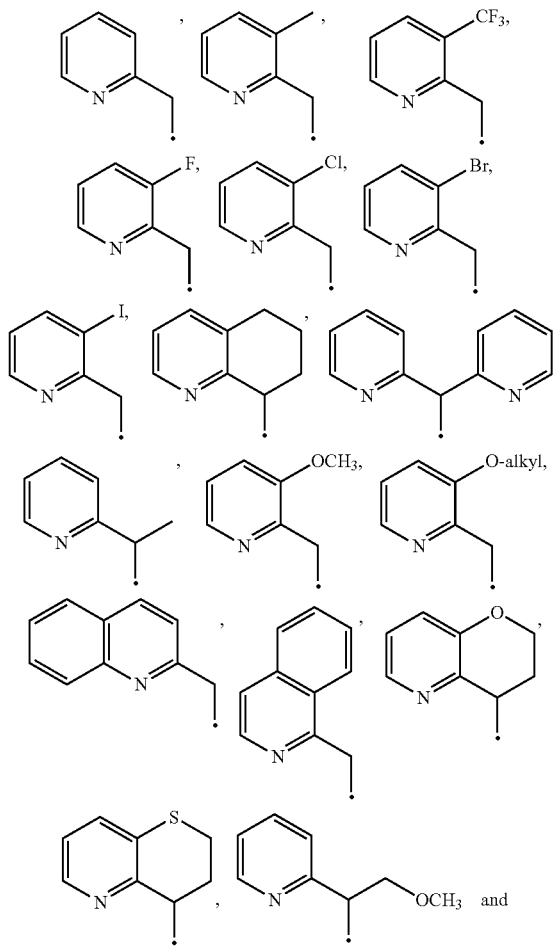

-continued

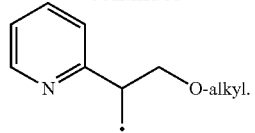

In a particular embodiment of Formula (I), the group

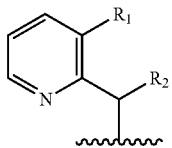
or
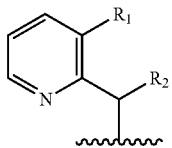
.

In some embodiments, when X, Y, or Z is $NR_aR_b$, $R_a$ and $R_b$, together with the nitrogen atom to which they are shown attached form a substituted or unsubstituted heterocyclyl. In certain embodiments, the heterocyclyl is selected from piperidyl, piperazyl, morpholinyl, pyridyl, pyrimidyl, pyrrolyl, diazinyl, triazinyl or the like.

When E is —W-J-$L_2$-Y, non limiting examples of —W-J-$L_2$-Y include substituted or unsubstituted heterocyclyl rings (including, as non-limiting examples, pyridyl, piperazyl, piperadyl and pyrimidyl) substituted with an aminoalkyl, carbocyclyl, heterocyclyl, or the like, any of which can be substituted or unsubstituted.

Non-limiting examples of groups formed when $R_3$ and $R_4$ taken together with the carbon atoms to which they are shown attached form a substituted or unsubstituted carbocyclyl or a substituted or unsubstituted heterocyclyl include:

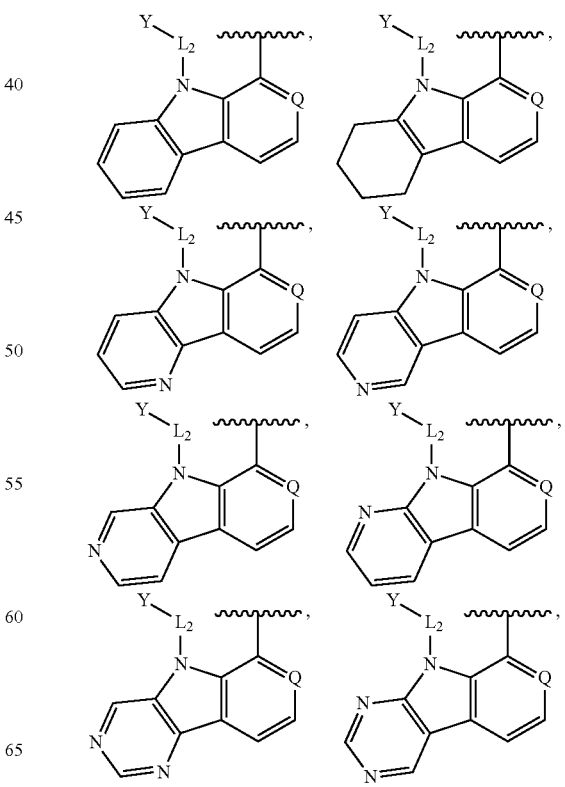

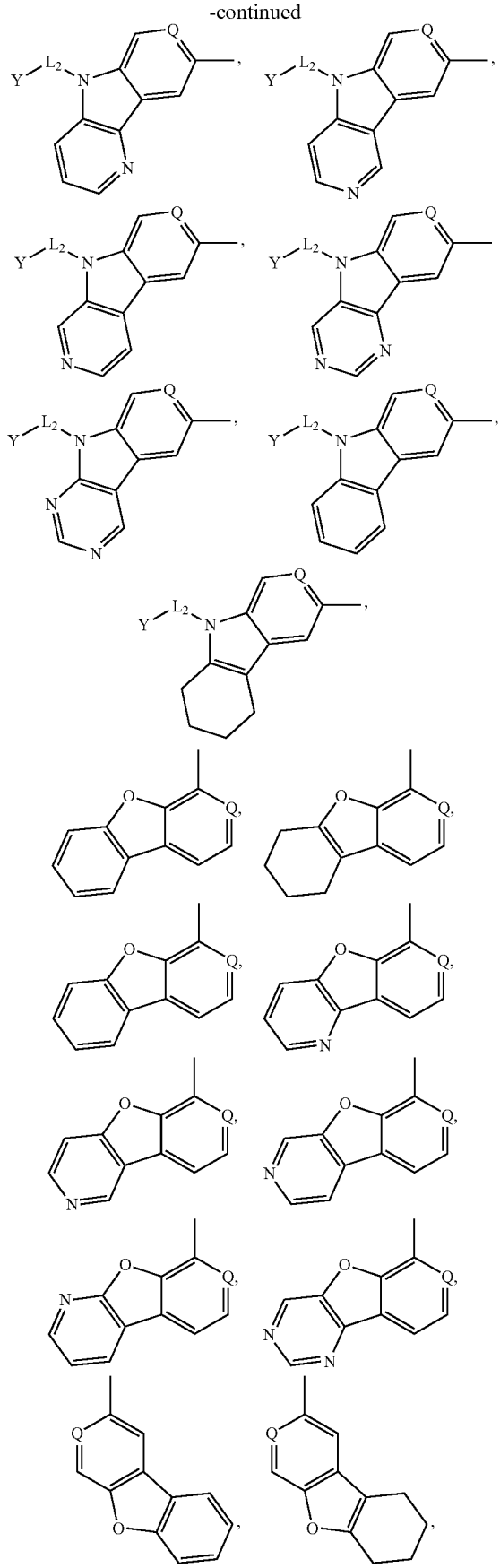

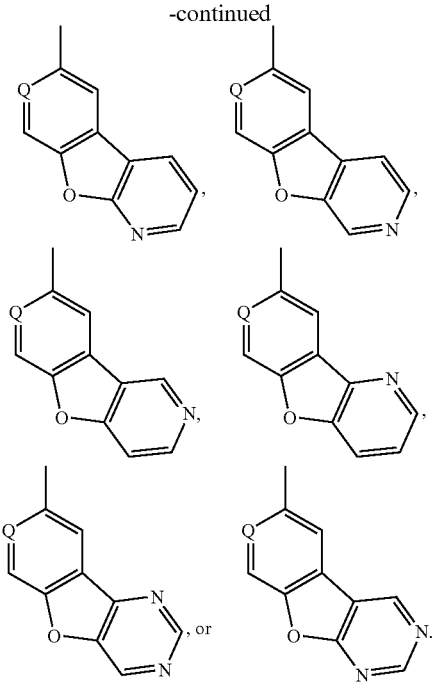

Each of the preceeding may be further substituted with one or more substituents.

Compounds of Formula IA

In one embodiment, the compounds of the present invention have the following Formula (IA):

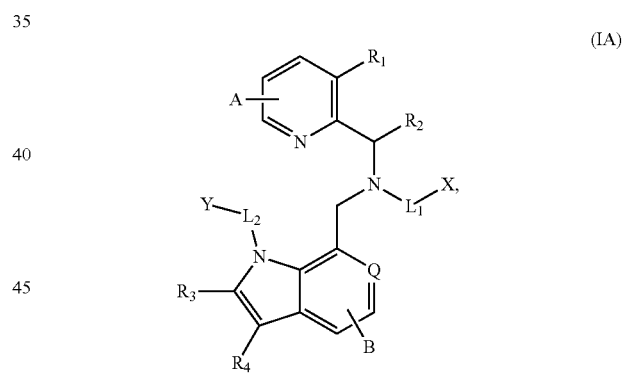

wherein each of $R_1$, $R_2$, $R_3$, $R_4$, $L_1$, $L_2$, X, Y, Q, A, and B are as defined or described herein.

In a particular embodiment of the compounds of Formula (IA), $R_1$ and $R_2$ are each independently H or alkyl; or $R_1$ and $R_2$, taken together with the carbon atoms to which they are shown attached, form a substituted or unsubstituted carbocyclyl; $L_1$ and $L_2$ are each independently selected from the group consisting of a covalent bond, substituted or unsubstituted alkylene, substituted or unsubstituted alkenyl, and substituted or unsubstituted alkynyl; X and Y are each independently H or $NR_aR_b$ wherein $R_a$ and $R_b$ are each independently selected from the group consisting of H, substituted or unsubstituted alkyl, aldiminyl, substituted or unsubstituted carbocyclyl, substituted or unsubstituted carbocyclylalkyl, substituted or unsubstituted heterocyclylalkyl, and substituted or unsubstituted heterocyclyl; or $R_a$ and $R_b$, together with the nitrogen atom to which they are shown attached form a substituted or unsubstituted heterocyclyl; Q is $CR_e$ or N; $R_e$ is selected from the group consisting of H, alkyl, halo, substituted or unsubstituted amino, cyano, nitro, haloalkyl, hydroxyl, and alkoxyl; and $R_3$ and $R_4$ are each independently selected from the group consisting of H, substituted or unsubstituted aryl, substituted or unsubstituted heteroaryl, substituted or unsubstituted alkyl, substituted or unsubstituted alkenyl, and substituted or unsubstituted alkynyl; or $R_3$ and $R_4$, taken together with the carbon atoms to which they are shown attached, form a substituted or unsubstituted carbocyclyl or a substituted or unsubstituted heterocyclyl.

In another embodiment of the compounds of Formula (IA), $R_2$ is H; or $R_1$ and $R_2$, taken together with the carbon atoms to which they are shown attached, form a substituted or unsubstituted carbocyclyl; $L_1$ is substituted or unsubstituted alkylene; $L_2$ is a covalent bond or substituted or unsubstituted alkylene; X and Y are each independently H or $NR_aR_b$; $R_a$ and $R_b$ are each independently selected from the group consisting of H, alkyl, aldiminyl, substituted or unsubstituted carbocyclyl, substituted or unsubstituted carbocyclylalkyl, substituted or unsubstituted heterocyclylalkyl, and substituted or unsubstituted heterocyclyl; or $R_a$ and $R_b$, together with the nitrogen atom to which they are shown attached form a substituted or unsubstituted heterocyclyl; Q is CH or N; and $R_3$ and $R_4$ are each H; or $R_3$ and $R_4$, taken together with the carbon atoms to which they are shown attached, form a substituted or unsubstituted aryl.

In some embodiments of the compounds of Formula (IA), $R_3$ and $R_4$, taken together with the carbon atoms to which they are shown attached, form:

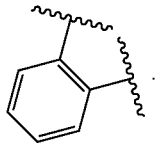

In other embodiments of the compounds of Formula (IA),

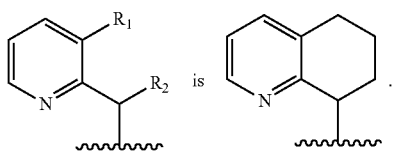

In other embodiments of the compounds of Formula (IA),

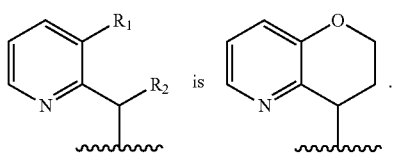

In other embodiments of the compounds of Formula (IA),

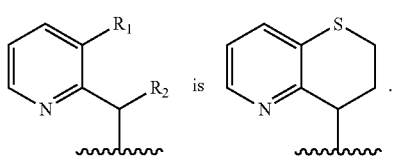

In some embodiments of the compounds of Formula (IA), Q is N.

In other embodiments of the compounds of Formula (IA), Q is CH.

In certain embodiments of the compounds of Formula (IA), $L_2Y$ is H.

In other embodiments of the compounds of Formula (IA), $L_2Y$ is -alkylene-$NR_aR_b$.

In yet other embodiments of the compounds of Formula (IA), $L_2Y$ is -alkylene-$NH_2$.

In further embodiments of the compounds of Formula (IA), $L_2Y$ is -alkylene-$N(alkyl)_2$.

In further embodiments of the compounds of Formula (IA), $L_2Y$ is —$(CH_2)_2$—$NR_aR_b$.

In another embodiment of the compounds of Formula (IA), $L_2Y$ is —$(CH_2)_2$—$NH_2$.

In another embodiment of the compounds of Formula (IA), $L_2Y$ is —$(CH_2)_2$—$N(alkyl)_2$.

In another embodiment of the compounds of Formula (IA), $L_2Y$ is —$(CH_2)_3$—$NR_aR_b$.

In another embodiment of the compounds of Formula (IA), $L_2Y$ is —$(CH_2)_3$—$NH_2$.

In another embodiment of the compounds of Formula (IA), $L_2Y$ is —$(CH_2)_3$—$N(alkyl)_2$.

In another embodiment of the compounds of Formula (IA), $L_2Y$ is —$(CH_2)_4$—$NR_aR_b$.

In another embodiment of the compounds of Formula (IA), $L_2Y$ is —$(CH_2)_4$—$NH_2$.

In another embodiment of the compounds of Formula (IA), $L_2Y$ is —$(CH_2)_4$—$N(alkyl)_2$.

In some embodiments of the compounds of Formula (IA), $L_1X$ is H.

In other embodiments of the compounds of Formula (IA), $L_1X$ is -alkylene-$NR_aR_b$.

In another embodiment of the compounds of Formula (IA), $L_1X$ is -alkylene-$NH_2$.

In another embodiment of the compounds of Formula (IA), $L_1X$ is -alkylene-$N(alkyl)_2$.

In another embodiment of the compounds of Formula (IA), $L_1X$ is —$(CH_2)_2$—$NR_aR_b$.

In another embodiment of the compounds of Formula (IA), $L_1X$ is —$(CH_2)_2$—$NH_2$.

In another embodiment of the compounds of Formula (IA), $L_1X$ is —$(CH_2)_2$—$N(alkyl)_2$.

In another embodiment of the compounds of Formula (IA), $L_1X$ is —$(CH_2)_3$—$NR_aR_b$.

In another embodiment of the compounds of Formula (IA), $L_1X$ is —$(CH_2)_3$—$NH_2$.

In another embodiment of the compounds of Formula (IA), $L_1X$ is —$(CH_2)_3$—$N(alkyl)_2$.

In another embodiment of the compounds of Formula (IA), $L_1X$ is —$(CH_2)_4$—$NR_aR_b$.

In another embodiment of the compounds of Formula (IA), $L_1X$ is —$(CH_2)_4$—$NH_2$.

In another embodiment of the compounds of Formula (IA), $L_1X$ is —$(CH_2)_4$—$N(alkyl)_2$.

In certain embodiments of the compounds of Formula (IA), $R_3$ and $R_4$, taken together with the carbon atoms to which they are shown attached, form:

In other embodiments of the compounds of Formula (IA), R₃ and R₄, taken together with the carbon atoms to which they are shown attached, form:

In another embodiment of the compounds of Formula (IA), R₃ and R₄, taken together with the carbon atoms to which they are shown attached, form:

In some embodiments of the compounds of Formula (IA), L₁X is alkyl; and L₂Y is -alkylene-NR$_a$R$_b$.
In other embodiments of the compounds of Formula (IA), L₁X is CH₃; and L₂Y is -alkylene-NR$_a$R$_b$.
In another embodiment of the compounds of Formula (IA), L₁X is CH₃; and L₂Y is -alkylene-NH₂.
In another embodiment of the compounds of Formula (IA), L₁X is CH₃; and L₂Y is -alkylene-NH(heterocyclyl).
In another embodiment of the compounds of Formula (IA), L₁X is CH₃; and L₂Y is -alkylene-NH(heteroarylalkyl).
In another embodiment of the compounds of Formula (IA), L₁X is CH₃; and L₂Y is -alkylene-NH(arylalkyl).
In another embodiment of the compounds of Formula (IA), L₁X is CH₃; and L₂Y is -alkylene-N(heteroarylalkyl)₂.
In another embodiment of the compounds of Formula (IA), L₁X is CH₃; and L₂Y is -alkylene-N(arylalkyl)₂.
In another embodiment of the compounds of Formula (IA), L₁X is CH₃; and L₂Y is -alkylene-N(alkyl)$_z$.

In another embodiment of the compounds of Formula (IA), L₁X is -alkylene-NR$_a$R$_b$; and L₂Y is H.
In another embodiment of the compounds of Formula (IA), L₁X is -alkylene-NH₂; and L₂Y is H.
In another embodiment of the compounds of Formula (IA), L₁X is —(CH₂)₂—NH₂; and L₂Y is H.
In another embodiment of the compounds of Formula (IA), L₁X is —(CH₂)₃—NH₂; and L₂Y is H.
In another embodiment of the compounds of Formula (IA), L₁X is —(CH₂)₄—NH₂; and L₂Y is H.
In another embodiment of the compounds of Formula (IA), L₁X is -alkylene-N(alkyl)$_z$; and L₂Y is H.
In another embodiment of the compounds of Formula (IA), L₁X is —(CH₂)₂—N(alkyl)₂; and L₂Y is H.
In another embodiment of the compounds of Formula (IA), L₁X is —(CH₂)₃—N(alkyl)₂; and L₂Y is H.
In another embodiment of the compounds of Formula (IA), L₁X is —(CH₂)₄—N(alkyl)₂; and L₂Y is H.
In another embodiment of the compounds of Formula (IA), L₁X is -alkylene-NH(alkyl); and L₂Y is H.
In another embodiment of the compounds of Formula (IA), L₁X is —(CH₂)₂—NH(alkyl); and L₂Y is H.
In another embodiment of the compounds of Formula (IA), L₁X is —(CH₂)₃—NH(alkyl); and L₂Y is H.
In another embodiment of the compounds of Formula (IA), L₁X is —(CH₂)₄—NH(alkyl); and L₂Y is H.
In another embodiment of the compounds of Formula (IA), L₁X is -alkylene-NH(heterocyclyl); and L₂Y is H.
In another embodiment of the compounds of Formula (IA), L₁X is —(CH₂)₂—NH(heterocyclyl); and L₂Y is H.
In another embodiment of the compounds of Formula (IA), L₁X is —(CH₂)₃—NH(heterocyclyl); and L₂Y is H.
In another embodiment of the compounds of Formula (IA), L₁X is —(CH₂)₄—NH(heterocyclyl); and L₂Y is H.
In another embodiment of the compounds of Formula (IA), L₁X is -alkylene-NH(heterocyclylalkyl); and L₂Y is H.
In another embodiment of the compounds of Formula (IA), L₁X is —(CH₂)₂—NH(heterocyclylalkyl); and L₂Y is H.
In another embodiment of the compounds of Formula (IA), L₁X is —(CH₂)₃—NH(heterocyclylalkyl); and L₂Y is H.
In another embodiment of the compounds of Formula (IA), L₁X is —(CH₂)₄—NH(heterocyclylalkyl); and L₂Y is H.
In another embodiment of the compounds of Formula (IA), L₁X is -alkylene-NH(heteroarylalkyl); and L₂Y is H.
In another embodiment of the compounds of Formula (IA), L₁X is —(CH₂)₂—NH(heteroarylalkyl); and L₂Y is H.
In another embodiment of the compounds of Formula (IA), L₁X is —(CH₂)₃—NH(heteroarylalkyl); and L₂Y is H.
In another embodiment of the compounds of Formula (IA), L₁X is —(CH₂)₄—NH(heteroarylalkyl); and L₂Y is H.
In another embodiment of the compounds of Formula (IA), L₁X is -alkylene-NH(arylalkyl); and L₂Y is H.
In another embodiment of the compounds of Formula (IA), L₁X is —(CH₂)₂—NH(arylalkyl); and L₂Y is H.
In another embodiment of the compounds of Formula (IA), L₁X is —(CH₂)₃—NH(arylalkyl); and L₂Y is H.
In another embodiment of the compounds of Formula (IA), L₁X is —(CH₂)₄—NH(arylalkyl); and L₂Y is H.

In one embodiment of the compounds of Formula (IA), R₃ and R₄, taken together with the carbon atoms to which they are shown attached, form:

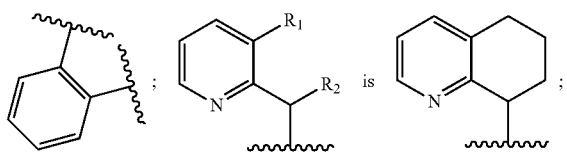

$L_1X$ is alkyl; and $L_2Y$ is -alkylene-$NR_aR_b$.

In another embodiment of the compounds of Formula (IA), $R_3$ and $R_4$, taken together with the carbon atoms to which they are shown attached, form:

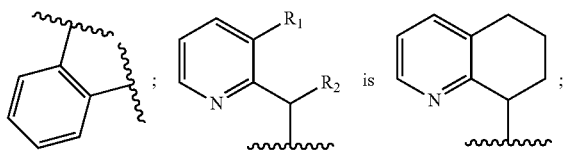

$L_1X$ is $CH_3$; and $L_2Y$ is -alkylene-$NR_aR_b$.

In another embodiment of the compounds of Formula (IA), $R_3$ and $R_4$, taken together with the carbon atoms to which they are shown attached, form:

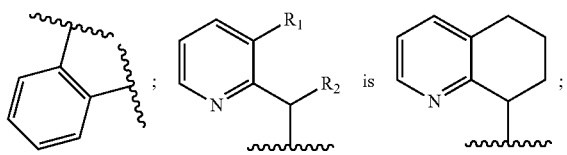

$L_1X$ is $CH_3$; and $L_2Y$ is -alkylene-$NH_2$.

In another embodiment of the compounds of Formula (IA), $R_3$ and $R_4$, taken together with the carbon atoms to which they are shown attached, form:

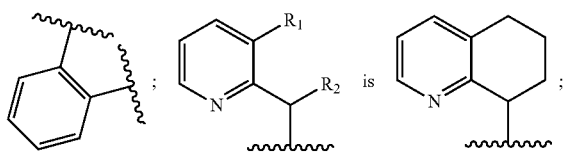

$L_1X$ is $CH_3$; and $L_2Y$ is -alkylene-NH(alkyl).

In another embodiment of the compounds of Formula (IA), $R_3$ and $R_4$, taken together with the carbon atoms to which they are shown attached, form:

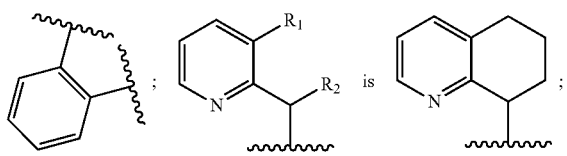

$L_1X$ is $CH_3$; and $L_2Y$ is -alkylene-NH(heterocyclyl).

In another embodiment of the compounds of Formula (IA), $R_3$ and $R_4$, taken together with the carbon atoms to which they are shown attached, form:

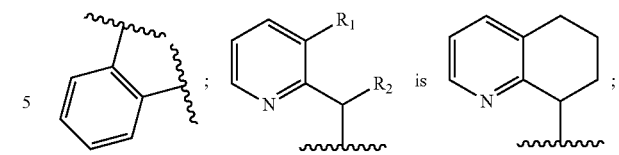

$L_1X$ is $CH_3$; and $L_2Y$ is -alkylene-NH(heterocyclylalkyl).

In another embodiment of the compounds of Formula (IA), $R_3$ and $R_4$, taken together with the carbon atoms to which they are shown attached, form:

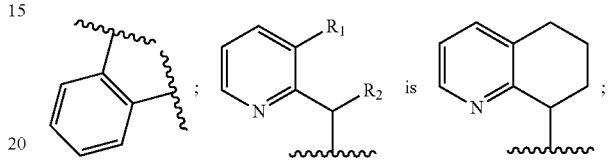

$L_1X$ is $CH_3$; and $L_2Y$ is -alkylene-NH(heteroarylalkyl).

In another embodiment of the compounds of Formula (IA), $R_3$ and $R_4$, taken together with the carbon atoms to which they are shown attached, form:

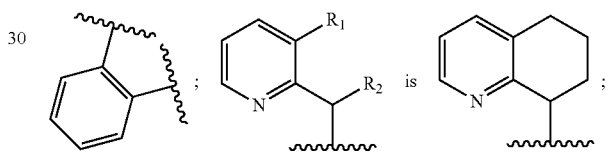

$L_1X$ is $CH_3$; and $L_2Y$ is -alkylene-NH(arylalkyl).

In another embodiment of the compounds of Formula (IA), $R_3$ and $R_4$, taken together with the carbon atoms to which they are shown attached, form:

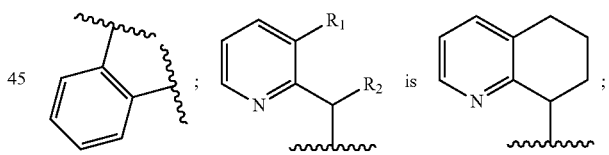

$L_1X$ is $CH_3$; and $L_2Y$ is —$(CH_2)_2$—$NH_2$.

In another embodiment of the compounds of Formula (IA), $R_3$ and $R_4$, taken together with the carbon atoms to which they are shown attached, form:

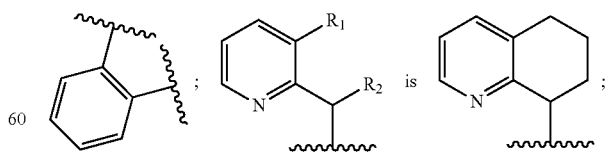

$L_1X$ is $CH_3$; and $L_2Y$ is —$(CH_2)_2$—NH(alkyl).

In another embodiment of the compounds of Formula (IA), $R_3$ and $R_4$, taken together with the carbon atoms to which they are shown attached, form:

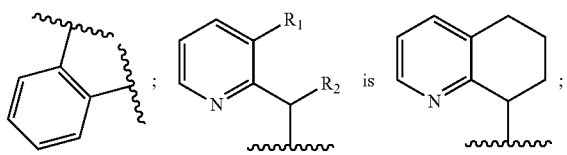

L$_1$X is CH$_3$; and L$_2$Y is —(CH$_2$)$_2$—NH(heterocyclyl).

In another embodiment of the compounds of Formula (IA), R$_3$ and R$_4$, taken together with the carbon atoms to which they are shown attached, form:

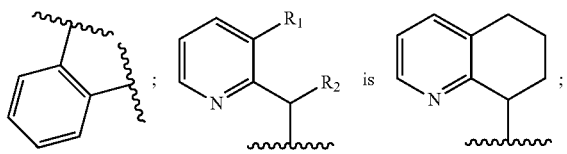

L$_1$X is CH$_3$; and L$_2$Y is —(CH$_2$)$_2$—NH(heterocyclylalkyl).

In another embodiment of the compounds of Formula (IA), R$_3$ and R$_4$, taken together with the carbon atoms to which they are shown attached, form:

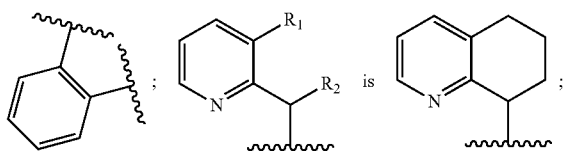

L$_1$X is CH$_3$; and L$_2$Y is —(CH$_2$)$_2$—NH(heteroarylalkyl).

In another embodiment of the compounds of Formula (IA), R$_3$ and R$_4$, taken together with the carbon atoms to which they are shown attached, form:

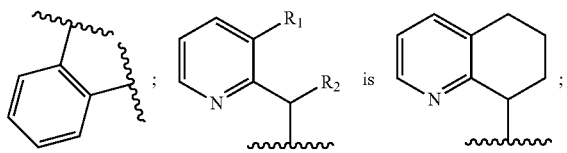

L$_1$X is CH$_3$; and L$_2$Y is —(CH$_2$)$_2$—NH(arylalkyl).

In another embodiment of the compounds of Formula (IA), R$_3$ and R$_4$, taken together with the carbon atoms to which they are shown attached, form:

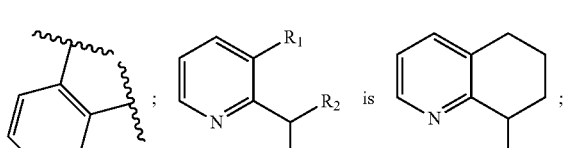

L$_1$X is CH$_3$; and L$_2$Y is —(CH$_2$)$_3$—NH$_2$.

In another embodiment of the compounds of Formula (IA), R$_3$ and R$_4$, taken together with the carbon atoms to which they are shown attached, form:

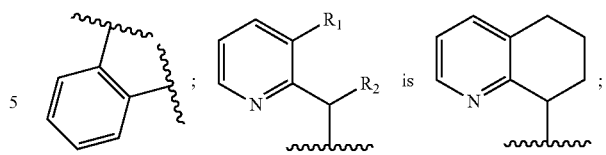

L$_1$X is CH$_3$; and L$_2$Y is —(CH$_2$)$_3$—NH(alkyl).

In another embodiment of the compounds of Formula (IA), R$_3$ and R$_4$, taken together with the carbon atoms to which they are shown attached, form:

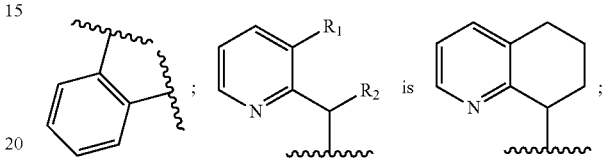

L$_1$X is CH$_3$; and L$_2$Y is —(CH$_2$)$_3$—NH(heterocyclyl).

In another embodiment of the compounds of Formula (IA), R$_3$ and R$_4$, taken together with the carbon atoms to which they are shown attached, form:

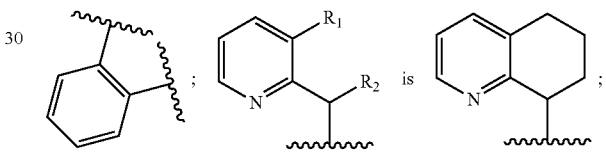

L$_1$X is CH$_3$; and L$_2$Y is —(CH$_2$)$_3$—NH(heterocyclylalkyl).

In another embodiment of the compounds of Formula (IA), R$_3$ and R$_4$, taken together with the carbon atoms to which they are shown attached, form:

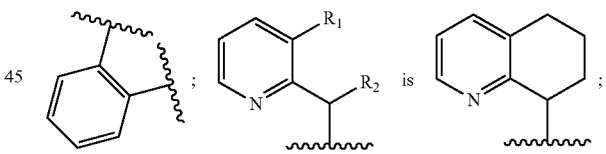

L$_1$X is CH$_3$; and L$_2$Y is —(CH$_2$)$_3$—NH(heteroarylalkyl).

In another embodiment of the compounds of Formula (IA), R$_3$ and R$_4$, taken together with the carbon atoms to which they are shown attached, form:

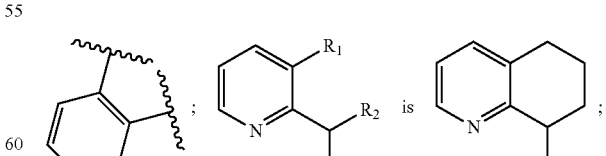

L$_1$X is CH$_3$; and L$_2$Y is —(CH$_2$)$_3$—NH(arylalkyl).

In another embodiment of the compounds of Formula (IA), R$_3$ and R$_4$, taken together with the carbon atoms to which they are shown attached, form:

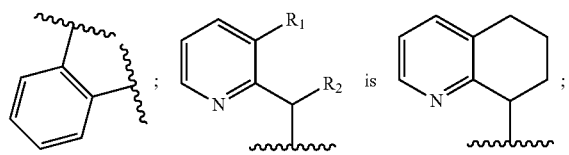

$L_1X$ is $CH_3$; and $L_2Y$ is —$(CH_2)_4$—$NH_2$.

In another embodiment of the compounds of Formula (IA), $R_3$ and $R_4$, taken together with the carbon atoms to which they are shown attached, form:

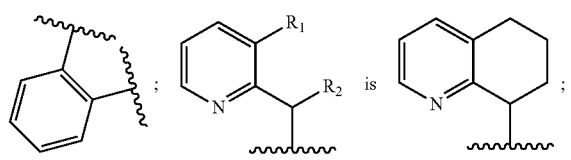

$L_1X$ is $CH_3$; and $L_2Y$ is —$(CH_2)_4$—NH(alkyl).

In another embodiment of the compounds of Formula (IA), $R_3$ and $R_4$, taken together with the carbon atoms to which they are shown attached, form:

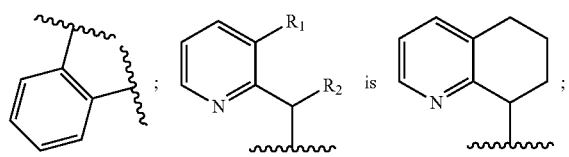

$L_1X$ is $CH_3$; and $L_2Y$ is —$(CH_2)_4$—NH(heterocyclyl).

In another embodiment of the compounds of Formula (IA), $R_3$ and $R_4$, taken together with the carbon atoms to which they are shown attached, form:

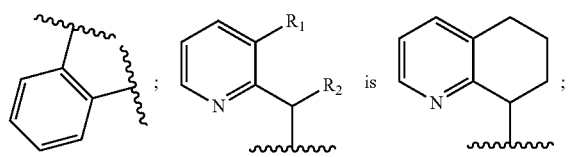

$L_1X$ is $CH_3$; and $L_2Y$ is —$(CH_2)_4$—NH(heterocyclylalkyl).

In another embodiment of the compounds of Formula (IA), $R_3$ and $R_4$, taken together with the carbon atoms to which they are shown attached, form:

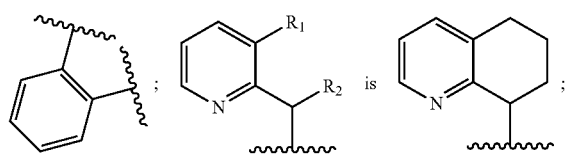

$L_1X$ is $CH_3$; and $L_2Y$ is —$(CH_2)_4$—NH(heteroarylalkyl).

In another embodiment of the compounds of Formula (IA), $R_3$ and $R_4$, taken together with the carbon atoms to which they are shown attached, form:

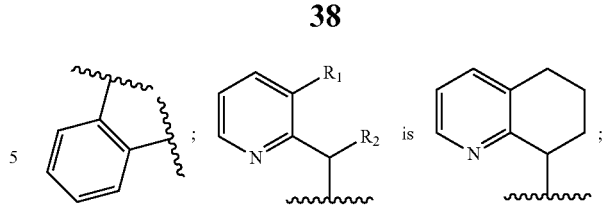

$L_1X$ is $CH_3$; and $L_2Y$ is —$(CH_2)_4$—NH(arylalkyl).

In another embodiment of the compounds of Formula (IA), $R_3$ and $R_4$, taken together with the carbon atoms to which they are shown attached, form:

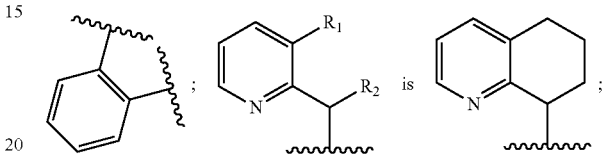

$L_1X$ is -alkylene-$NR_aR_b$; and $L_2Y$ is H.

In another embodiment of the compounds of Formula (IA), $R_3$ and $R_4$, taken together with the carbon atoms to which they are shown attached, form:

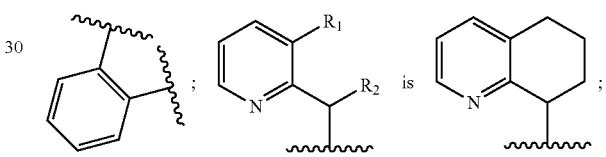

$L_1X$ is -alkylene-$NH_2$; and $L_2Y$ is H.

In another embodiment of the compounds of Formula (IA), $R_3$ and $R_4$, taken together with the carbon atoms to which they are shown attached, form:

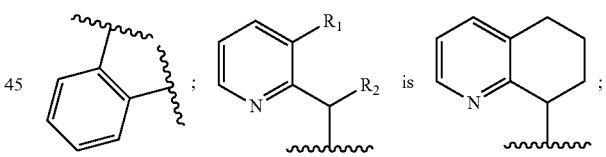

$L_1X$ is -alkylene-N(alkyl)$_2$; and $L_2Y$ is H.

In another embodiment of the compounds of Formula (IA), $R_3$ and $R_4$, taken together with the carbon atoms to which they are shown attached, form:

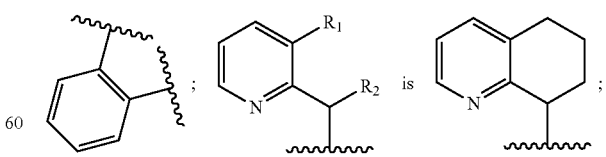

$L_1X$ is -alkylene-NH(alkyl); and $L_2Y$ is H.

In another embodiment of the compounds of Formula (IA), $R_3$ and $R_4$, taken together with the carbon atoms to which they are shown attached, form:

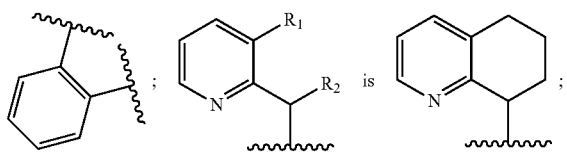

$L_1X$ is -alkylene-NH(heterocyclyl); and $L_2Y$ is H.

In another embodiment of the compounds of Formula (IA), $R_3$ and $R_4$, taken together with the carbon atoms to which they are shown attached, form:

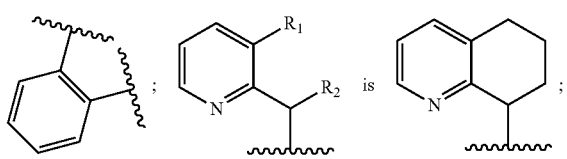

$L_1X$ is -alkylene-NH(heterocyclylalkyl); and $L_2Y$ is H.

In another embodiment of the compounds of Formula (IA), $R_3$ and $R_4$, taken together with the carbon atoms to which they are shown attached, form:

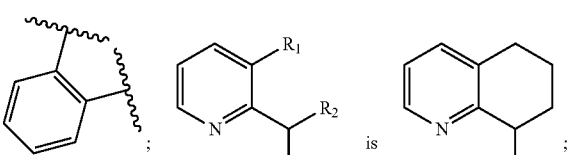

$L_1X$ is -alkylene-NH(heteroarylalkyl); and $L_2Y$ is H.

In another embodiment of the compounds of Formula (IA), $R_3$ and $R_4$, taken together with the carbon atoms to which they are shown attached, form:

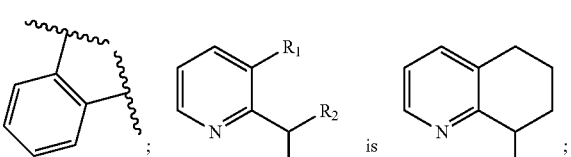

$L_1X$ is -alkylene-NH(arylalkyl); and $L_2Y$ is H.

In another embodiment of the compounds of Formula (IA), $R_3$ and $R_4$, taken together with the carbon atoms to which they are shown attached, form:

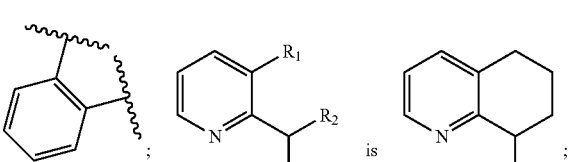

$L_1X$ is —$(CH_2)_2$—$NH_2$; and $L_2Y$ is H.

In another embodiment of the compounds of Formula (IA), $R_3$ and $R_4$, taken together with the carbon atoms to which they are shown attached, form:

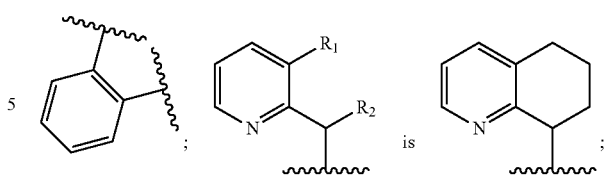

$L_1X$ is —$(CH_2)_2$—$N(alkyl)_2$; and $L_2Y$ is H.

In another embodiment of the compounds of Formula (IA), $R_3$ and $R_4$, taken together with the carbon atoms to which they are shown attached, form:

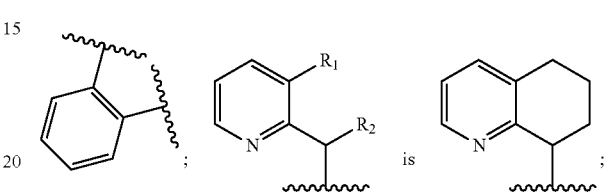

$L_1X$ is —$(CH_2)_2$—NH(alkyl); and $L_2Y$ is H.

In another embodiment of the compounds of Formula (IA), $R_3$ and $R_4$, taken together with the carbon atoms to which they are shown attached, form:

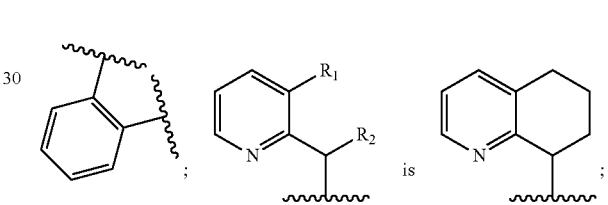

$L_1X$ is —$(CH_2)_2$—NH(heterocyclyl); and $L_2Y$ is H.

In another embodiment of the compounds of Formula (IA), $R_3$ and $R_4$, taken together with the carbon atoms to which they are shown attached, form:

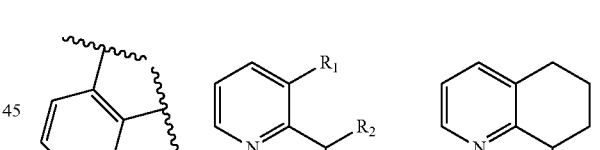

$L_1X$ is —$(CH_2)_2$—NH(heterocyclylalkyl); and $L_2Y$ is H.

In another embodiment of the compounds of Formula (IA), $R_3$ and $R_4$, taken together with the carbon atoms to which they are shown attached, form:

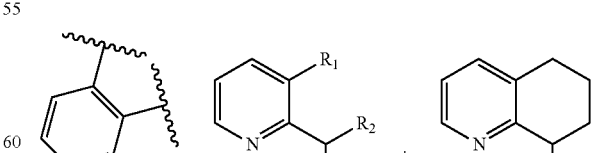

$L_1X$ is —$(CH_2)_2$—NH(heteroarylalkyl); and $L_2Y$ is H.

In another embodiment of the compounds of Formula (IA), $R_3$ and $R_4$, taken together with the carbon atoms to which they are shown attached, form:

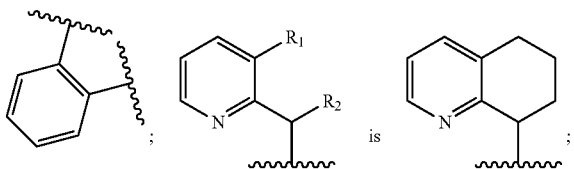

$L_1X$ is —$(CH_2)_2$—NH(arylalkyl); and $L_2Y$ is H.

In another embodiment of the compounds of Formula (IA), $R_3$ and $R_4$, taken together with the carbon atoms to which they are shown attached, form:

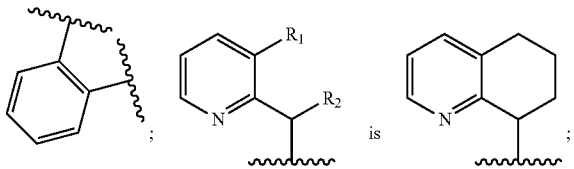

$L_1X$ is —$(CH_2)_3$—$NH_2$; and $L_2Y$ is H.

In another embodiment of the compounds of Formula (IA), $R_3$ and $R_4$, taken together with the carbon atoms to which they are shown attached, form:

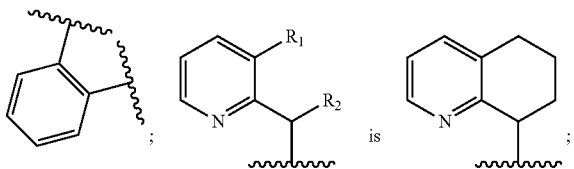

$L_1X$ is —$(CH_2)_3$—$N(alkyl)_2$; and $L_2Y$ is H.

In another embodiment of the compounds of Formula (IA), $R_3$ and $R_4$, taken together with the carbon atoms to which they are shown attached, form:

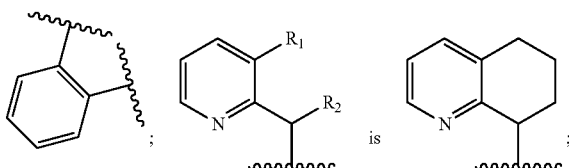

$L_1X$ is —$(CH_2)_3$—NH(alkyl); and $L_2Y$ is H.

In another embodiment of the compounds of Formula (IA), $R_3$ and $R_4$, taken together with the carbon atoms to which they are shown attached, form:

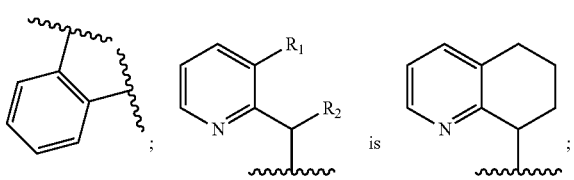

$L_1X$ is —$(CH_2)_3$—NH(heterocyclyl); and $L_2Y$ is H.

In another embodiment of the compounds of Formula (IA), $R_3$ and $R_4$, taken together with the carbon atoms to which they are shown attached, form:

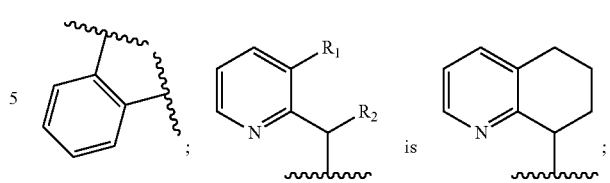

$L_1X$ is —$(CH_2)_3$—NH(heterocyclylalkyl); and $L_2Y$ is H.

In another embodiment of the compounds of Formula (IA), $R_3$ and $R_4$, taken together with the carbon atoms to which they are shown attached, form:

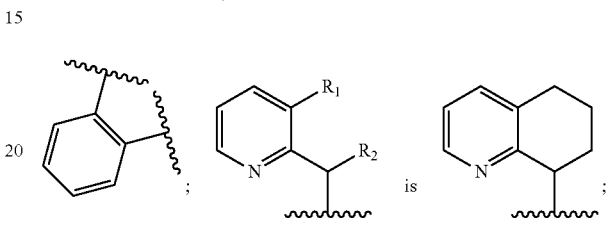

$L_1X$ is —$(CH_2)_3$—NH(heteroarylalkyl); and $L_2Y$ is H.

In another embodiment of the compounds of Formula (IA), $R_3$ and $R_4$, taken together with the carbon atoms to which they are shown attached, form:

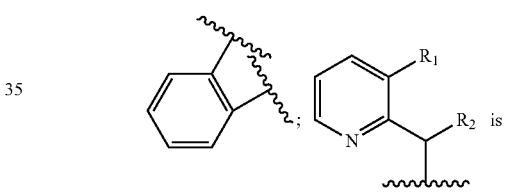

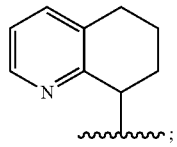

$L_1X$ is —$(CH_2)_3$—NH(arylalkyl); and $L_2Y$ is H.

In another embodiment of the compounds of Formula (IA), $R_3$ and $R_4$, taken together with the carbon atoms to which they are shown attached, form:

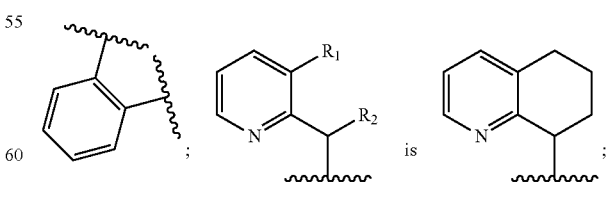

$L_1X$ is —$(CH_2)_4$—$NH_2$; and $L_2Y$ is H.

In another embodiment of the compounds of Formula (IA), $R_3$ and $R_4$, taken together with the carbon atoms to which they are shown attached, form:

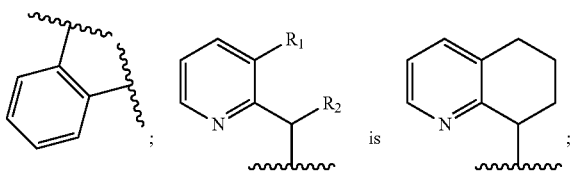

$L_1X$ is —$(CH_2)_4$—$N(alkyl)_2$; and $L_2Y$ is H.

In another embodiment of the compounds of Formula (IA), $R_3$ and $R_4$, taken together with the carbon atoms to which they are shown attached, form:

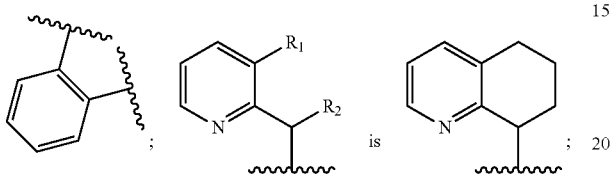

$L_1X$ is —$(CH_2)_4$—NH(alkyl); and $L_2Y$ is H.

In another embodiment of the compounds of Formula (IA), $R_3$ and $R_4$, taken together with the carbon atoms to which they are shown attached, form:

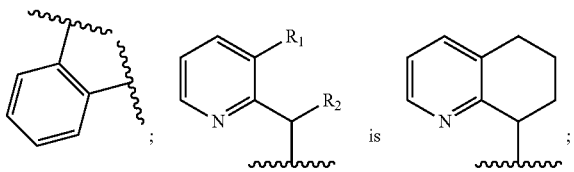

$L_1X$ is —$(CH_2)_4$—NH(heterocyclyl); and $L_2Y$ is H.

In another embodiment of the compounds of Formula (IA), $R_3$ and $R_4$, taken together with the carbon atoms to which they are shown attached, form:

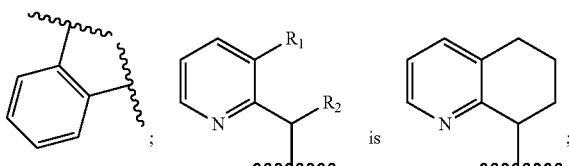

$L_1X$ is —$(CH_2)_4$—NH(heterocyclylalkyl); and $L_2Y$ is H.

In another embodiment of the compounds of Formula (IA), $R_3$ and $R_4$, taken together with the carbon atoms to which they are shown attached, form:

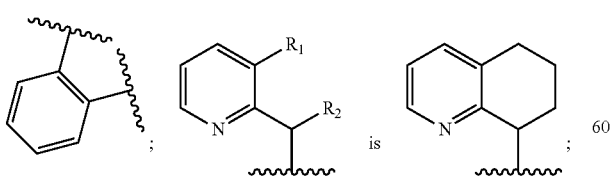

$L_1X$ is —$(CH_2)_4$—NH(heteroarylalkyl); and $L_2Y$ is H.

In another embodiment of the compounds of Formula (IA), $R_3$ and $R_4$, taken together with the carbon atoms to which they are shown attached, form:

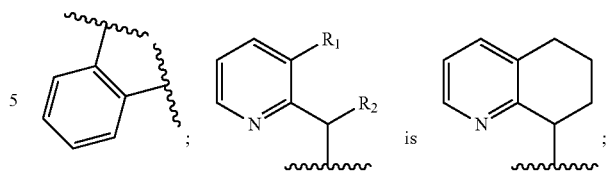

$L_1X$ is —$(CH_2)_4$—NH(arylalkyl); and $L_2Y$ is H.

In certain specific embodiments, the invention provides compounds of Formula (IA-1), or a pharmaceutically acceptable salt, solvate, tautomer, stereoisomer, and/or ester thereof:

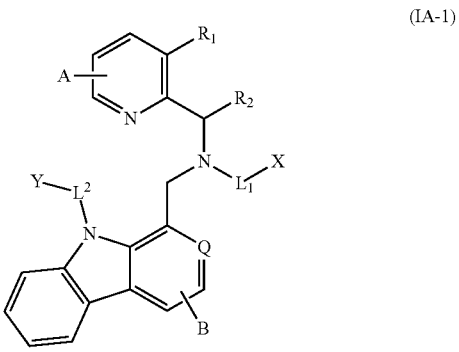

(IA-1)

wherein variables A, B, $R_1$, $R_2$, $L_1$, $L_2$, Q, X, and Y are as defined above for Formula (I).

In one embodiment of Formula IA-1, Q is nitrogen. In another embodiment of Formula IA-1, Q is $CR_e$.

In another embodiment of Formula IA-1,

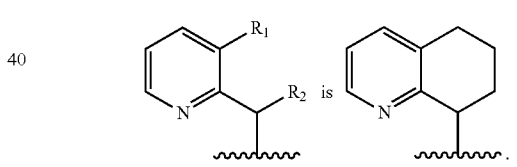

In still another embodiment of Formula IA-1, Q is nitrogen and

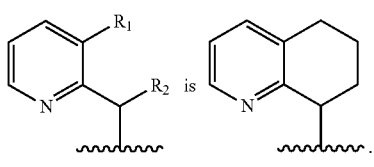

In yet another embodiment of Formula IA-1,

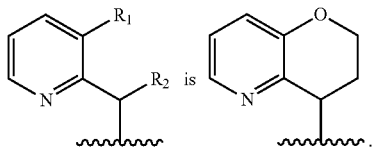

In another embodiment of Formula IA-1, Q is nitrogen and

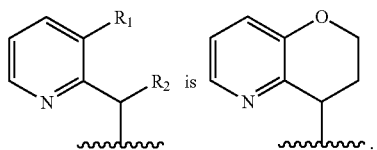

In another embodiment of Formula IA-1, Q is nitrogen, and R₁ is hydrogen, alkyl, halogen, hydroxy, amino, alkyl or dialkyl amino, alkoxy, acyl, alkoxycarbonyl or CF₃; and R₂ is hydrogen, alkyl, heteroalkyl, hydroxyalkyl, alkoxyalkyl, carbocyclyl, or heterocyclyl.

In another embodiment of Formula IA-1, Q is nitrogen and R₁ is hydrogen, alkyl, halogen or CF₃.

In another embodiment of Formula IA-1, Q is nitrogen,

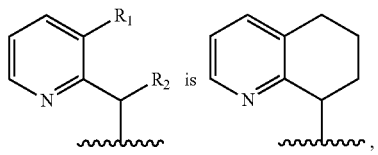

$L_1$ is an optionally substituted alkylene group, and X is optionally substituted carbocyclyl, optionally substituted heterocyclyl or $NR_aR_b$.

In still another embodiment of Formula IA-1, Q is nitrogen,

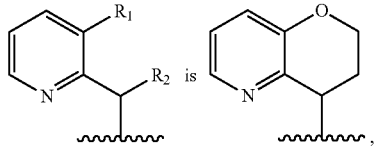

$L_1$ is an optionally substituted alkylene group, and X is optionally substituted carbocyclyl, optionally substituted heterocyclyl or $NR_aR_b$.

In another embodiment of Formula IA-1, Q is nitrogen,

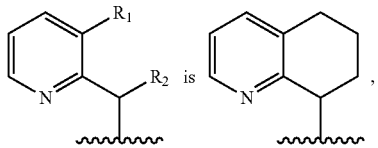

and $L_1$-X is

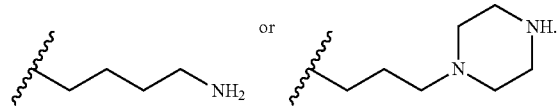

In yet another embodiment of Formula IA-1, Q is nitrogen,

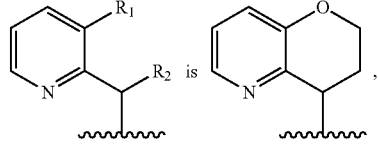

and $L_1$-X is

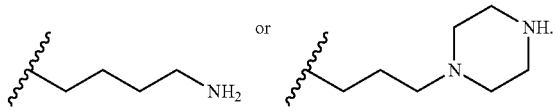

In still another embodiment of Formula IA-1, R₁ is hydrogen, alkyl, halogen, alkoxy, acyl, alkoxycarbonyl or CF₃; R₂ is hydrogen, alkyl, heteroalkyl, hydroxyalkyl, alkoxyalkyl, carbocyclyl, or heterocyclyl; and $L_1$-X is

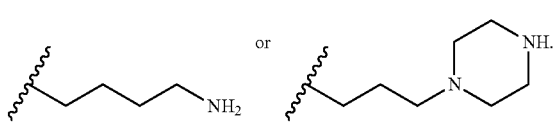

In another embodiment of Formula IA-1, $L_2$ is a bond or alkylene, and Y is H, $NR_aR_b$, —$OR_c$, carbocyclyl, heterocyclyl including triazolyl and tetrazolyl, acyl, alkoxycarbonyl, aminocarbonyl, alkyl- or dialkylaminocarbonyl, heterocyclylacyl, cyano, halogen or CF₃.

In still another embodiment of Formula IA-1, $L_2$ is a bond or alkylene, and Y is H, $NR_aR_b$, —$OR_c$, carbocyclyl, heterocyclyl including triazolyl and tetrazolyl, acyl, alkoxycarbonyl, aminocarbonyl, alkyl- or dialkylaminocarbonyl, heterocyclylacyl, cyano, halogen or CF₃; and $L_1$-X is

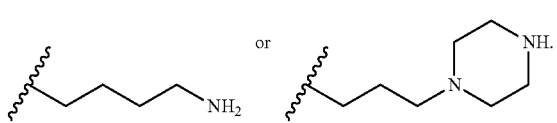

In certain embodiments of Formula IA-1, the compound has the stereochemical configuration of Formula IA-1S:

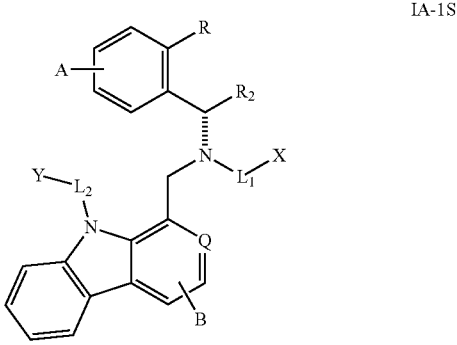

IA-1S wherein the variables R₁, R₂, A, B, L₁, L₂, Q, X, and Y are as defined for Formula IA-1.

In another embodiment of Formula IA-1, the compound has the stereochemical configuration of Formula IA-1R:

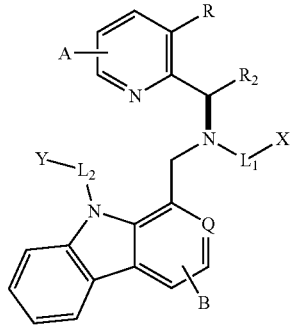

IA-1R wherein the variables $R_1$, $R_2$, A, B, $L_1$, $L_2$, Q, X, and Y are as defined for Formula IA-1.

In another embodiment, the invention provides compounds of Formula (IA-2), or a pharmaceutically acceptable salt, solvate, tautomer, stereoisomer, and/or ester thereof:

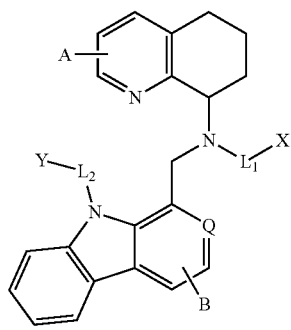

(IA-2)

wherein variables A, B, $L_1$, $L_2$, Q, X, and Y are as defined above for Formula (I).

In one embodiment of Formula IA-2, Q is nitrogen. In another embodiment of Formula IA-2, Q is $CR_e$.

In another embodiment of Formula IA-2, Q is nitrogen, $L_1$ is an optionally substituted alkylene group, and X is optionally substituted carbocyclyl, optionally substituted heterocyclyl or $NR_aR_b$.

In another embodiment of Formula IA-2, Q is nitrogen, and $L_1$-X is

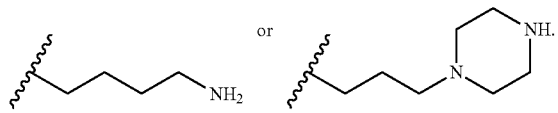 [SMILES: *CCCCN ; "or" ; *CCCN1CCNCC1]

In certain embodiments of Formula IA-2, Q is nitrogen, $L_2$ is a bond or alkylene, and Y is H, $NR_aR_b$, —$OR_c$, carbocyclyl, heterocyclyl including triazolyl and tetrazolyl, acyl, alkoxycarbonyl, aminocarbonyl, alkyl- or dialkylaminocarbonyl, heterocyclylacyl, cyano, halogen or $CF_3$.

In still another embodiment of Formula IA-2, Q is nitrogen, $L_1$ and $L_2$ are independently a bond or alkylene, Y is H, $NR_aR_b$, —$OR_c$, carbocyclyl, heterocyclyl including triazolyl and tetrazolyl, acyl, alkoxycarbonyl, aminocarbonyl, alkyl- or dialkylaminocarbonyl, heterocyclylacyl, cyano, halogen, or $CF_3$, and X is $NR_aR_b$.

In still another embodiment of Formula IA-2, Q is nitrogen, $L_1$ and $L_2$ are independently a bond or alkylene, Y is H, $NR_aR_b$, —$OR_c$, carbocyclyl, heterocyclyl including triazolyl and tetrazolyl, acyl, alkoxycarbonyl, aminocarbonyl, alkyl- or dialkylaminocarbonyl, heterocyclylacyl, cyano, halogen, or $CF_3$, and $L_1$-X is

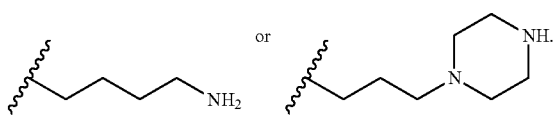

In one embodiment of Formula IA-2, the compound has the stereochemical configuration of Formula IA-2S:

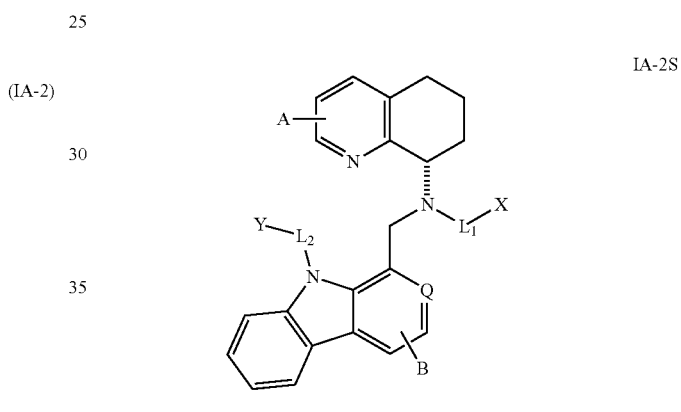

IA-2S wherein the variables A, B, $L_1$, $L_2$, Q, X, and Y are as defined for Formula IA-2.

In another embodiment of Formula IA-2, the compound has the stereochemical configuration of Formula IA-2R:

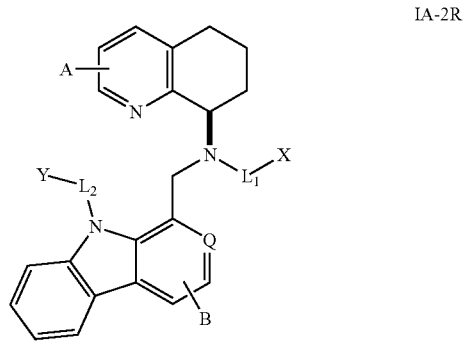

IA-2R wherein the variables A, B, $L_1$, $L_2$, Q, X, and Y are as defined for Formula IA-2.

In another embodiment, the invention provides compounds of Formula (IA-3), or a pharmaceutically acceptable salt, solvate, tautomer, stereoisomer, and/or ester thereof:

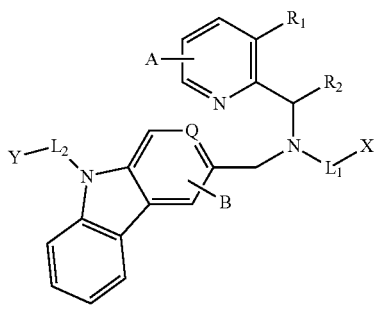

(IA-3)

wherein variables A, B, $R_1$, $R_2$, $L_1$, $L_2$, Q, X, and Y are as defined above for Formula (I).

In one embodiment of Formula IA-3, Q is nitrogen. In another embodiment of Formula IA-3, Q is $CR_e$.

In another embodiment of Formula IA-3,

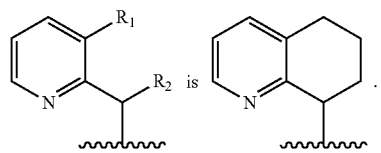

In still another embodiment of Formula IA-3, Q is nitrogen and

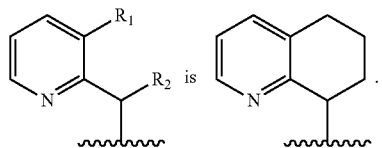

In yet another embodiment of Formula IA-3,

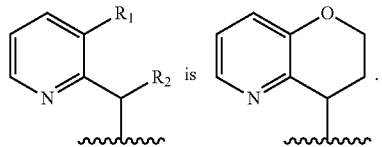

In another embodiment of Formula IA-3, Q is nitrogen and

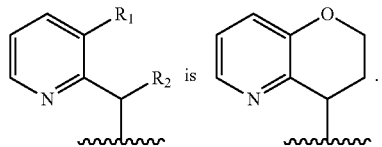

In another embodiment of Formula IA-3, Q is nitrogen, $R_1$ is hydrogen, alkyl, halogen, hydroxy, amino, alkyl or dialkyl amino, alkoxy, acyl, alkoxycarbonyl or $CF_3$; and $R_2$ is hydrogen, alkyl, heteroalkyl, hydroxyalkyl, alkoxyalkyl, carbocyclyl, or heterocyclyl.

In another embodiment of Formula IA-3, Q is nitrogen and $R_1$ is hydrogen, alkyl, halogen or $CF_3$.

In another embodiment of Formula IA-3, Q is nitrogen,

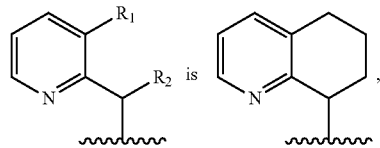

$L_1$ is an optionally substituted alkylene group, and X is optionally substituted carbocyclyl, optionally substituted heterocyclyl or $NR_aR_b$.

In still another embodiment of Formula IA-3, Q is nitrogen,

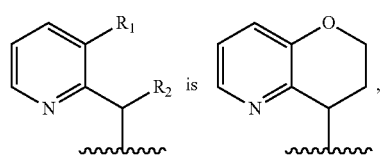

$L_1$ is an optionally substituted alkylene group, and X is optionally substituted carbocyclyl, optionally substituted heterocyclyl or $NR_aR_b$.

In another embodiment of Formula IA-3, Q is nitrogen,

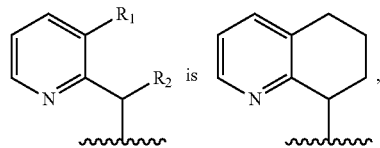

and $L_1$-X is

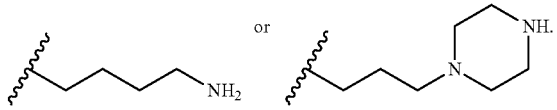 [SMILES: *CCCCN ; *CCCN1CCNCC1]

In yet another embodiment of Formula IA-3, Q is nitrogen,

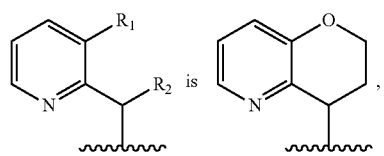

and $L_1$-X is

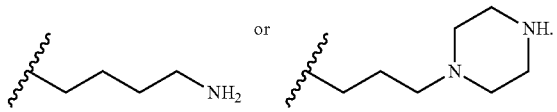 [SMILES: *CCCCN ; *CCCN1CCNCC1]

In still another embodiment of Formula IA-3, $R_1$ is hydrogen, alkyl, halogen, alkoxy, acyl, alkoxycarbonyl or $CF_3$; $R_2$ is hydrogen, alkyl, heteroalkyl, hydroxyalkyl, alkoxyalkyl, carbocyclyl, or heterocyclyl; and $L_1$-X is

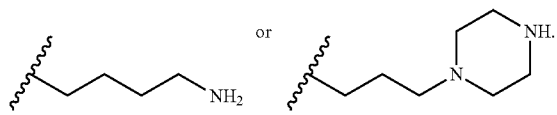

In another embodiment of Formula IA-3, $L_2$ is a bond or alkylene, and Y is H, $NR_aR_b$, —$OR_c$, carbocyclyl, heterocyclyl including triazolyl and tetrazolyl, acyl, alkoxycarbonyl, aminocarbonyl, alkyl- or dialkylaminocarbonyl, heterocyclylacyl, cyano, halogen or $CF_3$.

In still another embodiment of Formula IA-3, $L_2$ is a bond or alkylene, Y is H, $NR_aR_b$, —$OR_c$, carbocyclyl, heterocyclyl including triazolyl and tetrazolyl, acyl, alkoxycarbonyl, aminocarbonyl, alkyl- or dialkylaminocarbonyl, heterocyclylacyl, cyano, halogen or $CF_3$; and $L_1$-X is

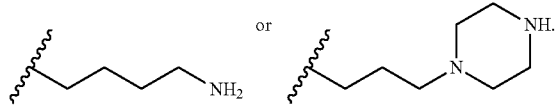

In one embodiment of Formula IA-3, the compound has the stereochemical configuration of Formula IA-3S:

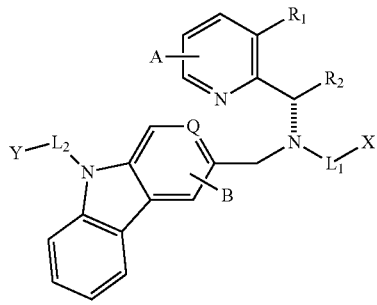

IA-3S wherein the variables $R_1$, $R_2$, A, B, $L_1$, $L_2$, Q, X, and Y are as defined for Formula IA-3.

In another embodiment of Formula IA-3, the compound has the stereochemical configuration of Formula IA-3R:

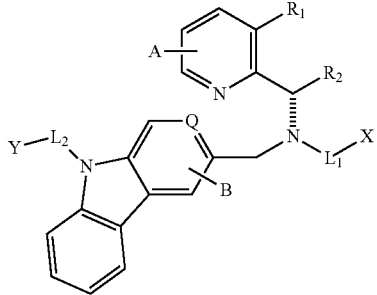

IA-3R wherein the variables $R_1$, $R_2$, A, B, $L_1$, $L_2$, Q, X, and Y are as defined for Formula IA-3.

In another embodiment, the invention provides compounds of Formula (IA-4), or a pharmaceutically acceptable salt, solvate, tautomer, stereoisomer, and/or ester thereof:

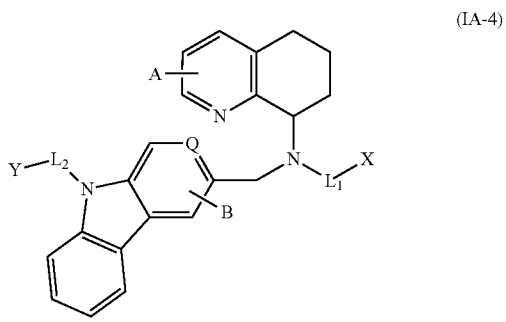

(IA-4)

wherein variables A, B, $L_1$, $L_2$, Q, X, and Y are as defined above for Formula (I).

In one embodiment of Formula IA-4, Q is nitrogen. In another embodiment of Formula IA-2, Q is $CR_e$.

In certain embodiments of Formula IA-4, Q is nitrogen, $L_1$ is an optionally substituted alkylene group, and X is optionally substituted carbocyclyl, optionally substituted heterocyclyl or $NR_aR_b$.

In another embodiment of Formula IA-4, Q is nitrogen, and $L_1$-X is

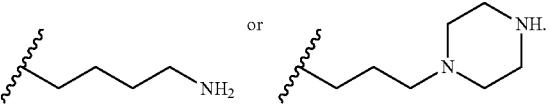 [SMILES: *CCCCN ; *CCCN1CCNCC1]

In another embodiment of Formula IA-4, Q is nitrogen, $L_2$ is a bond or alkylene, and Y is H, $NR_aR_b$, —$OR_c$, carbocyclyl, heterocyclyl including triazolyl and tetrazolyl, acyl, alkoxycarbonyl, aminocarbonyl, alkyl- or dialkylaminocarbonyl, heterocyclylacyl, cyano, halogen or $CF_3$.

In still another embodiment of Formula IA-4, Q is nitrogen, $L_1$ and $L_2$ are independently a bond or alkylene, Y is H, $NR_aR_b$, —$OR_c$, carbocyclyl, heterocyclyl including triazolyl and tetrazolyl, acyl, alkoxycarbonyl, aminocarbonyl, alkyl- or dialkylaminocarbonyl, heterocyclylacyl, cyano, halogen, or $CF_3$, and X is $NR_aR_b$.

In still another embodiment of Formula IA-4, Q is nitrogen, $L_1$ and $L_2$ are independently a bond or alkylene, Y is H, $NR_aR_b$, —$OR_c$, carbocyclyl, heterocyclyl including triazolyl and tetrazolyl, acyl, alkoxycarbonyl, aminocarbonyl, alkyl- or dialkylaminocarbonyl, heterocyclylacyl, cyano, halogen, or $CF_3$, and $L_1$-X is

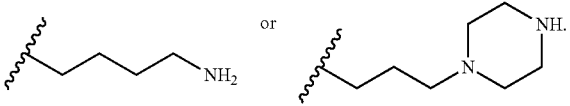 [SMILES: *CCCCN ; "or" ; *CCCN1CCNCC1]

In one embodiment of Formula IA-4, the compound has the stereochemical configuration of Formula IA-4S:

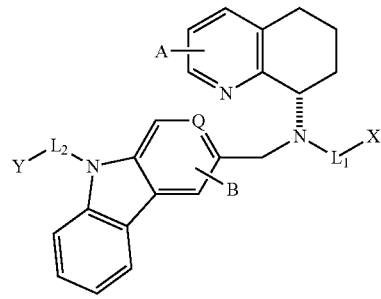

IA-4S wherein the variables A, B, L$_1$, L$_2$, Q, X, and Y are as defined for Formula IA-4.

In another embodiment of Formula IA-4, the compound has the stereochemical configuration of Formula IA-4R:

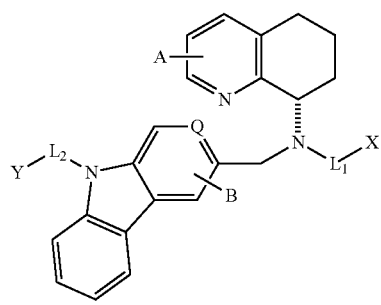

IA-4R wherein the variables A, B, L$_1$, L$_2$, Q, X, and Y are as defined for Formula IA-4.

In various embodiments of Formulae IA, IA-1, IA-1S, IA-1R, IA-2, IA-2S, IA-2R, IA-3, IA-3S, IA-3R, IA-4, IA-4S and IA-4R, -L$_2$-Y is selected from:

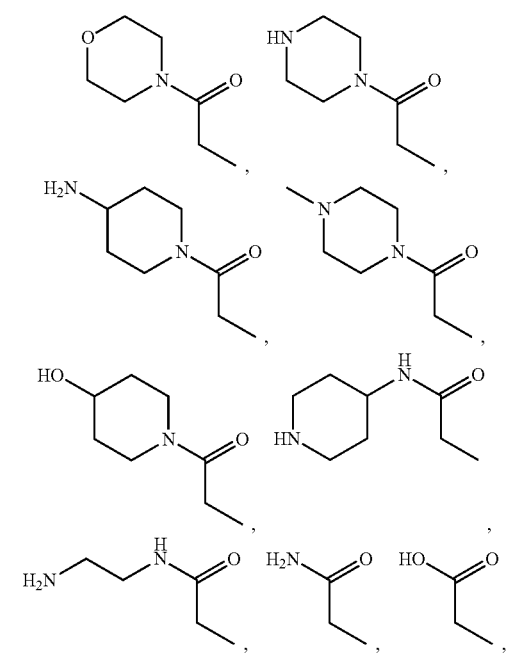

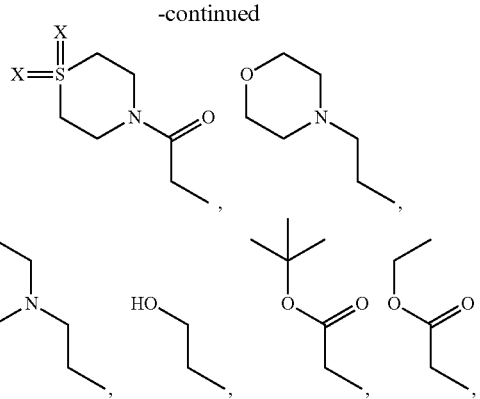

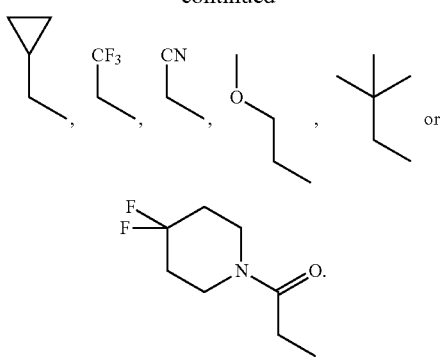
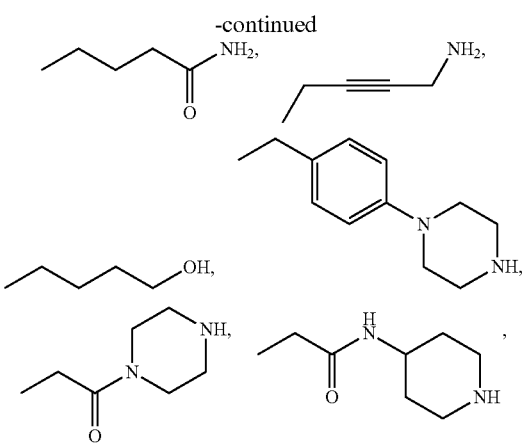
In various embodiments of Formulae IA, IA-1, IA-1S, IA-1R, IA-2, IA-2S, IA-2R, IA-3, IA-3S, IA-3R, IA-4, IA-4S and IA-4R, $L_1$-X is selected from:
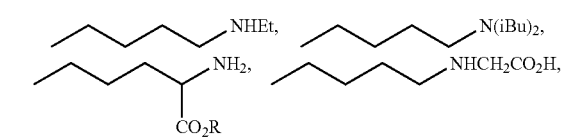
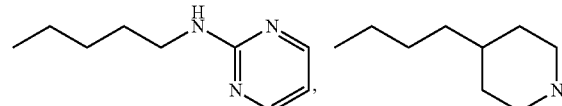
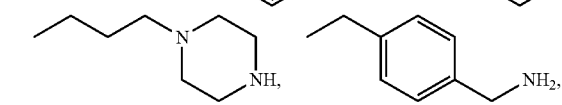
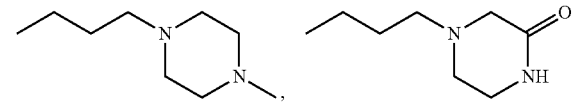
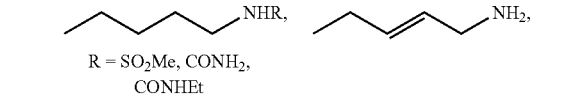
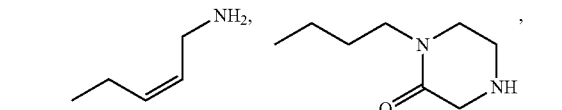
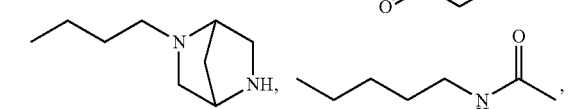
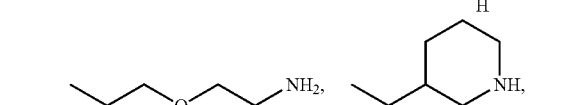
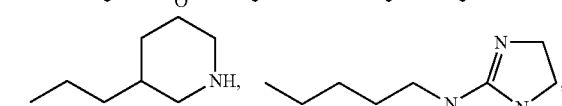
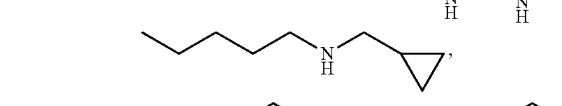

Compounds of Formula 1B and 1C

In another embodiment, the compounds of the present invention have the following Formula (IB) or (IC):

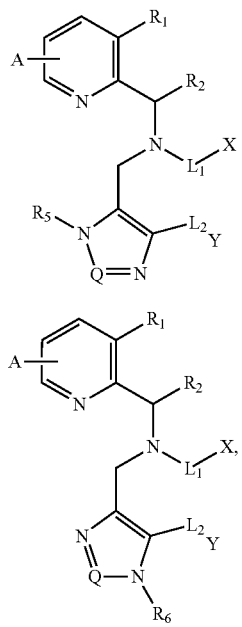

or a pharmaceutically acceptable salt, solvate, tautomer, stereoisomer, and/or ester thereof wherein variables A, X, Q, $R_1$, $R_2$, $R_5$, $R_6$, $L_1$, $L_2$ are all defined as in Formula I.

In certain embodiments of the compounds of Formula (IB) or (IC), $R_1$ and $R_2$, taken together with the carbon atoms to which they are shown attached, form a substituted or unsubstituted carbocyclyl or a substituted or unsubstituted heterocyclyl; $L_1$ is a substituted or unsubstituted alkylene; $L_2$ a covalent bond or a substituted or unsubstituted alkylene; X is H or $NR_aR_b$; Y is H, substituted or unsubstituted carbocyclyl, or substituted or unsubstituted heterocyclyl; $R_a$ and $R_b$ are each independently selected from the group consisting of H, substituted or unsubstituted alkyl, aldiminyl, substituted or unsubstituted carbocyclyl, substituted or unsubstituted carbocyclylalkyl, substituted or unsubstituted heterocyclylalkyl, and substituted or unsubstituted heterocyclyl; Q is N; $R_5$ is substituted or unsubstituted aminoalkyl, substituted or unsubstituted carbocyclyl, or substituted or unsubstituted heterocyclylalkyl; and $R_6$ is substituted or unsubstituted aminoalkyl, substituted or unsubstituted carbocyclyl, substituted or unsubstituted carbocyclylalkyl, substituted or unsubstituted heterocyclyl, substituted or unsubstituted heterocyclylalkyl, alkyl, alkenyl, and alkynyl.

In another embodiment of the compounds of Formula (IB) or (IC), $R_1$ and $R_2$, taken together with the carbon atoms to which they are shown attached, form a substituted or unsubstituted carbocyclyl or a substituted or unsubstituted heterocyclyl; $L_1$ is a substituted or unsubstituted alkylene; $L_2$ a covalent bond or a substituted or unsubstituted alkylene; X is H or $NR_aR_b$; Y is H, substituted or unsubstituted carbocyclyl, or substituted or unsubstituted heterocyclyl; $R_a$ and $R_b$ are each independently selected from the group consisting of H, substituted or unsubstituted alkyl, aldiminyl, substituted or unsubstituted carbocyclyl, substituted or unsubstituted carbocyclylalkyl, substituted or unsubstituted heterocyclylalkyl, and substituted or unsubstituted heterocyclyl; Q is CH; $R_5$ is substituted or unsubstituted aminoalkyl, substituted or unsubstituted carbocyclyl, or substituted or unsubstituted heterocyclylalkyl; and $R_6$ is substituted or unsubstituted aminoalkyl, substituted or unsubstituted carbocyclyl, substituted or unsubstituted carbocyclylalkyl, substituted or unsubstituted heterocyclyl, substituted or unsubstituted heterocyclylalkyl, alkyl, alkenyl, and alkynyl.

In another embodiment of the compounds of Formula (IB) or (IC),

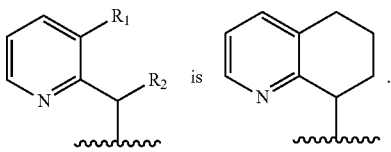

In another embodiment of the compounds of Formula (IB) or (IC),

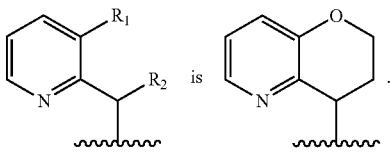

In another embodiment of the compounds of Formula (IB) or (IC),

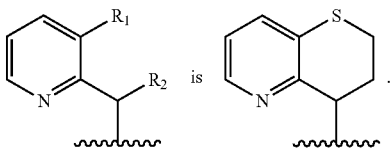

In another embodiment of the compounds of Formula (IB) or (IC), $L_2Y$ is H.

In another embodiment of the compounds of Formula (IB) or (IC), $L_2Y$ is substituted or unsubstituted heterocyclylalkyl.

In another embodiment of the compounds of Formula (IB) or (IC), $L_1X$ is alkyl.

In another embodiment of the compounds of Formula (IB) or (IC), $L_1X$ is $CH_3$.

In another embodiment of the compounds of Formula (IB) or (IC), $L_1X$ is -alkylene-$NR_aR_b$.

In another embodiment of the compounds of Formula (IB) or (IC), $L_1X$ is -alkylene-$NH_2$.

In another embodiment of the compounds of Formula (IB) or (IC), $L_1X$ is -alkylene-$N(alkyl)_2$.

In another embodiment of the compounds of Formula (IB) or (IC), $L_1X$ is -alkylene-NH(alkyl).

In another embodiment of the compounds of Formula (IB) or (IC), $L_1X$ is -alkylene-NH(heterocyclyl).

In another embodiment of the compounds of Formula (IB) or (IC), $L_1X$ is -alkylene-NH(heterocyclylalkyl).

In another embodiment of the compounds of Formula (IB) or (IC), $L_1X$ is -alkylene-NH(heteroarylalkyl).

In another embodiment of the compounds of Formula (IB) or (IC), $L_1X$ is -alkylene-NH(arylalkyl).

In another embodiment of the compounds of Formula (IB) or (IC), $L_1X$ is —$(CH_2)_2$—$NR_aR_b$.

In another embodiment of the compounds of Formula (IB) or (IC), $L_1X$ is —$(CH_2)_2$—$NH_2$.
In another embodiment of the compounds of Formula (IB) or (IC), $L_1X$ is —$(CH_2)_2$—$N(alkyl)_2$.
In another embodiment of the compounds of Formula (IB) or (IC), $L_1X$ is —$(CH_2)_2$—$NH(alkyl)$.
In another embodiment of the compounds of Formula (IB) or (IC), $L_1X$ is —$(CH_2)_2$—$NH(heterocyclyl)$.
In another embodiment of the compounds of Formula (IB) or (IC), $L_1X$ is —$(CH_2)_2$—$NH(heterocyclylalkyl)$.
In another embodiment of the compounds of Formula (IB) or (IC), $L_1X$ is —$(CH_2)_2$—$NH(heteroarylalkyl)$.
In another embodiment of the compounds of Formula (IB) or (IC), $L_1X$ is —$(CH_2)_2$—$NH(arylalkyl)$.
In another embodiment of the compounds of Formula (IB) or (IC), $L_1X$ is —$(CH_2)_3$—$NR_aR_b$.
In another embodiment of the compounds of Formula (IB) or (IC), $L_1X$ is —$(CH_2)_3$—$NH_2$.
In another embodiment of the compounds of Formula (IB) or (IC), $L_1X$ is —$(CH_2)_3$—$N(alkyl)_2$.
In another embodiment of the compounds of Formula (IB) or (IC), $L_1X$ is —$(CH_2)_3$—$NH(alkyl)$.
In another embodiment of the compounds of Formula (IB) or (IC), $L_1X$ is —$(CH_2)_3$—$NH(heterocyclyl)$.
In another embodiment of the compounds of Formula (IB) or (IC), $L_1X$ is —$(CH_2)_3$—$NH(heterocyclylalkyl)$.
In another embodiment of the compounds of Formula (IB) or (IC), $L_1X$ is —$(CH_2)_3$—$NH(heteroarylalkyl)$.
In another embodiment of the compounds of Formula (IB) or (IC), $L_1X$ is —$(CH_2)_3$—$NH(arylalkyl)$.
In another embodiment of the compounds of Formula (IB) or (IC), $L_1X$ is —$(CH_2)_4$—$NR_aR_b$.
In another embodiment of the compounds of Formula (IB) or (IC), $L_1X$ is —$(CH_2)_4$—$NH_2$.
In another embodiment of the compounds of Formula (IB) or (IC), $L_1X$ is —$(CH_2)_4$—$N(alkyl)_2$.
In another embodiment of the compounds of Formula (IB) or (IC), $L_1X$ is —$(CH_2)_4$—$NH(alkyl)$.
In another embodiment of the compounds of Formula (TB) or (IC), $L_1X$ is —$(CH_2)_4$—$NH(heterocyclyl)$.
In another embodiment of the compounds of Formula (IB) or (IC), $L_1X$ is —$(CH_2)_4$—$NH(heterocyclylalkyl)$.
In another embodiment of the compounds of Formula (IB) or (IC), $L_1X$ is —$(CH_2)_4$—$NH(heteroarylalkyl)$.
In another embodiment of the compounds of Formula (IB) or (IC), $L_1X$ is —$(CH_2)_4$—$NH(arylalkyl)$.
In another embodiment of the compounds of Formula (IB), $R_5$ is -alkylene-$NR_aR_b$.
In another embodiment of the compounds of Formula (IB), $R_5$ is -alkylene-$NH_2$.
In another embodiment of the compounds of Formula (IB), $R_5$ is -alkylene-$N(alkyl)_2$.
In another embodiment of the compounds of Formula (IB), $R_5$ is -alkylene-$NH(alkyl)$.
In another embodiment of the compounds of Formula (IB), $R_5$ is -alkylene-$NH(heterocyclyl)$.
In another embodiment of the compounds of Formula (IB), $R_5$ is -alkylene-$NH(heterocyclylalkyl)$.
In another embodiment of the compounds of Formula (IB), $R_5$ is -alkylene-$NH(heteroarylalkyl)$.
In another embodiment of the compounds of Formula (IB), $R_5$ is -alkylene-$NH(arylalkyl)$.
In another embodiment of the compounds of Formula (IB), $R_5$ is —$(CH_2)_2$—$NR_aR_b$.
In another embodiment of the compounds of Formula (IB), $R_5$ is —$(CH_2)_2$—$NH_2$.
In another embodiment of the compounds of Formula (IB), $R_5$ is —$(CH_2)_2$—$N(alkyl)_2$.
In another embodiment of the compounds of Formula (IB), $R_5$ is —$(CH_2)_2$—$NH(alkyl)$.
In another embodiment of the compounds of Formula (IB), $R_5$ is —$(CH_2)_2$—$NH(heterocyclyl)$.
In another embodiment of the compounds of Formula (IB), $R_5$ is —$(CH_2)_2$—$NH(heterocyclylalkyl)$.
In another embodiment of the compounds of Formula (IB), $R_5$ is —$(CH_2)_2$—$NH(heteroarylalkyl)$.
In another embodiment of the compounds of Formula (IB), $R_5$ is —$(CH_2)_2$—$NH(arylalkyl)$.
In another embodiment of the compounds of Formula (IB), $R_5$ is —$(CH_2)_3$—$NR_aR_b$.
In another embodiment of the compounds of Formula (IB), $R_5$ is —$(CH_2)_3$—$NH_2$.
In another embodiment of the compounds of Formula (IB), $R_5$ is —$(CH_2)_3$—$N(alkyl)_2$.
In another embodiment of the compounds of Formula (IB), $R_5$ is —$(CH_2)_3$—$NH(alkyl)$.
In another embodiment of the compounds of Formula (IB), $R_5$ is —$(CH_2)_3$—$NH(heterocyclyl)$.
In another embodiment of the compounds of Formula (IB), $R_5$ is —$(CH_2)_3$—$NH(heterocyclylalkyl)$.
In another embodiment of the compounds of Formula (IB), $R_5$ is —$(CH_2)_3$—$NH(heteroarylalkyl)$.
In another embodiment of the compounds of Formula (IB), $R_5$ is —$(CH_2)_3$—$NH(arylalkyl)$.
In another embodiment of the compounds of Formula (IB), $R_5$ is —$(CH_2)_4$—$NR_aR_b$.
In another embodiment of the compounds of Formula (IB), $R_5$ is —$(CH_2)_4$—$NH_2$.
In another embodiment of the compounds of Formula (IB), $R_5$ is —$(CH_2)_4$—$N(alkyl)_2$.
In another embodiment of the compounds of Formula (IB), $R_5$ is —$(CH_2)_4$—$NH(alkyl)$.
In another embodiment of the compounds of Formula (IB), $R_5$ is —$(CH_2)_4$—$NH(heterocyclyl)$.
In another embodiment of the compounds of Formula (IB), $R_5$ is —$(CH_2)_4$—$NH(heterocyclylalkyl)$.
In another embodiment of the compounds of Formula (IB), $R_5$ is —$(CH_2)_4$—$NH(heteroarylalkyl)$.
In another embodiment of the compounds of Formula (IB), $R_5$ is —$(CH_2)_4$—$NH(arylalkyl)$.
In another embodiment of the compounds of Formula (IB), $R_5$ is substituted or unsubstituted aryl.
In another embodiment of the compounds of Formula (IB), $R_5$ is substituted or unsubstituted phenyl.
In another embodiment of the compounds of Formula (IB), $R_5$ is substituted or unsubstituted heterocyclylalkyl.
In another embodiment of the compounds of Formula (IB), $R_5$ is H.
In another embodiment of the compounds of Formula (IC), $R_6$ is -alkylene-$NR_aR_b$.
In another embodiment of the compounds of Formula (IB), $R_6$ is -alkylene-$NH_2$.
In another embodiment of the compounds of Formula (IB), $R_6$ is -alkylene-$N(alkyl)_2$.
In another embodiment of the compounds of Formula (IB), $R_6$ is -alkylene-$NH(alkyl)$.
In another embodiment of the compounds of Formula (IB), $R_6$ is -alkylene-$NH(heterocyclyl)$.
In another embodiment of the compounds of Formula (IB), $R_6$ is -alkylene-$NH(heterocyclylalkyl)$.
In another embodiment of the compounds of Formula (IB), $R_6$ is -alkylene-$NH(heteroarylalkyl)$.

In another embodiment of the compounds of Formula (IB), $R_6$ is -alkylene-NH(arylalkyl).

In another embodiment of the compounds of Formula (IB), $R_6$ is —$(CH_2)_2$—$NR_aR_b$.

In another embodiment of the compounds of Formula (IB), $R_6$ is —$(CH_2)_2NH_2$.

In another embodiment of the compounds of Formula (IB), $R_6$ is —$(CH_2)_2$—$N(alkyl)_2$.

In another embodiment of the compounds of Formula (IB), $R_6$ is —$(CH_2)_2$—NH(alkyl).

In another embodiment of the compounds of Formula (IB), $R_6$ is —$(CH_2)_2$—NH(heterocyclyl).

In another embodiment of the compounds of Formula (IB), $R_6$ is —$(CH_2)_2$—NH(heterocyclylalkyl).

In another embodiment of the compounds of Formula (IB), $R_6$ is —$(CH_2)_2$—NH(heteroarylalkyl).

In another embodiment of the compounds of Formula (IB), $R_6$ is —$(CH_2)_2$—NH(arylalkyl).

In another embodiment of the compounds of Formula (IB), $R_6$ is —$(CH_2)_3$—$NR_aR_b$.

In another embodiment of the compounds of Formula (IB), $R_6$ is —$(CH_2)_3$—$NH_2$.

In another embodiment of the compounds of Formula (IB), $R_6$ is —$(CH_2)_3$—$N(alkyl)_2$.

In another embodiment of the compounds of Formula (IB), $R_6$ is —$(CH_2)_3$—NH(alkyl).

In another embodiment of the compounds of Formula (IB), $R_6$ is —$(CH_2)_3$—NH(heterocyclyl).

In another embodiment of the compounds of Formula (IB), $R_6$ is —$(CH_2)_3$—NH(heterocyclylalkyl).

In another embodiment of the compounds of Formula (IB), $R_6$ is —$(CH_2)_3$—NH(heteroarylalkyl).

In another embodiment of the compounds of Formula (IB), $R_6$ is —$(CH_2)_3$—NH(arylalkyl).

In another embodiment of the compounds of Formula (IB), $R_6$ is —$(CH_2)_4$—$NR_aR_b$.

In another embodiment of the compounds of Formula (IB), $R_6$ is —$(CH_2)_4$—$NH_2$.

In another embodiment of the compounds of Formula (IB), $R_6$ is —$(CH_2)_4$—$N(alkyl)_2$.

In another embodiment of the compounds of Formula (IB), $R_6$ is —$(CH_2)_4$—NH(alkyl).

In another embodiment of the compounds of Formula (IB), $R_6$ is —$(CH_2)_4$—NH(heterocyclyl).

In another embodiment of the compounds of Formula (IB), $R_6$ is —$(CH_2)_4$—NH(heterocyclylalkyl).

In another embodiment of the compounds of Formula (IB), $R_6$ is —$(CH_2)_4$—NH(heteroarylalkyl).

In another embodiment of the compounds of Formula (IB), $R_6$ is —$(CH_2)_4$—NH(arylalkyl).

In another embodiment of the compounds of Formula (IC), $R_6$ is substituted or unsubstituted aryl.

In another embodiment of the compounds of Formula (IC), $R_6$ is substituted or unsubstituted phenyl.

In another embodiment of the compounds of Formula (IC), $R_6$ is substituted or unsubstituted heterocyclylalkyl.

In another embodiment of the compounds of Formula (IC), $R_6$ is substituted or unsubstituted arylalkyl.

In another embodiment of the compounds of Formula (IC), $R_6$ is substituted or unsubstituted benzyl.

In another embodiment of the compounds of Formula (IC), $R_6$ is alkenyl.

In another embodiment of the compounds of Formula (IC), $R_6$ is H.

In another embodiment of the compounds of Formula (IB) or (IC),

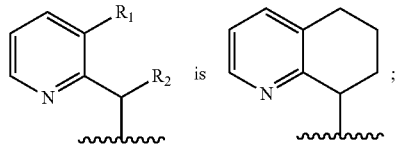

$L_2Y$ is H; and $L_1X$ is alkyl.

In another embodiment of the compounds of Formula (IB) or (IC),

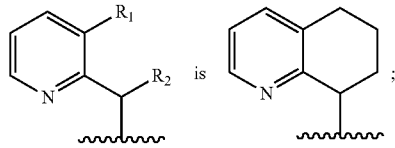

$L_2Y$ is H; and $L_1X$ is $CH_3$.

In another embodiment of the compounds of Formula (IC), $R_6$ is substituted or unsubstituted

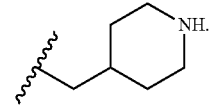

Compounds of Formula ID

In another embodiment, the compounds of the present invention have the following Formula (ID):

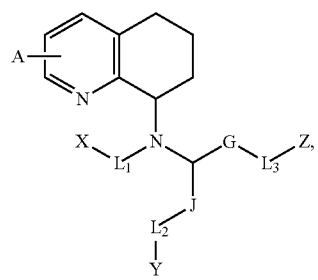

(ID)

or a pharmaceutically acceptable salt, solvate, tautomer, stereoisomer, and/or ester thereof wherein variables A, X, Y, Z, G, J, $L_1$, $L_2$ and $L_3$ are as defined in Formula I.

In some embodiments of the compounds of Formula (ID), $L_1X$ is H; $L_2$ is a covalent bond or a substituted or unsubstituted alkylene; $L_3$ is substituted or unsubstituted alkylene; Y is substituted or unsubstituted carbocyclyl, substituted or unsubstituted heterocyclyl, or $NR_aR_b$; Z is $NR_aR_b$; $R_a$ and $R_b$ are each independently selected from the group consisting of H, substituted or unsubstituted alkyl, substituted or unsubstituted carbocyclyl, substituted or unsubstituted carbocyclylalkyl, substituted or unsubstituted heterocyclylalkyl, and substituted or unsubstituted heterocyclyl; J is a covalent bond, —C(O)—$NR_d$—, or —C(O)—; $R_d$ is selected from the group consisting of H, alkyl, and substituted or unsubstituted arylalkyl; and G is a covalent bond or —C(O)—$NR_d$—.

In another embodiment of the compounds of Formula (ID), $L_1X$ is H.

In another embodiment of the compounds of Formula (ID), G is a covalent bond.

In another embodiment of the compounds of Formula (ID), G is —C(O)NH—.

In another embodiment of the compounds of Formula (ID), $L_3Z$ is -alkylene-$NR_aR_b$.

In another embodiment of the compounds of Formula (ID), $L_3Z$ is -alkylene-$NH_2$.

In another embodiment of the compounds of Formula (ID), $L_3Z$ is -alkylene-N(alkyl)$_2$.

In another embodiment of the compounds of Formula (ID), $L_3Z$ is -alkylene-NH(alkyl).

In another embodiment of the compounds of Formula (ID), $L_3Z$ is -alkylene-NH(heterocyclyl).

In another embodiment of the compounds of Formula (ID), $L_3Z$ is -alkylene-NH(heterocyclylalkyl).

In another embodiment of the compounds of Formula (ID), $L_3Z$ is -alkylene-NH(heteroarylalkyl).

In another embodiment of the compounds of Formula (ID), $L_3Z$ is -alkylene-NH(arylalkyl).

In another embodiment of the compounds of Formula (ID), $L_3Z$ is —$(CH_2)_2$—$NH_2$.

In another embodiment of the compounds of Formula (ID), $L_3Z$ is —$(CH_2)_2$—N(alkyl)$_2$.

In another embodiment of the compounds of Formula (ID), $L_3Z$ is —$(CH_2)_2$—NH(alkyl).

In another embodiment of the compounds of Formula (ID), $L_3Z$ is —$(CH_2)_2$—NH(heterocyclyl).

In another embodiment of the compounds of Formula (ID), $L_3Z$ is —$(CH_2)_2$—NH(heterocyclylalkyl).

In another embodiment of the compounds of Formula (ID), $L_3Z$ is —$(CH_2)_2$—NH(heteroarylalkyl).

In another embodiment of the compounds of Formula (ID), $L_3Z$ is —$(CH_2)_2$—NH(arylalkyl).

In another embodiment of the compounds of Formula (ID), $L_3Z$ is —$(CH_2)_3$—$NH_2$.

In another embodiment of the compounds of Formula (ID), $L_3Z$ is —$(CH_2)_3$—N(alkyl)$_2$.

In another embodiment of the compounds of Formula (ID), $L_3Z$ is —$(CH_2)_3$—NH(alkyl).

In another embodiment of the compounds of Formula (ID), $L_3Z$ is —$(CH_2)_3$—NH(heterocyclyl).

In another embodiment of the compounds of Formula (ID), $L_3Z$ is —$(CH_2)_3$—NH(heterocyclylalkyl).

In another embodiment of the compounds of Formula (ID), $L_3Z$ is —$(CH_2)_3$—NH(heteroarylalkyl).

In another embodiment of the compounds of Formula (ID), $L_3Z$ is —$(CH_2)_3$—NH(arylalkyl).

In another embodiment of the compounds of Formula (ID), $L_3Z$ is —$(CH_2)_4$—$NH_2$.

In another embodiment of the compounds of Formula (ID), $L_3Z$ is —$(CH_2)_4$—N(alkyl)$_2$.

In another embodiment of the compounds of Formula (ID), $L_3Z$ is —$(CH_2)_4$—NH(alkyl).

In another embodiment of the compounds of Formula (ID), $L_3Z$ is —$(CH_2)_4$—NH(heterocyclyl).

In another embodiment of the compounds of Formula (ID), $L_3Z$ is —$(CH_2)_4$—NH(heterocyclylalkyl).

In another embodiment of the compounds of Formula (ID), $L_3Z$ is —$(CH_2)_4$—NH(heteroarylalkyl).

In another embodiment of the compounds of Formula (ID), $L_3Z$ is —$(CH_2)_4$—NH(arylalkyl).

In another embodiment of the compounds of Formula (ID), $L_2Y$ is substituted or unsubstituted carbocyclylalkyl.

In another embodiment of the compounds of Formula (ID), $L_2Y$ is substituted or unsubstituted heterocyclylalkyl.

In another embodiment of the compounds of Formula (ID), $L_2Y$ is -alkylene-$NR_aR_b$.

In another embodiment of the compounds of Formula (ID), $L_2Y$ is -alkylene-$NH_2$.

In another embodiment of the compounds of Formula (ID), $L_2Y$ is -alkylene-N(alkyl)$_2$.

In another embodiment of the compounds of Formula (ID), $L_2Y$ is -alkylene-NH(alkyl).

In another embodiment of the compounds of Formula (ID), $L_2Y$ is -alkylene-NH(heterocyclyl).

In another embodiment of the compounds of Formula (ID), $L_2Y$ is -alkylene-NH(heterocyclylalkyl).

In another embodiment of the compounds of Formula (ID), $L_2Y$ is -alkylene-NH(heteroarylalkyl).

In another embodiment of the compounds of Formula (ID), $L_2Y$ is -alkylene-NH(arylalkyl).

In another embodiment of the compounds of Formula (ID), $L_2Y$ is —$(CH_2)_2$—$NH_2$.

In another embodiment of the compounds of Formula (ID), $L_2Y$ is —$(CH_2)_2$—N(alkyl)$_2$.

In another embodiment of the compounds of Formula (ID), $L_2Y$ is —$(CH_2)_2$—NH(alkyl).

In another embodiment of the compounds of Formula (ID), $L_2Y$ is —$(CH_2)_2$—NH(heterocyclyl).

In another embodiment of the compounds of Formula (ID), $L_2Y$ is —$(CH_2)_2$—NH(heterocyclylalkyl).

In another embodiment of the compounds of Formula (ID), $L_2Y$ is —$(CH_2)_2$—NH(heteroarylalkyl).

In another embodiment of the compounds of Formula (ID), $L_2Y$ is —$(CH_2)_2$—NH(arylalkyl).

In another embodiment of the compounds of Formula (ID), $L_2Y$ is —$(CH_2)_3$—$NH_2$.

In another embodiment of the compounds of Formula (ID), $L_2Y$ is —$(CH_2)_3$—N(alkyl)$_2$.

In another embodiment of the compounds of Formula (ID), $L_2Y$ is —$(CH_2)_3$—NH(alkyl).

In another embodiment of the compounds of Formula (ID), $L_2Y$ is —$(CH_2)_3$—NH(heterocyclyl).

In another embodiment of the compounds of Formula (ID), $L_2Y$ is —$(CH_2)_3$—NH(heterocyclylalkyl).

In another embodiment of the compounds of Formula (ID), $L_2Y$ is —$(CH_2)_3$—NH(heteroarylalkyl).

In another embodiment of the compounds of Formula (ID), $L_2Y$ is —$(CH_2)_3$—NH(arylalkyl).

In another embodiment of the compounds of Formula (ID), $L_2Y$ is —$(CH_2)_4$—$NH_2$.

In another embodiment of the compounds of Formula (ID), $L_2Y$ is —$(CH_2)_4$—N(alkyl)$_2$.

In another embodiment of the compounds of Formula (ID), $L_2Y$ is —$(CH_2)_4$—NH(alkyl).

In another embodiment of the compounds of Formula (ID), $L_2Y$ is —$(CH_2)_4$—NH(heterocyclyl).

In another embodiment of the compounds of Formula (ID), $L_2Y$ is —$(CH_2)_4$—NH(heterocyclylalkyl).

In another embodiment of the compounds of Formula (ID), $L_2Y$ is —$(CH_2)_4$—NH(heteroarylalkyl).

In another embodiment of the compounds of Formula (ID), $L_2Y$ is —$(CH_2)_4$—NH(arylalkyl).

In another embodiment of the compounds of Formula (ID), J is —C(O)NH—.

In another embodiment of the compounds of Formula (ID), J is a covalent bond.

In another embodiment of the compounds of Formula (ID), J is —C(O)—.

In another embodiment of the compounds of Formula (ID), L₁X is H; G is a covalent bond; L₃Z is -alkylene-NR_aR_b; J is —C(O)NH—; and L₂Y is substituted or unsubstituted carbocyclylalkyl or substituted or unsubstituted heterocyclylalkyl.

In another embodiment of the compounds of Formula (ID), L₁X is H; G is —C(O)NH—;

L₃Z is -alkylene-NR_aR_b; J is a covalent bond; and L₂Y is substituted or unsubstituted carbocyclylalkyl or substituted or unsubstituted heterocyclylalkyl.

In another embodiment of the compounds of Formula (ID), L₁X is H; G is a covalent bond; L₃Z is -alkylene-NR_aR_b; J is —C(O)—; and L₂Y is -alkylene-NR_aR_b.

Compounds of Formula 1E

In another embodiment, the compounds of the present invention have the following Formula (IE):

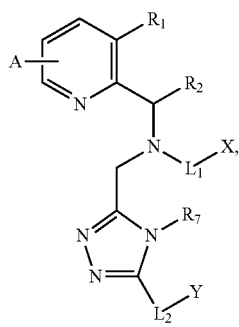
(IE)

or a pharmaceutically acceptable salt, solvate, tautomer, stereoisomer, and/or ester thereof, wherein variables R₁, R₂, A, X, Y, L₁ and L₂ are defined as in Formula I.

In one embodiment of the compounds of Formula (IE), R₁ and R₂, taken together with the carbon atoms to which they are shown attached, form a substituted or unsubstituted carbocyclyl; L₁ is substituted or unsubstituted alkylene; L₂ is a covalent bond or a substituted or unsubstituted alkylene; X is H or NR_aR_b; Y is a substituted or unsubstituted carbocyclyl, or a substituted or unsubstituted heterocyclyl; R_a and R_b are each independently selected from the group consisting of H, substituted or unsubstituted alkyl, substituted or unsubstituted carbocyclyl, substituted or unsubstituted carbocyclylalkyl, substituted or unsubstituted heterocyclylalkyl, and substituted or unsubstituted heterocyclyl; and R₇ is a substituted or unsubstituted alkyl or a substituted or unsubstituted aminoalkyl.

In certain embodiments of the compounds of Formula (IE),

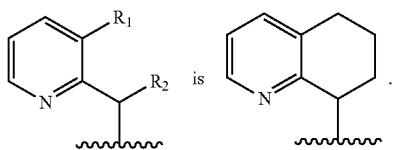

In another embodiment of the compounds of Formula (IE), R₇ is alkyl.

In another embodiment of the compounds of Formula (IE), R₇ is CH₃.

In another embodiment of the compounds of Formula (IE), R₇ is aminoalkyl.

In another embodiment of the compounds of Formula (IE), R₇ is (CH₂)₂NH₂.

In another embodiment of the compounds of Formula (IE), R₇ is (CH₂)₃NH₂.

In another embodiment of the compounds of Formula (IE), R₇ is (CH₂)₄NH₂.

In another embodiment of the compounds of Formula (IE), L₁X is alkyl or alkylene-NR_aR_b.

In another embodiment of the compounds of Formula (IE), L₂Y is substituted or unsubstituted aryl, substituted or unsubstituted arylalkyl, or substituted or unsubstituted heterocyclylalkyl.

In another embodiment of the compounds of Formula (IE),

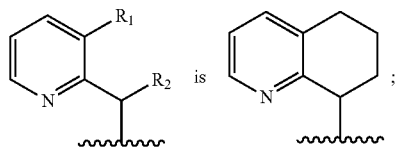

and R₂ is alkyl.

In another embodiment of the compounds of Formula (IE),

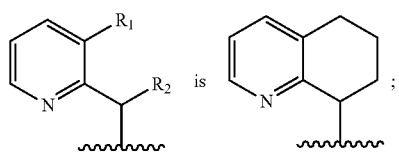

R₇ is alkyl; and L₂Y is substituted or unsubstituted aryl.

In another embodiment of the compounds of Formula (IE),

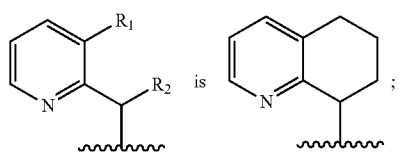

R₇ is alkyl; and L₂Y is substituted or unsubstituted

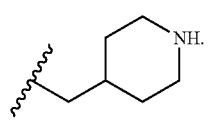 [SMILES: *CC1CCNCC1]

Compounds of Formula 1F

In another embodiment, the compounds of the present invention have the following Formula (IF):

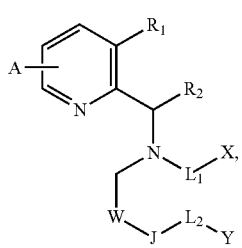
(IF)

or a pharmaceutically acceptable salt, solvate, tautomer, stereoisomer, and/or ester thereof wherein variables $R_1$, $R_2$, A, X, Y, J, W, $L_1$ and $L_2$ are defined as in Formula I.

In one embodiment of the compounds of Formula (IF), $R_1$ and $R_2$, taken together with the carbon atoms to which they are shown attached, form a substituted or unsubstituted carbocyclyl or a substituted or unsubstituted heterocyclyl; $L_1$ is substituted or unsubstituted alkylene; $L_2$, is a covalent bond or a substituted or unsubstituted alkylene; X is H; Y is $NR_aR_b$ or a substituted or unsubstituted heterocyclyl; $R_a$ and $R_b$ are each independently selected from the group consisting of H, substituted or unsubstituted alkyl, substituted or unsubstituted carbocyclyl, substituted or unsubstituted carbocyclylalkyl, substituted or unsubstituted heterocyclylalkyl, and substituted or unsubstituted heterocyclyl; or $R_a$ and $R_b$, together with the nitrogen atom to which they are shown attached form a substituted or unsubstituted heterocyclyl; W is a substituted or unsubstituted heterocyclyl; J is a covalent bond, alkylene, —C(O)—$NR_d$—, —$NR_d$—, or —C(O)—; and $R_d$ is selected from the group consisting of H, alkyl, and substituted or substituted arylalkyl.

In certain embodiments of the compounds of Formula (IF), J is a covalent bond.

In another embodiment of the compounds of Formula (IF), J is —NH—.

In another embodiment of the compounds of Formula (IF), J is —C(O)—.

In another embodiment of the compounds of Formula (IF), J is —C(O)—NH—.

In another embodiment of the compounds of Formula (IF), $L_1X$ is substituted or unsubstituted alkyl.

In another embodiment of the compounds of Formula (IF), $L_1X$ is substituted or unsubstituted $CH_3$.

In another embodiment of the compounds of Formula (IF), $L_2Y$ is -alkylene-$NR_aR_b$.

In another embodiment of the compounds of Formula (IF), $L_2Y$ is -alkylene-$NH_2$.

In another embodiment of the compounds of Formula (IF), $L_2Y$ is -alkylene-$N(alkyl)_2$.

In another embodiment of the compounds of Formula (IF), $L_2Y$ is -alkylene-NH(alkyl).

In another embodiment of the compounds of Formula (IF), $L_2Y$ is -alkylene-NH(heterocyclyl).

In another embodiment of the compounds of Formula (IF), $L_2Y$ is -alkylene-NH(heterocyclylalkyl).

In another embodiment of the compounds of Formula (IF), $L_2Y$ is -alkylene-NH(heteroarylalkyl).

In another embodiment of the compounds of Formula (IF), $L_2Y$ is -alkylene-NH(arylalkyl).

In another embodiment of the compounds of Formula (IF), $L_2Y$ is —$(CH_2)_2$—$NR_aR_b$.

In another embodiment of the compounds of Formula (IF), $L_2Y$ is —$(CH_2)_2$—$NH_2$.

In another embodiment of the compounds of Formula (IF), $L_2Y$ is —$(CH_2)_2$—$N(alkyl)_2$.

In another embodiment of the compounds of Formula (IF), $L_2Y$ is —$(CH_2)_2$—NH(alkyl).

In another embodiment of the compounds of Formula (IF), $L_2Y$ is —$(CH_2)_2$—NH(heterocyclyl).

In another embodiment of the compounds of Formula (IF), $L_2Y$ is —$(CH_2)_2$—NH(heterocyclylalkyl).

In another embodiment of the compounds of Formula (IF), $L_2Y$ is —$(CH_2)_2$—NH(heteroarylalkyl).

In another embodiment of the compounds of Formula (IF), $L_2Y$ is —$(CH_2)_2$—NH(arylalkyl).

In another embodiment of the compounds of Formula (IF), $L_2Y$ is —$(CH_2)_3$—$NR_aR_b$.

In another embodiment of the compounds of Formula (IF), $L_2Y$ is —$(CH_2)_3$—$NH_2$.

In another embodiment of the compounds of Formula (IF), $L_2Y$ is —$(CH_2)_3$—$N(alkyl)_2$.

In another embodiment of the compounds of Formula (IF), $L_2Y$ is —$(CH_2)_3$—NH(alkyl).

In another embodiment of the compounds of Formula (IF), $L_2Y$ is —$(CH_2)_3$—NH(heterocyclyl).

In another embodiment of the compounds of Formula (IF), $L_2Y$ is —$(CH_2)_3$—NH(heterocyclylalkyl).

In another embodiment of the compounds of Formula (IF), $L_2Y$ is —$(CH_2)_3$—NH(heteroarylalkyl).

In another embodiment of the compounds of Formula (IF), $L_2Y$ is —$(CH_2)_3$—NH(arylalkyl).

In another embodiment of the compounds of Formula (IF), $L_2Y$ is —$(CH_2)_4$—$NR_aR_b$.

In another embodiment of the compounds of Formula (IF), $L_2Y$ is —$(CH_2)_4$—$NH_2$.

In another embodiment of the compounds of Formula (IF), $L_2Y$ is —$(CH_2)_4$—$N(alkyl)_2$.

In another embodiment of the compounds of Formula (IF), $L_2Y$ is —$(CH_2)_4$—NH(alkyl).

In another embodiment of the compounds of Formula (IF), $L_2Y$ is —$(CH_2)_4$—NH(heterocyclyl).

In another embodiment of the compounds of Formula (IF), $L_2Y$ is —$(CH_2)_4$—NH(heterocyclylalkyl).

In another embodiment of the compounds of Formula (IF), $L_2Y$ is —$(CH_2)_4$—NH(heteroarylalkyl).

In another embodiment of the compounds of Formula (IF), $L_2Y$ is —$(CH_2)_4$—NH(arylalkyl).

In another embodiment of the compounds of Formula (IF), $L_2Y$ is substituted or unsubstituted heterocyclylalkyl.

In another embodiment of the compounds of Formula (IF),

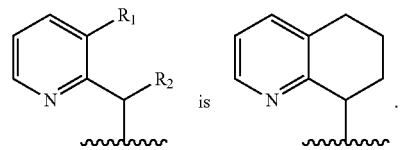

In another embodiment of the compounds of Formula (IF),

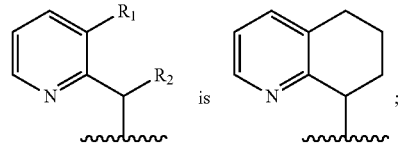

W is a substituted or unsubstituted heterocyclyl; $L_1X$ is substituted or unsubstituted alkyl; and $L_2Y$ is -alkylene-$NR_aR_b$.

In another embodiment of the compounds of Formula (IF), J is a covalent bond.

In another embodiment of the compounds of Formula (IF), J is NH.

In another embodiment of the compounds of Formula (IF), J is —C(O)—.

In another embodiment of the compounds of Formula (IF), J is —C(O)—NH—.

In another embodiment of the compounds of Formula (IF), W is substituted or unsubstituted substitutent selected from:

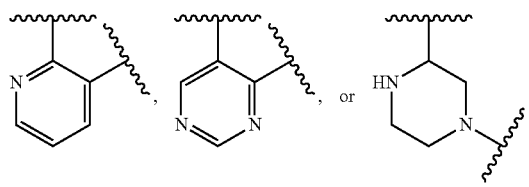

Compounds of Formula 1G

In yet another embodiment, the compounds of the present invention have the following Formula (IG):

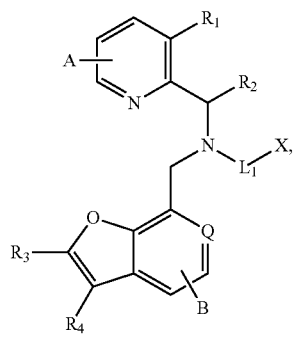

(IG)

wherein each of $R_1$, $R_2$, $R_3$, $R_4$, $L_1$, X, Q, A, and B are as defined for Formula I.

In a particular embodiment of the compounds of Formula (IG), $R_1$ and $R_2$ are each independently H or alkyl; or $R_1$ and $R_2$, taken together with the carbon atoms to which they are shown attached, form a substituted or unsubstituted carbocyclyl; $L_1$ is selected from the group consisting of a covalent bond, substituted or unsubstituted alkylene, substituted or unsubstituted alkenyl, and substituted or unsubstituted alkynyl; X is H or $NR_aR_b$; $R_a$ and $R_b$ are each independently selected from the group consisting of H, substituted or unsubstituted alkyl, aldiminyl, substituted or unsubstituted carbocyclyl, substituted or unsubstituted carbocyclylalkyl, substituted or unsubstituted heterocyclylalkyl, and substituted or unsubstituted heterocyclyl; or $R_a$ and $R_b$, together with the nitrogen atom to which they are shown attached form a substituted or unsubstituted heterocyclyl; Q is $CR_e$ or N; $R_e$ is selected from the group consisting of H, alkyl, halo, substituted or unsubstituted amino, cyano, nitro, haloalkyl, hydroxyl, and alkoxyl; and $R_3$ and $R_4$ are each independently selected from the group consisting of H, substituted or unsubstituted aryl, substituted or unsubstituted heteroaryl, substituted or unsubstituted alkyl, substituted or unsubstituted alkenyl, and substituted or unsubstituted alkynyl; or $R_3$ and $R_4$, taken together with the carbon atoms to which they are shown attached, form a substituted or unsubstituted carbocyclyl or a substituted or unsubstituted heterocyclyl.

In another embodiment of the compounds of Formula (IG), $R_2$ is H; or $R_1$ and $R_2$, taken together with the carbon atoms to which they are shown attached, form a substituted or unsubstituted carbocyclyl; $L_1$ is substituted or unsubstituted alkylene; X is H or $NR_aR_b$; $R_a$ and $R_b$ are each independently selected from the group consisting of H, alkyl, aldiminyl, substituted or unsubstituted carbocyclyl, substituted or unsubstituted carbocyclylalkyl, substituted or unsubstituted heterocyclylalkyl, and substituted or unsubstituted heterocyclyl; or $R_a$ and $R_b$, together with the nitrogen atom to which they are shown attached form a substituted or unsubstituted heterocyclyl; Q is CH or N; and $R_3$ and $R_4$ are each H; or $R_3$ and $R_4$, taken together with the carbon atoms to which they are shown attached, form a substituted or unsubstituted aryl.

In another embodiment of the compounds of Formula (IG), $R_3$ and $R_4$, taken together with the carbon atoms to which they are shown attached, form:

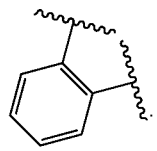 [SMILES: *c1ccccc1*]

In another embodiment of the compounds of Formula (IG),

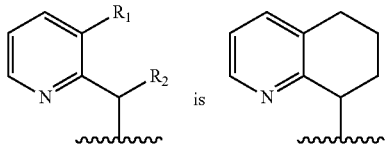

In another embodiment of the compounds of Formula (IG),

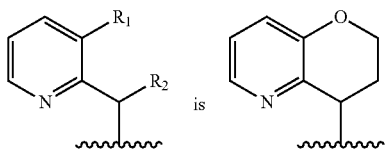

In another embodiment of the compounds of Formula (IG),

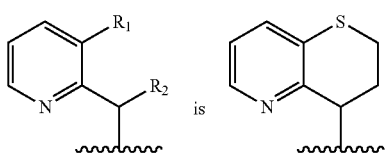

In another embodiment of the compounds of Formula (IG), Q is N.

In another embodiment of the compounds of Formula (IG), Q is CH.

In another embodiment of the compounds of Formula (IG), $L_1X$ is H.

In another embodiment of the compounds of Formula (IG), $L_1X$ is -alkylene-$NR_aR_b$.

In another embodiment of the compounds of Formula (IG), $L_1X$ is -alkylene-$NH_2$.

In another embodiment of the compounds of Formula (IG), $L_1X$ is -alkylene-$N(alkyl)_2$.

In another embodiment of the compounds of Formula (IG), $L_1X$ is —$(CH_2)_2$—$NR_aR_b$.

In another embodiment of the compounds of Formula (IG), $L_1X$ is —$(CH_2)_2$—$NH_2$.

In another embodiment of the compounds of Formula (IG), $L_1X$ is —$(CH_2)_2$—$N(alkyl)_2$.

In another embodiment of the compounds of Formula (IG), $L_1X$ is —$(CH_2)_3$—$NR_aR_b$.
In another embodiment of the compounds of Formula (IG), $L_1X$ is —$(CH_2)_3$—$NH_2$.
In another embodiment of the compounds of Formula (IG), $L_1X$ is —$(CH_2)_3$—$N(alkyl)_2$.
In another embodiment of the compounds of Formula (IG), $L_1X$ is —$(CH_2)_4$—$NR_aR_b$.
In another embodiment of the compounds of Formula (IG), $L_1X$ is —$(CH_2)_4$—$NH_2$.
In another embodiment of the compounds of Formula (IG), $L_1X$ is —$(CH_2)_4$—$N(alkyl)_2$.
In another embodiment of the compounds of Formula (IG), $R_3$ and $R_4$, taken together with the carbon atoms to which they are shown attached, form:

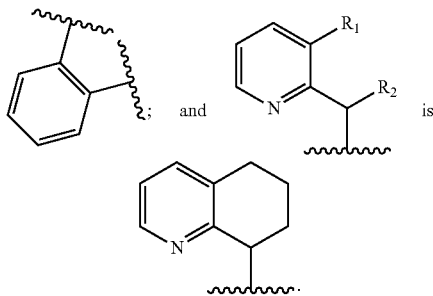

In another embodiment of the compounds of Formula (IG), $R_3$ and $R_4$, taken together with the carbon atoms to which they are shown attached, form:

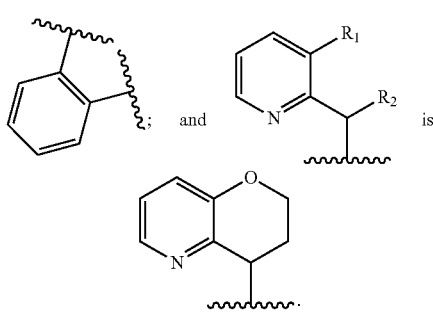

In another embodiment of the compounds of Formula (IG), $R_3$ and $R_4$, taken together with the carbon atoms to which they are shown attached, form:

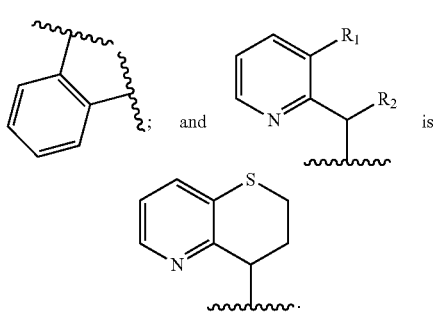

In another embodiment of the compounds of Formula (IG), $L_1X$ is alkyl.

In another embodiment of the compounds of Formula (IG), $L_1X$ is $CH_3$.
In another embodiment of the compounds of Formula (IG), $L_1X$ is -alkylene-$NR_aR_b$.
In another embodiment of the compounds of Formula (IG), $L_1X$ is -alkylene-$NH_2$.
In another embodiment of the compounds of Formula (IG), $L_1X$ is —$(CH_2)_2$—$NH_2$.
In another embodiment of the compounds of Formula (IG), $L_1X$ is —$(CH_2)_3$—$NH_2$.
In another embodiment of the compounds of Formula (IG), $L_1X$ is —$(CH_2)_4$—$NH_2$.
In another embodiment of the compounds of Formula (IG), $L_1X$ is -alkylene-$N(alkyl)_2$.
In another embodiment of the compounds of Formula (IG), $L_1X$ is —$(CH_2)_2$—$N(alkyl)_2$.
In another embodiment of the compounds of Formula (IG), $L_1X$ is —$(CH_2)_3$—$N(alkyl)_2$.
In another embodiment of the compounds of Formula (IG), $L_1X$ is —$(CH_2)_4$—$N(alkyl)_2$.
In another embodiment of the compounds of Formula (IG), $L_1X$ is -alkylene-NH(alkyl).
In another embodiment of the compounds of Formula (IG), $L_1X$ is —$(CH_2)_2$—NH(alkyl).
In another embodiment of the compounds of Formula (IG), $L_1X$ is —$(CH_2)_3$—NH(alkyl).
In another embodiment of the compounds of Formula (IG), $L_1X$ is —$(CH_2)_4$—NH(alkyl).
In another embodiment of the compounds of Formula (IG), $L_1X$ is -alkylene-NH(heterocyclyl).
In another embodiment of the compounds of Formula (IG), $L_1X$ is —$(CH_2)_2$—NH(heterocyclyl).
In another embodiment of the compounds of Formula (IG), $L_1X$ is —$(CH_2)_3$—NH(heterocyclyl).
In another embodiment of the compounds of Formula (IG), $L_1X$ is —$(CH_2)_4$—NH(heterocyclyl).
In another embodiment of the compounds of Formula (IG), $L_1X$ is -alkylene-NH(heterocyclylalkyl).
In another embodiment of the compounds of Formula (IG), $L_1X$ is —$(CH_2)_2$—NH(heterocyclylalkyl).
In another embodiment of the compounds of Formula (IG), $L_1X$ is —$(CH_2)_3$—NH(heterocyclylalkyl).
In another embodiment of the compounds of Formula (IG), $L_1X$ is —$(CH_2)_4$—NH(heterocyclylalkyl).
In another embodiment of the compounds of Formula (IG), $L_1X$ is -alkylene-NH(heteroarylalkyl).
In another embodiment of the compounds of Formula (IG), $L_1X$ is —$(CH_2)_2$—NH(heteroarylalkyl).
In another embodiment of the compounds of Formula (IG), $L_1X$ is —$(CH_2)_3$—NH(heteroarylalkyl).
In another embodiment of the compounds of Formula (IG), $L_1X$ is —$(CH_2)_4$—NH(heteroarylalkyl).
In another embodiment of the compounds of Formula (IG), $L_1X$ is -alkylene-NH(arylalkyl).
In another embodiment of the compounds of Formula (IG), $L_1X$ is —$(CH_2)_2$—NH(arylalkyl).
In another embodiment of the compounds of Formula (IG), $L_1X$ is —$(CH_2)_3$—NH(arylalkyl).
In another embodiment of the compounds of Formula (IG), $L_1X$ is —$(CH_2)_4$—NH(arylalkyl).
In another embodiment of the compounds of Formula (IG), $R_3$ and $R_4$, taken together with the carbon atoms to which they are shown attached, form:

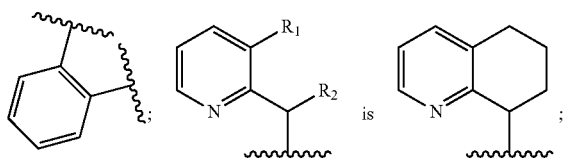

and L₁X is alkyl.

In another embodiment of the compounds of Formula (IG), $R_3$ and $R_4$, taken together with the carbon atoms to which they are shown attached, form:

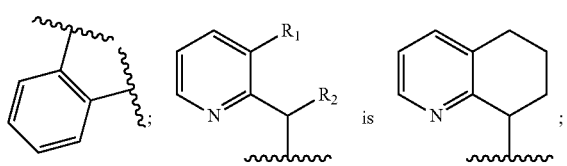

and $L_1X$ is $CH_3$.

In another embodiment of the compounds of Formula (IG), $R_3$ and $R_4$, taken together with the carbon atoms to which they are shown attached, form:

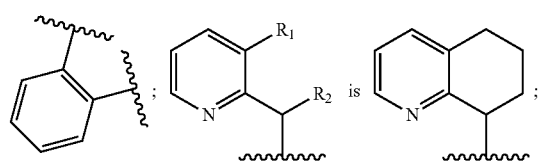

and $L_1X$ is -alkylene-$NR_aR_b$.

In another embodiment of the compounds of Formula (IG), $R_3$ and $R_4$, taken together with the carbon atoms to which they are shown attached, form:

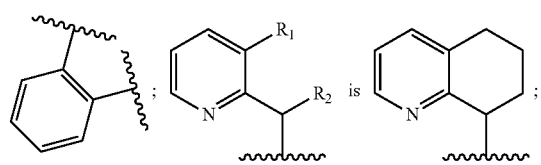

and $L_1X$ is -alkylene-$NH_2$.

In another embodiment of the compounds of Formula (IG), $R_3$ and $R_4$, taken together with the carbon atoms to which they are shown attached, form:

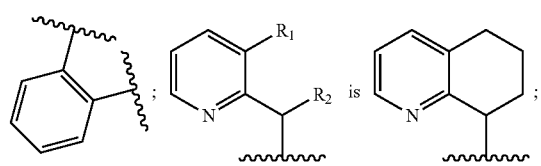

and $L_1X$ is -alkylene-N(alkyl)₂.

In another embodiment of the compounds of Formula (IG), $R_3$ and $R_4$, taken together with the carbon atoms to which they are shown attached, form:

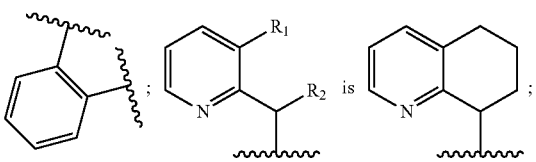

and $L_1X$ is -alkylene-NH(alkyl).

In another embodiment of the compounds of Formula (IG), $R_3$ and $R_4$, taken together with the carbon atoms to which they are shown attached, form:

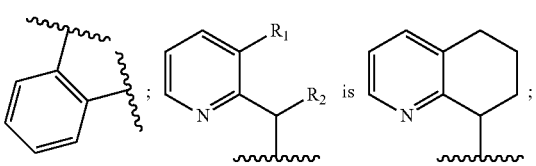

and $L_1X$ is -alkylene-NH(heterocyclyl).

In another embodiment of the compounds of Formula (IG), $R_3$ and $R_4$, taken together with the carbon atoms to which they are shown attached, form:

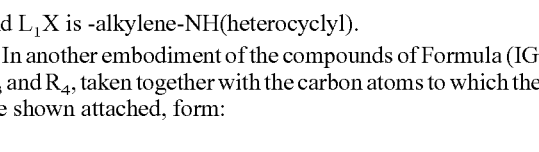

and $L_1X$ is -alkylene-NH(heterocyclylalkyl).

In another embodiment of the compounds of Formula (IG), $R_3$ and $R_4$, taken together with the carbon atoms to which they are shown attached, form:

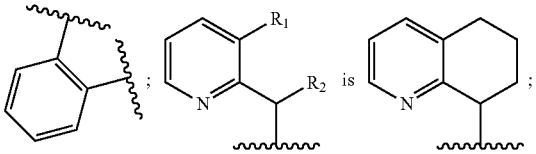

and $L_1X$ is -alkylene-NH(heteroarylalkyl).

In another embodiment of the compounds of Formula (IG), $R_3$ and $R_4$, taken together with the carbon atoms to which they are shown attached, form:

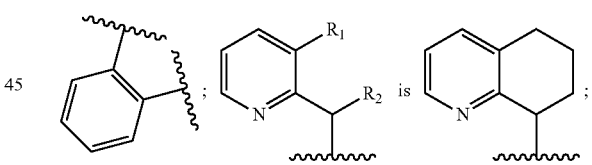

and $L_1X$ is -alkylene-NH(arylalkyl).

In another embodiment of the compounds of Formula (IG), $R_3$ and $R_4$, taken together with the carbon atoms to which they are shown attached, form:

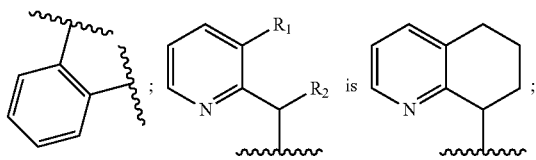

and L$_1$X is —(CH$_2$)$_2$—NH$_2$.

In another embodiment of the compounds of Formula (IG), R$_3$ and R$_4$, taken together with the carbon atoms to which they are shown attached, form:

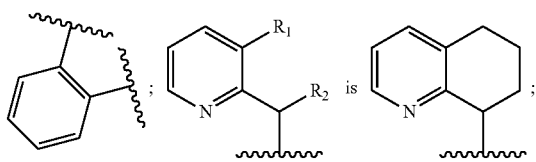

and L$_1$X is —(CH$_2$)$_2$—N(alkyl)$_2$.

In another embodiment of the compounds of Formula (IG), R$_3$ and R$_4$, taken together with the carbon atoms to which they are shown attached, form:

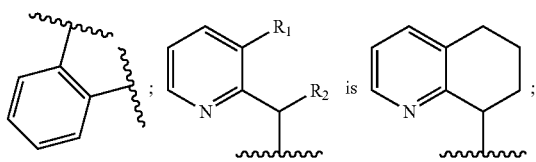

and L$_1$X is —(CH$_2$)$_2$—NH(alkyl).

In another embodiment of the compounds of Formula (IG), R$_3$ and R$_4$, taken together with the carbon atoms to which they are shown attached, form:

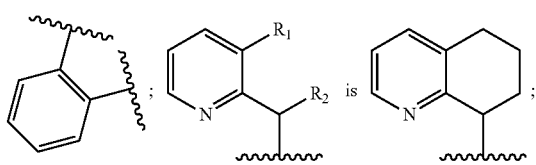

and L$_1$X is —(CH$_2$)$_2$—NH(heterocyclyl).

In another embodiment of the compounds of Formula (IG), R$_3$ and R$_4$, taken together with the carbon atoms to which they are shown attached, form:

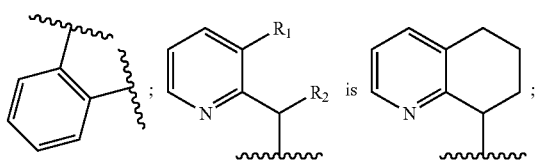

and L$_1$X is —(CH$_2$)$_2$—NH(heterocyclylalkyl).

In another embodiment of the compounds of Formula (IG), R$_3$ and R$_4$, taken together with the carbon atoms to which they are shown attached, form:

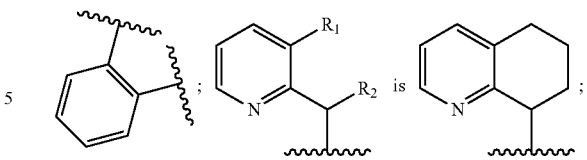

and L$_1$X is —(CH$_2$)$_2$—NH(heteroarylalkyl).

In another embodiment of the compounds of Formula (IG), R$_3$ and R$_4$, taken together with the carbon atoms to which they are shown attached, form:

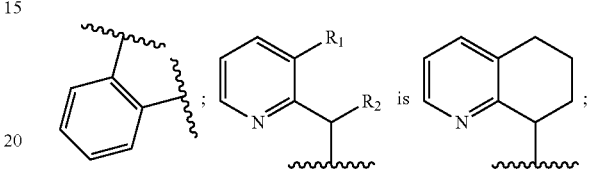

and L$_1$X is —(CH$_2$)$_2$—NH(arylalkyl).

In another embodiment of the compounds of Formula (IG), R$_3$ and R$_4$, taken together with the carbon atoms to which they are shown attached, form:

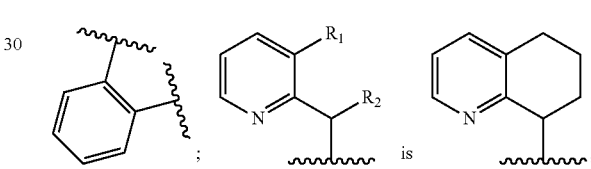

and L$_1$X is —(CH$_2$)$_3$—NH$_2$.

In another embodiment of the compounds of Formula (IG), R$_3$ and R$_4$, taken together with the carbon atoms to which they are shown attached, form:

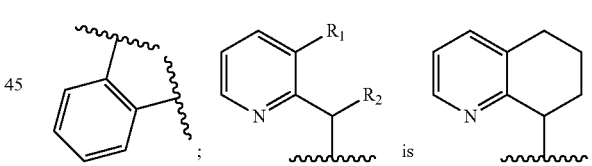

and L$_1$X is —(CH$_2$)$_3$—N(alkyl)$_2$.

In another embodiment of the compounds of Formula (IG), R$_3$ and R$_4$, taken together with the carbon atoms to which they are shown attached, form:

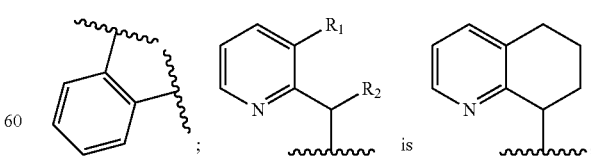

and L$_1$X is —(CH$_2$)$_3$—NH(alkyl).

In another embodiment of the compounds of Formula (IG), R$_3$ and R$_4$, taken together with the carbon atoms to which they are shown attached, form:

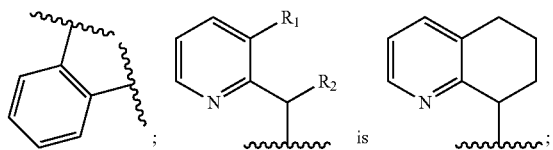

and L₁X is —(CH$_2$)$_3$—NH(heterocyclyl).

In another embodiment of the compounds of Formula (IG), R$_3$ and R$_4$, taken together with the carbon atoms to which they are shown attached, form:

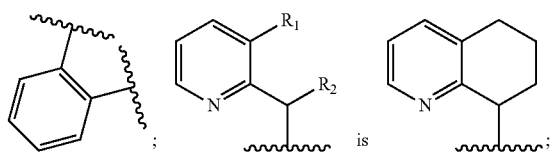

and L₁X is —(CH$_2$)$_3$—NH(heterocyclylalkyl).

In another embodiment of the compounds of Formula (IG), R$_3$ and R$_4$, taken together with the carbon atoms to which they are shown attached, form:

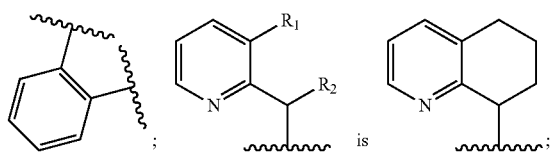

and L₁X is —(CH$_2$)$_3$—NH(heteroarylalkyl).

In another embodiment of the compounds of Formula (IG), R$_3$ and R$_4$, taken together with the carbon atoms to which they are shown attached, form:

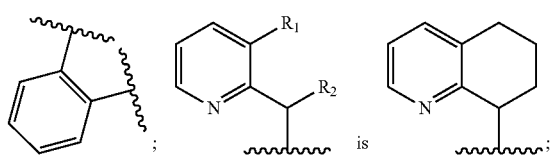

and L₁X is —(CH$_2$)$_3$—NH(arylalkyl).

In another embodiment of the compounds of Formula (IG), R$_3$ and R$_4$, taken together with the carbon atoms to which they are shown attached, form:

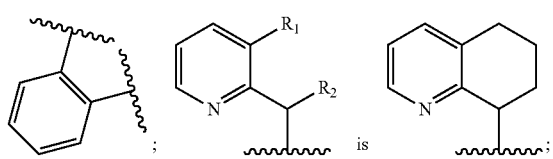

and L₁X is —(CH$_2$)$_4$—NH$_2$.

In another embodiment of the compounds of Formula (IG), R$_3$ and R$_4$, taken together with the carbon atoms to which they are shown attached, form:

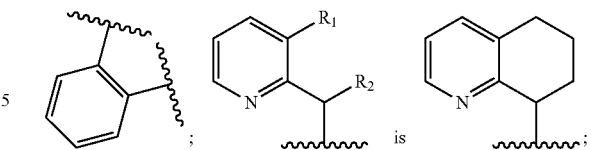

and L₁X is —(CH$_2$)$_4$—N(alkyl)$_2$.

In another embodiment of the compounds of Formula (IG), R$_3$ and R$_4$, taken together with the carbon atoms to which they are shown attached, form:

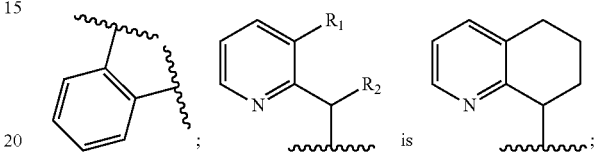

and L₁X is —(CH$_2$)$_4$—NH(alkyl).

In another embodiment of the compounds of Formula (IG), R$_3$ and R$_4$, taken together with the carbon atoms to which they are shown attached, form:

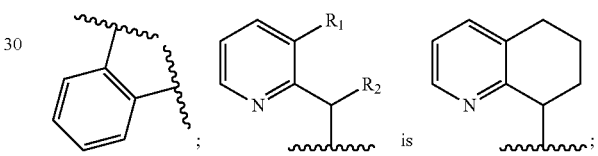

and L₁X is —(CH$_2$)$_4$—NH(heterocyclyl).

In another embodiment of the compounds of Formula (IG), R$_3$ and R$_4$, taken together with the carbon atoms to which they are shown attached, form:

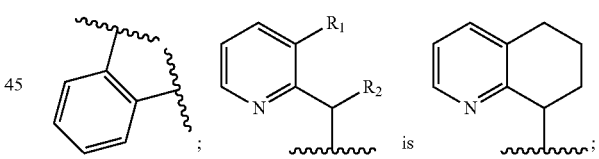

and L₁X is —(CH$_2$)$_4$—NH(heterocyclylalkyl).

In another embodiment of the compounds of Formula (IG), R$_3$ and R$_4$, taken together with the carbon atoms to which they are shown attached, form:

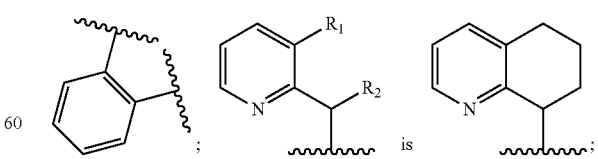

and L₁X is —(CH$_2$)$_4$—NH(heteroarylalkyl).

In another embodiment of the compounds of Formula (IG), R$_3$ and R$_4$, taken together with the carbon atoms to which they are shown attached, form:

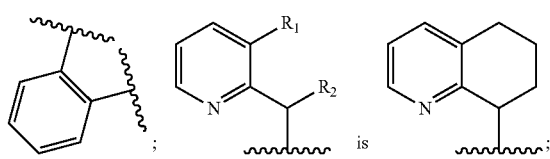

and $L_1X$ is —$(CH_2)_4$—NH(arylalkyl).

In one embodiment, the invention provides compounds of Formula (IG-1), or a pharmaceutically acceptable salt, solvate, tautomer, stereoisomer, and/or ester thereof:

(IG-1)

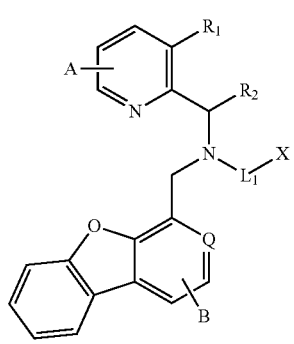

wherein variables A, B, $R_1$, $R_2$, $L_1$, Q, and X are as defined above for Formula (I).

In one embodiment of Formula IG-1, Q is nitrogen. In another embodiment of Formula IA-1, Q is $CR_e$.

In another embodiment of Formula IG-1,

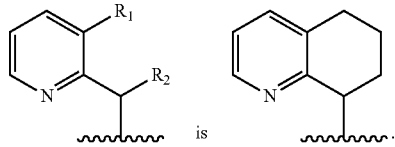

In still another embodiment of Formula IG-1, Q is nitrogen and

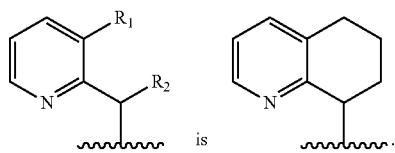

In yet another embodiment of Formula IG-1,

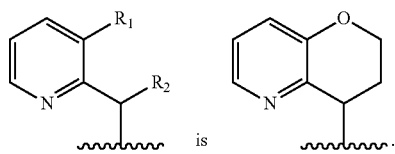

In another embodiment of Formula IG-1, Q is nitrogen and

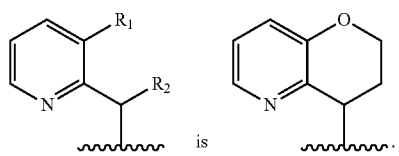

In another embodiment of Formula IG-1, Q is nitrogen, and $R_1$ is hydrogen, alkyl, halogen, hydroxy, amino, alkyl or dialkyl amino, alkoxy, acyl, alkoxycarbonyl or $CF_3$; and $R_2$ is hydrogen, alkyl, heteroalkyl, hydroxyalkyl, alkoxyalkyl, carbocyclyl, or heterocyclyl.

In another embodiment of Formula IG-1, Q is nitrogen and $R_1$ is hydrogen, alkyl, halogen or $CF_3$.

In another embodiment of Formula IG-1, Q is nitrogen,

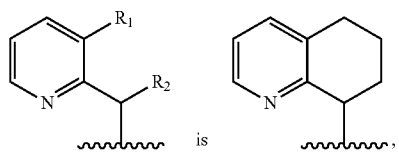

$L_1$ is an optionally substituted alkylene group, and X is heterocyclyl or $NR_aR_b$.

In still another embodiment of Formula IG-1, Q is nitrogen,

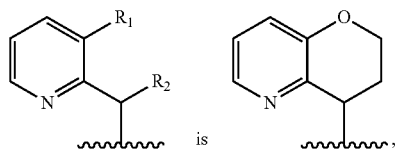

$L_1$ is an optionally substituted alkylene group, and X is heterocyclyl or $NR_aR_b$.

In another embodiment of Formula IG-1, Q is nitrogen,

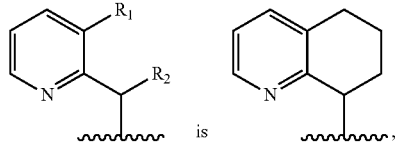

and $L_1$-X is

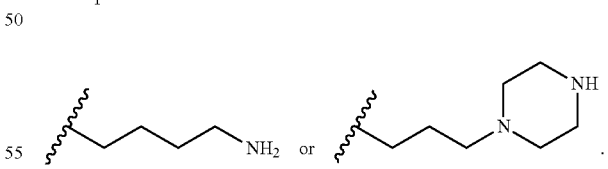

In yet another embodiment of Formula IG-1, Q is nitrogen,

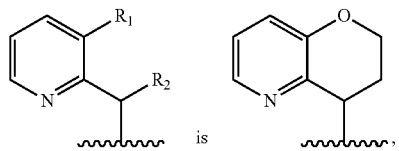

and L$_1$-X is

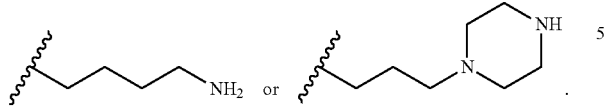

In still another embodiment of Formula IG-1, R$_1$ is hydrogen, alkyl, halogen, alkoxy, acyl, alkoxycarbonyl or CF$_3$; R$_2$ is hydrogen, alkyl, heteroalkyl, hydroxyalkyl, alkoxyalkyl, carbocyclyl, or heterocyclyl; and L$_1$-X is

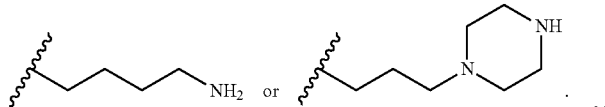

In one embodiment of Formula IG-1, the compound has the stereochemical configuration of Formula IG-1S:

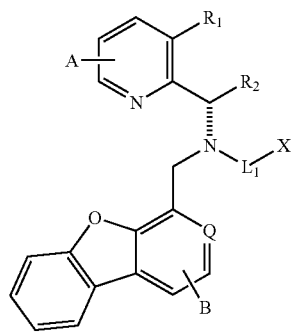

IG-1S wherein the variables A, B, L$_1$, L$_2$, Q, and X are as defined for Formula IG-1.

In another embodiment of Formula IG-1, the compound has the stereochemical configuration of Formula IG-1R:

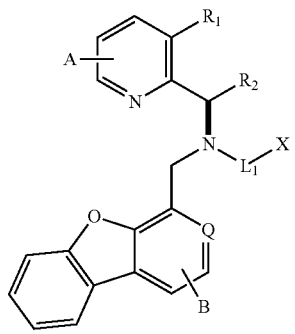

IG-1R wherein the variables A, B, L$_1$, Q, and X are as defined for Formula IG-1.

In another embodiment, the invention provides compounds of Formula (IA-2), or a pharmaceutically acceptable salt, solvate, tautomer, stereoisomer, and/or ester thereof:

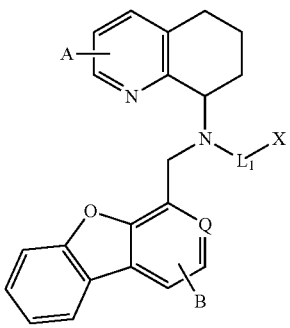

(IG-2)

wherein variables A, B, L$_1$, Q, and X are as defined above for Formula (I). In one embodiment of Formula IG-2, Q is nitrogen. In another embodiment of Formula IA-2, Q is CR$_e$.

In another embodiment of Formula IG-2, Q is nitrogen, L$_1$ is an optionally substituted alkylene group, and X is heterocyclyl or NR$_a$R$_b$.

In another embodiment of Formula IG-2, Q is nitrogen, and L$_1$-X is

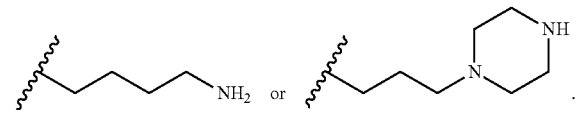 [SMILES: *CCCCN ; *CCCN1CCNCC1]

In one embodiment of Formula IG-2, the compound has the stereochemical configuration of Formula IG-2S:

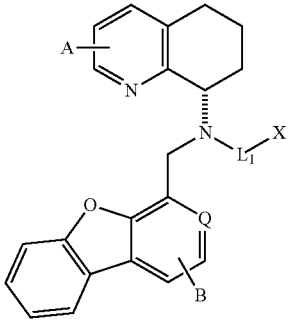

IG-2S

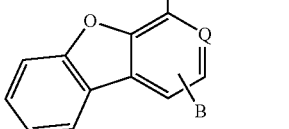

wherein the variables A, B, L$_1$, Q, and X are as defined for Formula IG-2.

In another embodiment of Formula IG-2, the compound has the stereochemical configuration of Formula IG-2R:

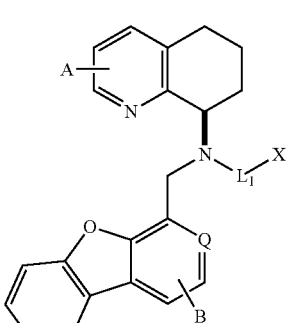

IG-2R wherein the variables A, B, L$_1$, Q, and XY are as defined for Formula IA-2.

In another embodiment, the invention provides compounds of Formula (IG-3), or a pharmaceutically acceptable salt, solvate, tautomer, stereoisomer, and/or ester thereof:

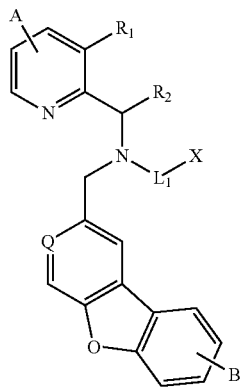
(IG-3)

wherein variables A, B, $R_1$, $R_2$, $L_1$, Q, and X are as defined above for Formula (I).

In one embodiment of Formula IG-3, Q is nitrogen. In another embodiment of Formula IA-1, Q is $CR_e$.

In another embodiment of Formula IG-3,

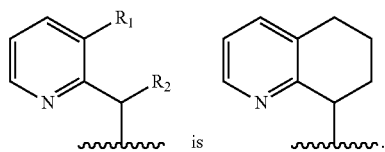

In still another embodiment of Formula IG-3, Q is nitrogen and

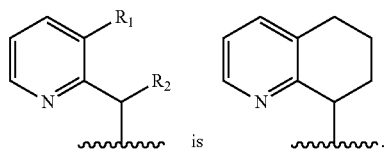

In yet another embodiment of Formula IG-3,

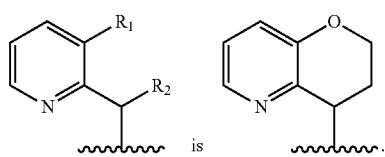

In another embodiment of Formula IG-3, Q is nitrogen and

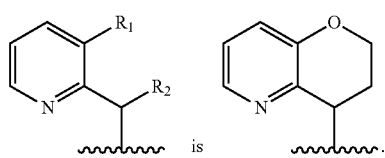

In another embodiment of Formula IG-3, Q is nitrogen, and $R_1$ is hydrogen, alkyl, halogen, hydroxy, amino, alkyl or dialkyl amino, alkoxy, acyl, alkoxycarbonyl or $CF_3$; and $R_2$ is hydrogen, alkyl, heteroalkyl, hydroxyalkyl, alkoxyalkyl, carbocyclyl, or heterocyclyl.

In another embodiment of Formula IG-3, Q is nitrogen and $R_1$ is hydrogen, alkyl, halogen or $CF_3$.

In another embodiment of Formula IG-3, Q is nitrogen,

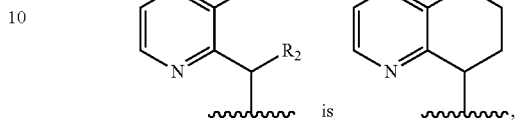

$L_1$ is an optionally substituted alkylene group, and X is heterocyclyl or $NR_aR_b$.

In still another embodiment of Formula IG-3, Q is nitrogen,

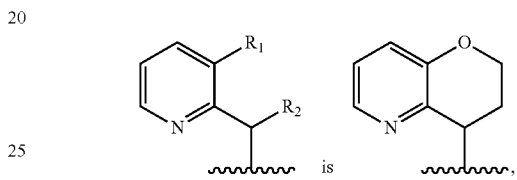

$L_1$ is an optionally substituted alkylene group, and X is heterocyclyl or $NR_aR_b$.

In another embodiment of Formula IG-3, Q is nitrogen,

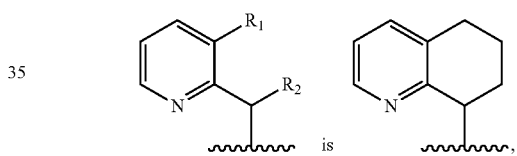

and $L_1$-X is

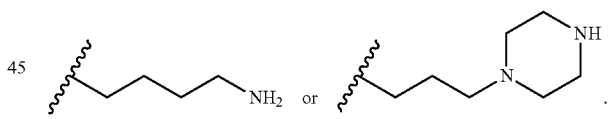

In yet another embodiment of Formula IG-3, Q is nitrogen,

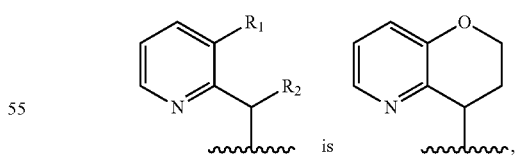

and $L_1$-X is

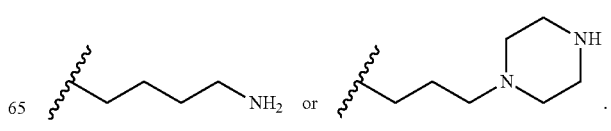

In still another embodiment of Formula IG-3, $R_1$ is hydrogen, alkyl, halogen, alkoxy, acyl, alkoxycarbonyl or $CF_3$; $R_2$ is hydrogen, alkyl, heteroalkyl, hydroxyalkyl, alkoxyalkyl, carbocyclyl, or heterocyclyl; and $L_1$-X is

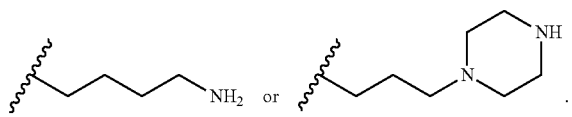 [SMILES: *CCCCN ; *CCCN1CCNCC1]

In another embodiment, the invention provides compounds of Formula (IG-4), or a pharmaceutically acceptable salt, solvate, tautomer, stereoisomer, and/or ester thereof:

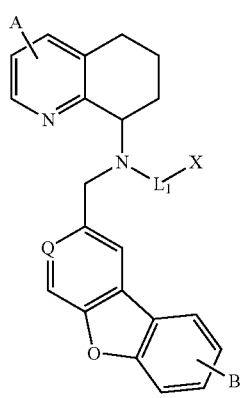

(IG-4)

wherein variables A, B, $L_1$, Q, and X are as defined above for Formula (I). In one embodiment of Formula IG-2, Q is nitrogen. In another embodiment of Formula IA-4, Q is $CR_e$.

In another embodiment of Formula IG-4, Q is nitrogen, $L_1$ is an optionally substituted alkylene group, and X is heterocyclyl or $NR_aR_b$.

In another embodiment of Formula IG-4, Q is nitrogen, and $L_1$-X is

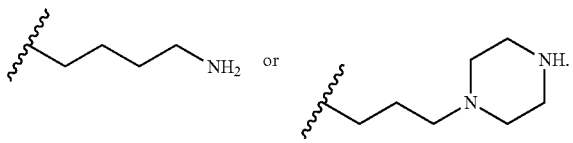 [SMILES: *CCCCN ; *CCCN1CCNCC1]

In one embodiment of Formula IG-4, the compound has the stereochemical configuration of Formula IG-4S:

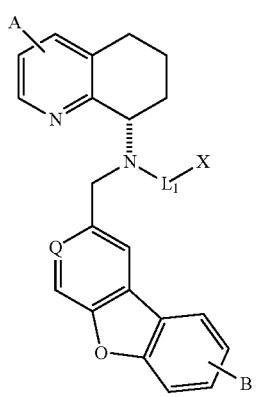

IG-4S wherein the variables A, B, $L_1$, Q, and X are as defined for Formula IG-4.

In another embodiment of Formula IG-2, the compound has the stereochemical configuration of Formula IG-4R:

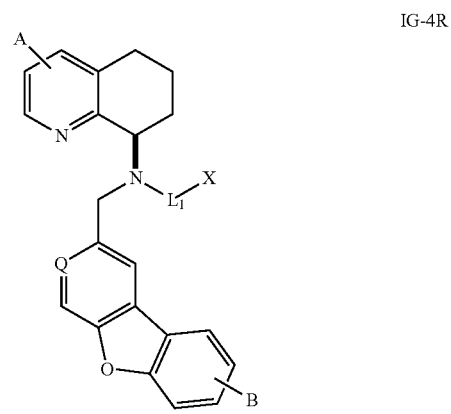

IG-4R wherein the variables A, B, $L_1$, Q, and XY are as defined for Formula IA-4.

In certain specific embodiments of the compounds of Formula (I), said compounds are selected from the group consisting of:

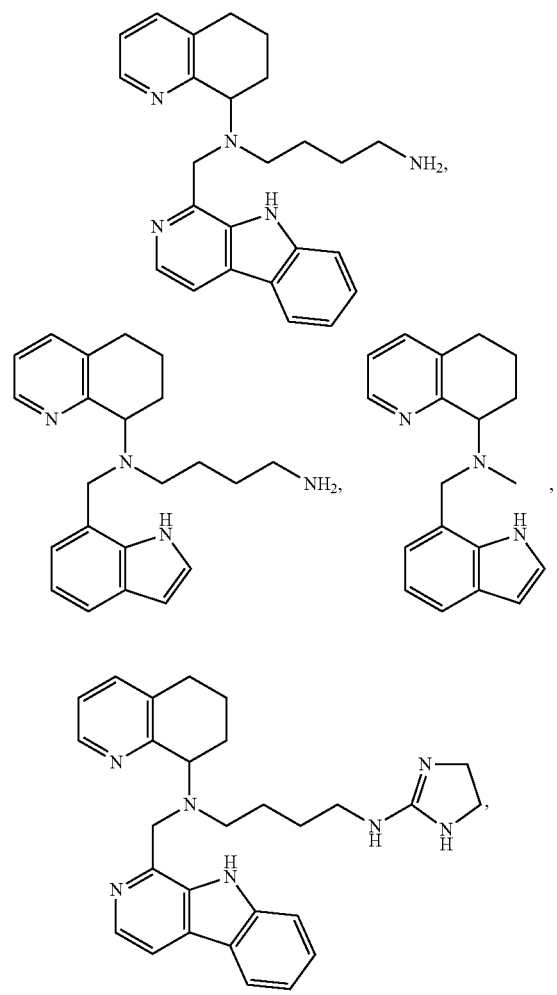

87
-continued
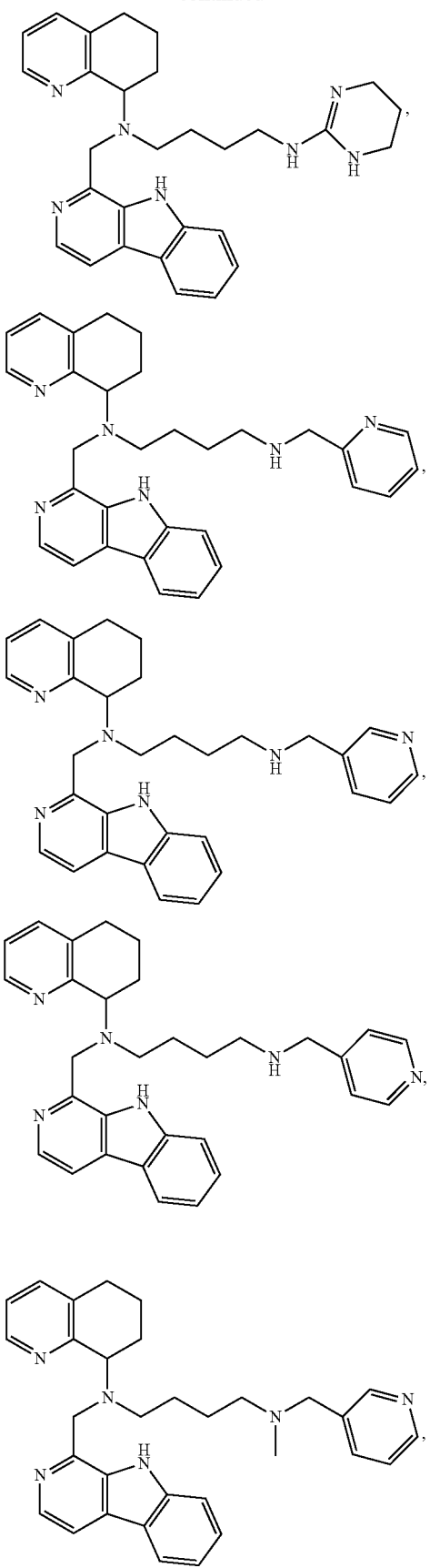
88
-continued
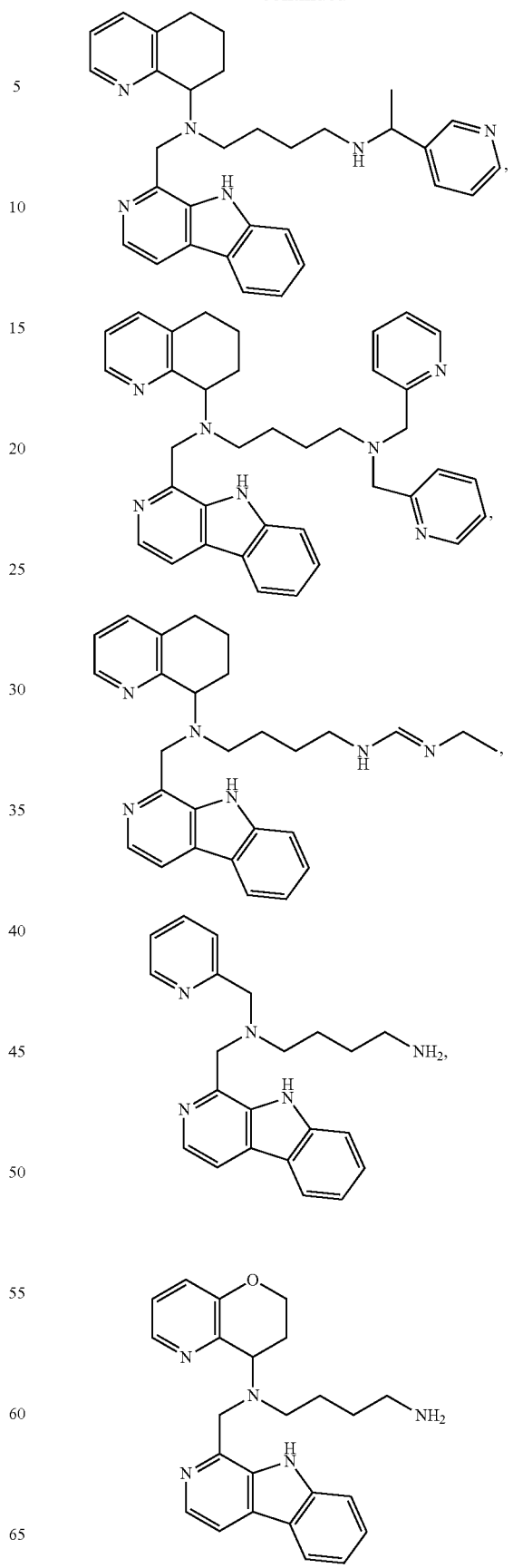

89
-continued
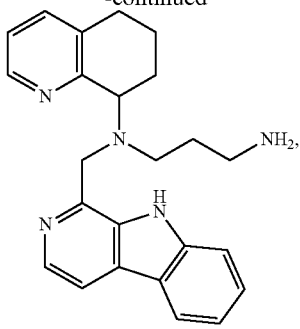
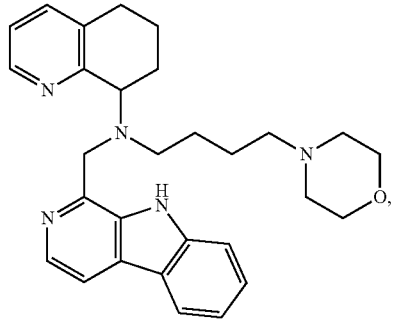
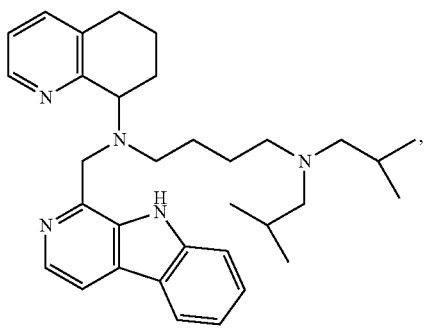
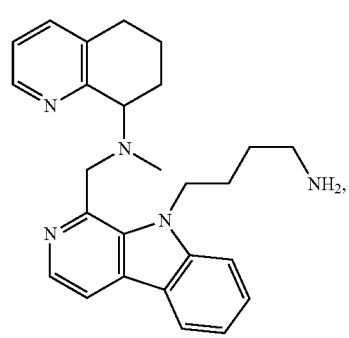
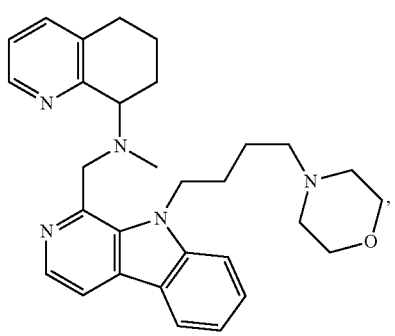
90
-continued
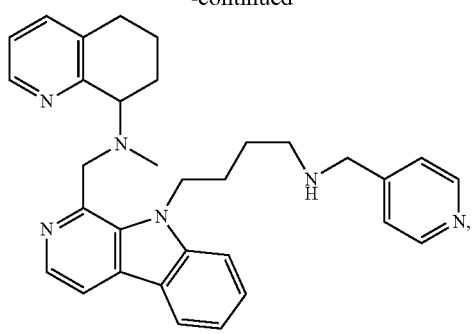
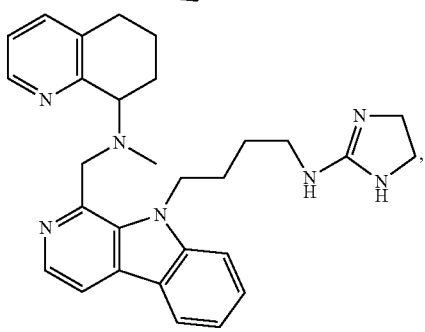
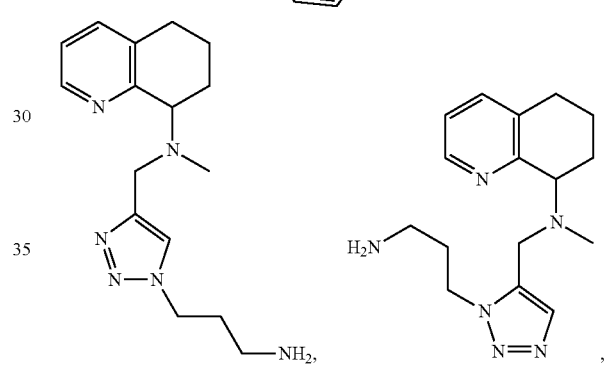
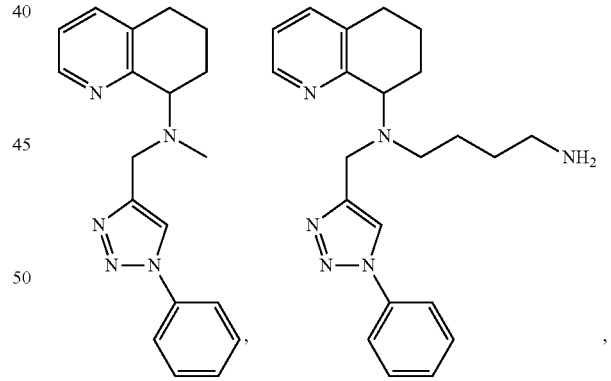
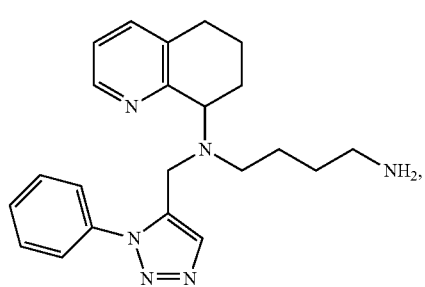

91
-continued
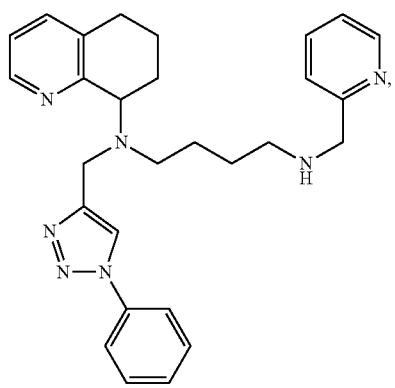
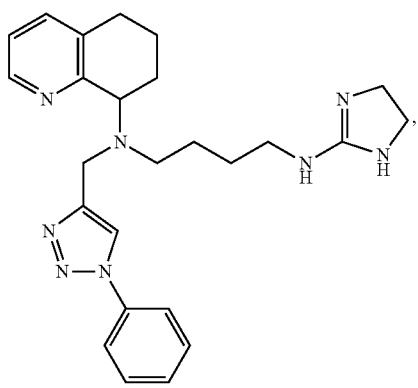
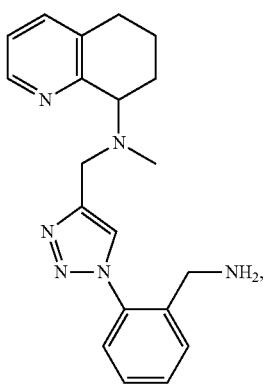
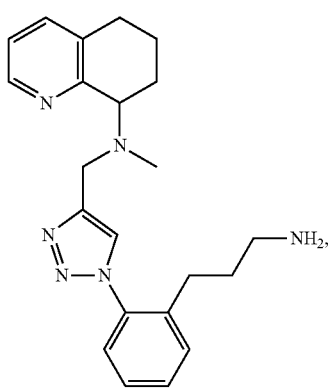
92
-continued
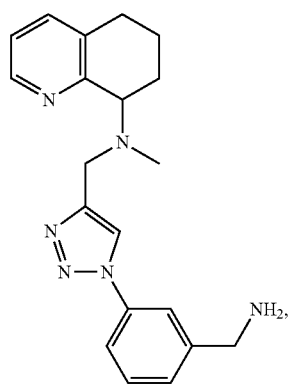
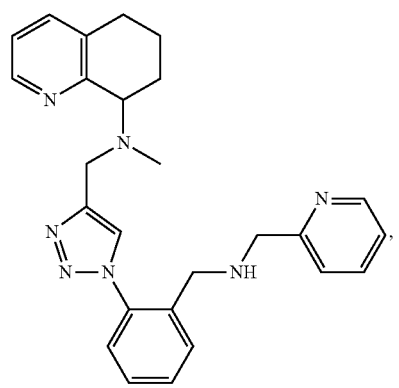
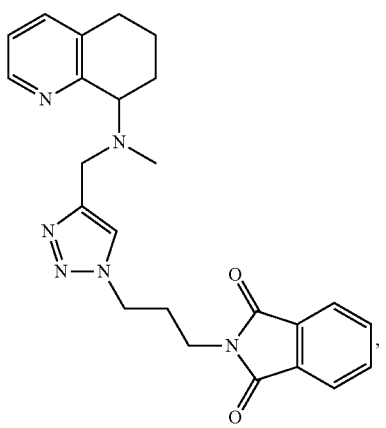
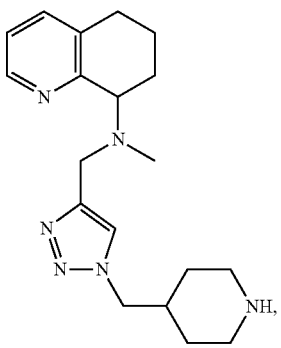

-continued
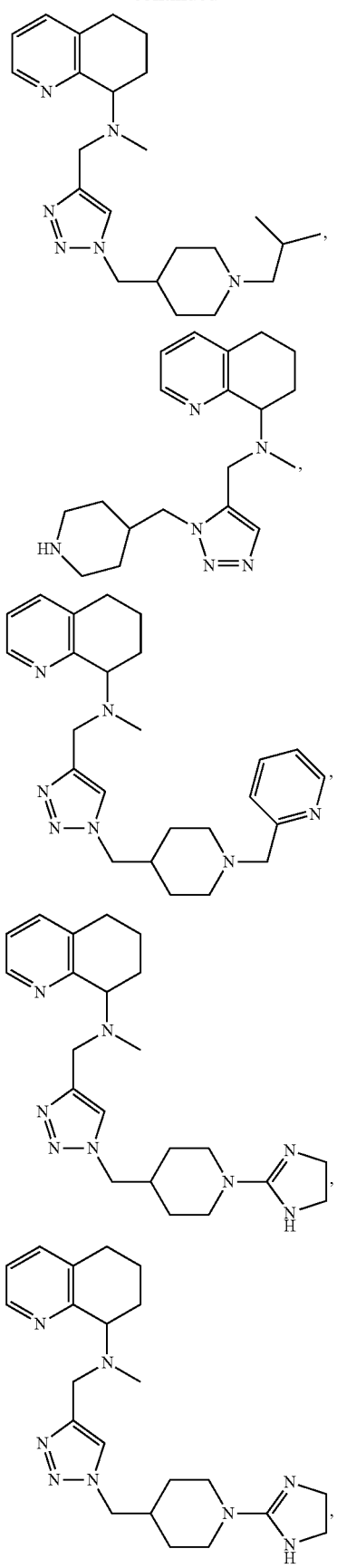
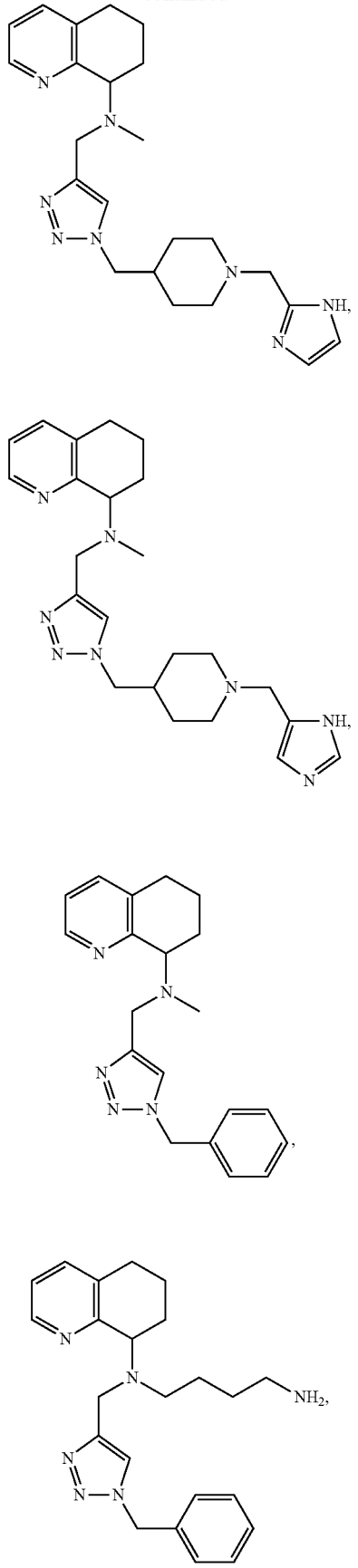

95
-continued
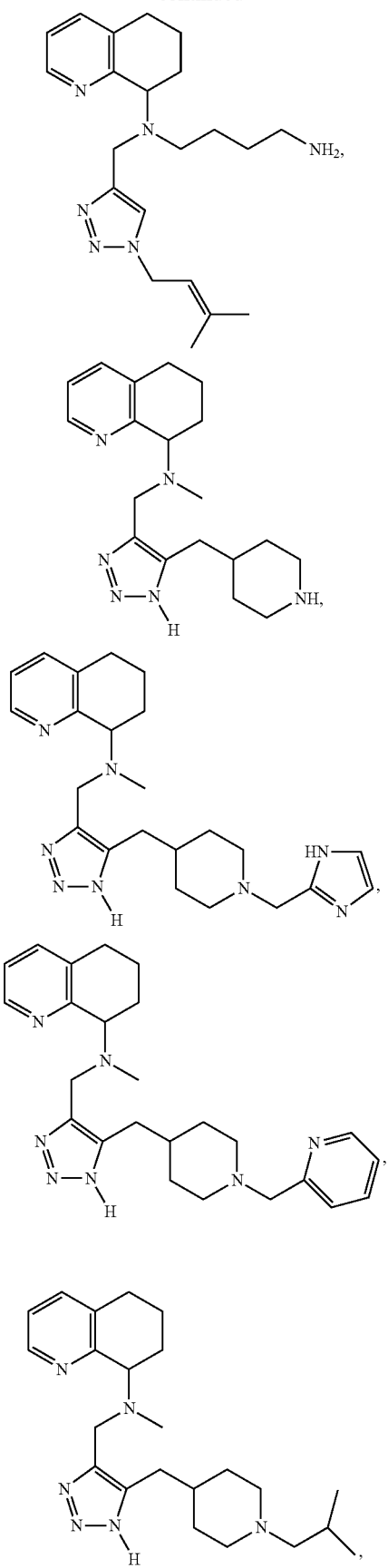
96
-continued
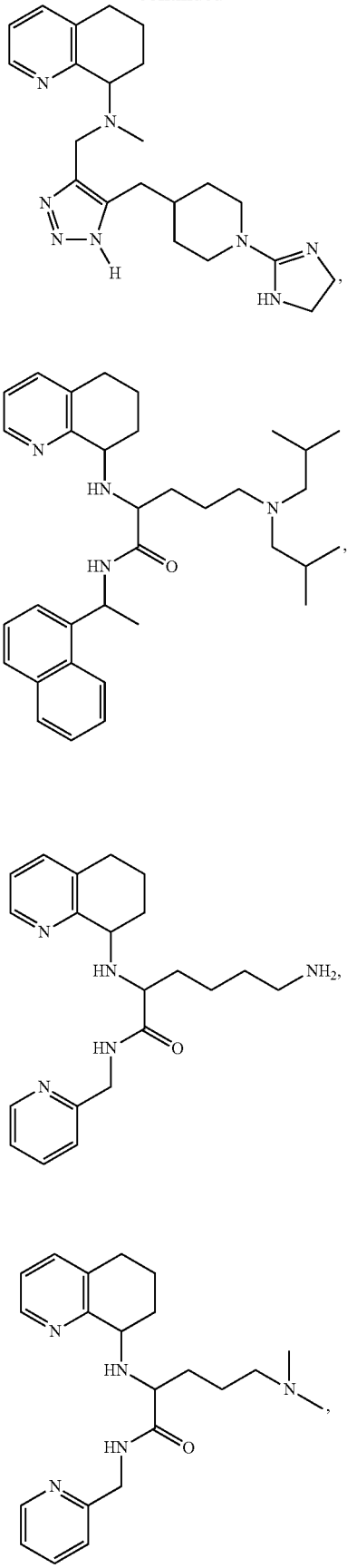

97
-continued
98
-continued
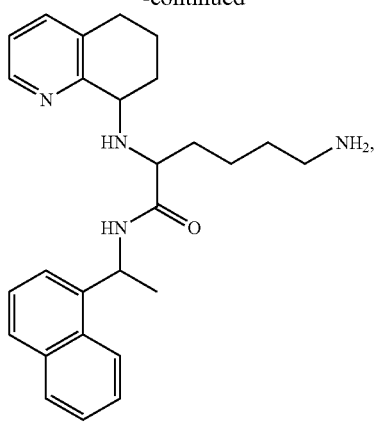
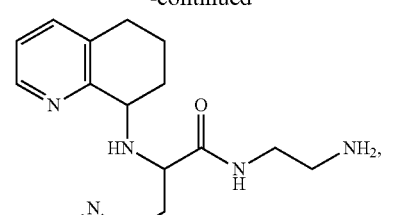
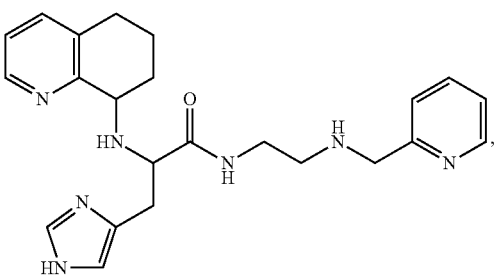
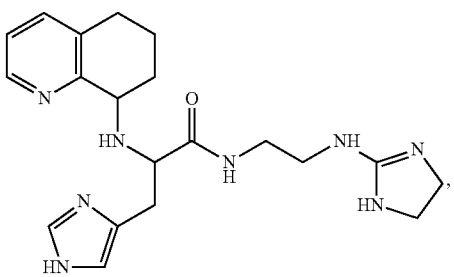
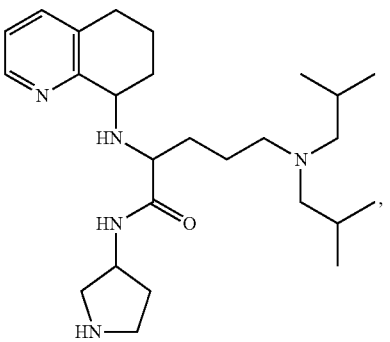

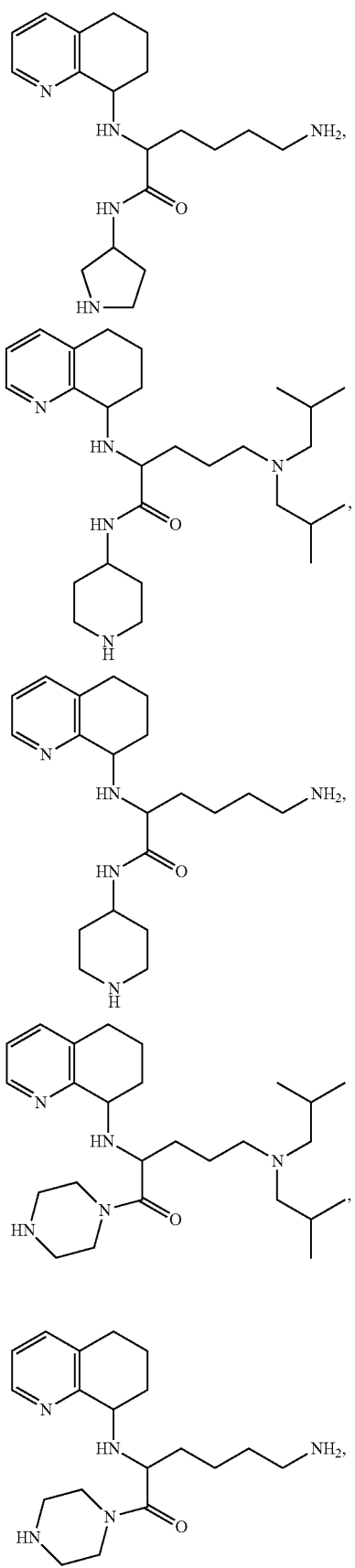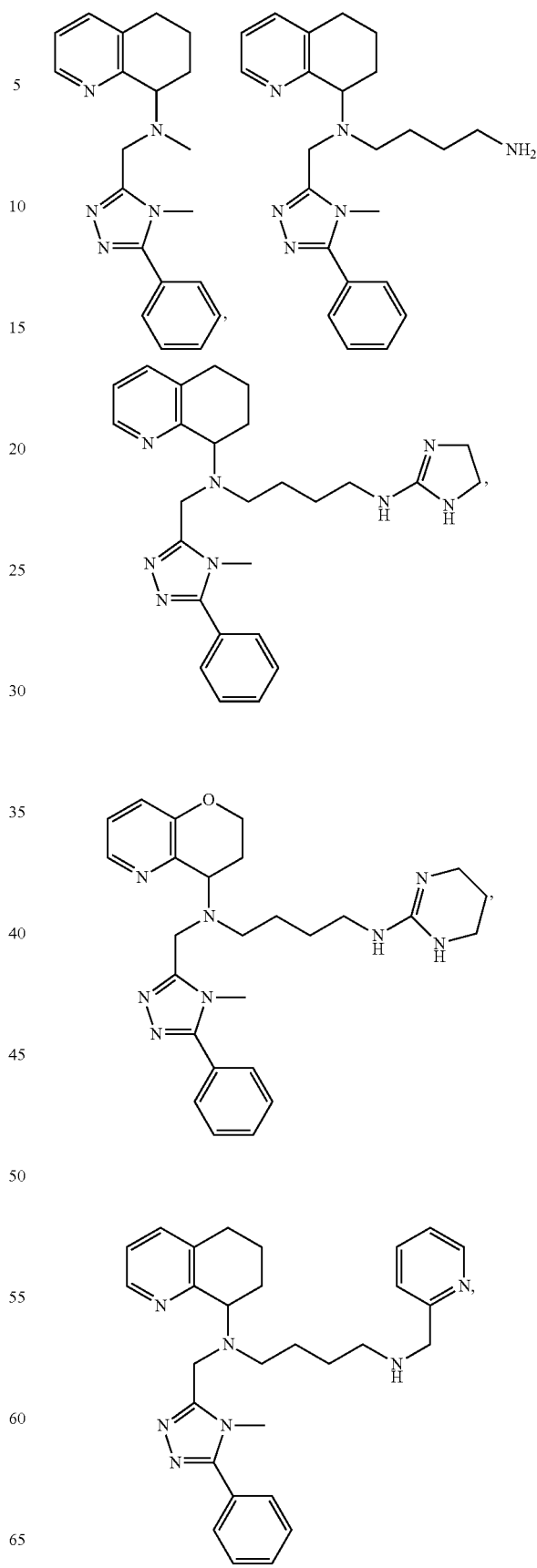

101
-continued
102
-continued
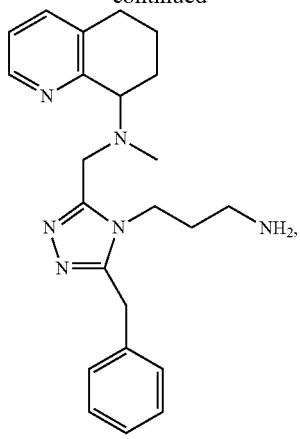
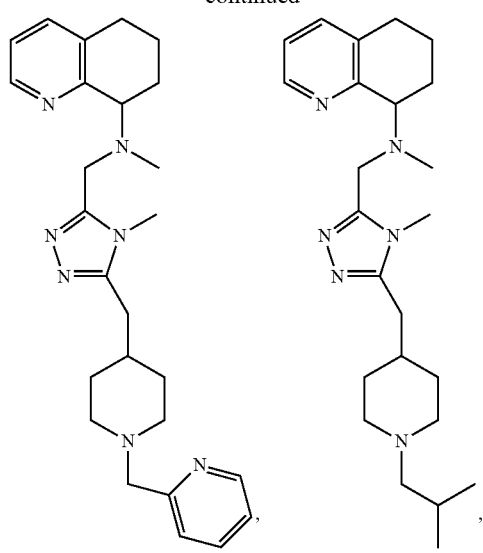
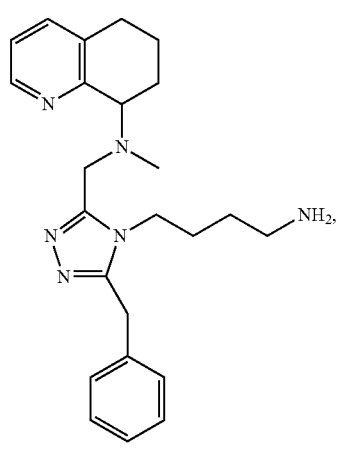
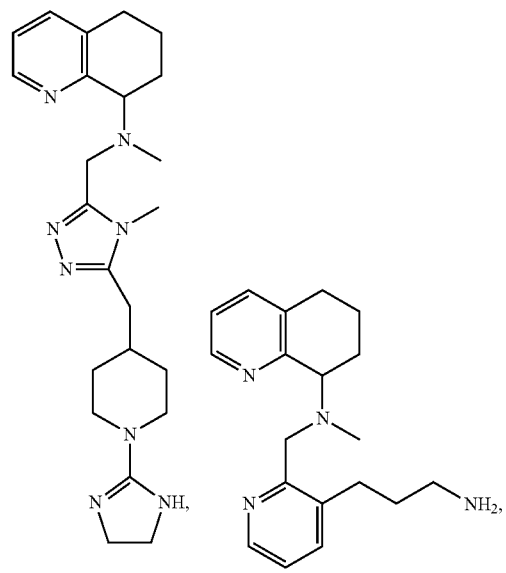
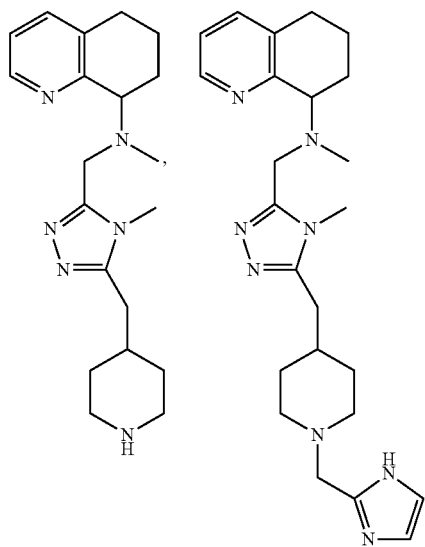

103
-continued
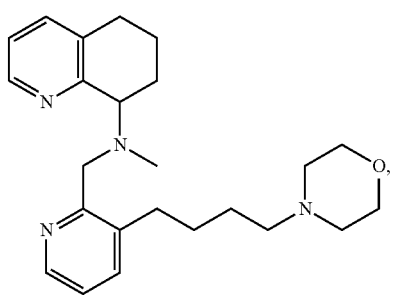
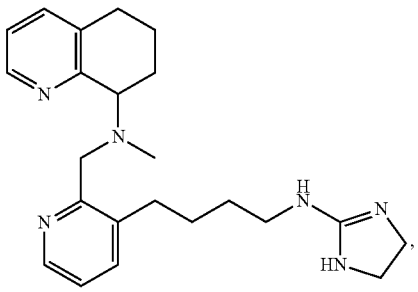
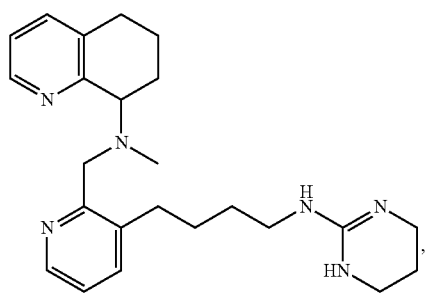
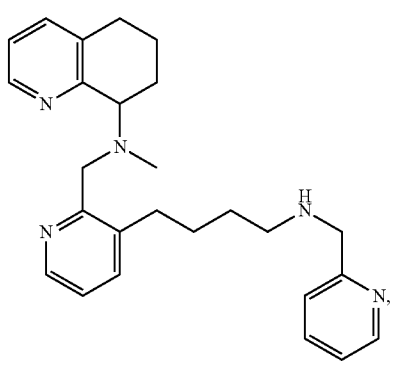
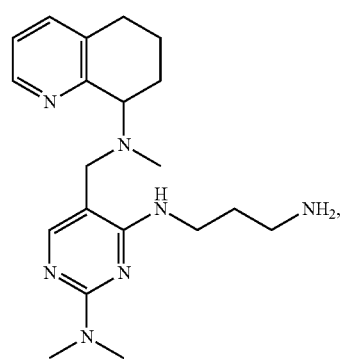
104
-continued
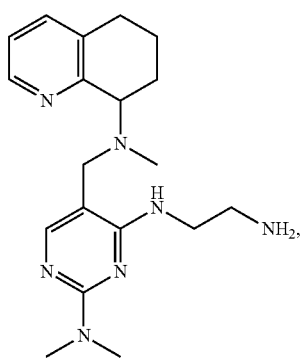
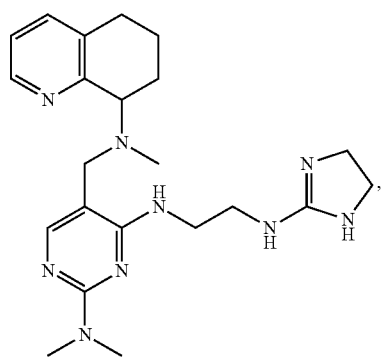
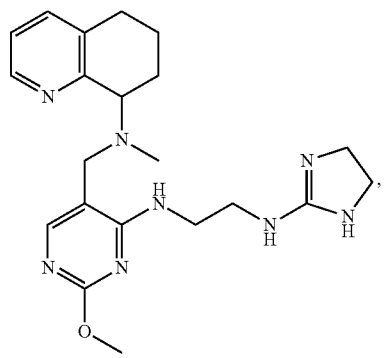
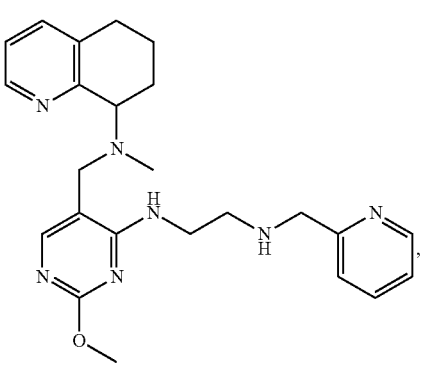

105
-continued
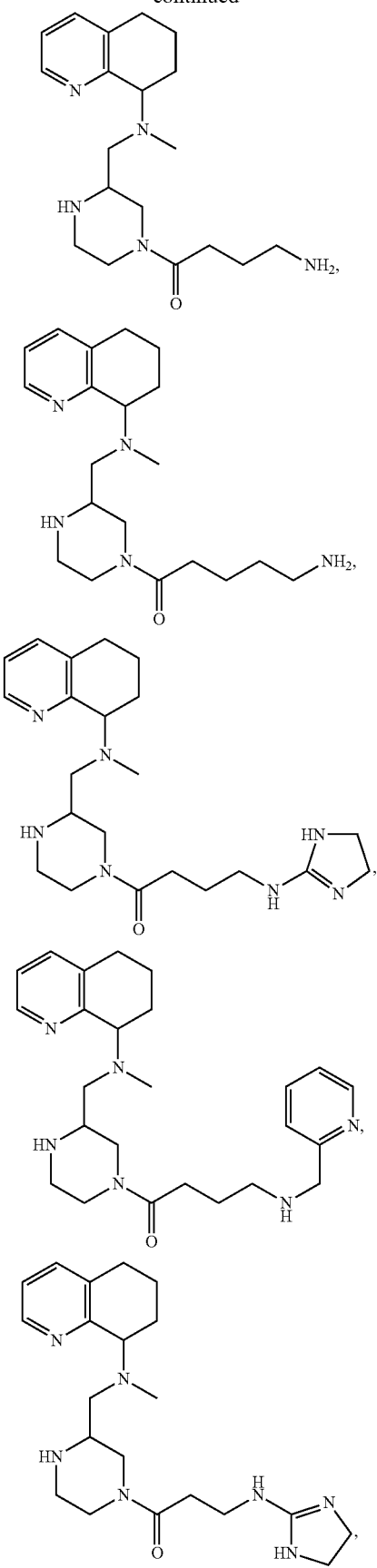
106
-continued
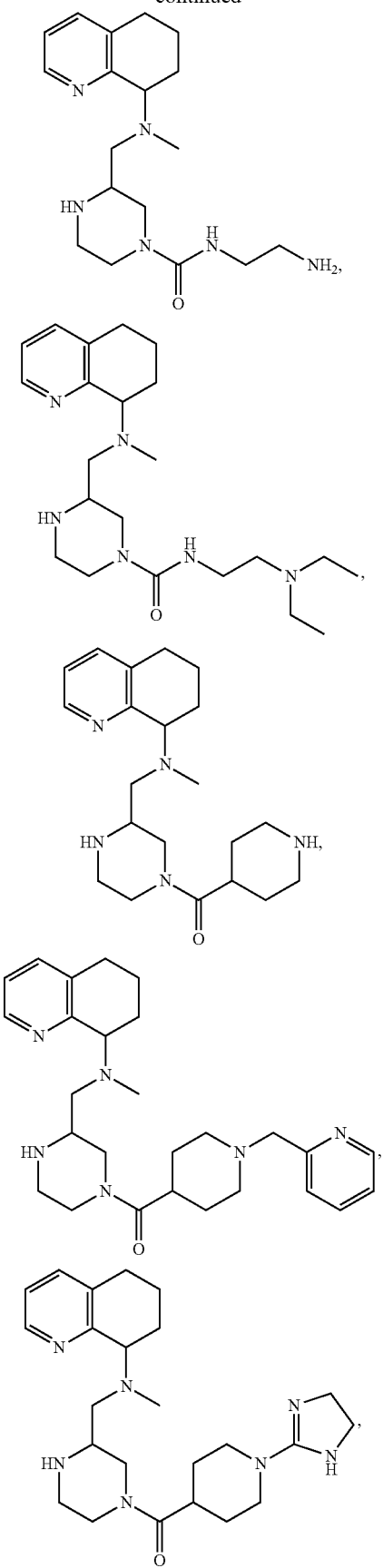

107
-continued
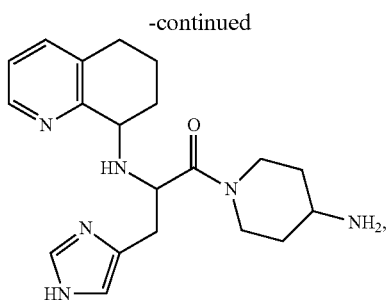
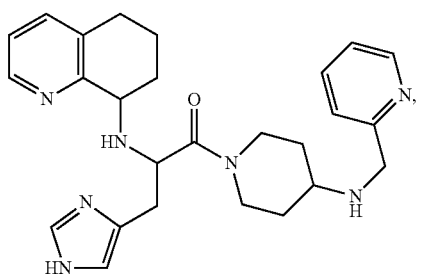
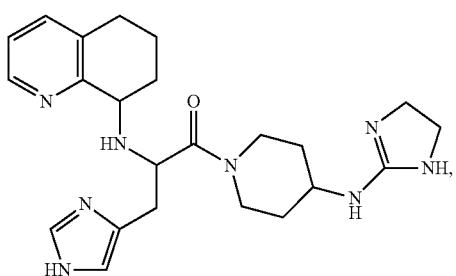
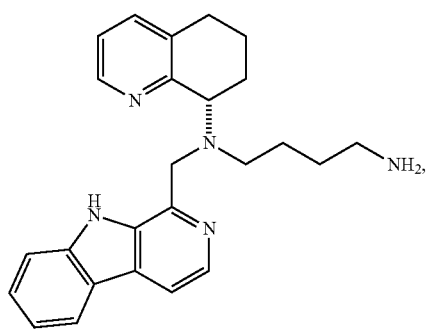
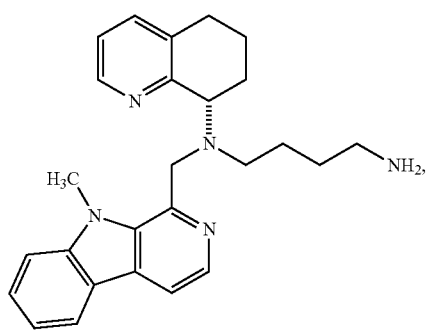
108
-continued
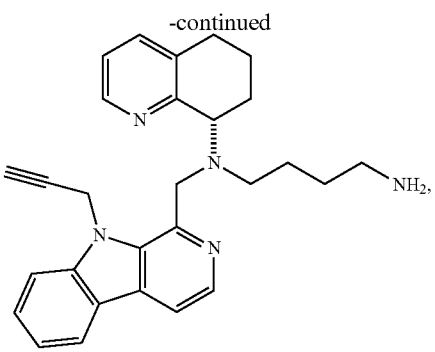
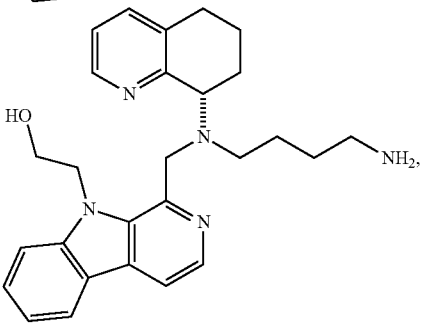
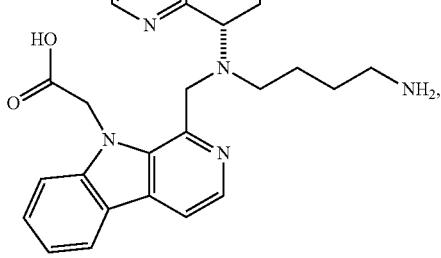
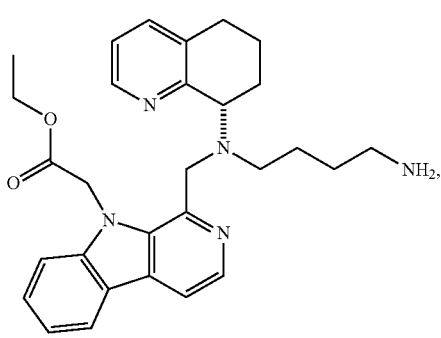
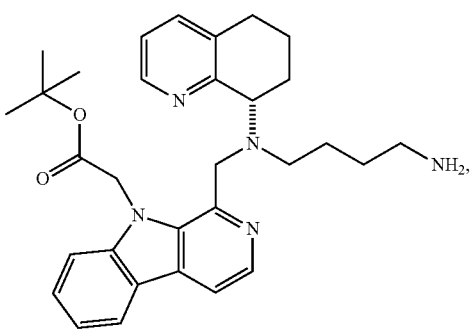

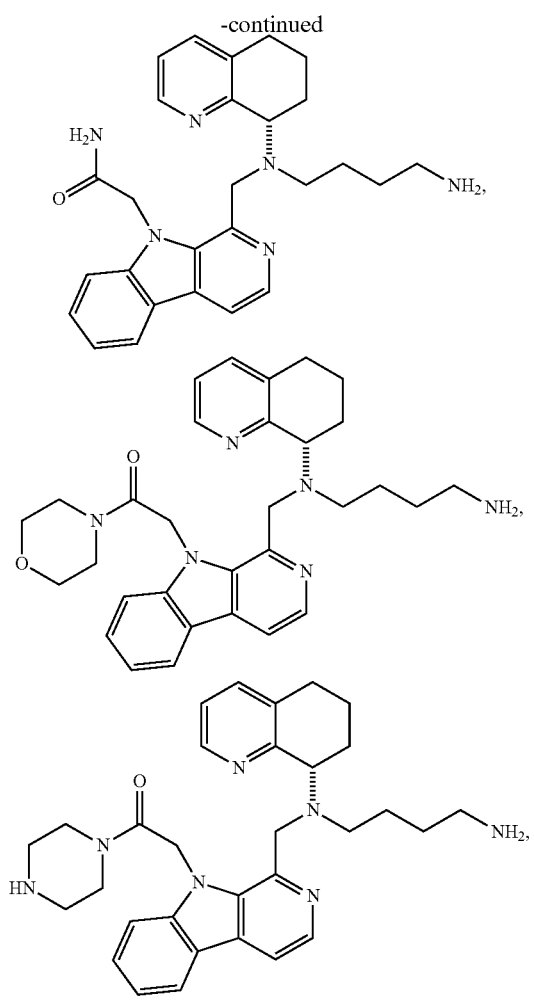

111
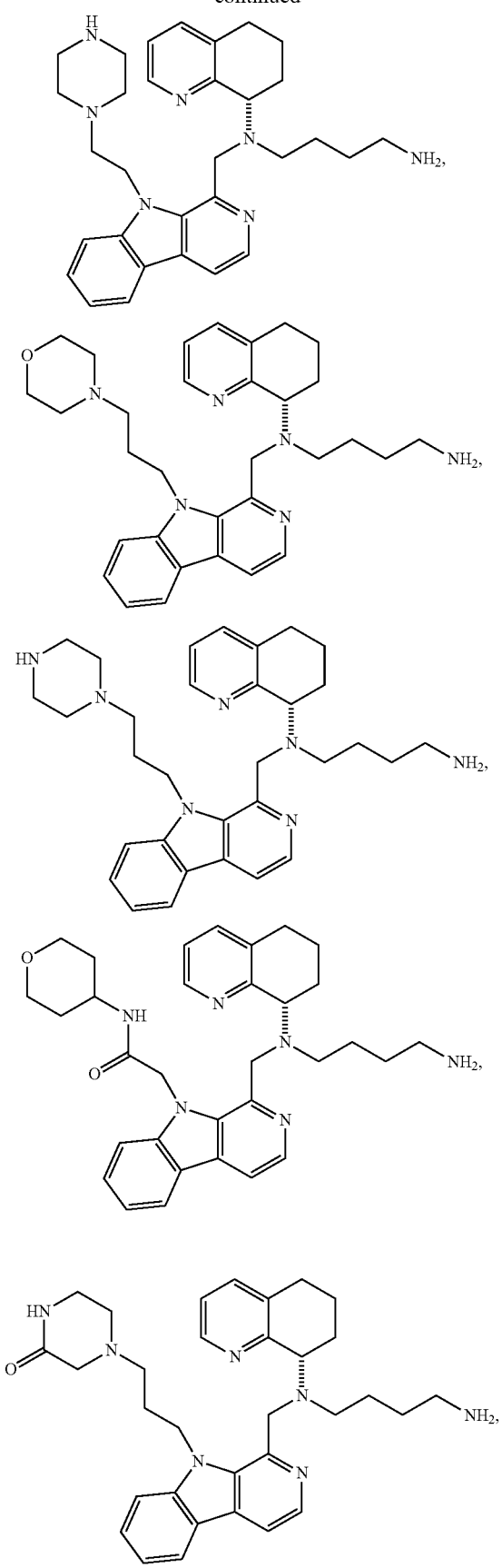
112
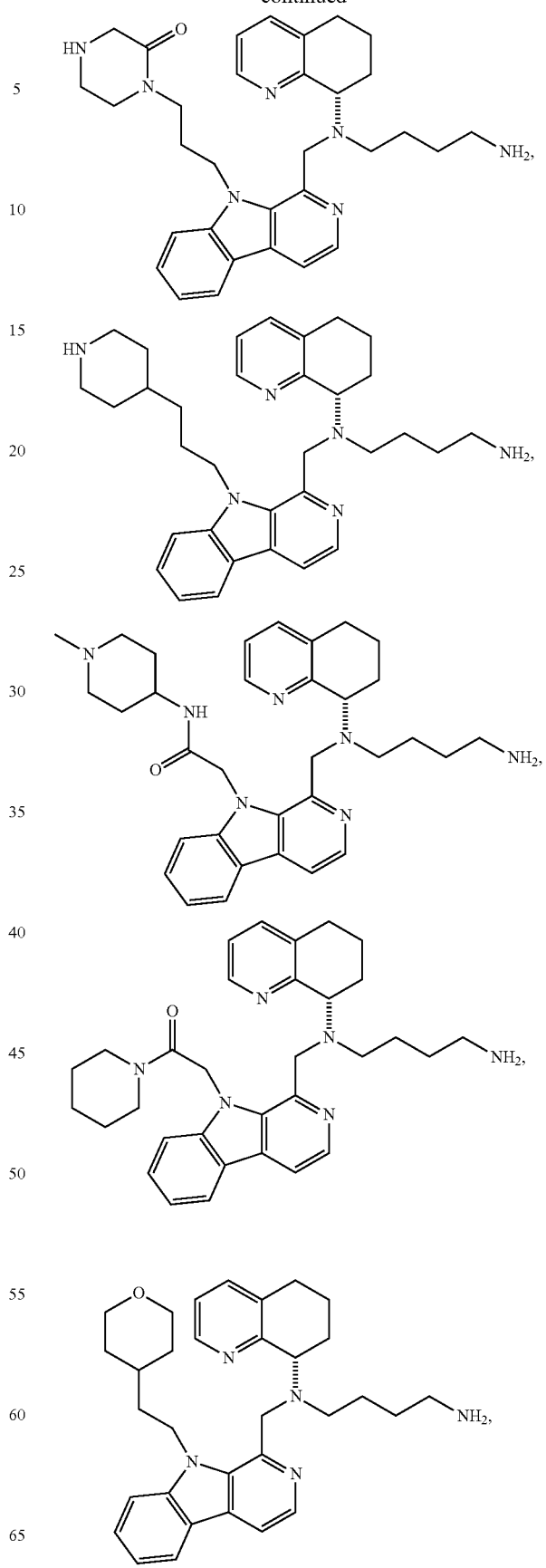

113
-continued
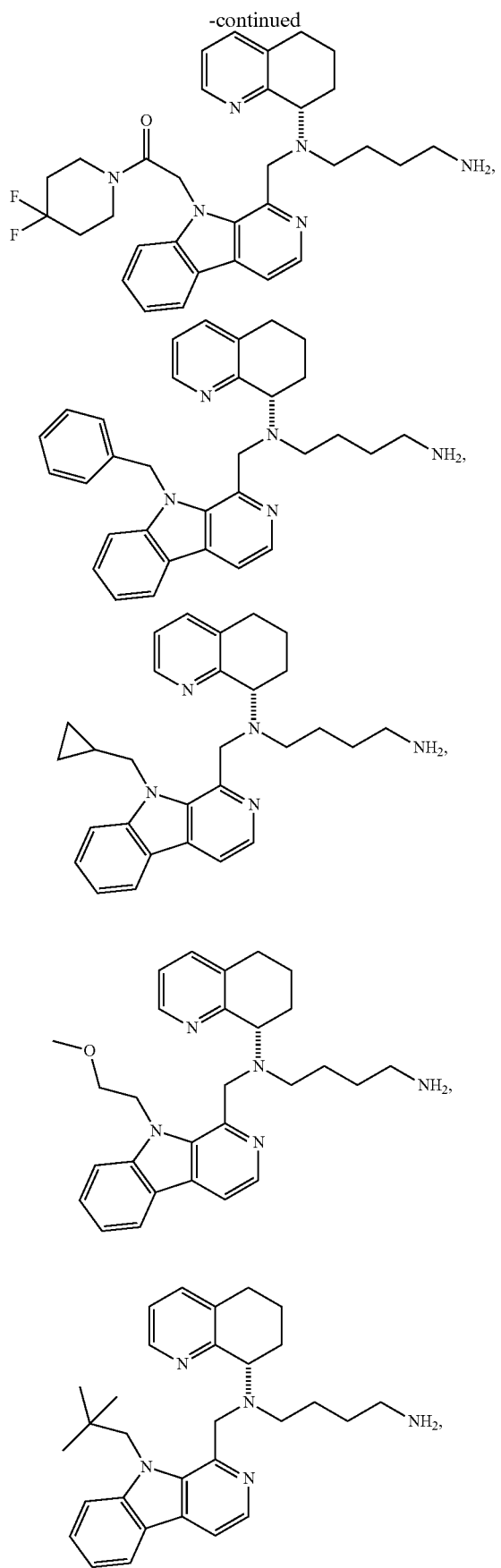
114
-continued
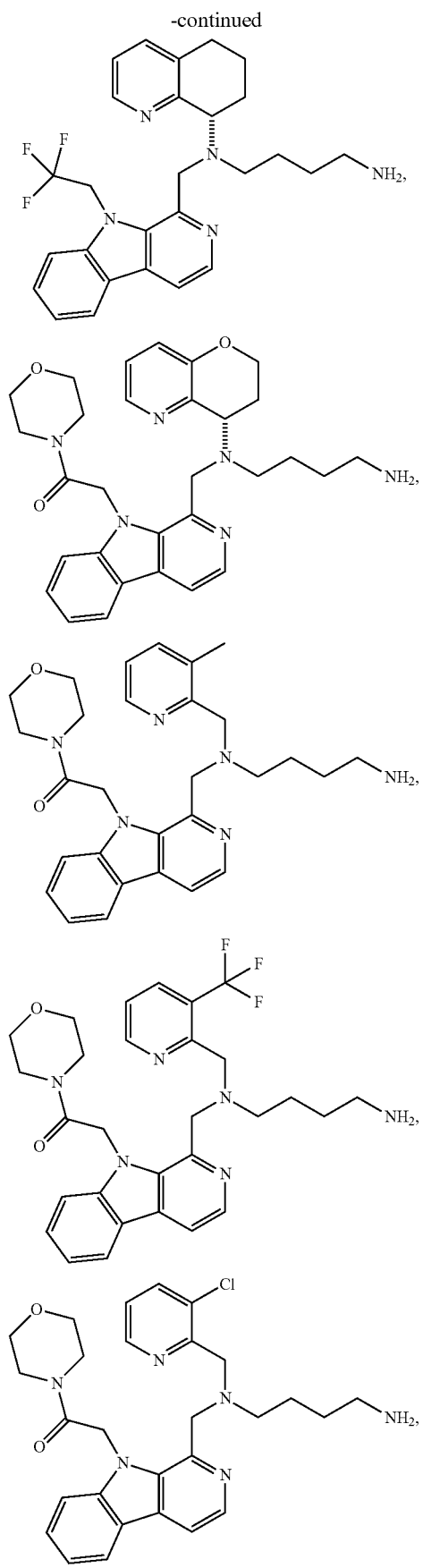

115
-continued
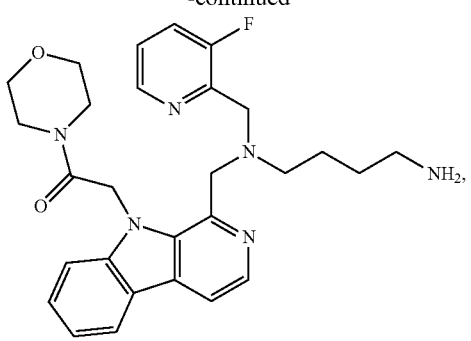
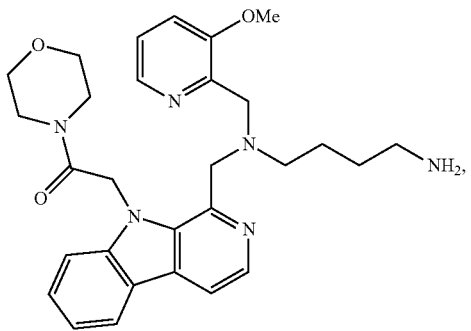
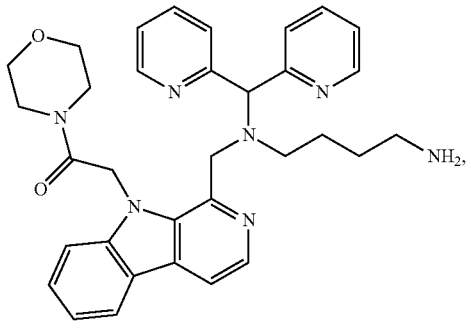
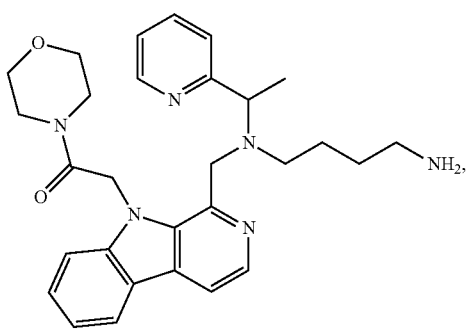
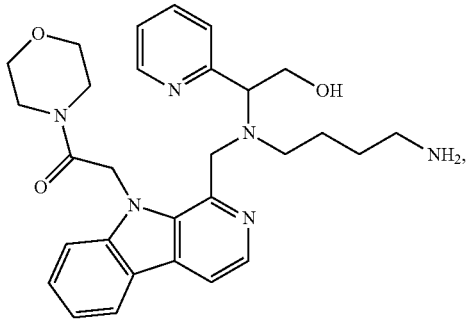
116
-continued
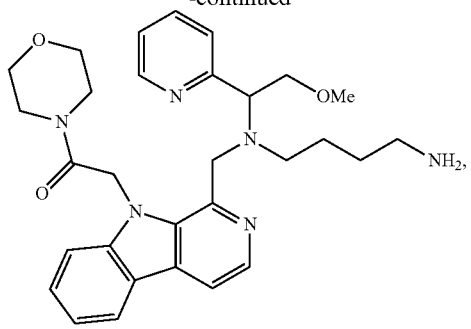
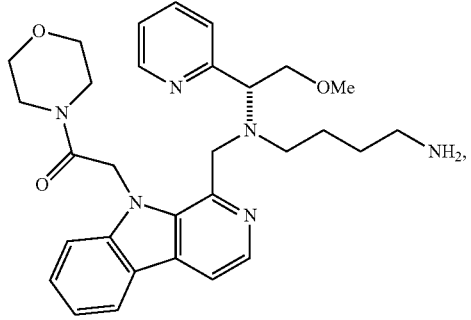
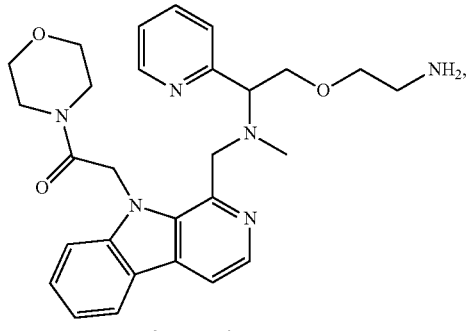
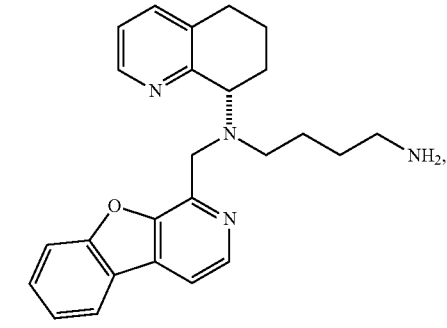
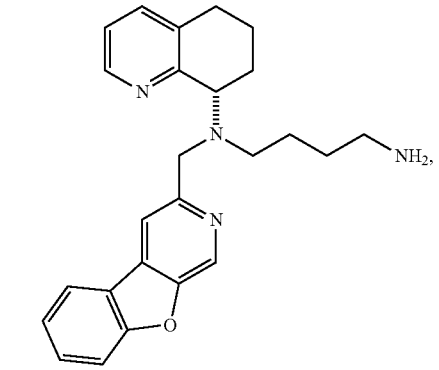

117
-continued
118
-continued
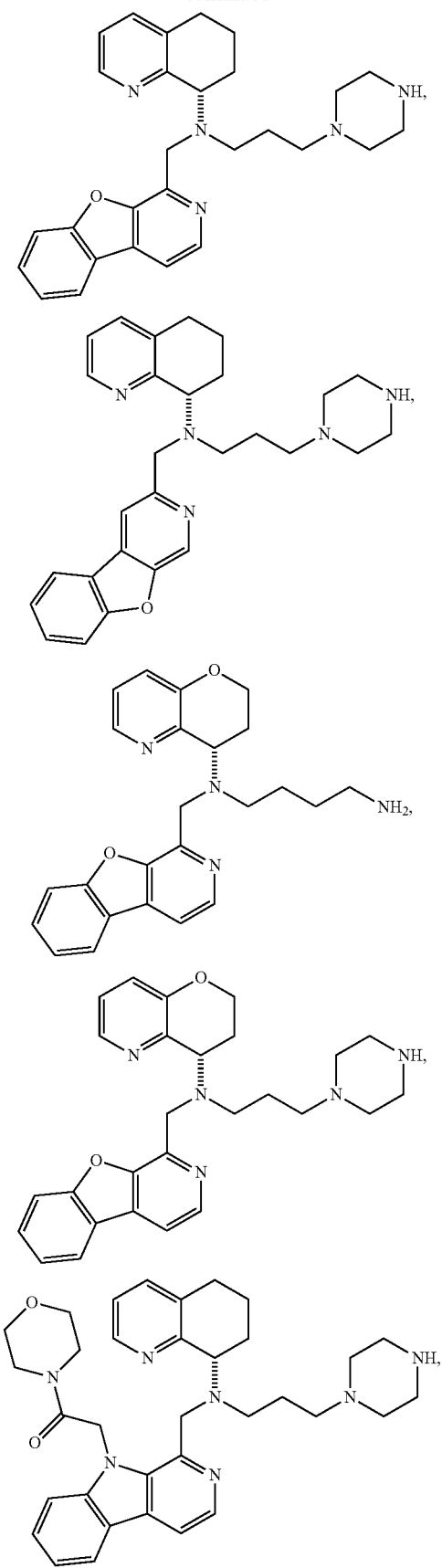
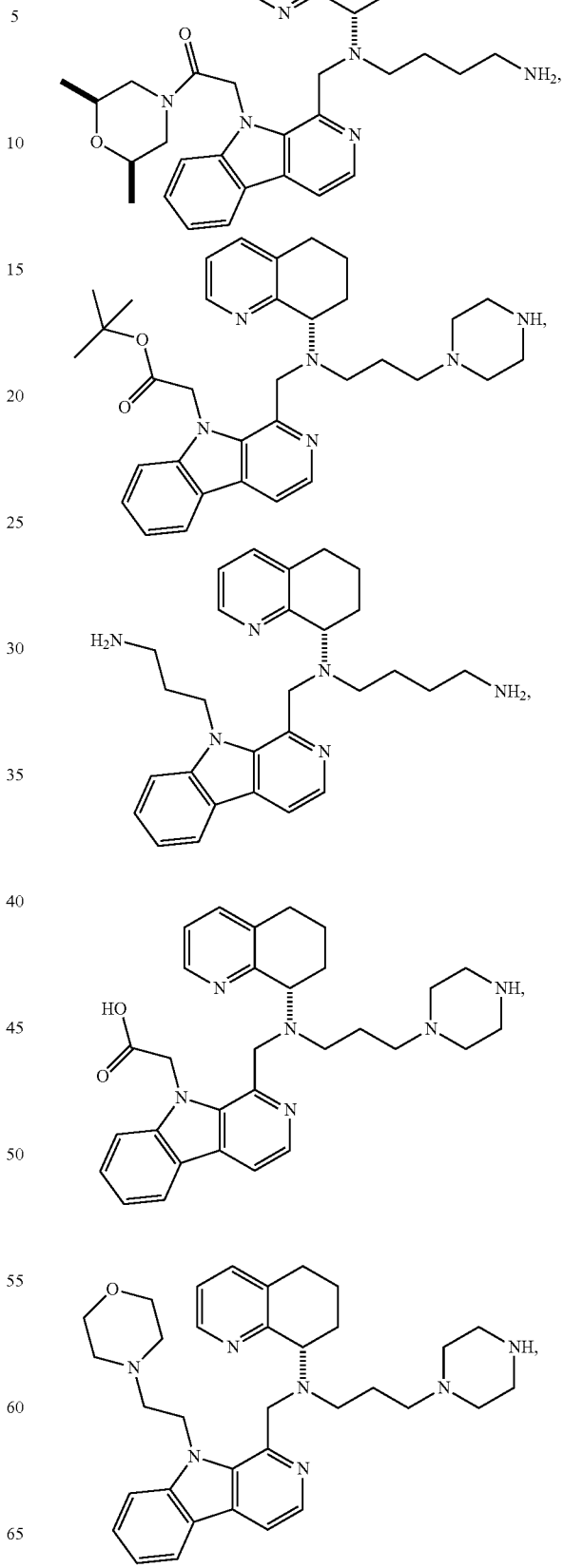

119
-continued
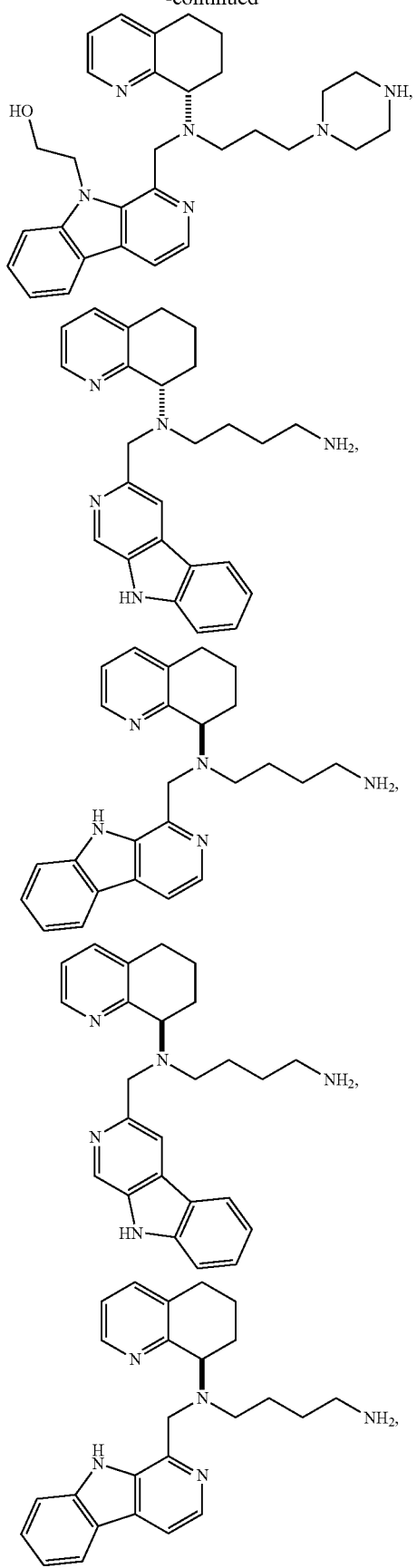
120
-continued
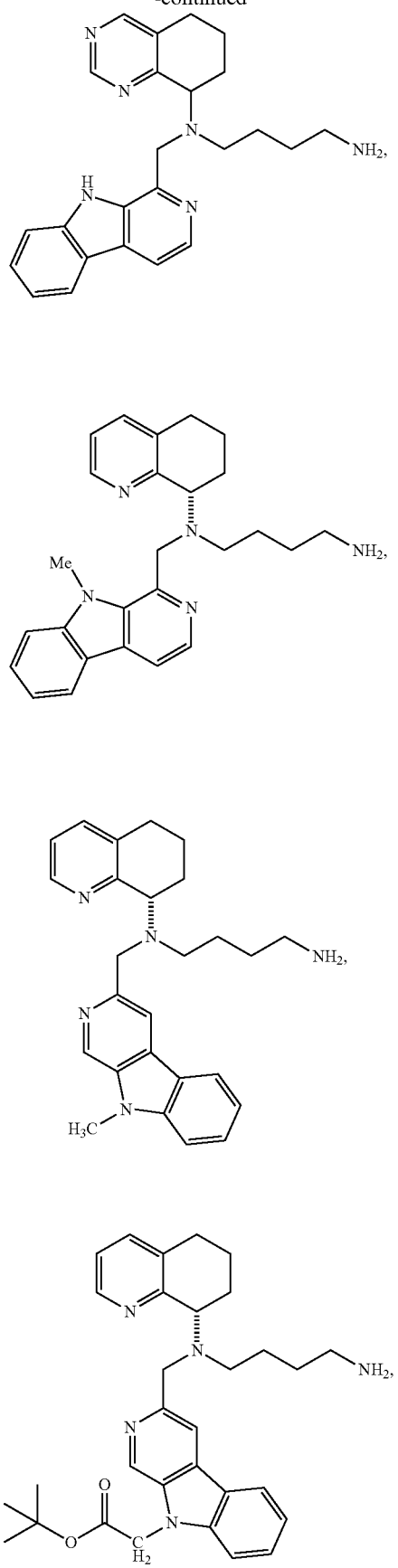

-continued
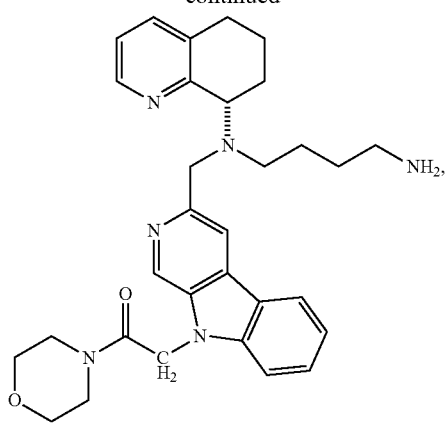
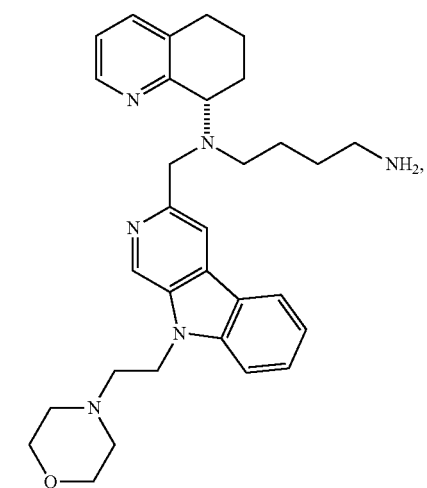
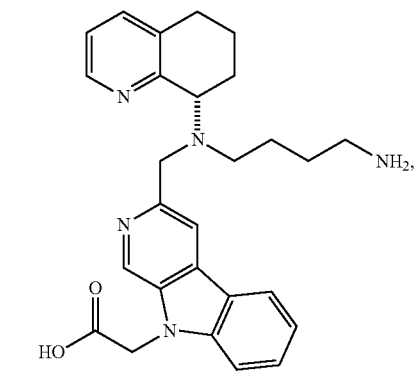
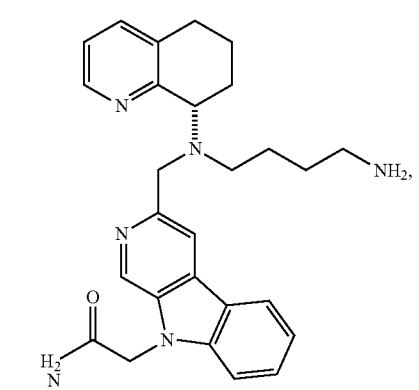
-continued
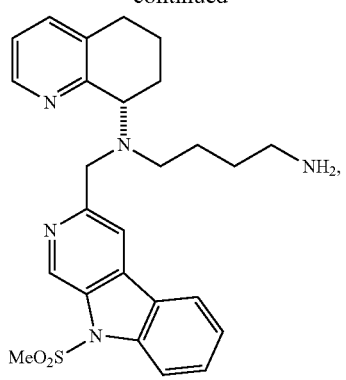
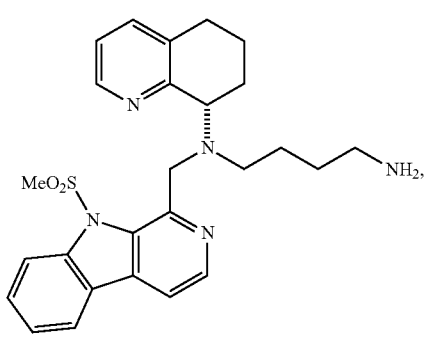
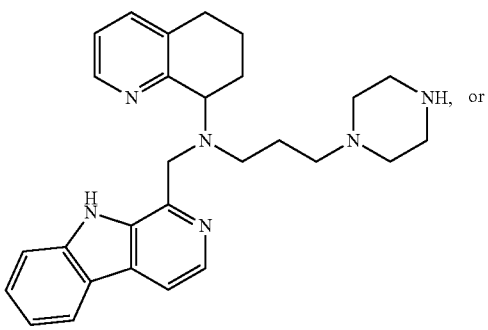
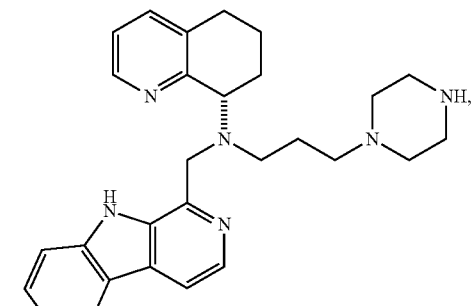
or a pharmaceutically acceptable salt, solvate, tautomer, stereoisomer, and/or ester thereof.

In certain other embodiments, the compounds can be selected from:
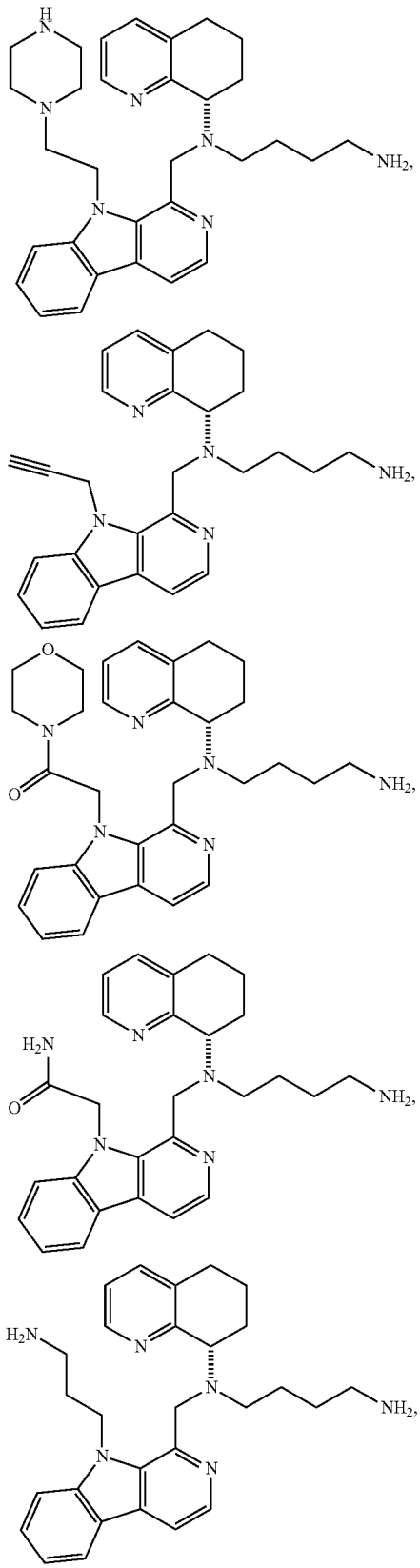
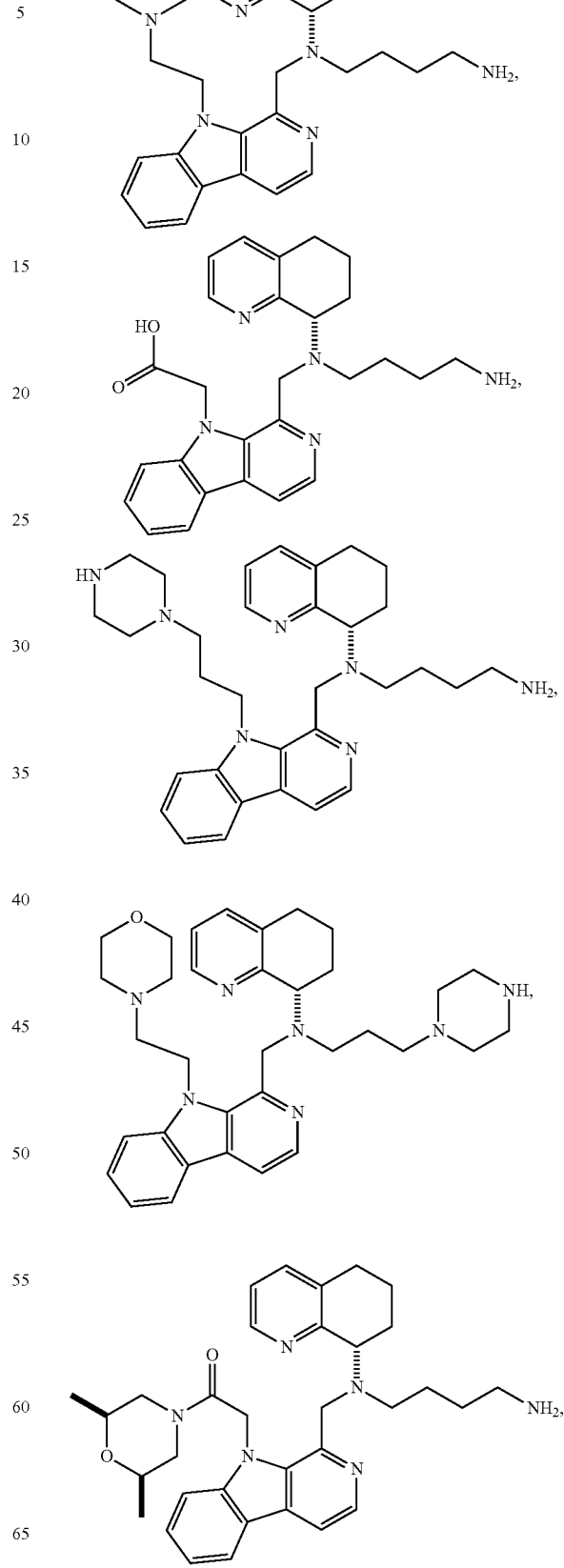

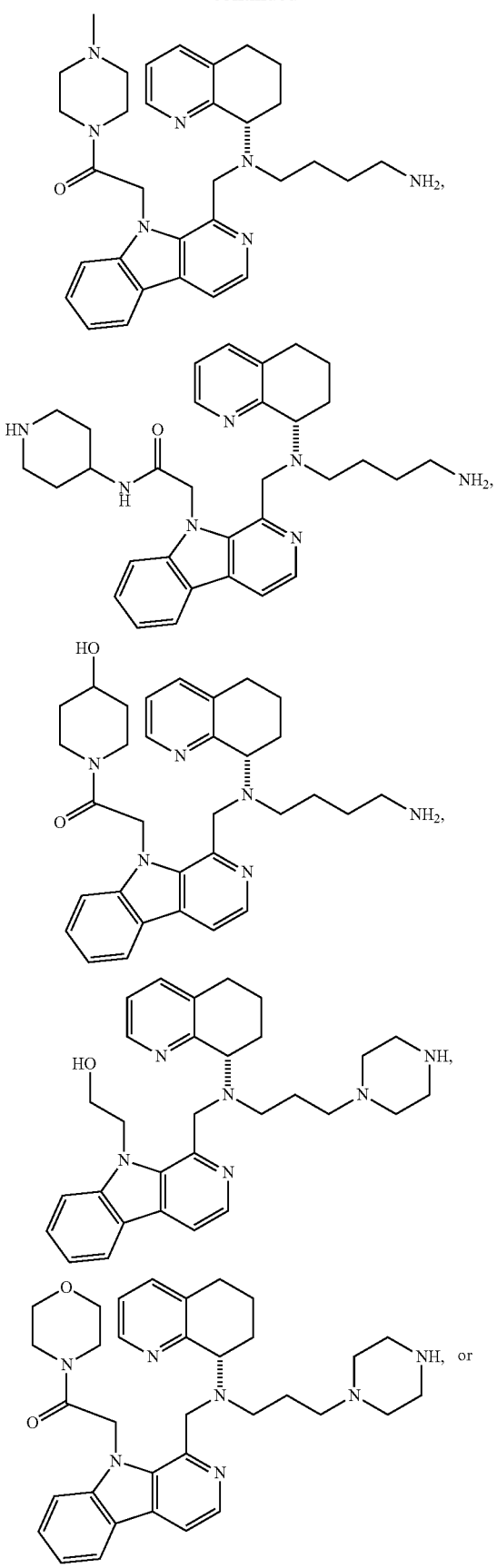

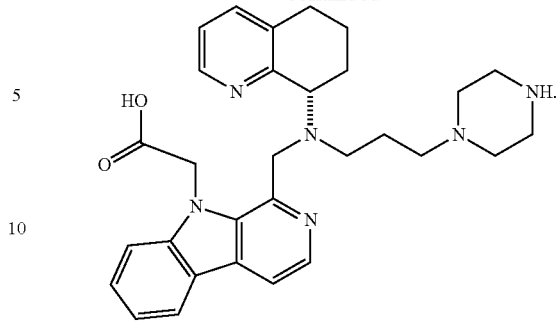

In certain embodiments, a compound that is useful in the methods of the invention can be identified based on in vitro criteria. In some embodiments, a compound can be considered to inhibit a chemokine signal, be a chemokine antagonist, or be useful in the methods of treatment described herein, if it interferes with Ca+ mobilization in vitro or in vivo by a chemokine receptor agonist at an $IC_{50}$ of less than about 1000 nM. In certain embodiments, the $IC_{50}$ is less than about 500 nM, 450 nM, 400 nM, 350 nM, 300 nM, 250 nM, 200 nM, 100 nM, 90 nM, 80 nM, 70 nM, 60 nM, 50 nM, 40 nM, 30 nM, 25 nM, 20 nM, 10 nM, 5 nM, 1 nM, 0.5 nM, or 0.1 nM. In particular embodiments, the $IC_{50}$ is in the range of about 500 nM to about 1 nM, about 400 nM to about 5 nM, about 350 nM to about 10 nM, about 300 nM to about 25 nM, about 250 nM to about 50 nM, about 200 nM to about 50 nM, about 100 nM to about 10 nM, about 70 nM to about 1 nM, or about 50 nM to about 1 nM. In some embodiments, the receptor is a CXCR4 receptor. In specific embodiments, the chemokine agonist is a natural agonist and in specific embodiments is SDF-1. In particular embodiments, the Ca+ mobilization is measured in vitro. The Ca+ flux can, for example, be measured in cells that naturally express high levels of chemokine receptor or, alternatively, a chemokine receptor can be recombinantly expressed.

In certain other embodiments, the compound is considered to inhibit a chemokine signal, be a chemokine antagonist, or be useful in the methods of treatment described herein when it inhibits impedance caused by a chemokine agonist. In particular embodiments, the impedance is stimulated by a natural agonist and in specific embodiments is SDF-1. The chemokine receptor can be any chemokine receptor but in certain embodiments is CXCR4. In particular embodiments, the $IC_{50}$ of impedance is less than about 500 nM, 450 nM, 400 nM, 350 nM, 300 nM, 250 nM, 200 nM, 100 nM, 90 nM, 80 nM, 70 nM, 60 nM, 50 nM, 40 nM, 30 nM, 25 nM, 20 nM, 10 nM, 5 nM, 1 nM, 0.5 nM, or 0.1 nM. In particular embodiments, the $IC_{50}$ of impedance is in the range of about 500 nM to about 1 nM, about 400 nM to about 5 nM, about 350 nM to about 10 nM, about 300 nM to about 25 nM, about 250 nM to about 50 nM, about 200 nM to about 50 nM, about 100 nM to about 10 nM, about 70 nM to about 1 nM, or about 50 nM to about 1 nM.

In one embodiment, the compound demonstrates inhibition of a chemokine agonist response in vitro or in vivo that is greater than that of AMD3100. In specific embodiments, the potency of inhibition of the compound as measured by an $IC_{50}$ is at least 2 times, at least 3 times, at least 4 times, at least 5 times, at least 6 times, at least 7 times, at least 8 times, at least 9 times, at least 10 times, at least 15 times, or at least 20 times that of AMD3100. In a particular embodiment, the potency of inhibition of the compound as measured by an $IC_{50}$ is in the range of about 2 times to about 20 times, about 3 times to about 15 times, about 2 times to about 10 times, or about 5 times to about 10 times that of AMD3100.

In certain embodiments, the compounds exhibit an enhanced safety profile. The safety profile can be tested in vitro or in vivo, but in certain embodiments is tested in vitro. Preferably, the dose at which cytotoxicity of a compound occurs in vitro or in vivo is at least 2 times, at least 3 times, at least 4 times, at least 5 times, at least 10 times, at least 25 times, at least 50 times, at least 100 times, at least 250 times, at least 500 times, or at least 1000 times the $IC_{50}$ of the compound in acting as a chemokine receptor antagonist.

In other embodiments, the compound exhibits reduced hERG binding. In particular embodiments, the compound exhibits hERG binding of less than 50% at its $IC_{50}$ for inhibition of a chemokine receptor. In other embodiments, the compound exhibits hERG binding of less than 50% at a concentration that is at least 2 times, at least 3 times, at least 4 times, at least 5 times, at least 10 times, at least 25 times, at least 50 times, at least 100 times, at least 250 times, at least 500 times, or at least 1000 times its $IC_{50}$.

Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

The active compound can also be provided as a prodrug, which is converted into a biologically active form in vivo. A prodrug may be converted into the parent drug by various mechanisms, including enzymatic processes and metabolic hydrolysis: T. Higuchi and V. Stella, *Pro-drugs as Novel Delivery Systems*, Vol. 14 of A.C.S. Symposium Series (1987) Harper, N.J. (1962) in Jucker, ed. *Progress in Drug Research*, 4:221-294; Morozowich et al. (1977) in E. B. Roche ed. *Design of Biopharmaceutical Properties through Prodrugs and Analogs*, APhA (Acad. Pharm. Sci.); E. B. Roche, ed. (1977) *Bioreversible Carriers in Drug in Drug Design, Theory and Application*, APhA; H. Bundgaard, ed. (1985) Design of Prodrugs, Elsevier; Wang et al. (1999) *Curr. Pharm. Design.* 5(4):265-287; Pauletti et al. (1997) *Adv. Drug. Delivery Rev.* 27:235-256; Mizen et al. (1998) *Pharm. Biotech.* 11:345-365; Gaignault et al. (1996) *Pract. Med. Chem.* 671-696; M. Asghamejad (2000) in G. L. Amidon, P. I. Lee and E. M. Topp, Eds., *Transport Proc. Pharm. Sys.*, Marcell Dekker, p. 185-218; Balant et al. (1990) *Eur. J. Drug Metab. Pharmacokinet.*, 15(2): 143-53; Balimane and Sinko (1999) *Adv. Drug Deliv. Rev.*, 39(1-3):183-209; Browne (1997). *Clin. Neuropharm.* 20(1): 1-12; Bundgaard (1979) *Arch. Pharm. Chemi.* 86(1): 1-39; H. Bundgaard, ed. (1985) *Design of Prodrugs*, New York: Elsevier; Fleisher et al. (1996) *Adv. Drug Delivery Rev*, 19(2): 115-130; Fleisher et al. (1985) *Methods Enzymol.* 112: 360-81; Farquhar D, et al. (1983) *J. Pharm. Sci.*, 72(3): 324-325; Han, H. K. et al. (2000) *AAPS Pharm Sci.*, 2(1): E6; Sadzuka Y. (2000) *Curr. Drug Metab.*, 1:31-48; D. M. Lambert (2000) *Eur. J. Pharm. Sci.*, 11 Suppl 2:S15-27; Wang, W. et al. (1999) *Curr. Pharm. Des.*, 5(4):265, each of which is incorporated herein by reference in its entirety.

The active compound can also be provided as a lipid prodrug. Nonlimiting examples of U.S. patents that disclose suitable lipophilic substituents that can be covalently incorporated into the compound or in lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.).

Preferably, the pharmaceutical preparation is in a unit dosage form. In such form, the preparation is subdivided into suitably sized unit doses containing appropriate quantities of the active compound, e.g., an effective amount to achieve the desired purpose.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 0.1 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), *Mack Publishing Co., Easton, Pa.*

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Methods of Treatment

The compounds described herein, are particularly useful for the treatment or prevention of a disorder associated with chemokine receptor binding or activation. The methods of treatment or prevention of diseases or disorders herein by administration of a compound as described herein may alternatively be a method of use of the compounds for treatment or prevention of the diseases or disorders, or may be a method of use of the compound in the manufacture of a medicament for treatment or prevention of the disease or disorder in a host. In certain embodiments, the host is a human, an in particular, a human in need of chemokine receptor inhibition. In certain embodiments, the host in need is at risk of suffering from a disorder causing a reduction in lymphocytes or myeloid cells.

Generally, the disclosure provides compositions and methods for treating or preventing a chemokine receptor mediated pathology by administering a compound of the present invention, or a pharmaceutically acceptable salt, solvate, prodrug, or ester thereof to a host in a therapeutic amount, for example in an amount sufficient to inhibit chemokine signal transduction in a cell expressing a chemokine receptor or homologue thereof.

In certain embodiments, the compounds are useful for treating disorders associated with reduced hematopoetic stem cell mobilization. The interaction between SDF-1 and CXCR4 is important in hematopoietic stem cell homing to the bone marrow and in hematopoietic stem cell quiescence. Hematopoietic stem cells can be mobilized into all blood cell types including myeloid (monocytes and macrophages, neutrophils, basophils, eosinophils, erythrocytes, megakaryocytes/platelets, dendritic cells), and lymphoid lineages (T-cells, B-cells, NK-cells).

Because the interaction between SDF-1 and CXCR4 plays an important role in holding hematopoietic stem cells in the bone marrow, the compounds described herein that are CXCR4 antagonist compounds are capable of "mobilizing" hematopoietic stem cells into the bloodstream as peripheral blood stem cells. Peripheral blood stem cell mobilization is very important in hematopoietic stem cell transplantation (an alternative to transplantation of surgically-harvested bone marrow) and is currently performed using drugs such as G-CSF.

In some embodiments, the compounds can be useful for affecting disorders that are associated with a disorder causing a hormone fluctuation or affecting the autonomic nervous system. In particular, such disorders can affect sensations involving temperature, such as hot flashes, cause dizziness or lightheadedness, or have similar somatosensory affects.

Another embodiment provides uses of a compound of the present invention, or a pharmaceutically acceptable salt, solvate, prodrug, or ester thereof for the treatment of, or for the manufacture of a medicament for the treatment of chemokine receptor mediated pathologies including, but not limited to cancer or inflammation. Still another embodiment provides uses of a chemokine peptide antagonist for the manufacture of medicament for the prevention of tumor cell metastasis in a mammal In a separate embodiment, a method for treating diseases of vasculature, inflammatory and degenerative diseases is provided including administering a compound of Formula (I)-(V) to a host. In one embodiment, a compound of Formula (I)-(V) is used to stimulate the production and proliferation of stem cells and progenitor cells.

In a separate embodiment, a method for the treatment of, prevention of, or reduced severity of inflammatory disease states, neovascularization, and wound healing including administering at least one compound described herein is provided.

Vascular endothelial cells express a multitude of chemokine receptors, with CXCR4 being particularly prominent (Gupta, et al. (1998) J Biol Ghem. 273: 4282; Volin, et al. (1998) Biochem Biophys Res ommnun. 242: 46). A RT-PCR based strategy which utilized CXCR4 specific primers demonstrated that mRNA for the chemokine receptor CXCR4 is expressed not only in primary culturs and transformed type II alveolar epithelial cells (pneumocytes) but also in a number of epithelial cell lines derived from various other tissues. (Murdoch, et al. (1998) Immunology. 98(1): 36-41). Unlike with endothelial cells, CXCR4 is the only chemokine receptor expressed on epithelial cells. The receptor may have a functional role in epithelial pathology. Whether CXCR4 participates in inflammatory responses remains unclear. CXCR4 expressed on the epithelium may facilitate the recruitment of phagocytic cells to sites of inflammation by direct effects on epithelial cells. CXCR4 may also have other functional roles within the immune response or participate in wound healing or neovascularization. CXCR4 may also be involved in the pathophysiology of several acute or chronic inflammatory disease states associated with the epithelium. (Murdoch, et al. (1999) Immunology. 98(1): 36-41).

In addition, the invention is directed to methods of treating animal subjects, in particular, veterinary and human subjects, to enhance or elevate the number of progenitor cells and/or stem cells. The progenitor and/or stem cells may be harvested and used in cell transplantation. In one embodiment, bone marrow progenitor and/or stem cells are mobilized for myocardial repair. Further, the invention is directed to methods of treating animal subjects, in particular, veterinary and human patients, who are defective in white blood cell (WBC) count, or who would benefit from elevation of WBC levels using the compounds disclosed herein. Moreover, the invention is directed to methods of effecting regeneration of cardiac tissue in a subject in need of such regeneration using the disclosed compounds.

The compounds of the invention may be used for the treatment of diseases that are associated with immunosuppression such as individuals undergoing chemotherapy, radiation therapy, enhanced wound healing and burn treatment, therapy for autoimmune disease or other drug therapy (e.g. corticosteroid therapy) or combination of conventional drugs used in the treatment of autoimmune diseases and graft transplantation rejection, which causes immunosuppression; immunosuppression due to congenital deficiency in receptor function or other causes; and infectious diseases, such as parasitic diseases, including but not limited to helminth infections, such as nematodes. The method of the invention thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the invention targets a broad spectrum of conditions characterized by a deficiency in white blood cell count, or which would benefit from elevation of said white blood cell count.

The term "progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocytemacrophage); CFU-GEMM (colony-forming units, -multipotential); BFU-E (burst-forming units, erythroid); HPP-CFC (high proliferative potential colony-forming cells); or other types of differentiated colonies which can be obtained in culture using known protocols. "Stem" cells are less differentiated forms of progenitor cells. Typically, such cells are often positive for CD34. Some stem cells do not contain this marker, however. In general, CD34+ cells are present only in low levels in the blood, but are present in large numbers in bone marrow.

The compounds of the invention may be administered as sole active ingredients, as mixtures of various compounds of Formula (I)-(V), and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-i), Interleukin-3 (IL-3), Interleukin-8 (IL-8), PIXY-32 1 (GM-CSF/IL-3 fusion protein), macrophage inflammatory protein, stem cell factor, thrombopoictin, growth related oncogene or chemotherapy and the like. In addition, the compounds of the invention may be administered in admixture with additional active ingredients that are therapeutically or nutritionally useful, such as antibiotics, vitamins, herbal extracts, anti-inflammatories, glucose, antipyretics, analgesics, and the like.

The binding of SDF-1 to CXCR4 has also been implicated in the pathogenesis of atherosclerosis (Abi-Younes et al. Circ. Res. 86, 131-138 (2000)), renal allograft rejection (Either et al. Transplantation 66, 1551-1557 (1998)), asthma and allergic airway inflammation (Yssel et al. Clinical and Experimental Aller 28, 104-109 (1998); JBC vol. 164, 59355943 (2000); Gonzalo et al. J. Immunol. 165, 499-508 (2000)), Alzheimer's disease (Xia et al. J. Neurovirology 5, 32-41 (1999)) and Arthritis (Nanici et al. J. Immunol. 164, 5010-5014 (2000)).

In one particular embodiment, a method of preventing metastasis of a malignant cell is provided that includes contacting the cells with a compound of Formula I-V, or a pharmaceutically acceptable salt, ester or prodrug thereof. In a separate embodiment, a method of treating proliferative disorders by administering a compound of Formulas (I)-(V) to a host in need of treatment is provided.

In another embodiment, the invention provides a method of reducing neovascularization, particularly VEGF-dependent neocascularization, by contacting a cell with a compound of Formula (I)-(V). The cell can be in a host animal.

In a separate embodiment, a method for treating diseases of vasculature, inflammatory and degenerative diseases is provided including administering a compound of Formula (I)-(V) to a host. In one embodiment, a compound of Formula (I)-(V) is used to stimulate the production and proliferation of stem cells and progenitor cells.

The compounds can prevent or reduce the severity of diseases associated with CXCR4 activity, and in particular of proliferative diseases in any host. However, typically the host is a mammal and more typically is a human. In certain sub-embodiments the host has been diagnosed with a hyperproliferative disorder prior to administration of the compound, however in other embodiments, the host is merely considered at risk of suffering from such a disorder.

Host, including humans suffering from, or at risk for, a proliferative disorder can be treated by administering an effective amount of a pharmaceutical composition of the active compound.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, mt. J. Dermatol. 18:111, 1979). Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers. Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross, R. Nature, 1993, 362:801-809) Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of msangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, B. D., Jr. (1990) The New England Journal of Medicine, 322:1277-1289), and to be caused by autoantibodies produced against collagen and IgE.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Examples of proliferative disorders which can be the primary tumor that is treated, or which can be the site from which metastasis is inhibited or reduced, include but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

Specific types of diseases include Acute Childhood Lymphoblastic Leukemia; Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphorria, Adult Lymphocytic Leukemia, Adult Non-Hodgkin's Lymphoma, Adult Primary Liver Cancer, Adult Soft Tissue Sarcoma, AIDS-Related Lymphorria, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphorria, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalanic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma. Endometrial Cancer, Ependymoma, Epithelial Cancei, Esophageal Cancer, Ewing's Sarcoma and Related Tumors, Exocrine Pancreatic Cancer, Extraeranial Germ Cell Tumor, Extragonadal Germ Cell Tumor, Extrahepatie Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypophaiyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Canner, Lung Cancer, Lympho proliferative Disorders, Macroglobulinemia, Male Breast Cancer, Malignant Mesothelioma, Malignant Thymoma, Medulloblastomia, Melanoma, Mesothelioma, Metastatie Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyigeal Cancer, Neuroblastorna, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, OsteolMalignant Fibrous Sarcoma, OsteosarcomalMalignant Fibrous Histiocytoma, OsteosarcomalMaligriant Fibrous Histiocytoma of Bone, Ovarian Epithelitj Cancer, Ovarian Germ Cell Tumor, Ovarian Low Malignant Potential Tumor, Pancreatic Cancer, Paraproteinemias, Purpura, Parathyroid, Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethial Cancer, Uterine Cancer, Uterine Sarcoma, Vaginal Cancer, Visual Pathway and Hypothalamic Glioma, Vulvar Cancer, Waldenstrom's Macroglobulinemia, Wilm's Tumor, and any other hyperproliferative disease located in an organ system listed above.

Hyperplastic disorders include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia; leukemia (including acute leukemia (e.g., acute lymphocytic leukemia, acute myelocytic leukemia (including myeloblastic, promyelocytic, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, Sarcomas and, carcinomas such as fibrosarcoma, myxosarcoma, liposarcoma, chondrosarcoma, osteogenic sarcoma, chordoma, anglosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

In a separate embodiment, a method for the treatment of, prevention of, or reduced severity of, age-related macular degeneration (ARMD) and other pathogenic states involving macular retinal pigment epithelial (RPE) cells including administering at least one compound described herein is provided.

CXCR4 plays a crucial role in ocular diseases involving the retina such as age-related macular degeneration (ARMD). The retinal pigment epithelium has a major role in the physiological renewal of photoreceptor outer segments in the provision of a transport and storage system or nutrients essential to the photoreceptor layer. The retinal pigment epithelial (RPE) cells predominantly express CXCR4 receptors. (Crane, et al. (2000) J. Immunol. 165: 4372-4278). CXCR4 receptor expression on human retinal pigment epithelial cells from the blood-retina barrier leads to chemokine secretion and migration in response to stromal cell-derived factor 1a. J. limmunol. 200; 165: 4372-4278). The level of CXCR4 mRNA expression increases upon stimulation with IL-i 3 or TNFa (Dwinell, et al. (1999) Gastroenterology. 117: 359-367). RPE cells also migrated in response to SDF-1a indicating that SDF-1a/CXCR4 interactions may modulate the affects of chronic inflammation and subretinal neovascularization at the RPE site of the blood-retina barrier. (Crane I J, Wallace C A, McKillop-Smith S, Forrester N. CXCR4 receptor expression on human retinal pigment epithelial cells from the blood-retina barrier leads to chemokine secretion and migration in response to stromal cellderived factor 1a J. Immunol. 200; 165: 4372-4278).

Age-related macular degeneration is characterized by both primary and secondary damage of macular RPE cells. Early stages of ARMD are characterized by macular drusen, and irregular proliferation and atrophy of the RPE. The late stages of ARMD present with geographic RPE atrophy, RPE detachment and rupture, choroidal neovascularaization and fibrovascular disciform scarring. Common first symptoms include metamorphopisia and/or general central vision loss resulting in reading disability and difficulties in detecting faces. Late stages of ARMD cause central scomota, which is extremely disabling if occurrence is bilateral (Bressler and Bressler (1995) Ophthalmology. 1995; 102: 1206-1211).

The compounds, or pharmaceutically acceptable salts, solvates, prodrugs, or esters thereof of the present invention described herein can be used to treat or prevent cancer, in particular the spread of cancer within an organism. Cancer is a general term for diseases in which abnormal cells divide without control. Cancer cells can invade nearby tissues and can spread through the bloodstream and lymphatic system to other parks of the body. It has been discovered that the administration of a chemokine receptor antagonist to a host, for example a mammal, inhibits or reduces the metastasis of tumor cells, in particular breast cancer and prostate cancer.

There are several main types of cancer, and the disclosed compounds or compositions can be used to treat any type of cancer. For example, carcinoma is cancer that begins in the skin or in tissues that line or cover internal organs. Sarcoma is cancer that begins in bone, cartilage, fat, muscle, blood vessels, or other connective or supportive tissue.

Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. A solid tumor is an abnormal mass of tissue that usually does not contain cysts or liquid areas. A single tumor may even have different populations of cells within it with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors. The compositions described herein can be used to reduce, inhibit, or diminish the proliferation of tumor cells, and thereby assist in reducing the size of a tumor.

Representative cancers that may treated with the disclosed compositions and methods include, but are not limited to, bladder cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, ostessarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness.

Ultimately, the tumor cells may even gain the ability to break away from the microscopic environment in which they originated, spread to another area of the body (with a very different environment, not normally conducive to their growth) and continue their rapid growth and division in this new location. This is called metastasis. Once malignant cells have metastasized, achieving cure is more difficult.

Benign tumors have less of a tendency to invade and are less likely to metastasize. They do divide in an uncontrolled manner, though. Depending on their location, they can be just as life threatening as malignant lesions. An example of this would be a benign tumor in the brain, which can grow and occupy space within the skull, leading to increased pressure on the brain. The compositions provided herein can be used to treat benign or malignant tumors.

In certain embodiments, the compounds described herein are useful for the treatment of HIV or AIDS in a host in need thereof.

In one embodiment, a method of treating or preventing HIV infection or reduction of symptoms associated with AIDS is provided including administering a compound of at least one of Formula (I)-(V) to a host. In certain embodiments, the compound can be provided to a host before treatment of infection with another compound. In a separate embodiment, the compound is provided to a patient that has been treated for HIV infection to reduce the likelihood of recurrence, or reduce mortality associated with AIDS related symptoms. In another embodiment, the compound is administered to a host at high risk of suffering from HIV infections.

Human and simian immunodeficiency viruses (HIV and SIV, respectively) enter cells through a fusion reaction triggered by the viral envelope glycoprotein (Env) and two cellular molecules: CD4 and a chemokine receptor, generally either CCR5 or CXCR5. (Alkhatib G, Combadiere C, Croder C, Feng Y, Kennedy P E, Murphy P M, Berger E A. CC CKR5. a RANTES, MIP-1alpha, MIP-1Beta receptor as a fusion cofactor for macrophage-tropic HIV-1. *Science*. 1996; 272: 1955-1988).

In approximately 50% of infected individuals, CXCR4-tropic (X4-tropic) viruses emerge later in HIV infection, and their appearance correlates with a more rapid CD4 decline and a faster progression to AIDS (Connor, et al. (1997) *J Exp. Med*. 185: 621-628). Dualtropic isolates that are able to use both CCR5 and CXCR4 are also seen and may represent intermediates in the switch from CCR5 to CXCR4 tropism (Doranz, et al. (1996) *Cell*. 85: 1149-1158).

Hosts, including humans suffering from, or at risk for, HIV infection can be treated by administering an effective amount of the active compound or a pharmaceutically acceptable prodrug or salt thereof in the presence of a pharmaceutically acceptable carrier or diluent.

The administration can be prophylactically for the prevention of HIV infection or reduction of symptoms associated with AIDS. The active materials can be administered by any appropriate route, for example, orally, parenterally, intravenously, intradermally, subcutaneously, or topically, in liquid or solid form. However, the compounds are particularly suited to oral delivery.

In a separate embodiment, a method for the treatment or prevention of HIV infection or reduction of symptoms associated with AIDS by administering a compound of the present invention, or a pharmaceutically acceptable salt, solvate, prodrug, or ester thereof to a host in need of treatment is provided. The compounds of the invention, or a pharmaceutically acceptable salt, solvate, prodrug, or ester thereof can be administered to a host in need thereof to reduce the severity of AIDS related disorders. In one embodiment of the invention, the host is a human.

In a separate embodiment, a method for the treatment of, prevention of, or reduced severity of liver disease associated with viral infections including administering at least one compound described herein is provided.

Chronic hepatitis C virus (HCV) and hepatitis B virus (HBC) infection is accompanied by inflammation and fibrosis eventually leading to cirrhosis. A study testing the expression and function of CXCR4 on liver-infiltrating lymphocytes (LIL) revealed an important role for the CXCL12/CXCR4 pathway in recruitment and retention of immune cells in the liver during chronic HCV and HBV infection (Wald, et al. (2004) *European Journal of Immunology*. 34(4): 1164-1174). High levels of CXCR4 and TGFβ have been detected in liver samples obtained from patients infected with HCV. (Mitra, et al. (1999) *Int. J. Oncol*. 14: 917-925). In vitro, TGF-β has been shown to up-regulate the expression of CXCR4 on naïve T cells and to increase their migration. The CD69/TGFβ/CXCR4 pathway may be involved in the retention of recently activated lymphocytes in the liver (Wald, et al. *European Journal of Immunology*. 2004; 34(4): 1164-1174).

In another embodiment, the invention provides a method of treating symptoms associated with other infections associated with chemokine receptor activation, for example, liver diseases associated with flavivirus or pestivirus infection, and in particular, HCV or HBV, by contacting a cell with a compound of the present invention, or a pharmaceutically acceptable salt, solvate, prodrug, or ester thereof. The cell can be in a host animal, in particular in a human.

The compounds can treat or prevent HIV infection, or reduce the severity of AIDS related symptoms and diseases in any host. However, typically the host is a mammal and more typically is a human. In certain embodiments the host has been diagnosed with AIDS prior to administration of the compound, however in other embodiments, the host is merely infected with HIV and asymptomatic.

An exemplary dose of the compound will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent compound to be delivered. If the salt, ester or prodrug exhibits activity in itself, the effective dosage can be estimated as above using the weight of the salt, ester, solvate, or prodrug, or by other means known to those skilled in the art.

The amount and frequency of administration of the compounds of the invention and/or the pharmaceutically acceptable salts thereof will be regulated according to the judgment of the attending clinician considering such factors as age, condition and size of the patient as well as the condition and/or severity of the symptoms being treated. A typical recommended daily dosage regimen for oral administration can range from about 0.1 mg/day to about 2000 mg/day, in one to four divided doses.

Pharmaceutical Compositions

In one embodiment, pharmaceutical compositions including at least one compound of the present invention, or a pharmaceutically acceptable salt, solvate, prodrug, or ester thereof is provided.

The compound of the present invention, or a pharmaceutically acceptable salt, solvate, prodrug, or ester thereof is conveniently administered in unit any suitable dosage form, including but not limited to one containing 7 to 3000 mg, preferably 70 to 1400 mg of active ingredient per unit dosage form. A oral dosage of 50-1000 mg is usually convenient. Ideally the active ingredient should be administered to achieve peak plasma concentrations of the active compound of from about 1 μM to 100 mM or from 0.2 to 700 μM, or about 1.0 to 10 μM.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or antiviral compounds, or with additional chemotherapeutic agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

In a preferred embodiment, the active compounds are prepared with carriers that will protect the compound against rapid elimination from the body, such as a controlled release Formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such Formulations will be apparent to those skilled in the art. The materials can also be obtained commercially from Alza Corporation. If administered intravenously, preferred carriers are physiological saline or phosphate buffered saline (PBS).

In certain embodiments, the active is provided an aqueous solution. The active can be dissolved in, for example, water, PBS, or a similar intert liquid. Similarly, when in a solid form, the active can be provided in conjunction with an inert carrier. Typically, the inert carrier makes up the remained of any given volume of liquid or solid Formulation, ie up to 100%. When actives are combined, the ratio of the actives can vary from about 1:10.000 to about 1:1, however the ratio is more typically from about 1:1 to about 1:50, or more typically about 1:1 to about 1:10. Ratios can be measured either on a molar basis or by weight.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome Formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Combination and Alternation Therapy

In one embodiment, the compounds described herein are administered in combination or alternation with another active compound.

In certain embodiments, at least a second active compound is administered in combination or alternation with the first compound.

The second active compound can be a chemotherapeutic agent, for example an agent active against a primary tumor. Hosts, including humans suffering from or at risk for a proliferative disorder can be treated by administering an effective amount of a pharmaceutical composition of the active compound. In particular embodiments, the compound is useful in disorders in which hematopoietic stem cell mobilization is desired, such as upon administration of a chemotherapeutic agent. In these embodiments, it may be beneficial to administer the compound described herein in combination or alternation with a chemotherapeutic agent to reduce side effects of chemotherapy.

In certain other embodiments, the second active compound can be an antiviral, particularly an agent active against a HIV and in a particular embodiment, active against HIV-1. Hosts, including humans suffering from or at risk of contracting HIV can be treated by administering an effective amount of a pharmaceutical composition of the active compound.

In one embodiment, the active compound is a compound that is used as a chemotherapeutic. The compound provided in combination or alternation can, for example, be selected from the following list:

| | | | |
|---|---|---|---|
| 13-cis-Retinoic Acid | 2-Amino-6-Mercaptopurine | 2-CdA | 2-Chlorodeoxyadenosine |
| 5-fluorouracil | 5-FU | 6-TG | 6-Thioguanine |
| 6-Mercaptopurine | 6-MP | Accutane | Actinomycin-D |
| Adriamycin | Adrucil | Agrylin | Ala-Cort |
| Aldesleukin | Alemtuzumab | Alitretinoin | Alkaban-AQ |
| Alkeran | All-transretinoic acid | Alpha interferon | Altretamine |
| Amethopterin | Amifostine | Aminoglutethimide | Anagrelide |
| Anandron | Anastrozole | Arabinosylcytosine | Ara-C |
| Aranesp | Aredia | Arimidex | Aromas in |
| Arsenic trioxide | Asparaginase | ATRA | Avastin |
| BCG | BCNU | Bevacizumab | Bexarotene |
| Bicalutamide | BiCNU | Blenoxane | Bleomycin |
| Bortezomib | Busulfan | Busulfex | C225 |
| Calcium Leucovorin | Campath | Camptosar | Camptothecin-11 |
| Capecitabine | Carac | Carboplatin | Carmustine |
| Carmustine wafer | Casodex | CCNU | CDDP |
| CeeNU | Cerubidine | cetuximab | Chlorambucil |
| Cisplatin | Citrovorum Factor | Cladribine | Cortisone |
| Cosmegen | CPT-11 | Cyclophosphamide | Cytadren |
| Cytarabine | Cytarabine liposomal | Cytosar-U | Cytoxan |
| Dacarbazine | Dactinomycin | Darbepoetin alfa | Daunomycin |
| Daunorubicin | Daunorubicin hydrochloride | Daunorubicin liposomal | DaunoXome |
| Decadron | Delta-Cortef | Deltasone | Denileukin diftitox |
| DepoCyt | Dexamethasone | Dexamethasone acetate | dexamethasone sodium phosphate |
| Dexasone | Dexrazoxane | DHAD | DIC |
| Diodex | Docetaxel | Doxil | Doxorubicin |
| Doxorubicin liposomal | Droxia | DTIC | DTIC-Dome |
| Duralone | Efudex | Eligard | Ellence |
| Eloxatin | Elspar | Emcyt | Epirubicin |
| Epoetin alfa | Erbitux | Erwinia L-asparaginase | Estramustine |
| Ethyol | Etopophos | Etoposide | Etoposide phosphate |
| Eulexin | Evista | Exemestane | Fareston |
| Faslodex | Femara | Filgrastim | Floxuridine |
| Fludara | Fludarabine | Fluoroplex | Fluorouracil |
| Fluorouracil (cream) | Fluoxymesterone | Flutamide | Folinic Acid |
| FUDR | Fulvestrant | G-CSF | Gefitinib |
| Gemcitabine | Gemtuzumab ozogamicin | Gemzar | Gleevec |
| Gliadel wafer | Glivec | GM-CSF | Goserelin |
| granulocyte colony stimulating factor | Granulocyte macrophage colony stimulating factor | Halotestin | Herceptin |
| Hexadrol | Hexalen | Hexamethylmelamine | HMM |
| Hycamtin | Hydrea | Hydrocort Acetate | Hydrocortisone |
| Hydrocortisone sodium phosphate | Hydrocortisone sodium succinate | Hydrocortone phosphate | Hydroxyurea |
| Ibritumomab | Ibritumomab Tiuxetan | Idamycin | Idarubicin |
| Ifex | IFN-alpha | Ifosfamide | IL-2 |
| IL-11 | Imatinib mesylate | Imidazole Carboxamide | Interferon alfa |
| Interferon Alfa-2b (PEG conjugate) | Interleukin-2 | Interleukin-11 | Intron A (interferon alfa-2b) |
| Iressa | Irinotecan | Isotretinoin | Kidrolase |
| Lanacort | L-asparaginase | LCR | Letrozole |
| Leucovorin | Leukeran | Leukine | Leuprolide |
| Leurocristine | Leustatin | Liposomal Ara-C | Liquid Pred |
| Lomustine | L-PAM | L-Sarcolysin | Lupron |
| Lupron Depot | Matulane | Maxidex | Mechlorethamine |
| Mechlorethamine Hydrochlorine | Medralone | Medrol | Megace |
| Megestrol | Megestrol Acetate | Melphalan | Mercaptopurine |
| Mesna | Mesnex | Methotrexate | Methotrexate Sodium |
| Methylprednisolone | Meticorten | Mitomycin | Mitomycin-C |
| Mitoxantrone | M-Prednisol | MTC | MTX |
| Mustargen | Mustine | Mutamycin | Myleran |
| Mylocel | Mylotarg | | Navelbine |
| Neosar | Neulasta | Neumega | Neupogen |
| Nilandron | | | |
| Nilutamide | Nitrogen Mustard | Novaldex | Novantrone |
| Octreotide | Octreotide acetate | Oncospar | Oncovin |
| Ontak | Onxal | Oprevelkin | Orapred |
| Orasone | Oxaliplatin | Paclitaxel | Pamidronate |
| Panretin | Paraplatin | Pediapred | PEG Interferon |
| Pegaspargase | Pegfilgrastim | PEG-INTRON | PEG-L-asparaginase |
| Phenylalanine Mustard | Platinol | Platinol-AQ | Prednisolone |
| Prednisone | Prelone | Procarbazine | PROCRIT |
| Proleukin | Prolifeprospan 20 with Carmustine implant | Purinethol | Raloxifene |
| Rheumatrex | Rituxan | Rituximab | Roveron-A (interferon α-2a) |
| Rubex | Rubidomycin hydrochloride | Sandostatin | Sandostatin LAR |
| Sargramostim | Solu-Cortef | Solu-Medrol | STI-571 |
| Streptozocin | Tamoxifen | Targretin | Taxol |
| Taxotere | Temodar | Temozolomide | Teniposide |
| TESPA | Thalidomide | Thalomid | TheraCys |

| | | | |
|---|---|---|---|
| Thioguanine | Thioguanine Tabloid | Thiophosphoamide | Thioplex |
| Thiotepa | TICE | Toposar | Topotecan |
| Toremifene | Trastuzumab | Tretinoin | Trexall |
| Trisenox | TSPA | VCR | Velban |
| Velcade | VePesid | Vesanoid | Viadur |
| Vinblastine | Vinblastine Sulfate | Vincasar Pfs | Vincristine |
| Vinorelbine | Vinorelbine tartrate | VLB | VM-26 |
| VP-16 | Vumon | Xeloda | Zanosar |
| Zevalin | Zinecard | Zoladex | Zoledronic acid |
| Zometa | | | |

In another embodiment, the second active compound is a compound that is used as an anti-HIV agent, including but not limited to a nucleoside or nonnucleoside reverse transcriptase inhibitor, a protease inhibitor, a fusion inhibitor, cytokine and interferon. The compound provided in combination or alternation can, as a nonlimiting example, be selected from the following lists:

| Brand Name | Generic Name |
|---|---|
| Agenerase | amprenavir |
| Combivir | lamivudine and zidovudine |
| Crixivan | indinavir, IDV, MK-639 |
| Emtriva | FTC, emtricitabine |
| Epivir | lamivudine, 3TC |
| Epzicom | abacavir/lamivudine |
| Fortovase | saquinavir |
| Fuzeon | enfuvirtide, T-20 |
| Hivid | zalcitabine, ddC, dideoxycytidine |
| Invirase | saquinavir mesylate, SQV |
| Kaletra | lopinavir and ritonavir |
| Lexiva | Fosamprenavir Calcium |
| Norvir | ritonavir, ABT-538 |
| Rescriptor | delavirdine, DLV |
| Retrovir | zidovudine, AZT, azidothymidine, ZDV |
| Reyataz | atazanavir sulfate |
| Sustiva | efavirenz |
| Trizivir | abacavir, zidovudine, and lamivudine |
| Truvada | tenofovir disoproxil/emtricitabine |
| Videx EC | enteric coated didanosine |
| Videx | didanosine, ddI, dideoxyinosine |
| Viracept | nelfinavir mesylate, NFV |
| Viramune | nevirapine, BI-RG-587 |
| Viread | tenofovir disoproxil fumarate |
| Zerit | stavudine, d4T |
| Ziagen | abacavir |

Further active agents include: GW5634 (GSK), (+) Calanolide A (Sarawak Med.), Capravirine (Agouron), MIV-150 (Medivir/Chiron), TMC125 (Tibotec), RO033-4649 (Roche), TMC114 (Tibotec), Tipranavir (B-I), GW640385 (GSK/Vertex), Elvucitabine (Achillion Ph.), Alovudine (FLT) (B-I), MIV-210 (GSK/Medivir), Racivir (Pharmasset), SPD754 (Shire Pharm.), Reverset (Incyte Corp.), FP21399 (Fuji Pharm.), AMD070 (AnorMed), GW873140 (GSK), BMS-488043 (BMS), Schering C/D (417690), PRO 542 (Progenics Pharm), TAK-220 (Takeda), TNX-355 (Tanox), UK-427,857 (Pfizer).

Further active agents include: Attachment and Fusion Inhibitors (i.e. AMD070, BMS-488043, FP21399, GW873140, PRO 542, Schering C, SCH 417690, TAK-220, TNX-355 and UK-427,857); Integrase Inhibitors; Maturation Inhibitors (i.e. PA457); Zinc Finger Inhibitors (i.e. azodicarbonamide (ADA)); Antisense Drugs (i.e. HGTV43 by Enzo Therapeutics, GEM92 by Hybridon); Immune Stimulators (i.e. Ampligen by Hemispherx Biopharma, IL-2 (Proleukin) by Chiron Corporation, Bay 50-4798 by Bayer Corporation, Multikine by Cel-Sci Corporation, IR103 combo); Vaccine-Like Treatment (i.e. HRG214 by Virionyx, DermaVir, VIR201 (Phase I/IIa)).

In one embodiment, the compounds of the invention are administered in combination with another active agent. The compounds can also be administered concurrently with the other active agent. In this case, the compounds can be administered in the same Formulation or in a separate Formulation. There is no requirement that the compounds be administered in the same manner. For example, the second active agent can be administered via intravenous injection while the compounds of the invention may be administered orally. In another embodiment, the compounds of the invention are administered in alternation with at least one other active compound. In a separate embodiment, the compounds of the invention are administered during treatment with an active agent, such as, for example, an agent listed above, and administration of the compounds of the invention is continued after cessation of administration of the other active compound.

The compounds of the invention can be administered prior to or after cessation of administration of another active compound. In certain cases, the compounds may be administered before beginning a course of treatment for viral infection or for secondary disease associated with HIV infections, for example. In a separate embodiment, the compounds can be administered after a course of treatment to reduce recurrence of viral infections.

In another embodiment, the active compound is a compound that is used as a chemotherapeutic. A compound provided in combination or alternation can, for example, be selected from the following list:

| | | | |
|---|---|---|---|
| 13-cis-Retinoic Acid | 2-Amino-6-Mercaptopurine | 2-CdA | 2-Chlorodeoxyadenosine |
| 5-fluorouracil | 5-FU | 6-TG | 6-Thioguanine |
| 6-Mercaptopurine | 6-MP | Accutane | Actinomycin-D |
| Adriamycin | Adrucil | Agrylin | Ala-Cort |
| Aldesleukin | Alemtuzumab | Alitretinoin | Alkaban-AQ |
| Alkeran | All-transretinoic acid | Alpha interferon | Altretamine |
| Amethopterin | Amifostine | Aminoglutethimide | Anagrelide |
| Anandron | Anastrozole | Arabinosylcytosine | Ara-C |
| Aranesp | Aredia | Arimidex | Aromasin |
| Arsenic trioxide | Asparaginase | ATRA | Avastin |
| BCG | BCNU | Bevacizumab | Bexarotene |
| Bicalutamide | BiCNU | Blenoxane | Bleomycin |
| Bortezomib | Busulfan | Busulfex | C225 |

-continued

| | | | |
|---|---|---|---|
| Calcium Leucovorin | Campath | Camptosar | Camptothecin-11 |
| Capecitabine | Carac | Carboplatin | Carmustine |
| Carmustine wafer | Casodex | CCNU | CDDP |
| CeeNU | Cerubidine | cetuximab | Chlorambucil |
| Cisplatin | Citrovorum Factor | Cladribine | Cortisone |
| Cosmegen | CPT-11 | Cyclophosphamide | Cytadren |
| Cytarabine | Cytarabine liposomal | Cytosar-U | Cytoxan |
| Dacarbazine | Dactinomycin | Darbepoetin alfa | Daunomycin |
| Daunorubicin | Daunorubicin hydrochloride | Daunorubicin liposomal | DaunoXome |
| Decadron | Delta-Cortef | Deltasone | Denileukin diftitox |
| DepoCyt | Dexamethasone | Dexamethason Acetate | dexamethasone sodium phosphate |
| Dexasone | Dexrazoxane | DHAD | DIC |
| Diodex | Docetaxel | Doxil | Doxorubicin |
| Doxorubicin liposomal | Droxia | DTIC | DTIC-Dome |
| Duralone | Efudex | Eligard | Ellence |
| Eloxatin | Elspar | Emcyt | Epirubicin |
| Epoetin alfa | Erbitux | Erwinia-L-asparaginase | Estramustine |
| Ethyol | Etopophos | Etoposide | Etoposide phosphate |
| Eulexin | Evista | Exemestane | Fareston |
| Faslodex | Femara | Filgrastim | Floxuridine |
| Fludara | Fludarabine | Fluoroplex | Fluorouracil |
| Fluorouracil (cream) | Fluoxymesterone | Flutamide | Folinic Acid |
| FUDR | Fulvestrant | G-CSF | Gefitinib |
| Gemcitabine | Gemtuzumab ozogamicin | Gemzar | Gleevec |
| Gliadel wafer | Glivec | GM-CSF | Goserelin |
| granulocyte colony stimulating factor | Granulocyte macrophage colony stimulating factor | Halotestin | Herceptin |
| Hexadrol | Hexalen | Hexamethylmelamine | HMM |
| Hycamtin | Hydrea | Hydrocort Acetate | Hydrocortisone |
| Hydrocortisone sodium phosphate | Hydrocortisone sodium succinate | Hydrocortone phosphate | Hydroxyurea |
| Ibritumomab | Ibritumomab Tiuxetan | Idamycin | Idarubicin |
| Ifex | IFN-alpha | Ifosfamide | IL-2 |
| IL-11 | Imatinib mesylate | Imidazole Carboxamide | Interferon alfa |
| Interferon Alfa-2b (PEG conjugate) | Interleukin-2 | Interleukin-11 | Intron A (interferon alfaL2b) |
| Iressa | Irinotecan | Isotretinoin | Kidrolase |
| Lanacort | L-asparaginase | LCR | Letrozole |
| Leucovorin | Leukeran | Leukine | Leuprolide |
| Leurocristine | Leustatin | Liposomal Ara-C | Liquid Pred |
| Lomustine | L-PAM | L-Sarcolysin | Lupron |
| Lupron Depot | Matulane | Maxidex | Mechlorethamine |
| Mechlorethamine hydrochloride | Medralone | Medrol | Megace |
| Megestrol | Megestrol Acetate | Melphalan | Mercaptopurine |
| Mesna | Mesnex | Methotrexate | Methotrexate Sodium |
| Methylprednisolone | Meticorten | Mitomycin | Mitomycin-C |
| Mitoxantrone | M-Prednisol | MTC | MTX |
| Mylocel | Mylotarg | Navelbine | Neosar |
| Neulasta | Neumega | Neupogen | Nilandron |
| Nilutamide | Nitrogen Mustard | Novaldex | Novantrone |
| Octreotide | Octreotide acetate | Oncospar | Oncovin |
| Ontak | Onxal | Oprevelkin | Orapred |
| Orasone | Oxaliplatin | Paclitaxel | Pamidronate |
| Panretin | Paraplatin | Pediapred | PEG Interferon |
| Pegaspargase | Pegfilgrastim | PEG-INTRON | PEG-L-asparaginase |
| Phenylalanine Mustard | Platinol | Platinol-AQ | Prednisolone |
| Prednisone | Prelone | Procarbazine | PROCRIT |
| Proleukin | Prolifeprospan 20 with Carmustine implant | Purinethol | Raloxifene |
| Rheumatrex | Rituxan | Rituximab | Roveron-A (interferon α-2a) |
| Rubex | Rubidomycin hydrochloride | Sandostatin | Sandostatin LAR |
| Sargramostim | Solu-Cortef | Solu-Medrol | STI-571 |
| Streptozocin | Tamoxifen | Targretin | Taxol |
| Taxotere | Temodar | Temozolomide | Teniposide |
| TESPA | Thalidomide | Thalomid | TheraCys |
| Thioguanine | Thioguanine Tabloid | Thiophosphoamide | Thioplex |
| Thiotepa | TICE | Toposar | Topotecan |
| Toremifene | Trastuzumab | Tretinoin | Trexall |
| Trisenox | TSPA | VCR | Velban |
| Velcade | VePesid | Vesanoid | Viadur |
| Vinorelbine | Vinorelbine tartrate | VLB | VM-26 |
| VP-16 | Vumon | Xeloda | Zanosar |
| Zevalin | Zinecard | Zoladex | Zoledronic acid |
| Zometa | | | |

EXAMPLES

Example 1

General Preparation of Compounds of Formula (IA)

Compounds of Formula (IA):

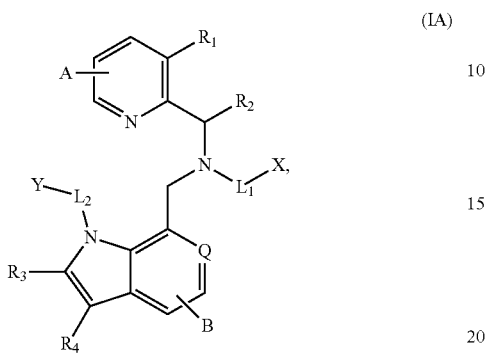

(IA)

wherein $R_1$, $R_2$, $R_3$, $R_4$, $L_1$, $L_2$, X, Y, Q, A, and B are as defined herein. Exemplary compounds of Formula (IA) are shown in Table 1.

TABLE 1

| Compound | —$R_3$ | —$R_4$ | —$L_2$—Y | Q | —$L_1$—X | ![R1/R2 group] |
|---|---|---|---|---|---|---|
| A | ⌇⃝⌇ (phenylene) | | H | N | ⌇~~~NH₂ | tetrahydroquinoline |
| B | H | H | H | CH | ⌇~~~NH₂ | tetrahydroquinoline |
| C | H | H | H | CH | CH₃ | tetrahydroquinoline |
| D | ⌇⃝⌇ (phenylene) | | H | N | ⌇~~~NH-C(=N)NH (imidazoline) | tetrahydroquinoline |
| E | ⌇⃝⌇ (phenylene) | | H | N | ⌇~~~NH-C(=N)NH (tetrahydropyrimidine) | tetrahydroquinoline |

TABLE 1-continued
| Compound | —R₃ —R₄ | —L₂—Y | Q | —L₁—X | (pyridine with R₁/R₂) |
|---|---|---|---|---|---|
| F | 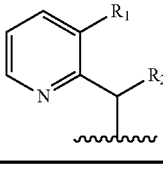 | H | N | 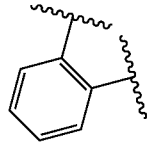 [SMILES: *c1ccccc1*] | 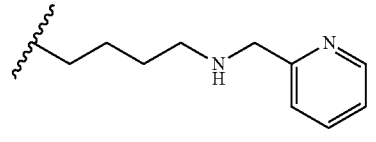 [SMILES: *CCCCNCc1ccccn1] |
| G | 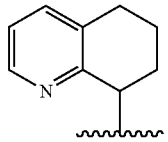 [SMILES: *C1CCCc2cccnc21] | H | N | 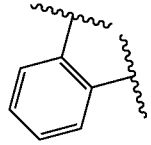 [SMILES: *c1ccccc1*] | 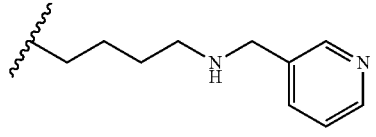 [SMILES: *CCCCNCc1cccnc1] |
| H | 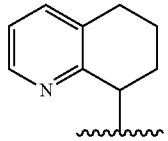 [SMILES: *C1CCCc2cccnc21] | H | N | 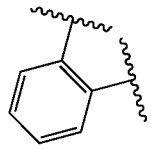 [SMILES: *c1ccccc1*] | 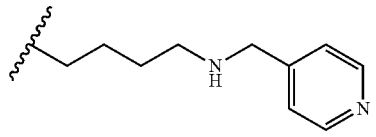 [SMILES: *CCCCNCc1ccncc1] |
| I | 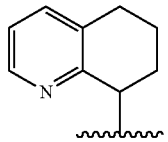 [SMILES: *C1CCCc2cccnc21] | H | N | 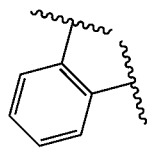 [SMILES: *c1ccccc1*] | 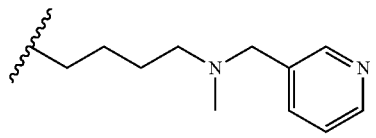 [SMILES: *CCCCN(C)Cc1cccnc1] |
| J | 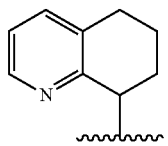 | H | N | 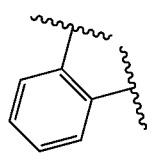 [SMILES: *c1ccccc1*] | 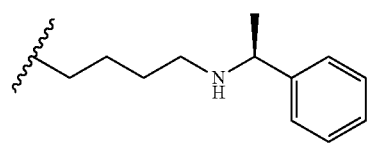 [SMILES: *CCCCN[C@@H](C)c1ccccc1] |
| K | 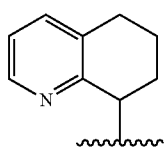 | H | N | 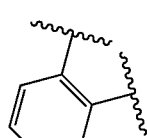 | 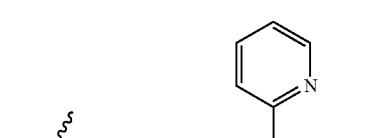 |
| L | 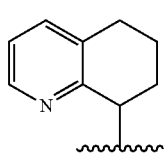 [SMILES: *C1CCCc2cccnc21] | H | N | 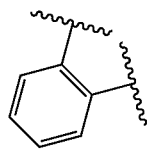 [SMILES: *c1ccccc1*] | 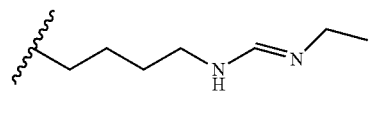 [SMILES: *CCCCN/C=N/CC] |
| M | 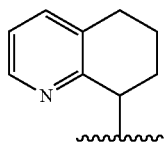 [SMILES: *C1CCCc2cccnc21] | H | N | 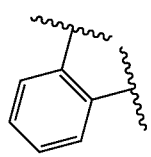 | 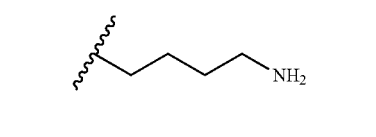 |

TABLE 1-continued
| Compound | —R₃ | —R₄ | —L₂—Y | Q | —L₁—X | 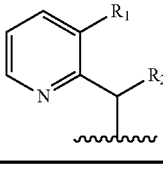 |
|---|---|---|---|---|---|---|
| N | 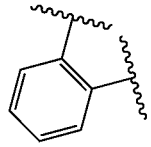 [SMILES: *c1ccccc1*] | | H | N | 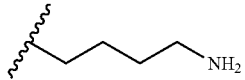 | 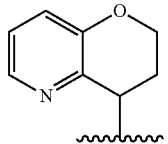 [SMILES: *C1CCOc2cccnc21] |
| O | 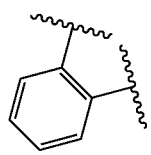 [SMILES: *c1ccccc1*] | | H | N | 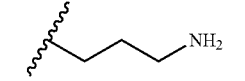 | 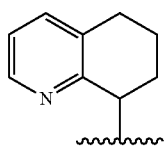 [SMILES: *C1CCCc2cccnc21] |
| P | 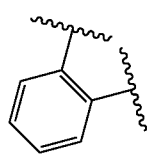 | | H | N | 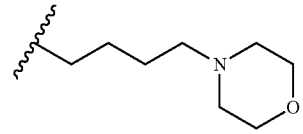 [SMILES: *CCCCN1CCOCC1] | 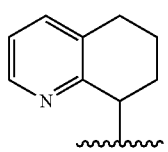 |
| Q | 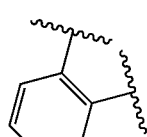 | | H | N | 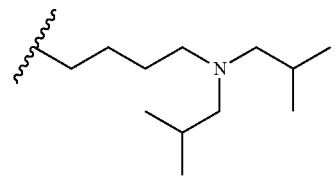 [SMILES: *CCCCN(CC(C)C)CC(C)C] | 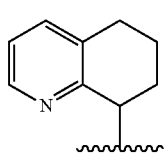 [SMILES: *C1CCCc2cccnc21] |
| R | 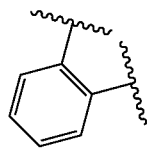 [SMILES: *c1ccccc1*] | | 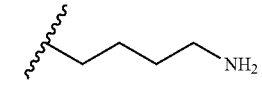 [SMILES: *CCCCN] | N | CH₃ |  |
| S | 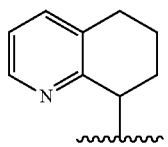 [SMILES: *C1CCCc2cccnc21] | | 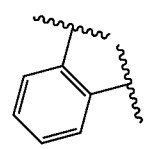 | N | CH₃ | 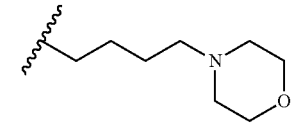 [SMILES: *CCCCN1CCOCC1] |
| T |  | | 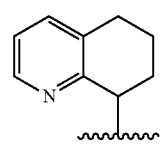 [SMILES: *C1CCCc2cccnc21] | N | CH₃ | 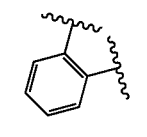 |
| U | 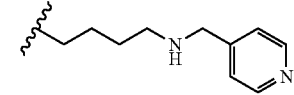 [SMILES: *CCCCNCc1ccncc1] | |  | N | CH₃ | 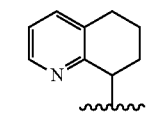 [SMILES: *C1CCCc2cccnc21] |
| V | 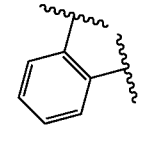 [SMILES: *c1ccccc1*] | | H | N | CH₃ | 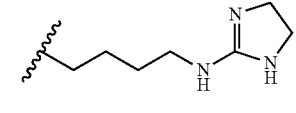 [SMILES: *CCCCNC1=NCCN1] |

TABLE 1-continued

| Compound | —R3 | —R4 | —L2—Y | Q | —L1—X | (pyridine with R1, R2) |
|---|---|---|---|---|---|---|
| V1 | (benzene) | | H | N | (chain-NH2) | (2-pyridyl-CH(CH3)-) |

The compounds of Formula (IA) can be prepared, for example, as described below.

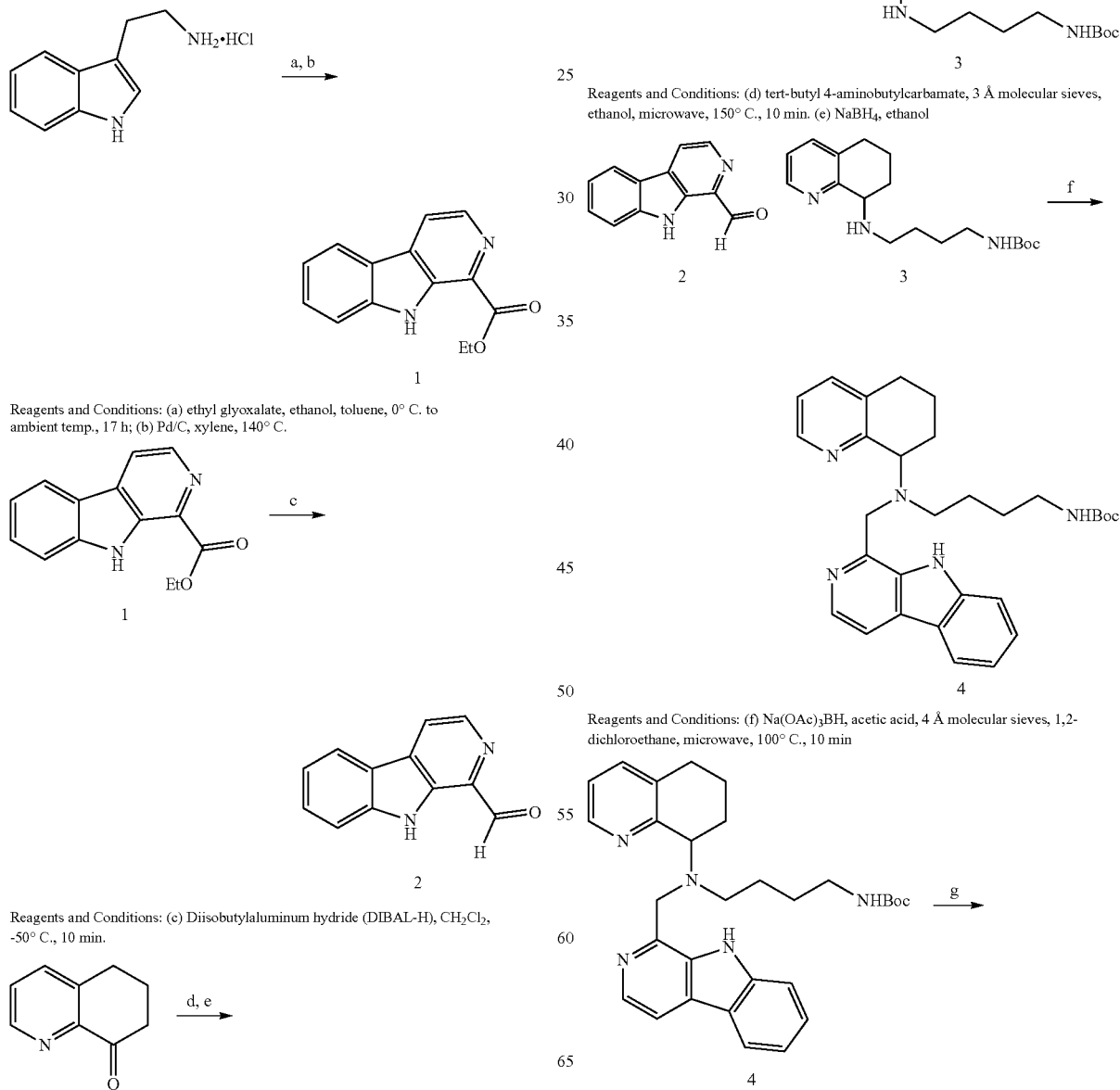

SCHEME 1

Reagents and Conditions: (a) ethyl glyoxalate, ethanol, toluene, 0° C. to ambient temp., 17 h; (b) Pd/C, xylene, 140° C.

Reagents and Conditions: (c) Diisobutylaluminum hydride (DIBAL-H), CH2Cl2, −50° C., 10 min.

Reagents and Conditions: (d) tert-butyl 4-aminobutylcarbamate, 3 Å molecular sieves, ethanol, microwave, 150° C., 10 min. (e) NaBH4, ethanol Reagents and Conditions: (f) Na(OAc)3BH, acetic acid, 4 Å molecular sieves, 1,2-dichloroethane, microwave, 100° C., 10 min -continued

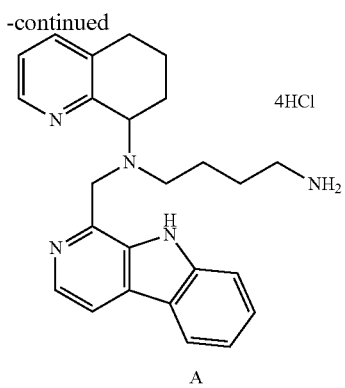

Reagents and Conditions: (g) thionyl chloride, methanol, ambient temp., 2 h

Example 2

Preparation of N-((9H-pyrido[3,4-b]indol-1-yl)methyl)-N-(4-aminobutyl)-5,6,7,8-tetrahydroquinolin-8-amine tetrahydrochloride (A)

Step a:

Preparation of ethyl-9H-pyrido[3,4-b]indole-1-carboxylate (1). To a suspension of tryptamine hydrochloride (2.00 g, 10.17 mmol) in ethanol (25 mL) was added a solution of glyoxylic acid ethyl ester (3.12 g, 15.26 mmol) in toluene (50% v/v) at 0° C. After the reaction mixture was stirred overnight at ambient temperature, the solvent was removed under reduced pressure. The resulting residue was treated with saturated aqueous sodium bicarbonate. The product was extracted with ethyl acetate. The combined organic layers were washed with brine, dried over sodium sulfate and concentrated under reduced pressure. The crude product was used in the next step without further purification.

Step b:

To a solution of the resulting crude residue in o-xylene (20 mL) at 0° C. was added 10% Pd/C (0.51 g). The mixture was stirred overnight at 140° C. under an air atmosphere. The reaction mixture was filtered through Celite, washed with chloroform and concentrated. The resulting residue was purified by chromatography on silica gel (0-20% ethyl acetate/hexanes) to afford 1.26 g (52% yield) of product 1: $^1$H NMR (400 MHz, CDCl$_3$) δ 9.92 (bs, 1H), 8.59 (d, J=4.8 Hz, 1H), 8.16-8.13 (m, 2H), 7.62-7.55 (m, 2H), 7.32 (dt, J=1.2, 7.0 Hz, 1H), 4.59 (q, J=7.2 Hz, 2H), 1.53 (t, J=7.2 Hz, 3H); ESI$^+$ MS: m/z (rel intensity) 241.1 (100, [M+H]$^+$).

Step c:

Preparation of 9H-pyrido[3,4-b]indole-1-carbaldehyde (2). To a stirred solution of ethyl-9H-pyrido[3,4-b]indole-1-carboxylate, 1, (1.26 g, 5.24 mmol) in CH$_2$Cl$_2$ (50 mL) was added a DIBAL-H solution (1.0 M in toluene; 36.0 mL, 36.71 mmol) at −50° C. The mixture was stirred at −50° C. for 10 min and quenched by sequential addition of methanol (14.0 mL) and 10% NaOH (10 mL) at −50° C. Then the mixture was stirred at ambient temperature for an additional 1 h. The precipitates were removed by filtration through Celite and washed with CHCl$_3$-methanol (10:1). The combined filtrates were washed with brine, dried over sodium sulfate and concentrated under reduced pressure. The product was purified by chromatography on silica gel (2-20% methanol/CH$_2$Cl$_2$) to afford 0.46 g (45% yield) of β-carboline-1-carbaldehyde, 2: $^1$H NMR (400 MHz, CDCl$_3$) δ 10.33 (s, 1H), 10.04 (bs, 1H), 8.63 (d, J=5.2 Hz, 1H), 8.18-8.15 (m, 2H), 7.64-7.57 (m, 2H), 7.35 (dt, J=1.6, 7.6 Hz, 1H); ESI$^+$ MS: m/z (rel intensity) 197.0 (100, [M+H]$^+$).

Steps d and e:

Preparation of tert-butyl 4-(5,6,7,8-tetrahydroquinolin-8-ylamino)butylcarbamate (3). To a solution of 6,7-dihydroquinolin-8(5H)-one (2.0 g, 13.6 mmol) in ethanol (15 mL) was added concentrated acetic acid (5 drops), tert-butyl 4-aminobutylcarbamate (2.7 g, 14.3 mmol) and 4 Å molecular sieves. The reaction mixture was heated at 150° C. in microwave reactor for 10 min. The mixture was cooled to room temperature and NaBH$_4$ (0.8 g, 20.4 mmol) was added all at once. The crude reaction mixture was absorbed onto silica gel and the product purified by silica gel chromatography (0% to 10% methanol/CH$_2$Cl$_2$) to afford the desired product: ESI$^+$ MS: m/z (rel intensity) 320.2 (100, [M+H]$^+$).

Step f:

Preparation of tert-butyl 4-(((9H-pyrido[3,4-b]indol-1-yl)methyl)(5,6,7,8-tetrahydroquinolin-8-yl)amino)butylcarbamate (4). A heavy-walled Pyrex tube was charged with a solution of 9H-pyrido[3,4-b]indole-1-carbaldehyde, 2, (0.20 g, 1.02 mmol) in 1,2-dichloroethane (5 mL). This solution was treated with tert-butyl 4-(5,6,7,8-tetrahydroquinolin-8-ylamino)butylcarbamate, 3, (0.36 g, 1.12 mmol), sodium triacetoxyborohydride (0.43 g, 2.04 mmol), 4 Å molecular sieves and a catalytic amount of acetic acid (2 drops). The reaction mixture was exposed to microwave irradiation for 10 min at a temperature of 100° C. After the irradiation, the reaction mixture was cooled with high-pressure air until the temperature had fallen below 40° C. The crude reaction mixture was poured onto a saturated aqueous solution of sodium bicarbonate. The product was extracted with dichloromethane. The combined organic layers were washed with brine, dried over potassium carbonate, filtered and concentrated in vacuo. The crude product was purified by silica gel chromatography (0-5% methanol/CH$_2$Cl$_2$) to afford 0.12 g (24% yield) of desired product 4: $^1$H NMR (400 MHz, CDCl$_3$) δ 13.43 (bs, 1H), 8.67 (d, J=3.6 Hz, 1H), 8.24 (d, J=5.6 Hz, 1H), 8.10 (d, J=7.6 Hz, 1H), 7.82 (d, J=5.2 Hz, 1H), 7.69 (d, J=8.4 Hz, 1H), 7.54 (dt, J=1.2, 7.4 Hz, 1H), 7.41 (d, J=7.2 Hz, 1H), 7.21 (dt, J=0.8, 7.2 Hz, 1H), 7.14 (dd, J=4.8, 7.6 Hz, 1H), 4.28-4.02 (m, 4H), 2.90-2.60 (m, 5H), 2.44-2.26 (m, 2H), 2.12-2.04 (m, 1H), 1.96-1.84 (m, 1H), 1.80-1.65 (m, 1H), 1.44-1.25 (m, 1H), 1.33 (s, 9H), 1.22-1.12 (m, 1H); ESI$^+$ MS: m/z (rel intensity) 500.2 (100, [M+H]$^+$).

Step g:

Preparation of N-((9H-pyrido[3,4-b]indol-1-yl)methyl)-N-(4-aminobutyl)-5,6,7,8-tetrahydroquinolin-8-amine tetrahydrochloride (A). A solution of tert-butyl 4-(((9H-pyrido[3,4-b]indol-1-yl)methyl)(5,6,7,8-tetrahydroquinolin-8-yl)amino)-butylcarbamate, 4, (0.12 g, 0.24 mmol) in methanol (5 mL) was treated with thionyl chloride (1 mL) at room temperature. The resulting mixture was stirred for 30 min. The reaction mixture was then concentrated and dried under reduced pressure to afford 0.11 g (80% yield) of the desired product A: $^1$H NMR (400 MHz, d$^6$-DMSO) δ 13.49 (bs, 1H), 8.80-8.41 (m, 3H), 8.00-7.82 (m, 3H), 7.80 (d, J=8.0 Hz, 1H), 7.78-7.70 (m, 1H), 7.39 (t, J=7.2 Hz, 1H), 4.95-4.85 (m, 1H), 4.68-4.50 (m, 2H), 2.98-2.82 (m, 2H), 2.61-2.50 (m, 2H), 2.47-2.35 (m, 3H), 2.12-1.94 (m, 2H), 1.80-1.30 (m, 5H); ESI$^+$ MS: m/z (rel intensity) 400.2 (100, [M+H]$^+$).

SCHEME 2

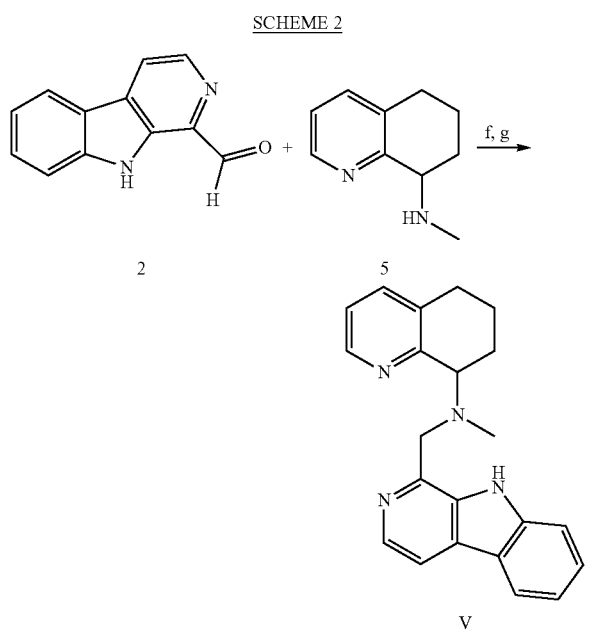

Reagents and Conditions:
(f) methanol, 65° C.;
(g) NaBH₄, methanol, 0° C. to room temperature.

Example 3

Preparation of N-((9H-pyrido[3,4-b]indol-1-yl)methyl)-N-methyl-5,6,7,8-tetrahydroquinolin-8-amine tetrahydrochloride (V)

A solution of β-carboline-1-carbaldehyde, 2, (0.10 g, 0.50 mmol) in methanol (10 mL) was treated with N-methyl-5,6,7,8-tetrahydroquinolin-8-amine, 5, (0.09 g, 0.56 mmol). The resulting mixture was warmed to 65° C. and stirred for 18 h. The reaction mixture was then cooled to 0° C. and sodium borohydride (0.08 g, 2.03 mmol) was added portionwise. The reaction mixture was slowly warmed to room temperature and stirred for 1 h. A saturated aqueous solution of sodium bicarbonate was added. The product was extracted with dichloromethane. The combined organic layers were dried over potassium carbonate, filtered and concentrated in vacuo. The product was purified by silica gel chromatography (0-5% methanol/CH₂Cl₂) to afford 0.07 g (40% yield) of the desired product V: $^1$H NMR (400 MHz, CDCl₃) δ13.20 (bs, 1H), 8.73 (d, J=4.4 Hz, 1H), 8.27 (d, J=5.6 Hz, 1H), 8.12 (d, J=7.6 Hz, 1H), 7.85 (d, J=5.2 Hz, 1H), 7.70 (d, J=8.4 Hz, 1H), 7.55 (t, J=7.6 Hz, 1H), 7.44 (d, J=8.0 Hz, 1H), 7.25-7.15 (m, 2H), 4.26-4.18 (m, 3H), 2.94-2.72 (m, 2H), 2.34-2.18 (m, 1H), 2.24 (s, 3H), 2.15-2.05 (m, 1H), 2.04-1.90 (m, 1H), 1.85-1.70 (m, 1H); ESI+ MS: m/z (rel intensity) 343.1 (90, [M+H]+).

SCHEME 3

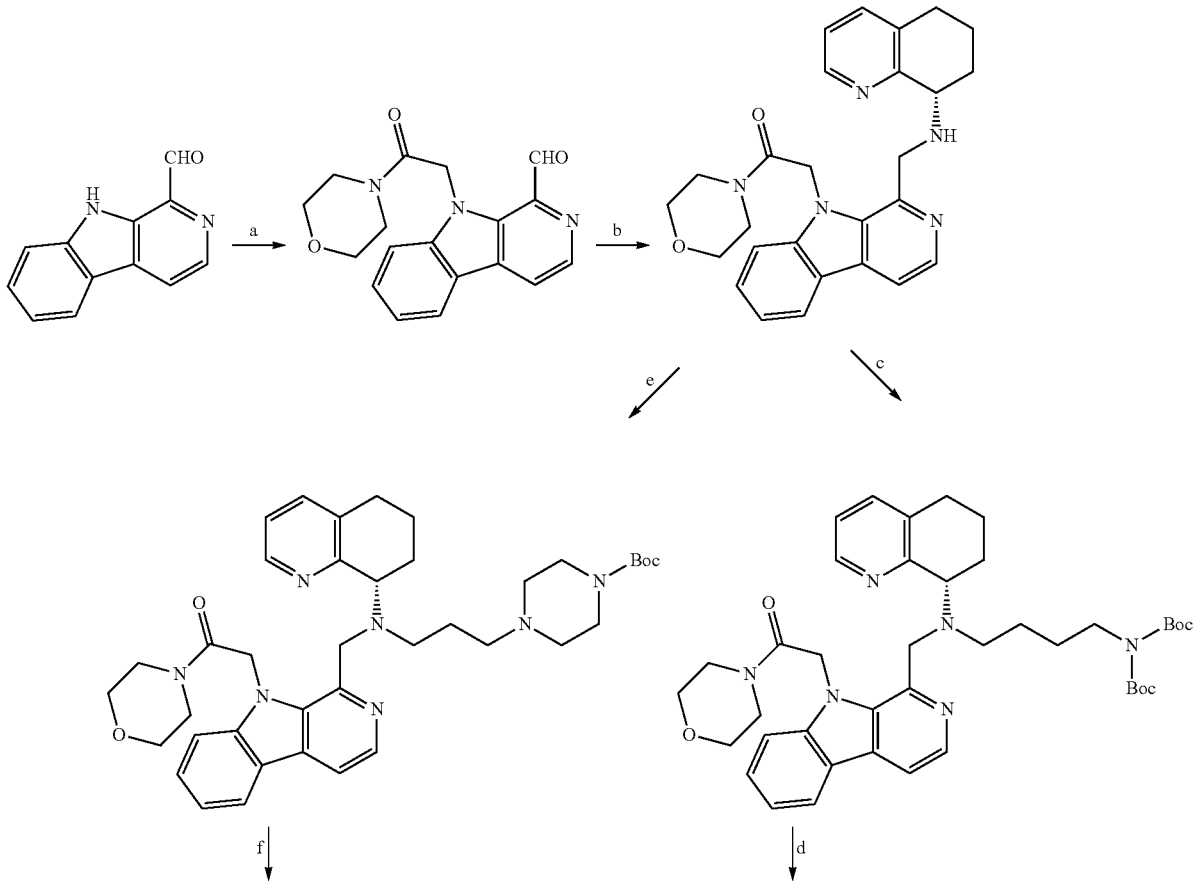

-continued

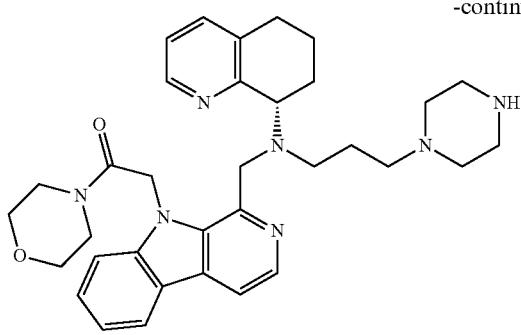

compound 1162

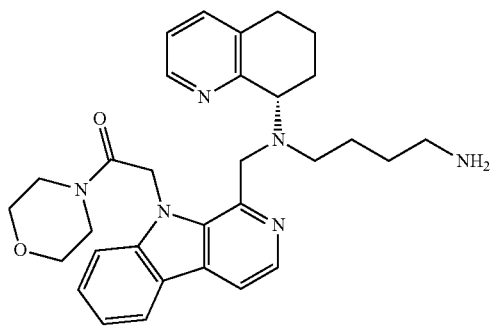

compound 1128

Reagents and Conditions:
(a) Cs₂CO₃, N-(chloroacetyl)morpholine, 65° C.;
(b) (S)-5,6,7,8-tetrahydroquinolin-8-amine, Na(OAc)₃BH, rt;
(c) bis-1-(N-tert-butoxycarbonyl)-4-oxobutylcarbamate, Na(OAc)₃BH, rt;
(d) trifluoroacetic acid, rt;
(e) tert-butyl-4-(3-bromopropyl)piperazine-1-carboxylate, triethylamine, reflux in acetonitrile;
(f) trifluoroacetic acid, ambient temp.

Example 4

Preparation of Compound 1128 of Scheme 3

Step a:
Preparation of 9-(2-morpholino-2-oxoethyl)-9H-pyrido[3,4-b]indole-1-carbaldehyde: 4.00 mmol of cesium carbonate was added to the solution of 2.00 mmol of carboline aldehyde in 20 ml DMF. After stirring 1 hour at room temperature 3.00 mmol of N-(chloroacetyl)morpholine was added to the reaction mixture. The reaction mixture was heated to 65° C. for 24 hours and then poured to ice-water. The precipitate was filtered off, and washed with water and dried. The product was pure enough to use for the next step (75% yield). ESI⁺ MS: m/z (rel intensity) 324.10 (100, [M+H]⁺). ¹H-NMR (400 MHz, CDCl₃): δ 10.21 (s, 1H), 8.66 (d, 1H, J=4.8 Hz), 8.20 (d, 1H, J=4.4 Hz), 8.17 (d, 1H, 6.8 Hz), 7.64 (dt, 1H, J=1.2, 7.2 Hz), 7.38 (q, 2H, J=7.2 Hz), 5.81 (s, 2H), 3.92 (t, 2H, J=4.4 Hz), 3.74 (t, 4H, J=4.8 Hz), 3.61 (t, 2H, J=4.8 Hz).

Step b:
Preparation of (S)-1-morpholino-2-(1-((5,6,7,8-tetrahydroquinolin-8-ylamino)methyl)-9H-pyrido[3,4-b]indol-9-yl)ethanone. 1.5 mmol of 9-(2-morpholino-2-oxoethyl)-9H-pyrido[3,4-b]indole-1-carbaldehyde, 1.5 mmol of (S)-5,6,7,8-tetrahydroquinolin-8-amine, and 3.00 mmol of sodium triacetoxyborohydride in 20 ml dichloromethane were stirred for 2 hours at room temperature, then reaction was quenched with saturated sodium bicarbonate solution. Organic layer was dried over magnesium sulfate, filtered off, and evaporated. Desired product was purified with column chromatography using dichloromethane:methanol:NH4OH (9:1:0.1) solvent system (85% yield). ESI⁺ MS: m/z (rel intensity) 456.2 (100, [M+H]⁺). ¹H-NMR (400 MHz, CDCl₃): δ 8.38 (d, 1H, J=4.8 Hz), 8.36 (d, 1H, J=1.6 Hz), 8.12 (d, 1H, J=7.6 Hz), 7.92 (d, 1H, J=5.6 Hz), 7.55 (dt, 1H, J=1.2, 8.0 Hz), 7.37 (d, 1H, J=7.6 Hz), 7.29 (q, 2H, J=4.8 Hz), 7.07 (q, 1H, 4.8 Hz), 6.11 (d, 1H, J=18.0 Hz), 5.74 (d, 1H, J=17.6 Hz), 4.46 (d, 1H, J=12.0 Hz), 4.33 (d, 1H, J=12.0 Hz), 4.00 (t, 1H, J=5.6 Hz), 3.82-3.76 (m, 1H), 3.73-3.60 (m, 6H), 3.55-3.50 (m, 1H), 2.78 (t, 2H, J=6.4 Hz), 2.18-2.08 (m, 1H), 1.96-1.66 (m, 4H).

Step c:
Preparation of (5)-4-(((9-(2-morpholino-2-oxoethyl)-9H-pyrido[3,4-b]indol-1-yl)methyl)(5,6,7,8-tetrahydroquinolin-8-yl)-(4-(Bis-N-tertbutoxycarbonyl)amino)butylcarbamate. 1.00 mmol of (S)-1-morpholino-2-(1-((5,6,7,8-tetrahydroquinolin-8-ylamino)methyl)₉H-pyrido[3,4-b]indol-9-yl)ethanone, 1.00 mmol of Bis-1-(N-tertbutoxycarbonyl)-4-oxobutylcarbamate, and 2.00 mmol of sodium triacetoxyborohydride in 20 ml 1,2-dichloroethane were stirred at room temperature for 2 hours. The reaction was quenched with saturated sodium bicarbonate solution. Organic layer was dried over magnesium sulfate, filtered off, and evaporated. The desired product was purified with column chromatography using dichloromethane:methanol:NH₄OH (9:1:0.1) in 50% dichloromethane (95% yield). ESI⁺ MS: m/z (rel intensity) 727.3 (100, [M+H]⁺). ¹H-NMR (400 MHz, CDCl₃): δ 8.29 (d, 1H, J=5.2 Hz), 8.21 (d, 1H, J=4.4 Hz), 8.09 (d, 1H, J=7.6 Hz), 7.86 (d, 1H, J=4.8 Hz), 7.56 (dt, 1H, J=1.2, 8.0 Hz), 7.30-7.23 (m, 3H), 7.17 (d, 1H, 18.4 Hz), 6.88 (dt, 1H, J=3.2, 4.4 Hz), 5.80 (d, 1H, J=17.2 Hz), 4.36 (s, 2H), 4.13 (q, 1H, J=6.8 Hz), 3.97 (d, 1H, J=12.8 Hz), 3.89 (d, 1H, J=14.4 Hz), 3.81-3.77 (m, 1H), 3.67-3.56 (m, 4H), 3.46-3.33 (m, 2H), 3.11-3.01 (m, 2H), 2.79-2.65 (m, 1H), 2.64-2.60 (m, 2H), 2.48-2.31 (m, 3H), 2.10-2.04 (m, 2H), 1.93-1.86 (m, 1H), 1.68-1.55 (m, 2H), 1.50 (s, 9H), 1.37 (s, 9H).

Step d:
Preparation of (S)-2-(1-(((4-aminobutyl)(5,6,7,8-tetrahydroquinolin-8-yl)amino)methyl)-9H-pyrido[3,4-b]indol-9-yl)-1-morpholinoethanone. 0.95 mmol of (S)-4-(((9-(2-morpholino-2-oxoethyl)-9H-pyrido[3,4-b]indol-1-yl)methyl)(5,6,7,8-tetrahydroquinolin-8-yl)-(4-(Bis-N-tertbutoxycarbonyl)amino)butylcarbamate was dissolved in 2 ml of dichloromethane and treated with 2 ml of trifluoroacetic acid. After the reaction was stirred at room temperature for 2 hours it was cooled to 0° C. with ice bath and then neutralized with 1M NaOH solution carefully. The mixture was warmed to ambient temperature. The organic layer was separated, dried over magnesium sulfate, filtered off, and evaporated. The desired product was purified with column chromatography using dichloromethane:methanol:NH₄OH (9:1:0.1). ESI⁺ MS: m/z (rel intensity) 527.2 (100, [M+H]⁺). ¹H-NMR (400 MHz, CDCl₃): δ 8.31 (d, 1H, J=5.2 Hz), 8.25 (d, 1H, J=4.0 Hz), 8.11 (d, 1H, J=8.0 Hz), 7.89 (d, 1H, J=4.8 Hz), 7.57 (dt, 1H, J=1.2, 8.0 Hz), 7.31-7.25 (m, 3H), 7.18 (d, 1H, 19.6 Hz), 6.90 (dt, 1H, J=2.8, 4.8 Hz), 5.76 (d, 1H, J=17.2 Hz), 4.36 (s, 2H), 4.12 (t, 1H, J=9.6 Hz), 3.97 (d, 1H, J=12.8 Hz), 3.89 (d, 1H, J=13.6 Hz), 3.79 (td, 1H, J=3.6, 12.0 Hz), 3.70-3.55 (m, 3H), 3.45-

3.40 (m, 1H), 3.35-3.30 (m, 1H), 2.82-2.76 (m, 1H), 2.68-2.59 (m, 2H), 2.42-2.32 (m, 2H), 2.21-2.17 (m, 2H), 2.10-2.04 (m, 2H), 1.63-1.59 (m, 1H), 1.25 (s, 2H), 0.97-0.76 (m, 4H). Elemental Analysis (C/H/N): $C_{31}H_{38}N_6O_2 \times 1.25$ mol $H_2O$; Calculated: 67.80/7.43/15.30. Found: 67.65/7.12/15.21.

Example 5

Preparation of Compound 1162 of Scheme 3

Step e:

Preparation of (S)-tert-butyl 4-(34(9-(2-morpholino-2-oxoethyl)-9H-pyrido[3,4-b]indol-1-yl)methyl)(5,6,7,8-tetrahydroquinolin-8-yl)amino)propyl)piperazine-1-carboxylate. 1.00 mmol of S)-1-morpholino-2-((5,6,7,8-tetrahydroquinolin-8-ylamino)methyl)₉H-pyrido[3,4-b]indol-9-yl)ethanone, 1.2 mmol tert-butyl-4-(3-bromopropyl)piperazine-1-carboxylate, and 2.5 mmol triethyl amine in 10 ml acetonitrile were heated to reflux for overnight. The reaction was cooled to room temperature and poured to saturated sodium bicarbonate solution. The mixture was extracted with ethyl acetate. Organic layer was dried over magnesium sulfate, filtered and evaporated. Desired product was purified with column chromatography using dichloromethane:methanol:NH₄OH (9:1:0.1) (46.88% yield). ESI⁺ MS: m/z (rel intensity) 682.4 (100, [M+H]⁺). ¹H-NMR (400 MHz, CDCl₃): δ 8.32 (d, 1H, J=4.4 Hz), 8.12 (d, 1H, J=7.6 Hz), 7.91 (d, 1H, J=4.8 Hz), 7.57 (t, 1H, J=8.0 Hz), 7.38 (d, 1H, J=17.6 Hz), 7.32-7.27 (m, 3H), 6.97 (dt, 1H, J=3.2, 4.4 Hz), 5.62 (d, 1H, J=17.6 Hz), 4.36 (s, 2H), 4.14 (t, 1H, J=8.8 Hz), 4.01 (d, 1H, J=14.4 Hz), 3.93 (d, 1H, J=14.0 Hz), 3.81-3.51 (m, 6H), 3.46-3.20 (m, 4H), 3.08-2.96 (m, 2H), 2.88-2.58 (m, 4H), 2.41-2.32 (m, 2H), 2.11-2.02 (m, 2H), 1.90-1.81 (m, 2H), 1.75-1.59 (m, 6H), 1.40 (s, 9H).

Step f:

Preparation of (S)-1-morpholino-2-(1(((3-(piperazin-1-yl)propyl)(5,6,7,8-tetrahydroquinolin-8-yl)amino)methyl)₉H-pyrido[3,4-b]indol-9-yl)ethanone. 0.50 mmol of (S)-tert-butyl 4-(3-(((9-(2-morpholino-2-oxoethyl)-9H-pyrido[3,4-b]indol-1-yl)methyl)(5,6,7,8-tetrahydroquinolin-8-yl)amino)propyl)piperazine-1-carboxylate was dissolved in 2 ml of dichloromethane and treated with 2 ml of trifluoroacetic acid. After the reaction was stirred at ambient temperature for 2 hours it was cooled to 0° C. with ice bath and then neutralized with 1M NaOH solution carefully. Let the mixture warmed up to room temperature. The organic layer was separated, dried over magnesium sulfate, filtered off, and evaporated. The desired product was purified with column chromatography using dichloromethane:methanol:NH4OH (9:1:0.1). ESI⁺ MS: m/z (rel intensity) 582.3 (100, [M+H]⁺). ¹H-NMR (400 MHz, CDCl₃): δ 8.31 (d, 1H, J=5.6 Hz), 8.28 (d, 1H, J=4.8 Hz), 8.11 (d, 1H, J=9.2 Hz), 7.89 (d, 1H, J=5.2 Hz), 7.57 (t, 1H, J=6.8 Hz), 7.32-7.25 (m, 5H), 6.94 (dt, 1H, J=2.8, 4.8 Hz), 5.67 (d, 1H, J=16.4 Hz), 4.37 (s, 2H), 4.14 (t, 1H, J=9.2 Hz), 4.05 (d, 1H, J=16.8 Hz), 3.93 (d, 1H, J=14.8 Hz), 3.83-3.76 (m, 1H), 3.72-3.47 (m, 4H), 3.45-3.30 (m, 1H), 3.29-3.26 (m, 1H), 2.88-2.51 (m, 6H), 2.41-2.32 (m, 2H), 2.11-2.02 (m, 2H), 1.90-1.59 (m, 8H), 1.02-0.96 (m, 1H), 0.95-0.80 (m, 1H). Elemental Analysis (C/H/N): $C_{34}H_{43}N_2O_2 \times$ 0.95 mol $H_2O$; Calculated: 68.19/7.56/16.37. Found: 68.18/7.38/16.23.

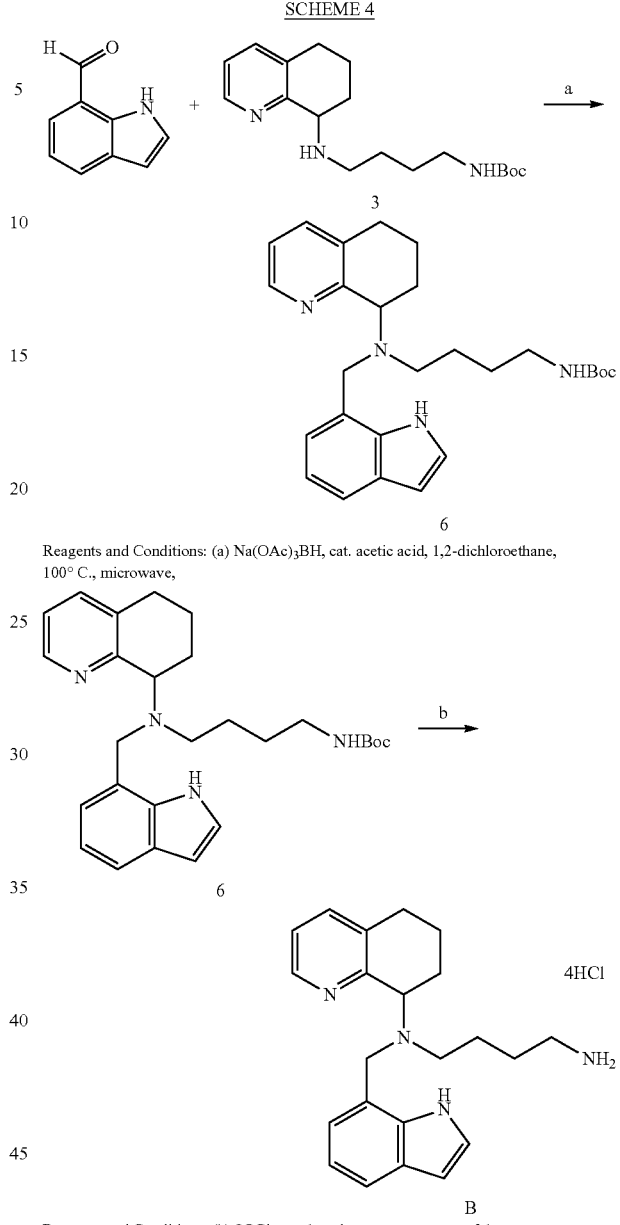

SCHEME 4

Reagents and Conditions: (a) Na(OAc)₃BH, cat. acetic acid, 1,2-dichloroethane, 100° C., microwave.

Reagents and Conditions: (b) SOCl₂, methanol, room temperature, 2 h.

Example 6

Preparation of N1-((1H-indol-7-yl)methyl)-N1-(5,6,7,8-tetrahydroquinolin-8-yl)butane-1,4-diamine (B)

Step a:

Preparation of tert-butyl 4-(((1H-indol-7-yl)methyl)(5,6,7,8-tetrahydroquinolin-8-yl)amino)butylcarbamate (6). A heavy-walled Pyrex tube was charged with a solution of indole-7-carboxaldehyde (0.50 g, 3.44 mmol) in 1,2-dichloroethane (5 mL). This solution was treated with tert-butyl 4-(5,6,7,8-tetrahydroquinolin-8-ylamino)butylcarbamate, 3, (1.21 g, 3.78 mmol), sodium triacetoxyborohydride (1.46 g, 6.88 mmol) and a catalytic amount of acetic acid (2 drops). The reaction mixture was exposed to microwave irradiation for 10 min at a temperature of 100° C. After the irradiation, the reaction tube was cooled with high-pressure air until the temperature had fallen below 40° C. The crude reaction mixture was poured onto a saturated aqueous solution of sodium bicarbonate. The product was extracted with dichloromethane. The combined organic layers were washed with brine, dried over potassium carbonate, filtered and concentrated in vacuo. The crude product was purified by silica gel chromatography (0-5% methanol/CH$_2$Cl$_2$) to afford 0.54 g (35% yield) of the desired product 6: $^1$H NMR (400 MHz, CDCl$_3$) δ 12.87 (bs, 1H), 8.56 (d, J=3.6 Hz, 1H), 7.53 (d, J=7.6 Hz, 1H), 7.41-7.37 (m, 2H), 7.10 (dd, J=5.2, 7.6 Hz, 1H), 6.97-6.88 (m, 2H), 6.51-6.49 (m, 1H), 4.26-4.20 (m, 2H), 3.96 (d, J=13.2 Hz, 1H), 3.60 (d, J=13.2 Hz, 1H), 2.92-2.72 (m, 3H), 2.65-2.55 (m, 2H), 2.50-2.40 (m, 1H), 2.29-2.20 (m, 1H), 2.14-2.04 (m, 1H), 1.95-1.68 (m, 2H), 1.47-1.15 (m, 2H), 1.39 (s, 9H); ESI$^+$ MS: m/z (rel intensity) 449.2 (100, [M+H]$^+$).

Step b:

Preparation of N1-((1H-indol-7-yl)methyl)-N1-(5,6,7,8-tetrahydroquinolin-8-yl)butane-1,4-diamine (B). A solution of tert-butyl 4-(((1H-indol-7-yl)methyl)(5,6,7,8-tetrahydroquinolin-8-yl)amino)butylcarbamate, 6, (0.27 g, 0.60 mmol) in methanol (5 mL) was treated with thionyl chloride (1 mL) at room temperature. The resulting mixture was stirred for 30 min. The reaction mixture was then concentrated and dried under reduced pressure to afford 0.26 g (87% yield) of the desired product, B: $^1$H NMR (400 MHz, d$^6$-DMSO) δ 11.97 (bs, 1H), 8.44 (d, J=4.8 Hz, 1H), 7.59 (d, J=7.2 Hz, 1H), 7.53 (d, J=7.2 Hz, 1H), 7.48-7.40 (m, 1H), 7.35-7.20 (m, 2H), 6.98 (t, J=6.8 Hz, 1H), 6.44 (bs, 1H), 4.90-4.78 (m, 2H), 3.60-3.53 (m, 2H), 3.10-3.00 (m, 2H), 2.80-2.60 (m, 4H), 2.50-2.39 (m, 1H), 2.30-1.40 (m, 7H); ESI$^+$ MS: m/z (rel intensity) 349.2 (100, [M+H]$^+$).

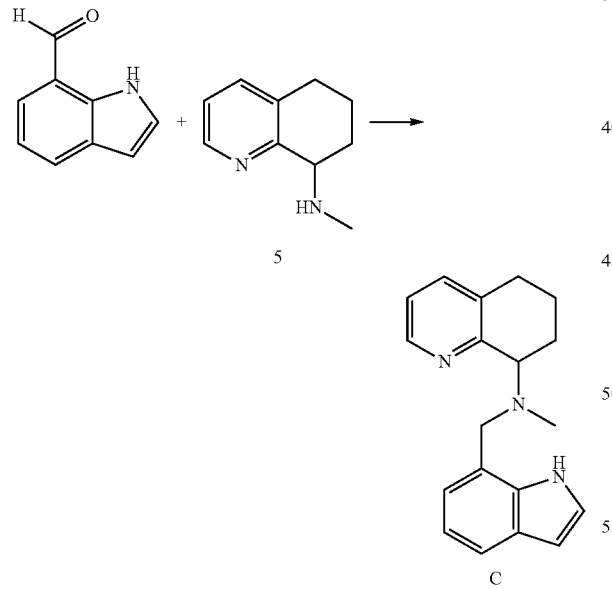

SCHEME 5

Example 7

Preparation of N-((1H-indol-7-yl)methyl)-N-methyl-5,6,7,8-tetrahydroquinolin-8-amine (C)

A solution of indole-7-carboxaldehyde (0.48 g, 3.36 mmol) in 1,2-dichloroethane (10 mL) was treated with N-methyl-5,6,7,8-tetrahydroquinolin-8-amine, 5, (0.60 g, 3.70 mmol), sodium triacetoxyborohydride (1.07 g, 5.05 mmol) and a catalytic amount of acetic acid (2 drops). The resulting mixture was warmed to 65° C. and stirred for 2 h. The reaction mixture was cooled to room temperature and a saturated aqueous solution of sodium bicarbonate was added. The product was extracted with dichloromethane. The combined organic layers were dried over potassium carbonate, filtered and concentrated in vacuo. The product was purified by silica gel chromatography (0-5% methanol/CH$_2$Cl$_2$) to afford 0.75 g (76% yield) of the desired product: $^1$H NMR (400 MHz, CDCl$_3$) δ 12.69 (bs, 1H), 8.61 (d, J=4.4 Hz, 1H), 7.85-7.81 (m, 1H), 7.68-7.65 (m, 1H), 7.59 (d, J=7.2 Hz, 1H), 7.44-7.38 (m, 2H), 7.12 (dd, J=4.4, 7.2 Hz, 1H), 7.03-6.96 (m, 2H), 6.55 (t, J=2.0 Hz, 1H), 4.22-4.17 (m, 1H), 4.00 (d, J=13.4 Hz, 1H), 3.84 (t, J=6.8 Hz, 1H), 3.73 (d, J=13.4 Hz, 1H), 3.42 (t, J=6.8 Hz, 1H), 2.92-2.72 (m, 2H), 2.28 (s, 3H), 2.14-2.04 (m, 1H), 2.00-1.88 (m, 1H), 1.85-1.70 (m, 1H); ESI$^+$ MS: m/z (rel intensity) 292.1 (90, [M+H]$^+$).

The skilled artisan will recognize that other compounds described in Table 1 can be prepared in a similar manner to the procedures described above, for example by substituting the appropriately substituted tetrahydroquinoline for compound 3.

Example 8

General Preparation of Compounds of Formulae (IB) and (IC)

Compounds of Formula (I), can have the following general structures (IB) and (IC):

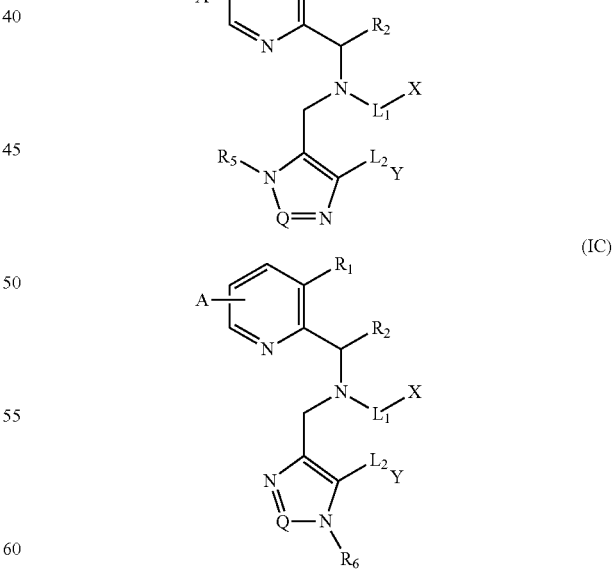

wherein R$_1$, R$_2$, R$_5$, R$_6$, L$_1$, L$_2$, X, Y, Q, A, and B are as defined herein. Specific embodiments of the compounds of Formula (IB) and (IC) are shown in Table 2, below. For each of the compounds of Table 2, Q is N.

TABLE 2
| Compound | —R5 | —R6 | —L2—Y | —L1—X |  |
|---|---|---|---|---|---|
| W | — | 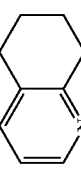 | H | CH3 | 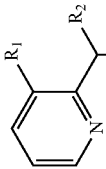 |
| X |  | — | H | CH3 | 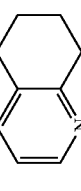 |
| Y | — | 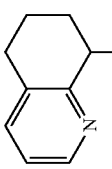 | H | CH3 | 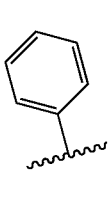 |
| Z | — | 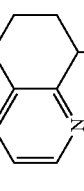 | H | 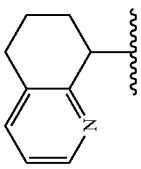 | 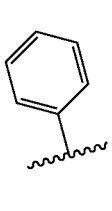 |
| AA | 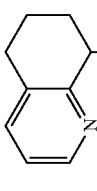 | — | H | 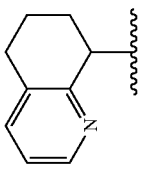 |  |

TABLE 2-continued

| Compound | —R₅ | —R₆ | —L₂—Y | —L₁—X | R₁ R₂ structure |
|---|---|---|---|---|---|
| AB | — | phenyl | H | pyridylmethyl-NH-(CH₂)ₙ- | tetrahydroquinoline |
| AC | — | phenyl | H | imidazolinyl-NH-(CH₂)ₙ- | tetrahydroquinoline |
| AD | — | 2-(aminomethyl)phenyl | H | CH₃ | tetrahydroquinoline |
| AE | — | 2-(3-aminopropyl)phenyl | H | CH₃ | tetrahydroquinoline |
| AF | — | 3-(aminomethyl)phenyl | H | CH₃ | tetrahydroquinoline |

TABLE 2-continued
| Compound | —R₅ | —R₆ | —L₂—Y | —L₁—X | <br>R₁ R₂ |
|---|---|---|---|---|---|
| AG | — | 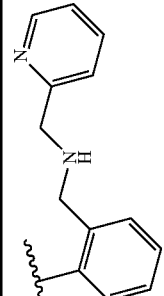 | H | CH₃ | 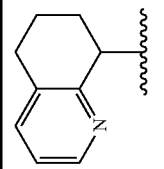 |
| AH | — | 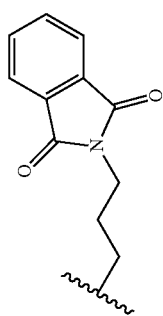 | H | CH₃ | 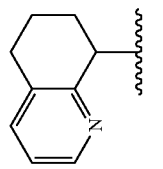 |
| AI | — | 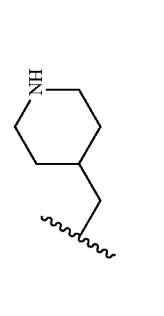 | H | CH₃ | 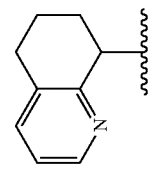 |
| AJ | — | 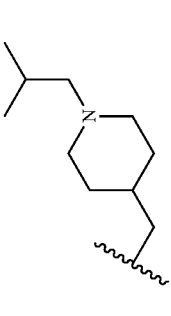 | H | CH₃ | 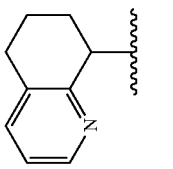 |
| AK |  | — | H | CH₃ | 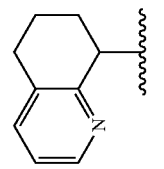 |

TABLE 2-continued

| Compound | —R₅ | —R₆ | —L₂—Y | —L₁—X | R₁ R₂ |
|---|---|---|---|---|---|
| AL | — | | H | CH₃ | |
| AM | — | | H | CH₃ | |
| AN | — | | H | CH₃ | |
| AO | — | | H | CH₃ | |
| AP | — | | H | CH₃ | |

US 9,314,468 B2

TABLE 2-continued

| Compound | —R₅ | —R₆ | —L₂—Y | —L₁—X | R₁ R₂ structure |
|---|---|---|---|---|---|
| AQ | — | benzyl | H | CH₃ | tetrahydroquinoline |
| AR | — | benzyl | H | (CH₂)₅NH₂ | tetrahydroquinoline |
| AS | — | isobutenyl | H | (CH₂)₅NH₂ | tetrahydroquinoline |
| AT | — | H | piperidinylmethyl (NH) | CH₃ | tetrahydroquinoline |
| AU | — | H | N-(imidazolylmethyl)piperidinylmethyl | CH₃ | tetrahydroquinoline |
| AV | — | H | N-(pyridylmethyl)piperidinylmethyl | CH₃ | tetrahydroquinoline |

TABLE 2-continued
| Compound | —R5 | —R6 | —L2—Y | —L1—X | R1, R2 group |
|---|---|---|---|---|---|
| AW | — | H | 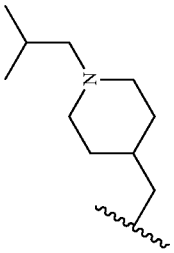 | CH3 |  |
| AX | — | H | 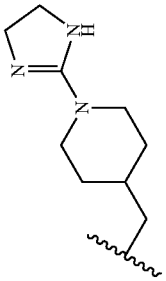 | CH3 | 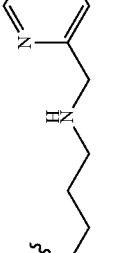 |
| AX1 | — | H | 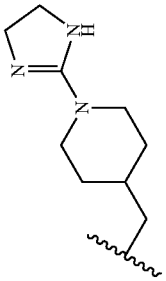 | CH3 | 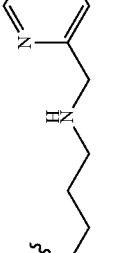 |
| AX2 | — | H | 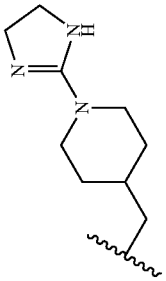 | CH3 | 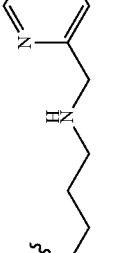 |
| AX3 | — | H | 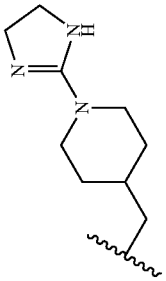 | CH3 | 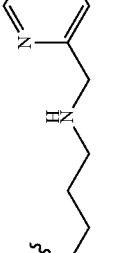 |

TABLE 2-continued
| Compound | —R$_5$ | —R$_6$ | —L$_2$—Y | —L$_1$—X | (R$_1$/R$_2$ group) |
|---|---|---|---|---|---|
| AX4 | — | H | 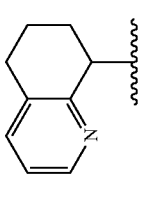 | CH$_3$ | 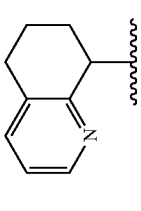 |
| AX5 | — | 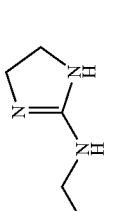 | 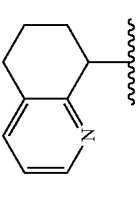 | CH$_3$ | 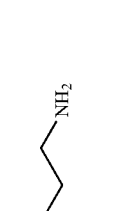 |
| AX6 | — | 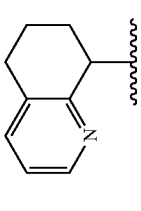 | (piperidine-NH with CH$_2$ linker) | CH$_3$ | (tetrahydroquinoline) |

SCHEME 6

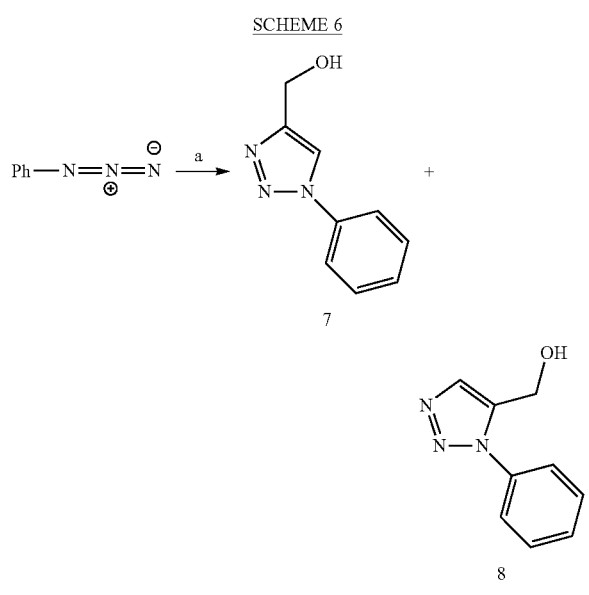

Reagents and Conditions: (a) propargyl alcohol, neat, 90° C.

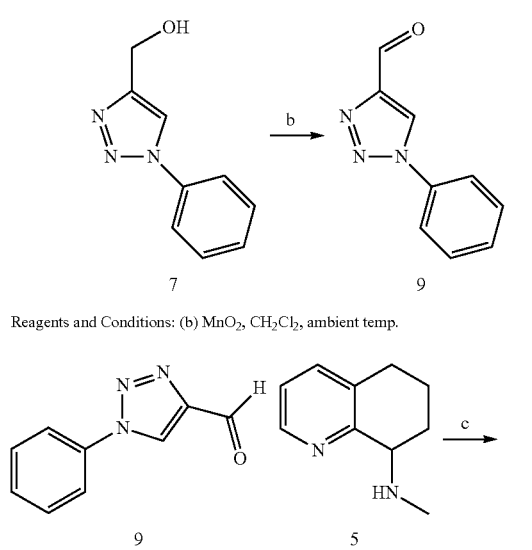

Reagents and Conditions: (b) MnO₂, CH₂Cl₂, ambient temp.

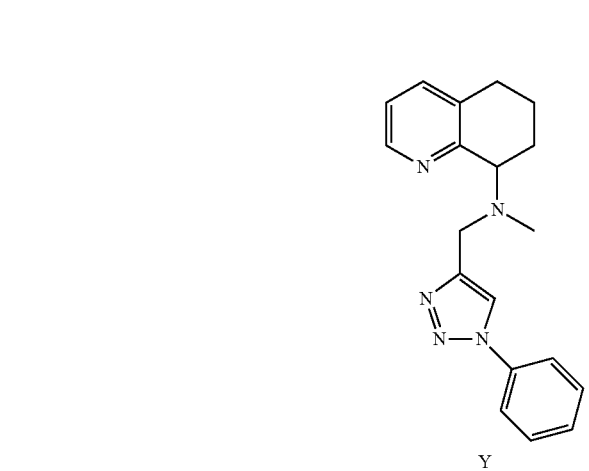

Reagents and Conditions: (c) Na(OAc)₃BH, cat. acetic acid, dichloroethane, 65° C.;

Example 9

Preparation of N-41H-benzo[d]imidazol-2-yl)methyl)-N-(4-aminobutyl)-5,6,7,8-tetrahydroquinolin-8-amine tetrahydrochloride (Y)

Step a:

Preparation of (1-phenyl-1H-1,2,3-triazol-4-yl)methanol (7). Phenyl azide (2.02 g, 17.0 mmol) was dissolved in neat propargyl alcohol (3 mL) and the mixture was heated to 90° C. for 2 h. The reaction mixture was cooled to room temperature and the reaction mixture was diluted into diethyl ether and left overnight during which time 7 precipitated as a crystalline solid to afford 1.03 g (35%) of the desired product 7 while the mother liquor contained primarily the regioisomer 9: $^1$H NMR (400 MHz, CDCl₃) δ 7.97, (s, 1H), 7.70, (d, J=8.40 Hz, 2H), 7.50, (m, 2H), 7.41 (m, 1H), 4.88, (d, J=6.00 Hz, 2H), 2.70, (bs, 1H).

Step b:

Preparation of 1-phenyl-1H-1,2,3-triazole-4-carbaldehyde (9). To a solution of (1-phenyl-1H-1,2,3-triazol-4-yl)methanol, 7, (1.03 g, 5.87 mmol) in CH₂Cl₂ (50 mL) was added MnO₂ (2.05 g, 23.5 mmol). The reaction mixture was stirred for 3 days at room temperature. The reaction mixture was then filtered through Celite® and the resulting filtrate was concentrated in vacuo. The crude material was purified by silica gel chromatography (0-5% methanol/dichloromethane) yielding 0.83 g (82%) of 9: $^1$H NMR (400 MHz, CDCl₃) δ 10.22 (s, 1H), 8.51 (s, 1H), 7.53, (d, J=9.6 Hz, 2H), 7.58-7.49, (m, 3H).

Step c:

Preparation of N-methyl-N-((1-phenyl-1H-1,2,3-triazol-4-yl)methyl)-5,6,7,8-tetrahydroquinolin-8-amine (Y). To a solution of 1-phenyl-1H-1,2,3-triazole-4-carbaldehyde, 9, (0.23 g, 1.35 mmol) in 1,2-dichloroethane (2 mL) was added N-methyl-5,6,7,8-tetrahydroquinolin-8-amine, 5, (0.20 g, 1.23 mmol), sodium triacetoxyborohydride (0.10 g, 1.60 mmol), and 3 drops of acetic acid. The reaction mixture was stirred for 16 h at room temperature. The reaction mixture was then poured into aqueous saturated NaCl (10 mL) and was extracted with ethyl acetate (10 mL). The organic phase was dried over MgSO₄, filtered, and concentrated in vacuo. The crude material was purified by silica gel chromatography (0-5% methanol/dichloromethane) yielding 35 mg (9%) of Y: $^1$H NMR (400 MHz, CDCl₃) δ 8.74 (s, 1H), 8.47 (s, 1H), 7.78, (d, J=8.4 Hz, 2H), 7.50-7.39, (m, 4H), 7.20, (m, 1H), 4.72, (d, J=13.6 Hz, 1H), 4.63-4.58 (m, 2H), 2.90-2.60 (m, 6H), 2.22-2.17 (m, 1H), 2.10-1.95, (m, 1H), 1.90-1.78, (m, 1H).

SCHEME 7

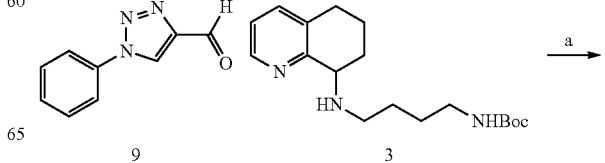

-continued

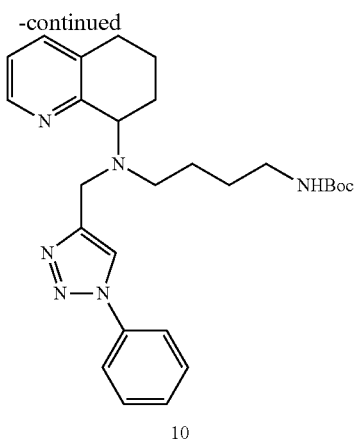

10

Reagents and Conditions:
(a) Na(OAc)₃BH, cat. acetic acid, dichloroethane, 65° C.

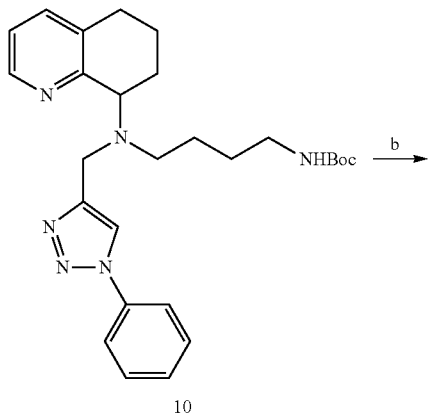

10

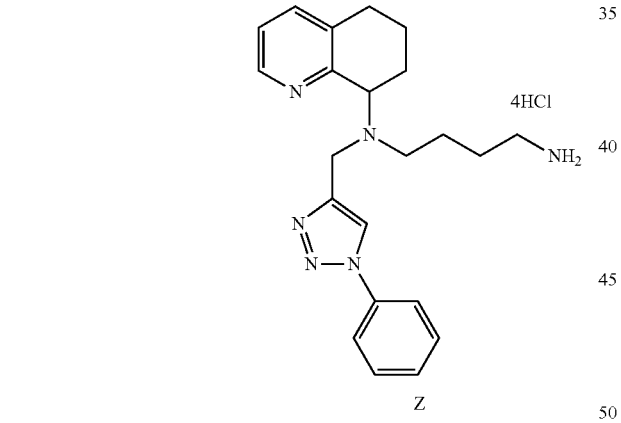

Z

Reagents and Conditions:
(b) SOCl₂, methanol, ambient temp.

Example 10

Preparation of N-(4-aminobutyl)-N-((1-phenyl-1H-1,2,3-triazol-4-yl)methyl)-5,6,7,8-tetrahydro-quinolin-8-amine tetrahydrochloride (Z)

Step a:

Preparation of tert-butyl 4-(((1-phenyl-1H-1,2,3-triazol-4-yl)methyl)(5,6,7,8-tetrahydroquinolin-8-yl)amino)butylcarbamate (10). To a solution of 1-phenyl-1H-1,2,3-triazole-4-carbaldehyde, 9, (0.54 g, 3.10 mmol) in 1,2-dichloroethane (15 mL) was added tert-butyl 4-(5,6,7,8-tetrahydroquinolin-8-ylamino)butylcarbamate, 3, (1.10 g, 3.40 mmol), sodium triacetoxyborohydride (1.00 g, 4.70 mmol), and 3 drops of acetic acid. The reaction mixture was stirred for 4 h at 65° C. The reaction mixture was then cooled to room temperature and poured into saturated aqueous NaHCO₃. The product was extracted with CH₂Cl₂ (3×10 mL) and the combined organic phases were dried over K₂CO₃, filtered, and concentrated in vacuo. The crude material was purified by silica gel chromatography (0-10% methanol/dichloromethane) yielding 850 mg (57%) of 13: $^1$H NMR (400 MHz, CDCl₃) δ 8.74 (d, J=4.0 Hz, 1H), 8.11 (s, 1H), 7.73, (d, J=8.0 Hz, 2H), 7.52-7.46, (m, 2H), 7.39, (d, J=7.6 Hz, 1H), 7.31, (d, J=8.0 Hz, 1H), 7.01, (dd, J=7.6, 4.4 Hz, 1H), 4.08, (m, 1H), 3.93, (d, J=14.8 Hz, 1H), 3.83, (d, J=14.8 Hz, 1H), 3.10-3.00 (m, 2H), 2.85-2.61 (m, 4H), 2.15-1.95 (m, 2H), 1.93-1.60, (m, 3H), 1.55-1.35, (m, 12H); ESI⁺ MS: m/z (rel intensity) 477 (100, M+H).

Step b:

Preparation of N-(4-aminobutyl)-N-((1-phenyl-1H-1,2,3-triazol-4-yl)methyl)-5,6,7,8-tetrahydro-quinolin-8-amine tetrahydrochloride (Z). To a solution of tert-butyl 4-(((1-phenyl-1H-1,2,3-triazol-4-yl)methyl)(5,6,7,8-tetrahydroquinolin-8-yl)-amino)butylcarbamate, 10 (0.85 g, 1.80 mmol) in methanol (20 mL) was added thionyl chloride (1.27 g, 10.7 mmol) at room temperature. The reaction mixture was stirred for 2 h. The reaction mixture was concentrated in vacuo yielding 790 mg (85%) of Z: $^1$H NMR (400 MHz, d₆-DMSO) δ 10.78, (bs, 1H), 8.93, (s, 1H), 8.51 (d, J=4.4 Hz, 1H), 8.25-8.06 (m, 3H), 7.84, (d, J=7.6 Hz, 2H), 7.71, (d, J=7.2 Hz, 2H), 7.62-7.55 (m, 2H), 7.52-7.46, (m, 1H), 7.40-7.35, (m, 1H), 4.77, (m, 1H), 4.50-4.38, (m, 2H), 3.32-3.22, (m, 1H), 3.15-3.02 (m, 1H), 2.88-2.66 (m, 4H), 2.50-2.39 (m, 1H), 2.15-2.00, (m, 2H), 1.95-1.68, (m, 3H), 1.64-1.50, (m, 2H), ESI⁺ MS: m/z (rel intensity) 377 (100, M+H).

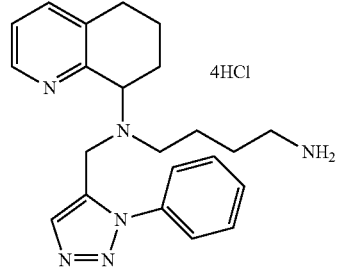

AA

Example 11

Preparation of N-(4-aminobutyl)-N4(3-phenyl-3H-1,2,3-triazol-4-yl)methyl)-5,6,7,8-tetrahydroquinolin-8-amine tetrahydrochloride (AA)

Compound AA was prepared using the procedure for compound Z, except that the aldehyde corresponding to compound 8 was used in place of compound 9. $^1$H NMR (400 MHz, d⁶-DMSO) δ 8.54 (d, J=4.8 Hz, 1H), 8.48 (s, 1H), 8.24-8.10 (m, 3H), 8.07 (d, J=7.6 Hz, 1H), 7.67-7.63 (m, 1H), 7.60-7.52 (m, 3H), 4.48-4.39 (m, 1H), 4.13 (d, J=15.2 Hz, 1H), 3.95 (d, J=15.2 Hz, 1H), 2.90-2.50 (m, 7H), 2.00-1.40 (m, 7H); ESI⁺ MS: m/z (rel intensity) 377.2 (90, [M+H]⁺).

SCHEME 8

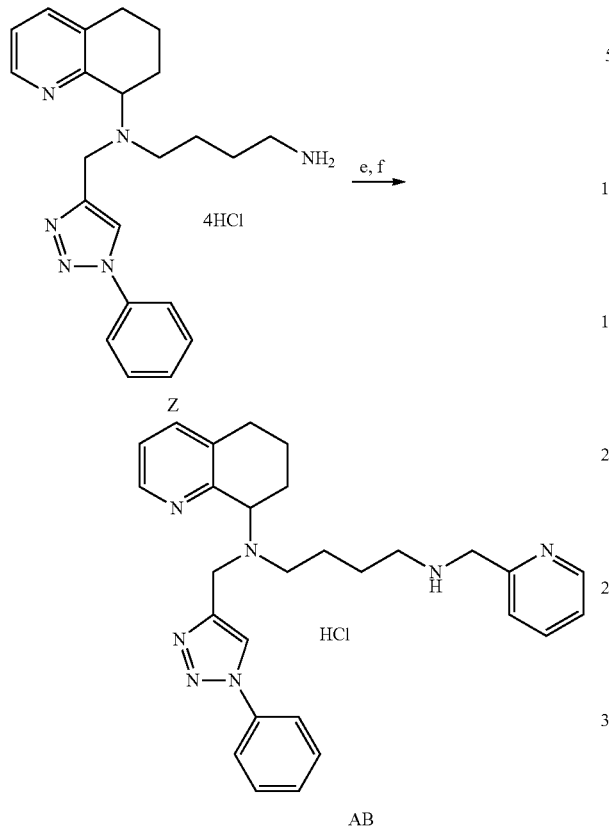

Reagents and Conditions:
(e) pyridinecarboxaldehyde, Na(OAc)$_3$BH, i-Pr$_2$NEt, cat. acetic acid, dichloroethane, 65° C.;
(f) 1N HCl, diethyl ether.

Example 12

Preparation of N1-((1-phenyl-1H-1,2,3-triazol-4-yl)methyl)-N4-(pyridin-2-ylmethyl)-N1-(5,6,7,8-tetrahydroquinolin-8-yl)butane-1,4-diamine hydrochloride (AB)

A solution of N-(4-aminobutyl)-N-((1-phenyl-1H-1,2,3-triazol-4-yl)methyl)-5,6,7,8-tetrahydro-quinolin-8-amine tetrahydrochloride, Z, (0.20 g, 0.38 mmol) in 1,2-dichloroethane (10 mL) was treated with Hünigs base (0.08 mL, 0.42 mmol), 2-pyridine carboxaldehyde (0.04 mL, 0.42 mmol), sodium triacetoxyborohydride (0.12 g, 0.57 mmol) and a catalytic amount of acetic acid (2 drops). The resulting mixture was warmed to 65° C. and stirred for 18 h. The reaction mixture was cooled to room temperature. A saturated aqueous solution of sodium bicarbonate was added. The product was extracted with dichloromethane. The combined organic layers were washed with brine, dried over potassium carbonate, filtered and concentrated in vacuo. The crude product was purified by silica gel chromatography (0-15% methanol/CH$_2$Cl$_2$) to afford 0.08 g (45% yield) of the desired product AB: $^1$H NMR (400 MHz, CDCl$_3$) δ 8.54-8.34 (m, 2H), 8.15 (bs, 1H), 7.71 (d, J=7.6 Hz, 1H), 7.60-7.52 (m, 1H), 7.45 (t, J=7.2 Hz, 2H), 7.39-7.32 (m, 1H), 7.32-7.22 (m, 2H), 7.14-7.04 (m, 1H), 7.02-6.84 (m, 1H), 4.15-4.04 (m, 1H), 3.92-3.70 (m, 4H), 2.82-2.50 (m, 6H), 2.15-2.04 (m, 1H), 2.04-1.82 (m, 1H), 1.82-1.78 (m, 1H), 1.70-1.40 (m, 5H); ESI$^+$ MS: m/z (rel intensity) 468.3 (100, [M+H]$^+$).

SCHEME 9

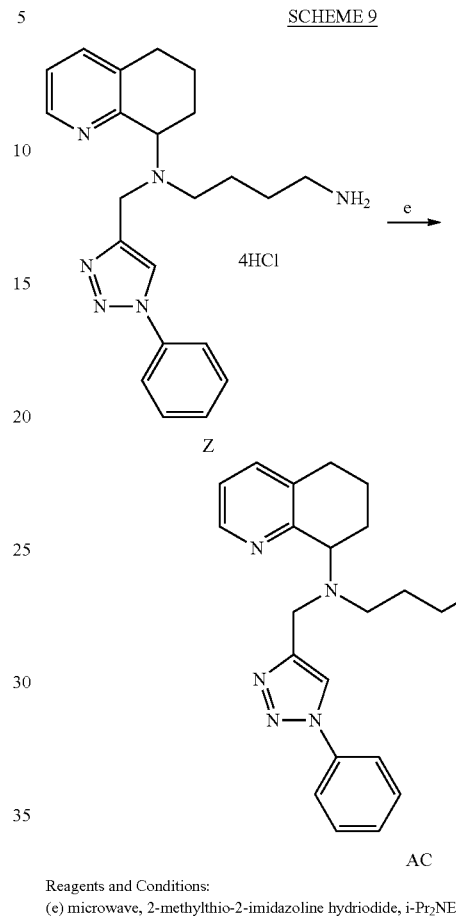

Reagents and Conditions:
(e) microwave, 2-methylthio-2-imidazoline hydriodide, i-Pr$_2$NEt, ethanol, 150° C., 10 min.

Example 13

Preparation of N1-(4,5-dihydro-1H-imidazol-2-yl)-N4((1-phenyl-1H-1,2,3-triazol-4-yl)methyl)-N4-(5,6,7,8-tetrahydroquinolin-8-yl)butane-1,4-diamine (AC)

A heavy-walled Pyrex tube was charged with a solution of Z (0.19 g, 0.36 mmol) in Ethanol (2 mL). The solution was treated with Hunig's base (N,N-diisopropylethylamine) (0.25 mL, 1.45 mmol) and 2-methylthio-2-imidazoline hydriodide (0.05 g, 0.40 mmol). The tube containing the resulting mixture was sealed with an aluminum crimp cap fitted with a silicon septum and then it was exposed to microwave irradiation for 10 min at a temperature of 150° C. After the irradiation, the reaction tube was cooled with high-pressure air until the temperature had fallen below 40° C. The crude reaction mixture was concentrated in vacuo. The crude product was purified by silica gel chromatography (0-10% methanol/CH$_2$Cl$_2$) to afford 0.07 g (44% yield) of the desired product AC: $^1$H NMR (400 MHz, CDCl$_3$) δ 9.13 (bs, 1H), 8.80 (t, J=5.6 Hz, 1H), 8.30 (d, J=3.6 Hz, 1H), 8.09 (s, 1H), 7.93 (bs, 1H), 7.75-7.68 (m, 2H), 7.48 (d, J=7.2 Hz, 2H), 7.44-7.32 (m, 2H), 7.05 (dd, J=4.8, 7.6 Hz, 1H), 4.12 (dd, J=6.0, 9.6 Hz, 1H), 4.00 (d, J=14.4 Hz, 1H), 3.79 (d, J=14.4

Hz, 1H), 3.40-3.22 (m, 2H), 2.80-2.48 (m, 4H), 2.20-2.10 (m, 1H), 2.05-1.90 (m, 1H), 1.90-1.45 (m, 6H); ESI⁺ MS: m/z (rel intensity) 445.2 (100, [M+H]⁺).

SCHEME 10

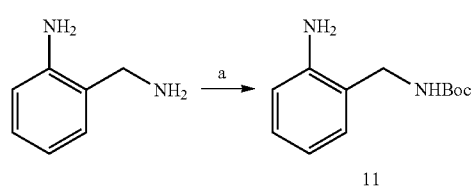

Reagents and Conditions: (a) Boc anhydride, triethylamine, THF, room temp.

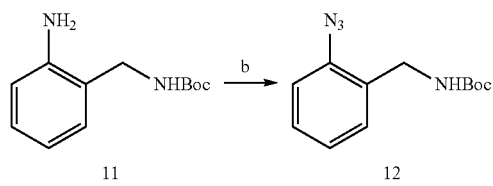

Reagents and Conditions: (b) t-BuONO, TMSN₃, CH₃CN, 0° C. to room temp.

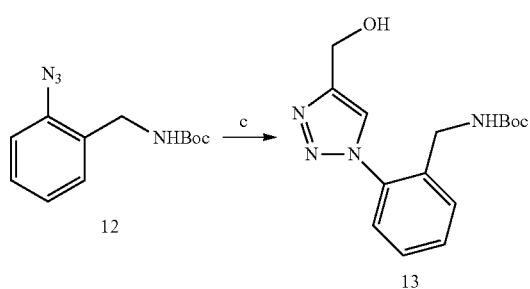

Reagents and Conditions: (c) propargyl alcohol, neat, 90° C.

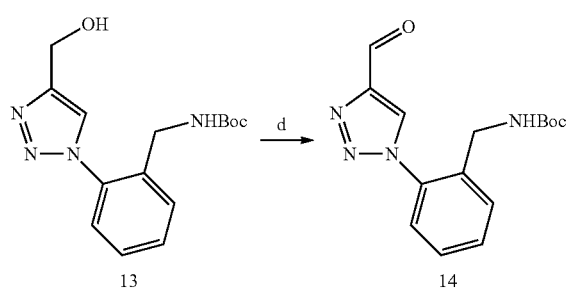

Reagents and Conditions: (d) MnO₂, CH₂Cl₂, room temp.

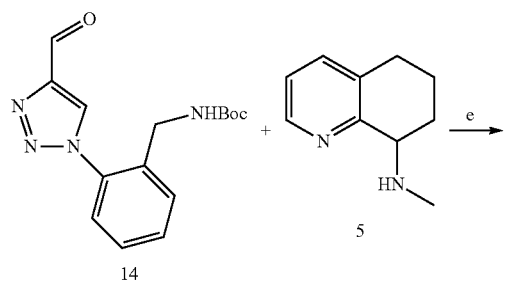

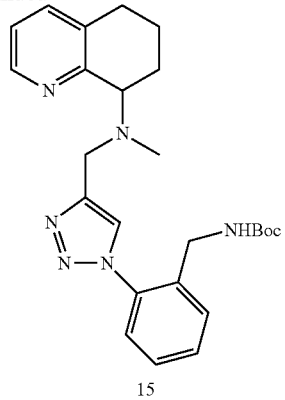

Reagents and Conditions: (e) Na(OAc)₃BH, cat. acetic acid, dichloroethane, 65° C.;

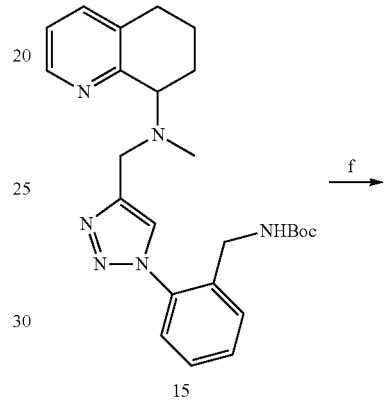

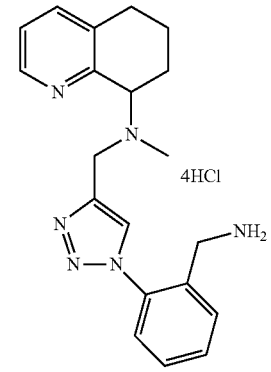

Reagents and Conditions: (f) SOCl₂, methanol, room temperature.

Example 14

Preparation of N-((1-(2-(aminomethyl)phenyl)-1H-1,2,3-triazol-4-yl)methyl)-N-methyl-1,2,3,4-tetrahydronaphthalen-1-amine tetrahydrochloride (AD)

Step a:
Preparation of tert-butyl 2-aminobenzylcarbamate (11). To a THF (30 mL) solution of 2-aminobenzyl amine (2.0 g, 16.4 mmol) was added triethylamine (4.60 mL, 32.7 mmol) and di-tert-butyldicarbonate (4.3 g, 19.6 mmol). The reaction mixture was stirred at room temperature for 16 h. The crude reaction mixture was then poured over saturated aqueous NaHCO₃ and the product was then extracted with ethyl acetate. The organic phase was washed with brine and then dried over MgSO₄, filtered and concentrated in vacuo. The crude product was purified by silica gel chromatography (0-5% methanol/dichloromethane) yielding 730 mg (20%) of 11: ¹H NMR (400 MHz, CDCl₃) δ 7.12-7.80, (m, 1H), 7.00 (d, J=7.6 Hz, 1H), 6.69-6.62 (m, 2H), 4.77, (bs, 1H), 4.29-4.11, (m, 4H), 1.43 (s, 9H); ESI⁺ MS: m/z (rel intensity) 223 (80, M+H).

Step b:

Preparation of tert-butyl 2-azidobenzylcarbamate (12). To a acetonitrile (40 mL) solution of 15 (5.00 g, 22.5 mmol) at 0° C. was added tert-butylnitrite (4.00 mL, 33.7 mmol) and trimethylsilylazide (33.55 mL, 26.9 mmol). The reaction stirred at 0° C. for 3 h. The reaction mixture was concentrated in vacuo, and the crude material was taken on to the next step without further purification. ESI⁺ MS: m/z (rel intensity) 271 (80, M+H).

Step c:

Preparation of tert-butyl 2-(4-(hydroxymethyl)-1H-1,2,3-triazol-1-yl)benzylcarbamate (13). tert-butyl 2-azidobenzylcarbamate, 12, (5.4 g, 21.7 mmol) was dissolved in neat propargyl alcohol (10 mL). The reaction mixture was stirred at 90° C. for 18 h. The reaction mixture was then concentrated in vacuo and the resulting residue dissolved in diethyl ether. Upon standing, triazole 13 crystallized. The crystals were collected by filtration yielding 2.5 g (38%) of 13: ¹H NMR (400 MHz, CDCl₃) δ 7.82, (s, 1H), 7.64-7.35 (m, 3H), 7.34-7.30 (m, 1H), 5.35, (bs, 1H), 4.87, (s, 2H), 4.15 (s, 2H), 1.42 (s, 9H); ESI⁺ MS: m/z (rel intensity) 249 (100, M-tBu).

Step d:

Preparation of tert-butyl 2-(4-formyl-1H-1,2,3-triazol-1-yl)benzylcarbamate (14). To a solution of tert-butyl 2-(4-(hydroxymethyl)-1H-1,2,3-triazol-1-yl)benzylcarbamate, 13, (2.5 g, 8.31 mmol) in CH₂Cl₂ (10 mL) was added MnO₂ (5.0 g, 57.5 mmol). The reaction mixture was stirred at room temperature for 18 h. The crude reaction mixture was then filtered through a plug of Celite® and then concentrated in vacuo. The crude material was purified by silica gel chromatography (0-5% methanol/dichloromethane) yielding 610 mg (25%) of 14: ESI⁺ MS: m/z (rel intensity) 225 (100, M+Na).

Step e:

Preparation of tert-butyl (2-(4-((methyl(5,6,7,8-tetrahydroquinolin-8-yl)amino)methyl)-1H-1,2,3-triazol-1-yl)phenyl) (15). To a solution of tert-butyl 2-(4-formyl-1H-1,2,3-triazol-1-yl)benzylcarbamate, 14, (0.61 g, 2.03 mmol) in 1,2-dichloroethane (4 mL) was added N-methyl-5,6,7,8-tetrahydroquinolin-8-amine, 11, (0.30 g, 1.85 mmol), sodium triacetoxyborohydride (0.70 g, 3.33 mmol), and AcOH (10 drops). The reaction mixture was heated to 65° C. and stirred for 18 h. The reaction mixture was poured into saturated aqueous NaHCO₃ (10 mL) and was extracted with EtOAc (2×10 mL). The organic phases were combined and washed with brine, dried over MgSO₄, filtered, and concentrated in vacuo. The crude material was purified by silica gel chromatography (0-5% methanol/dichloromethane) yielding 360 mg (44%) of 15: ¹H NMR (400 MHz, CDCl₃) δ 8.48 (d, J=4.4 Hz, 1H), 8.04 (s, 1H), 7.79 (bs, 1H), 7.64 (d, J=7.6 Hz, 1H), 7.47-7.30 (m, 4H), 7.08 (dd, J=8.0, 4.8 Hz, 1H), 4.18-3.95 (m, 5H), 2.88-2.65, (m, 2H), 2.41, (s, 3H), 2.24-2.14, (m, 1H), 2.10-1.90, (m, 2H), 1.76-1.64 (m, 1H), 1.39 (s, 9H); ESI⁺ MS: m/z (rel intensity) 449 (100, M+H).

Step f:

Preparation of N-((1-(2-(aminomethyl)phenyl)-1H-1,2,3-triazol-4-yl)methyl)-N-methyl-5,6,7,8-tetrahydroquinolin-8-amine tetrahydrochloride (AD). Through a methanol (2 mL) solution of tert-butyl (2-(4-((methyl(5,6,7,8-tetrahydroquinolin-8-yl)amino)methyl)-1H-1,2,3-triazol-1-yl)phenyl), 15, (0.36 g, 0.80 mmol) was bubbled HCl₍g₎ (generated by adding conc. H₂SO₄ to dry NaCl) until complete conversion was observed by LC-MS. The reaction mixture was then concentrated in vacuo yielding 250 mg (68%) of AD: ¹H NMR (400 MHz, d₆-DMSO) δ 8.81-8.68, (m, 4H), 8.52, (d, J=4.4 Hz, 1H), 7.87, (d, J=6.8 Hz, 1H), 7.75-7.50, (m, 4H), 7.38, (dd, J=7.6, 4.8 Hz, 1H), 4.81-4.73, (m, 1H), 4.61, (d, J=13.6 Hz, 1H), 4.47, (d, J=13.6 Hz, 1H), 3.91-3.83, (m, 2H), 2.90-2.70, (m, 5H), 2.51-2.49, (m, 1H), 2.15-2.03, (m, 2H), 1.72-1.60, (m, 1H); ESI⁺ MS: m/z (rel intensity) 349 (100, M+H).

SCHEME 11

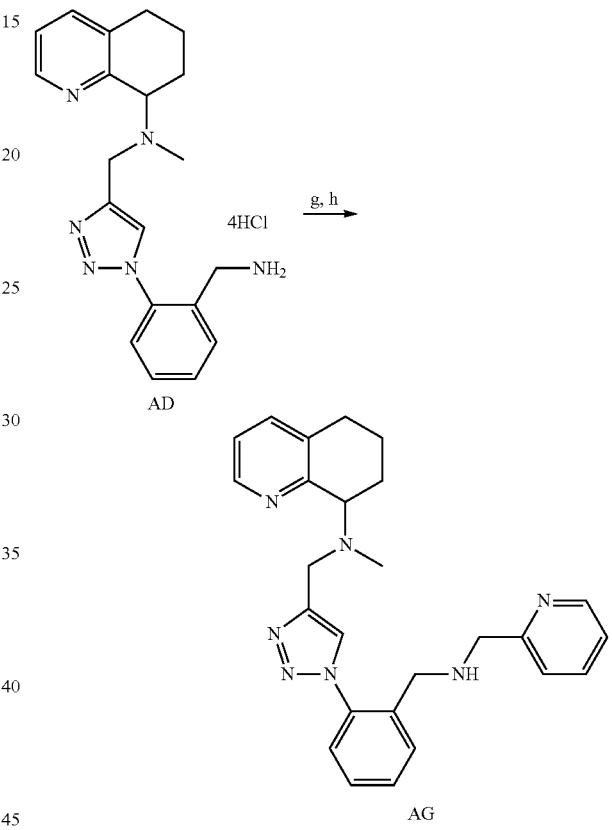

Reagents and Conditions:
(g) 2-pyridine carboxaldehyde, triethylamine, methanol, 60° C., 18 h;
(h) NaBH₄, room temperature, 1 h.

Example 15

Preparation of N-methyl-N-((1-(2-((pyridin-2-ylmethylamino)methyl)-phenyl)-1H-1,2,3-triazol-4-yl)methyl)-5,6,7,8-tetrahydroquinolin-8-amine (AG)

To a solution of N-((1-(2-(aminomethyl)phenyl)-1H-1,2,3-triazol-4-yl)methyl)-N-methyl-5,6,7,8-tetrahydroquinolin-8-amine tetrahydrochloride, AD, (0.20 g, 0.43 mmol) in methanol (2 mL) was added 2-pyridine carboxaldehyde (0.04 mL, 0.43 mmol) and triethylamine (0.18 mL, 1.30 mmol). The reaction mixture was heated to 60° C. and stirred for 18 h. The reaction mixture was then cooled to room temperature and NaBH₄ (0.05 g, 1.30 mmol) was added. The reaction stirred 1 h at room temperature. The reaction mixture was poured into brine (10 mL) and was extracted with ethyl acetate (2×10 mL). The combined organic phases were dried over MgSO₄, filtered, and concentrated in vacuo. The crude product was purified by chromatography on basic alumina (0-5% methanol/dichloromethane) yielding AG. ESI⁺ MS: m/z (rel intensity) 440 (100, M+H).

SCHEME 12

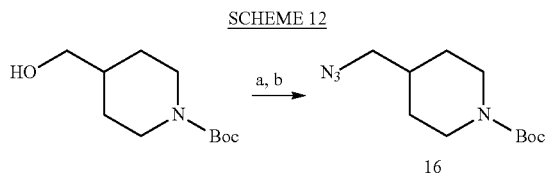

Reagents and Conditions: (a) methanesulfonyl chloride, triethylamine, CH₂Cl₂ (b) NaN₃, dimethylformamide, 70° C., 16 h.

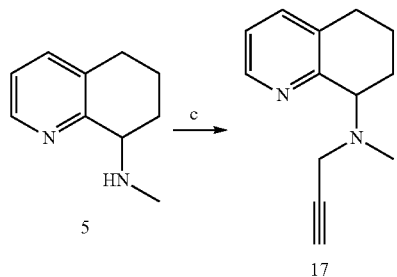

Reagents and Conditions: (a) propargyl bromide, Na₂CO₃, NaI, tetrahydrofuran, 3 h.

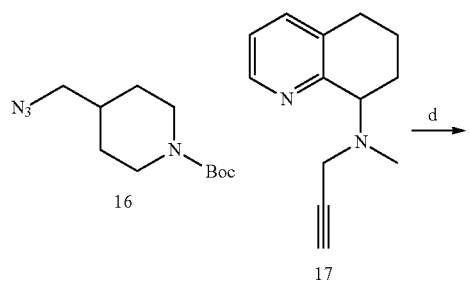

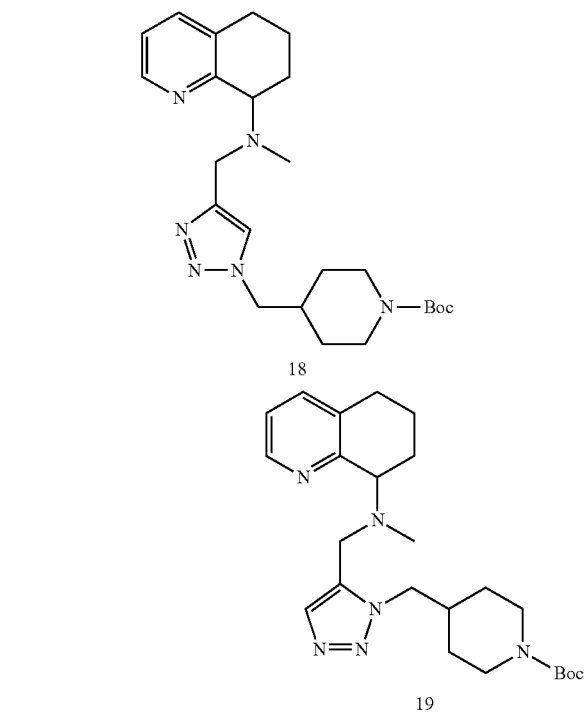

Reagents and Conditions: (d) neat, microwave, 150° C., 20 min.

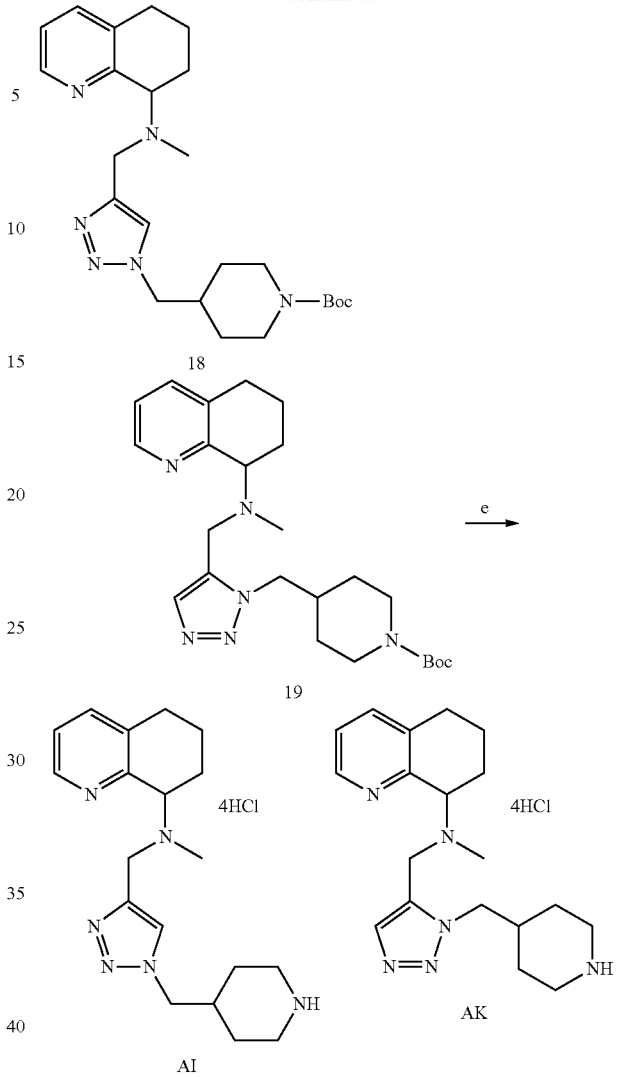

Reagents and Conditions: (e) HCl, methanol

Example 16

Preparation of N-methyl-N-((1-(piperidin-4-ylmethyl)-1H-1,2,3-triazol-4-yl)methyl)-5,6,7,8-tetrahydroquinolin-8-amine tetrahydrochloride (AI) and N-methyl-N-((3-(piperidin-4-ylmethyl)-3H-1,2,3-triazol-4-yl)methyl)-5,6,7,8-tetrahydroquinolin-8-amine (AK)

Step a:

Preparation of tert-butyl 4-(azidomethyl)piperidine-1-carboxylate (16). To a solution of tert-butyl 4-(hydroxymethyl)piperidine-1-carboxylate (2.00 g, 9.28 mmol) in CH₂Cl₂ (40 mL) was added methanesulfonyl chloride (0.76 mL, 9.75 mmol) followed by triethylamine (1.43 mL, 10.21 mmol). The reaction mixture was stirred at room temperature for 3 h. The mixture was diluted with NaHCO₃ and extracted with ethyl acetate. The organic phase was dried (MgSO₄), filtered and concentrated in vacuo. The crude solid was used without further purification: ¹H NMR (d6-DMSO) δ 4.02 (d, J=6.8 Hz, 2H), 3.95-3.85 (m 2H), 3.13 (s, 3H), 2.75-2.60 (m, 2H), 1.85-1.77 (m, 1H), 1.61 (d, J=13.2 Hz, 2H), 1.35 (s, 9H), 1.04 (ddd, J=12.4, 12.4, 4.4 Hz, 2H).

Step b:

To a solution of crude tert-butyl 4-((methylsulfonyloxy)methyl)piperidine-1-carboxylate (0.50 g, 1.71 mmol) in dimethylformamide (6 mL) was added sodium azide (0.14 g, 2.22 mmol). The reaction mixture was heated to 70° C. and stirred for 17 h. The mixture was diluted with water, extracted with ethyl acetate. The organic phase was dried (MgSO$_4$), filtered and concentrated in vacuo. The crude solid was used without further purification: $^1$H NMR (d6-DMSO) δ 3.22 (d, J=6.8 Hz, 2H), 2.68-2.55 (m 2H), 1.67-1.57 (m, 3H), 1.35 (s, 9H), 0.99 (ddd, J=12.4, 12.4, 4.4 Hz, 2H); ESI$^+$ MS: m/z (rel intensity) 263.1 (5, [M+H]$^+$).

Step c:

Preparation of N-methyl-N-(prop-2-ynyl)-5,6,7,8-tetrahydroquinolin-8-amine (17). To a solution of N-methyl-5,6,7,8-tetrahydroquinolin-8-amine, 5, (0.50 g, 3.08 mmol) in THF (15 mL) was added propargyl bromide (0.28 mL, 3.08 mmol), sodium iodide (0.05 g, 0.31 mmol) and sodium carbonate (0.98 g, 9.24 mmol). The reaction mixture was stirred at room temperature for 3 h. The mixture was diluted with water, extracted with ethyl acetate. The organic phase was dried (MgSO$_4$), filtered and concentrated in vacuo. The crude solid was used without further purification: $^1$H NMR (d6-DMSO) δ 8.30 (d, J=4.4 Hz, 1H), 7.44 (d, J=8.0 Hz, 1H), 7.13 (dd, J=8.0, 5.2 Hz, 1H), 3.74 (dd, J=4.8, 4.8 Hz, 1H), 3.47 (ddd, J=16.8, 2.4, 2.4 Hz, 2H), 3.06 (s, 1H), 2.80-2.60 (m, 2H), 2.12 (s, 3H), 2.12-1.87 (m, 2H), 1.74-1.68 (m, 1H), 1.62-1.55 (m, 1H); ESI$^+$ MS: m/z (rel intensity) 201.1 (100, [M+H]$^+$).

Step d:

Preparation of tert-butyl 4-((4-((methyl(5,6,7,8-tetrahydroquinolin-8-yl)amino)methyl)-1H-1,2,3-triazol-1-yl)methyl)piperidine-1-carboxylate (18) and tert-butyl 4-((5-((methyl(5,6,7,8-tetrahydroquinolin-8-yl)amino)methyl)-1H-1,2,3-triazol-1-yl)methyl)piperidine-1-carboxylate (19). A neat mixture of N-methyl-N-(prop-2-ynyl)-5,6,7,8-tetrahydroquinolin-8-amine, 5, (0.31 g, 1.54 mmol) and tert-butyl 4-(azidomethyl)piperidine-1-carboxylate, 16, (0.37 g, 1.54 mmol) was heated in microwave at 150° C. for 20 min. The resulting residue was partitioned between aqueous saturated NaHCO$_3$ solution and CH$_2$Cl$_2$. The organic phase was dried (MgSO$_4$), filtered and concentrated in vacuo. The crude solid was purified by column chromatography (basic alumina, 0% methanol/CH$_2$Cl$_2$ to 20% methanol/CH$_2$Cl$_2$) to afford a 1.4 to 1 ratio of the 1,4-substituted (18) and 1,5-substituted (19) triazole regioisomers: $^1$H NMR (d6-DMSO) δ 8.36 (d, J=5.6 Hz, 1H), 7.90 (s, 1H), 7.44 (dd, J=7.6 Hz, 1H), 4.27-4.24 (m, 1H), 4.22 (d, J=7.2 Hz, 1H), 3.88-3.77 (m, 2H), 3.88-3.77 (m, 4H), 2.72-2.07 (m, 4H), 1.95-1.85 (m, 4H), 1.64-1.55 (m, 1H), 1.42-1.35 (m, 1H), 1.35 (s, 9H), 1.05-0.98 (m, 1H); ESI$^+$ MS: m/z (rel intensity) 441.2 (100, [M+H]$^+$).

Step e:

Preparation of N-methyl-N-((1-(piperidin-4-ylmethyl)-1H-1,2,3-triazol-4-yl)methyl)-5,6,7,8-tetrahydroquinolin-8-amine tetrahydrochloride (AI) and N-methyl-N-((3-(piperidin-4-ylmethyl)-3H-1,2,3-triazol-4-yl)methyl)-5,6,7,8-tetrahydroquinolin-8-amine (AK). To a mixture of triazole regioisomers 18 and 19 (0.18 g, 0.42 mmol) in methanol (10 mL) was bubbled HCl gas (generated from H$_2$SO$_4$ and NaCl). The reaction mixture was stirred at room temp. for 30 minutes. The mixture was concentrated in vacuo to afford a 1.3 to 1 molar ratio of triazoles AI and AK. The tetrahydrochloride salt was used without further purification: ESI$^+$ MS: m/z (rel intensity) 341.2 (100, [M+H]$^+$).

SCHEME 13

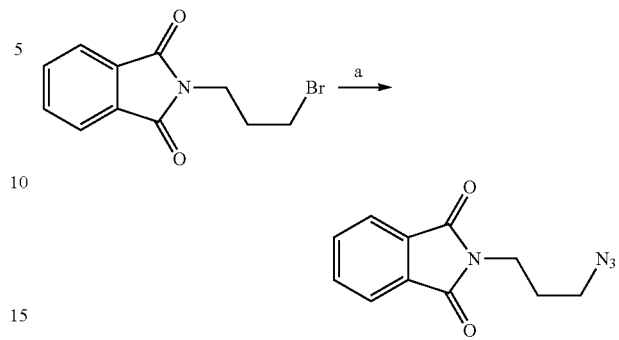

Reagents and Conditions: (a) sodium azide, H$_2$O, microwave, 120° C., 30 min

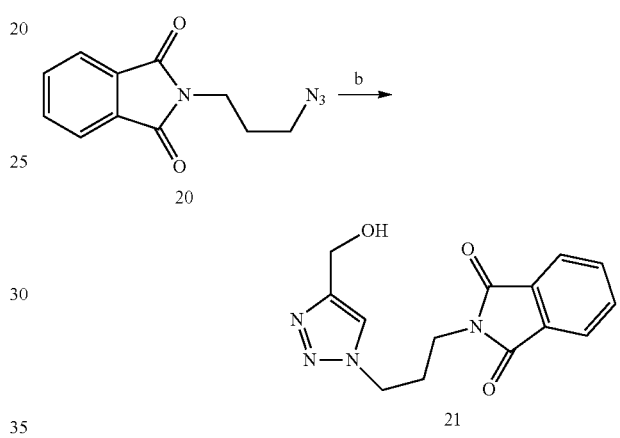

Reagents and Conditions: (b) propargyl alcohol, neat, 90° C.

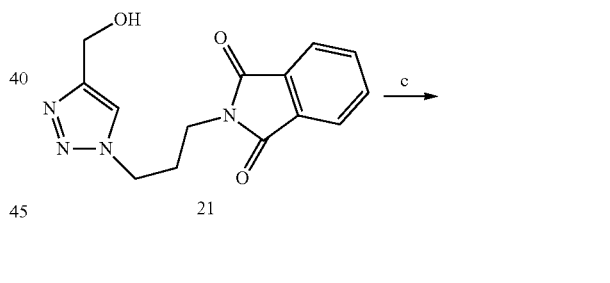

Reagents and Conditions: (c) MnO$_2$, CH$_2$Cl$_2$, room temp.

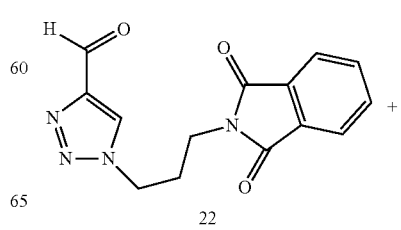

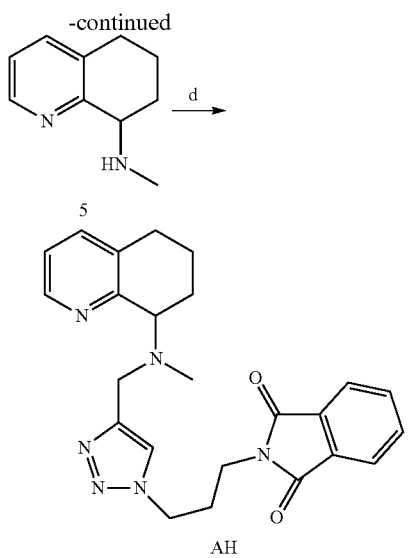

Reagents and Conditions: (e) Na(OAc)₃BH, cat. acetic acid, dichloroethane, 65° C.;

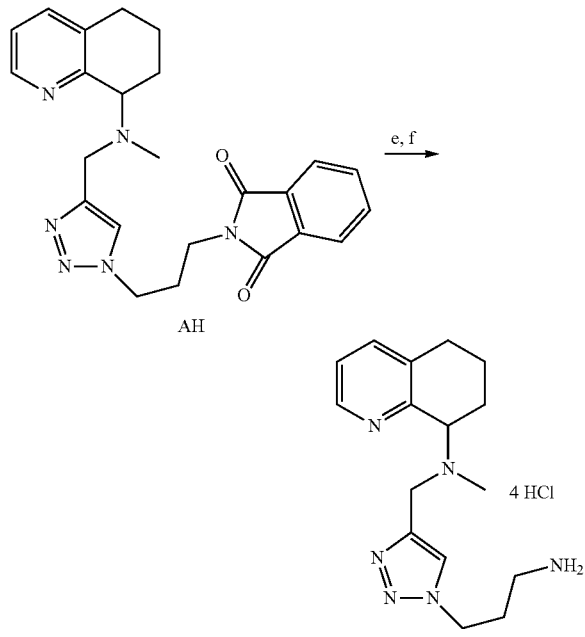

Reagents and Conditions: (e) NH₂NH₂, ethanol, 80° C., 20 h; (f) 1N HCl, diethyl ether.

Example 17

Preparation of N-((1-(3-aminopropyl)-1H-1,2,3-triazol-4-yl)methyl)-N-methyl-5,6,7,8-tetrahydroquinolin-8-amine tetrahydrochloride (W)

Step a:

Preparation of 2-(3-azidopropyl)isoindoline-1,3-dione (20). A heavy-walled Pyrex tube was charged with a suspension of N-(3-bromopropyl)phthalimide (1.00 g, 3.72 mmol) and sodium azide (0.32 g, 4.84 mmol) in H₂O (2 mL). The tube containing the resulting mixture was sealed with an aluminum crimp cap fitted with a silicon septum and then it was exposed to microwave irradiation for 30 min at a temperature of 120° C. After the irradiation, the reaction tube was cooled with high-pressure air until the temperature had fallen below 40° C. The product was extracted with ethyl acetate. The combined organic layers were dried with magnesium sulfate, filtered and concentrated in vacuo. The crude material (0.62 g, 72% yield) was used without further purification in the next step. $^1$H NMR (400 MHz, CDCl₃) δ 7.86-7.83 (m, 2H), 7.73-7.70 (m, 2H), 3.77 (t, J=6.4 Hz, 2H), 3.36 (t, J=8.0 Hz, 2H), 1.94 (m, 2H).

Step b:

Preparation of 2-(3-(4-(hydroxymethyl)-1H-1,2,3-triazol-1-yl)propyl)-isoindoline-1,3-dione (21). A solution of 2-(3-azidopropyl)isoindoline-1,3-dione, 20, (0.62 g, 2.69 mmol) in propargyl alcohol (4 mL) was warmed to 90° C. and stirred for 18 h. The reaction mixture was concentrated under reduced pressure. The crude product containing both regioisomers (~1:1 ratio) was used in the next step without further purification. ESI⁺ MS: m/z (rel intensity) 301.1 (100, [M+H]⁺).

Step c:

Preparation of 1-(3-(1,3-dioxoisoindolin-2-yl)propyl)-1H-1,2,3-triazole-4-carbaldehyde (22). A solution of the regioisomers 21 (0.77 g, 2.69 mmol) in dichloromethane (10 mL) was treated with manganese dioxide (0.94 g, 10.77 mmol). The resulting mixture was stirred at room temperature for 2 h. The reaction mixture was filtered through Celite and concentrated. The crude product was purified by silica gel chromatography (0-5% methanol/CH₂Cl₂) to afford 0.24 g (31% yield) of 22 as a single regioisomer: $^1$H NMR (400 MHz, CDCl₃) δ 10.08 (s, 1H), 8.34 (s, 1H), 7.85-7.65 (m, 4H), 4.45 (t, J=12.0 Hz, 2H), 3.77-3.71 (m, 2H), 2.42-2.34 (m, 2H); ESI⁺ MS: m/z (rel intensity) 285.0 (100, [M+H]⁺).

Step d:

Preparation of 2-(3-(4-((methyl(5,6,7,8-tetrahydroquinolin-8-yl)amino)-methyl)-1H-1,2,3-triazol-1-yl)propyl)isoindoline-1,3-dione (AH). A solution of 1-(3-(1,3-dioxoisoindolin-2-yl)propyl)-1H-1,2,3-triazole-4-carbaldehyde, 22, (0.24 g, 0.84 mmol), N-methyl-N-(prop-2-ynyl)-5,6,7,8-tetrahydroquinolin-8-amine, 5, (0.17 g, 1.01 mmol), sodium triacetoxyborohydride (0.27 g, 1.26 mmol) and a catalytic amount of acetic acid (2 drops) in 1,2-dichloroethane (10 mL) was warmed to 65° C. and stirred at this temperature for 24 h. The reaction mixture was cooled to room temperature. A saturated aqueous solution of sodium bicarbonate was added. The product was extracted with dichloromethane. The combined organic layers were dried over potassium carbonate, filtered and concentrated. The crude product was purified by silica gel chromatography (0-5% methanol/CH₂Cl₂) to afford 0.19 g (80% yield) of the desired product, AH: $^1$H NMR (400 MHz, CDCl₃) δ 8.45 (d, J=4.4 Hz, 1H), 7.79-7.76 (m, 2H), 7.71 (s, 1H), 7.68-7.65 (m, 2H), 7.30 (d, J=7.6 Hz, 1H), 7.00 (dd, J=4.8, 8.0 Hz, 1H), 4.32 (dt, J=3.2, 7.2 Hz, 2H), 3.91 (dd, J=6.0, 9.2 Hz, 1H), 3.77-3.66 (m, 4H), 2.82-2.70 (m, 1H), 2.70-2.60 (m, 1H), 2.29 (s, 3H), 2.29-2.23 (m, 2H), 2.12-2.02 (m, 1H), 2.02-1.92 (m, 1H), 1.92-1.80 (m, 1H), 1.70-1.56 (m, 1H); ESI⁺ MS: m/z (rel intensity) 431.2 (100, [M+H]⁺).

Step e:

Preparation of N-((1-(3-aminopropyl)-1H-1,2,3-triazol-4-yl)methyl)-N-methyl-5,6,7,8-tetrahydroquinolin-8-amine tetrahydrochloride (W). A solution of 2-(3-(4-((methyl(5,6,7,8-tetrahydroquinolin-8-yl)amino)-methyl)-1H-1,2,3-triazol-1-yl)propyl)isoindoline-1,3-dione, AH, (0.16 g, 0.37 mmol) in ethanol (5 mL) was treated with hydrazine (23 µL, 0.74 mmol). The resulting mixture was warmed to 80° C. and stirred for 20 h. The reaction mixture was cooled to room temperature. The white precipitate that formed was filtered and the filtrate was concentrated in vacuo. Chloroform was added. More of the precipitate crashed out and was filtered off. The solution was concentrated and dried under reduced pressure to afford 0.08 g (72% yield) of product W: $^1$H NMR (400 MHz, CDCl₃) δ 8.47 (d, J=3.6 Hz, 1H), 7.65 (s, 1H), 7.33 (d, J=7.6 Hz, 1H), 7.02 (d, J=4.8, 8.0 Hz, 1H), 4.39 (t, J=7.2 Hz, 1H), 3.95 (dd, J=5.6, 9.2 Hz, 1H), 3.75 (q, J=13.6 Hz, 2H), 2.85-2.60 (m, 2H), 2.68 (t, J=6.8 Hz, 2H), 2.31 (s, 3H), 2.25-2.05 (m, 2H), 2.05-1.95 (m, 2H), 1.95-1.80 (m, 1H), 1.75-1.58 (m, 1H); ESI$^+$ MS: m/z (rel intensity) 301.2 (95, [M+H]$^+$).

Example 18

General Preparation of Compounds of Formulae (IB) and (IC) in which $R_5$ and $R_6$ are Both H and $L_2Y$ is a Substituted or Unsubstituted Aminoalkyl Compounds of Formula (IB) and (IC) in which $R_5$ and $R_6$ are both H and $L_2Y$ is a substituted or unsubstituted aminoalkyl can be prepared, for example, as generally described in Scheme 14 below. The skilled artisan will recognize that substituted aminoalkyl compounds can be prepared by the appropriate derivatization of the unsubstituted aminoalkyl compound which is prepared according to Scheme 14. Other modifications (e.g., modifying the chain length of the alkylene portion of the aminoalkyl group, functionalization of the alcohol intermediate, etc.) are prepared by providing modified intermediates of Schemes 6-10.

SCHEME 14

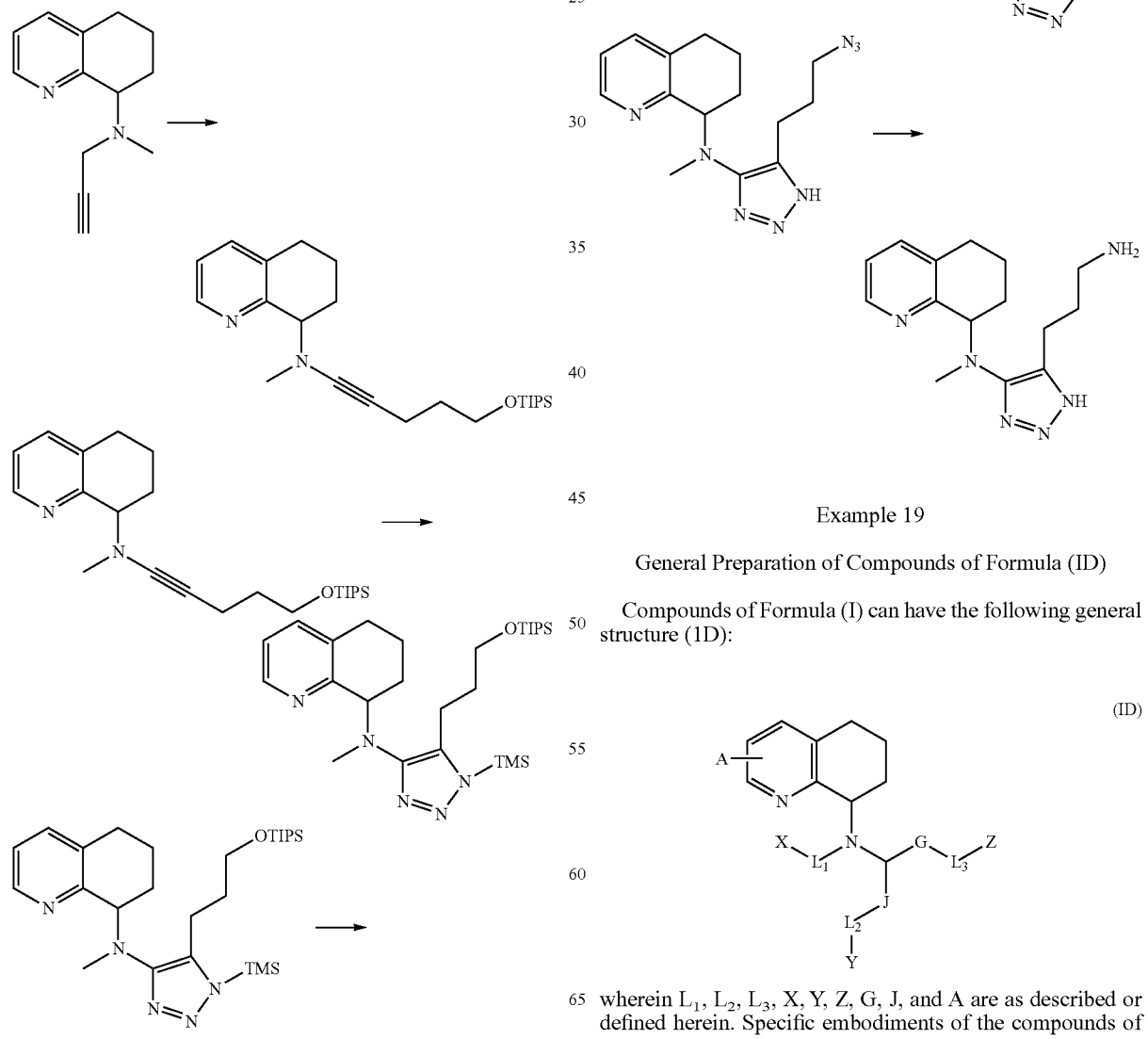

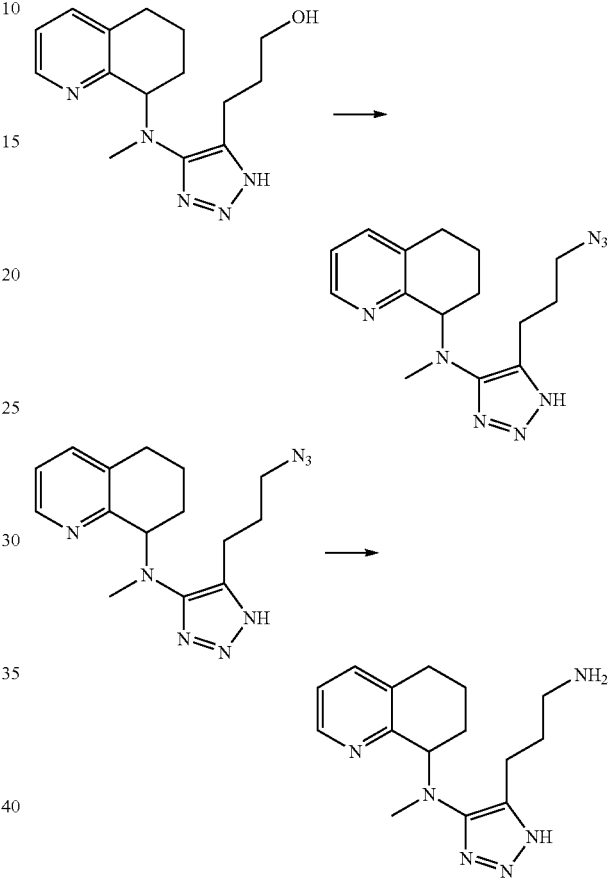

Example 19

General Preparation of Compounds of Formula (ID)

Compounds of Formula (I) can have the following general structure (1D):

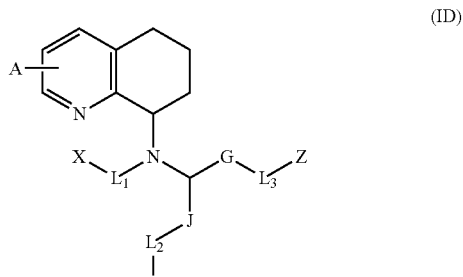

(ID)

wherein $L_1$, $L_2$, $L_3$, X, Y, Z, G, J, and A are as described or defined herein. Specific embodiments of the compounds of Formula (ID) are shown in Table 3, below.

TABLE 3
| Compound | —L₁—X | —G | —L₃—Z | —J | —L₂—Y |
|---|---|---|---|---|---|
| AY | H | — | 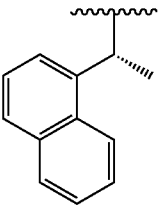 [SMILES: *[C@H](C)c1cccc2ccccc12] | CONH | 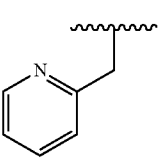 [SMILES: *Cc1ccccn1] |
| AZ | H | — | 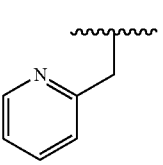 [SMILES: *Cc1ccccn1] | CONH | 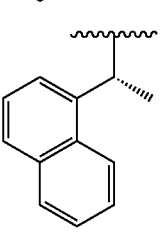 |
| BA | H | — | 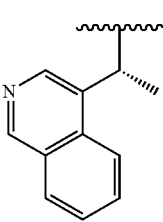 | CONH | 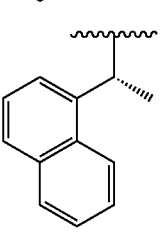 |
| BB | H | — | 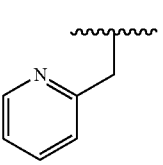 [SMILES: *Cc1ccccn1] | CONH | 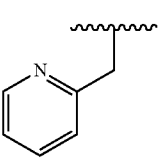 [SMILES: *Cc1ccccn1] |
| BC | H | — | 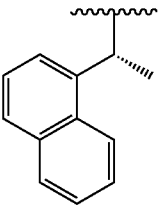 [SMILES: *[C@H](C)c1cccc2ccccc12] | CONH | 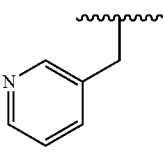 [SMILES: *Cc1cccnc1] |
| BD | H | — | 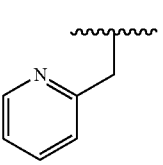 [SMILES: *Cc1ccccn1] | CONH | 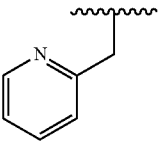 [SMILES: *Cc1ccccn1] |
| BE | H | — | 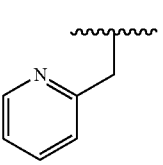 [SMILES: *Cc1ccccn1] | CONH | 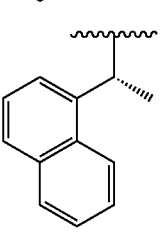 |
| BF | H | CONH | 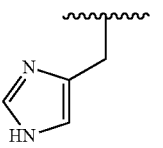 | — | 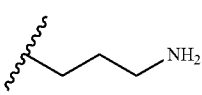 [SMILES: *CCCN] |
| BG | H | CONH | 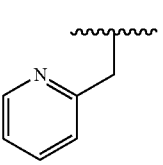 [SMILES: *Cc1ccccn1] | — | 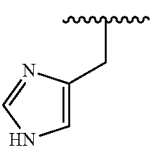 |

TABLE 3-continued
| Compound | —L₁—X | —G | —L₃—Z | —J | —L₂—Y |
|---|---|---|---|---|---|
| BH | H | CONH | 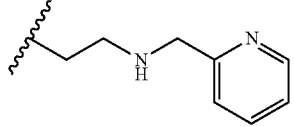 [SMILES: *CCNCc1ccccn1] | — | 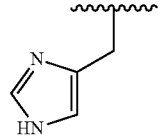 |
| BI | H | CONH | 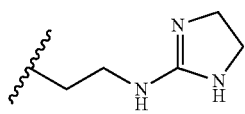 [SMILES: *CCNC1=NCCN1] | — | 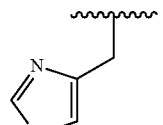 |
| BJ | H | — | 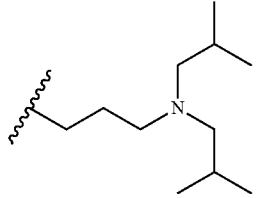 [SMILES: *CCCN(CC(C)C)CC(C)C] | CO | 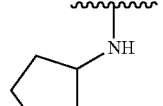 |
| BK | H | — | 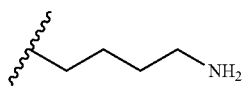 [SMILES: *CCCCN] | CO | 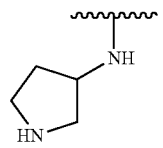 |
| BL | H | — | 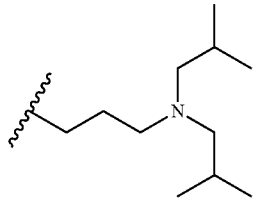 [SMILES: *CCCN(CC(C)C)CC(C)C] | CO | 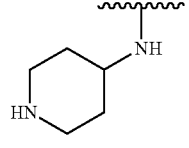 [SMILES: *NC1CCNCC1] |
| BM | H | — | 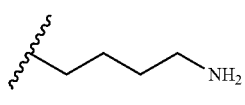 [SMILES: *CCCCN] | CO | 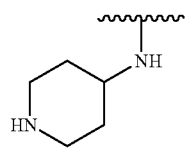 [SMILES: *NC1CCNCC1] |
| BN | H | — | 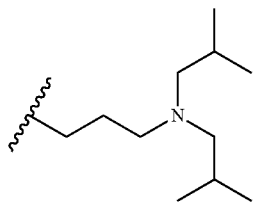 [SMILES: *CCCN(CC(C)C)CC(C)C] | CO | 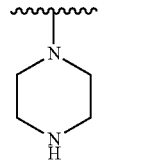 |
| BO | H | — | 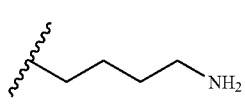 [SMILES: *CCCCN] | CO | 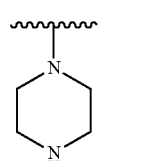 |
| BO1 | H | CO | 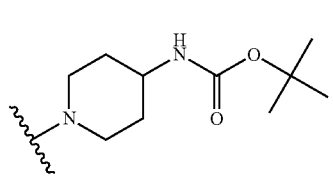 [SMILES: *N1CCC(NC(=O)OC(C)(C)C)CC1] | — | 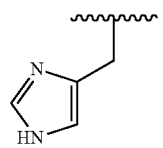 |

TABLE 3-continued

| Compound | —L₁—X | —G | —L₃—Z | —J | —L₂—Y |
|---|---|---|---|---|---|
| BO2 | H | CO | piperidine-4-amine | — | imidazole |
| BO3 | H | CO | N-(pyridin-2-ylmethyl)piperidin-4-amine | — | imidazole |
| BO4 | H | CO | N-(4,5-dihydro-1H-imidazol-2-yl)piperidin-4-amine | — | imidazole |

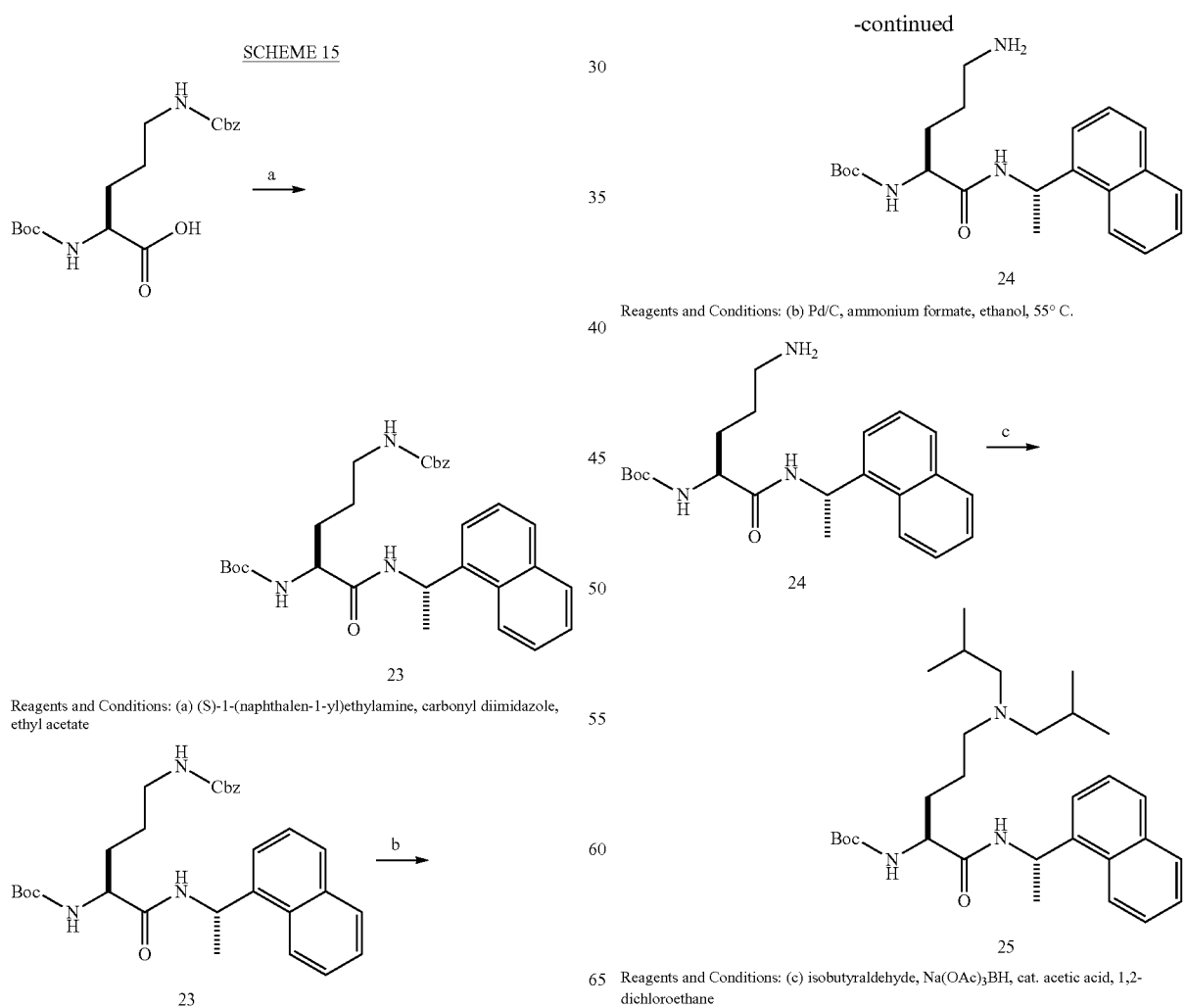

SCHEME 15

Reagents and Conditions: (a) (S)-1-(naphthalen-1-yl)ethylamine, carbonyl diimidazole, ethyl acetate Reagents and Conditions: (b) Pd/C, ammonium formate, ethanol, 55° C.

Reagents and Conditions: (c) isobutyraldehyde, Na(OAc)₃BH, cat. acetic acid, 1,2-dichloroethane -continued

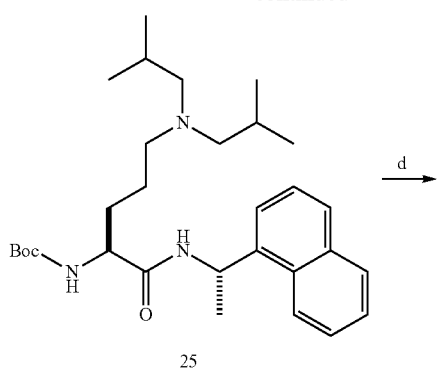

Reagents and Conditions: (d) Thionyl chloride, methanol

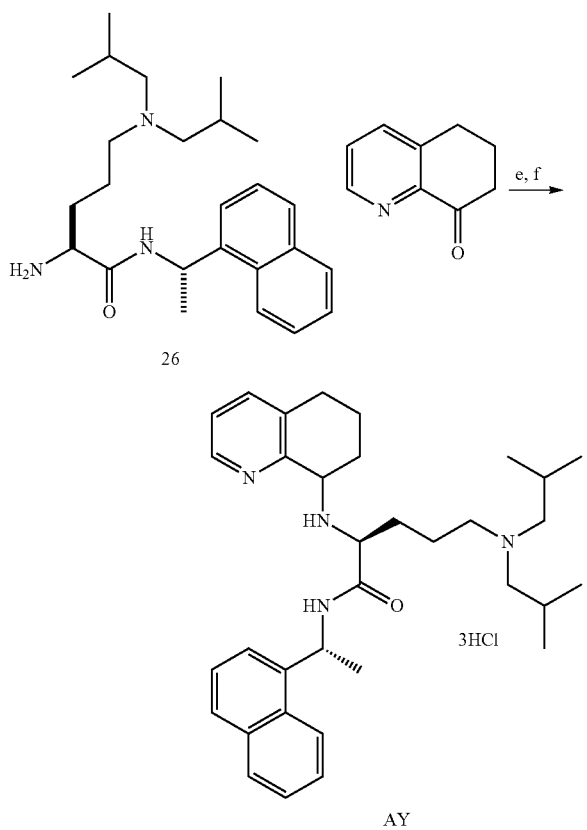

Reagents and Conditions: (e) methanol, microwave, 150° C., 15 min; (f) NaBH₄, methanol, room temp.

Example 20

Preparation of (S)-5-(diisobutylamino)-N-((R)-1-(naphthalen-1-yl)ethyl)-2-(5,6,7,8-tetrahydroquinolin-8-ylamino)pentanamide trihydrochloride (AY)

Step a:
Preparation of benzyl (S)-4-(tert-butoxycarbonyl)-amino-5-((S)-1-(naphthalen-1-yl)ethylamino)-5-oxopentylcarbamate (23). To a solution of Boc-Orn(Z)—OH (Bachem) (51.6 g, 141.0 mmol) in ethyl acetate (800 mL) was added 1,1-carbonyl diimidazole (24.0 g, 148.0 mmol). The mixture was stirred at room temp. for 30 min. A solution of (S)-(−)-(1)-(1-naphthyl)ethyl amine (25.3 g, 148.0 mmol) in CHCl₃ was added to the reaction mixture dropwise. The reaction mixture was stirred at room temperature for an additional 1 h. The mixture was diluted with water, extracted with ethyl acetate. The organic phase was washed with 0.3 N HCl (500 mL), water and then aqueous saturated NH₄Cl solution. The organic phase was dried (MgSO₄), filtered and concentrated in vacuo. The crude residue was purified by silica gel chromatography (0% to 20% methanol/CHCl₃) to afford the desired product 23: ESI⁺ MS: m/z (rel intensity) 520 (100, [M+H]⁺).

Step b:
Preparation of tert-butyl (5)-5-amino-1-((S)-1-(naphthalen-1-yl)ethylamino)-1-oxopentan-2-ylcarbamate (24). A solution of (S)-4-(tert-butoxycarbonyl)-amino-5-((S)-1-(naphthalen-1-yl)ethylamino)-5-oxopentylcarbamate, 23, (28.0 g, 54.0 mmol) in ethanol (600 mL) was added ammonium formate (10.2 g, 160.0 mmol) and palladium (10 wt % on carbon, 1.0 g). The reaction mixture was warmed to 55° C. and stirred for 18 h at 55° C. The mixture was filtered through Celite and washed with ethanol. The resulting filtrate was concentrated in vacuo. The residue was dissolved in ethyl acetate and the organic phase was washed with aqueous saturated NaCl solution. The organic phase was dried (MgSO₄), filtered and concentrated in vacuo. The crude residue was used without further purification: ¹H NMR (d6-DMSO) δ 8.55 (d, J=7.6 Hz, 1H), 8.04 (d, J=8.4 Hz, 1H), 7.89 (d, J=8.0 Hz, 1H), 7.78 (d, J=8.0 Hz, 1H), 7.53-7.42 (m, 4H), 6.81 (d, J=8.0 Hz, 1H), 5.65-5.62 (m, 1H), 3.96-3.89 (m, 1H), 2.60-2.53 (m, 2H), 1.46-1.40 (m, 7H), 1.33 (s, 9H); ESI⁺ MS: m/z (rel intensity) 386.2 (100, [M+H]⁺).

Step c:
Preparation of tert-butyl (5)-5-(diisobutylamino)-1-((S)-1-(naphthalen-1-yl)ethylamino)-1-oxopentan-2-ylcarbamate (25). To a solution of tert-butyl (S)-5-amino-1-((S)-1-(naphthalen-1-yl)ethylamino)-1-oxopentan-2-ylcarbamate, 24, (20.8 g, 54.0 mmol) in CH₂Cl₂ (600 mL) was added acetic acid (conc. 1 mL), followed by isobutyraldehyde (10.8 mL, 120.0 mmol) and sodium triacetoxyborohydride (28.6 g, 135 mmol). The reaction mixture was warmed to 65° C. and stirred for 30 min. The mixture was diluted with water, extracted with ethyl acetate. The organic phase was washed with aqueous saturated NaCl. The organic phase was dried (MgSO₄), filtered and concentrated in vacuo. The crude residue was used without further purification: ¹H NMR (d6-DMSO) δ 8.39 (d, J=7.6 Hz, 1H), 8.04 (d, J=7.2 Hz, 1H), 7.89 (d, J=8.0 Hz, 1H), 7.77 (d, J=8.0 Hz, 1H), 7.51-7.39 (m, 4H), 6.68 (d, J=8.4 Hz, 1H), 5.68-5.60 (m, 1H), 3.97-3.90 (m, 1H), 2.41-2.22 (m, 2H), 1.91 (d, J=7.2 Hz, 2H), 1.58-1.52 (m, 2H), 1.44 (d, J=6.8 Hz, 3H), 1.33 (s, 9H), 0.75 (d, J=6.8 Hz, 12H); ESI⁺ MS: m/z (rel intensity) 498.3 (100, [M+H]⁺).

Step d:
Preparation of (S)-2-amino-5-(diisobutylamino)-N-((S)-1-(naphthalen-1-yl)ethyl)pentanamide (26). To a solution of tert-butyl (S)-5-(diisobutylamino)-1-((S)-1-(naphthalen-1-yl)ethylamino)-1-oxopentan-2-ylcarbamate (2.0 g, 4.0 mmol) in CH$_2$Cl$_2$ (35 mL) was added trifluoroacetic acid (20 mL) dropwise. After stirring the reaction mixture for 45 min at room temperature, the mixture was concentrated in vacuo to afford the trifluoroacetic acid salt. The crude salt was used without further purification: ESI$^+$ MS: m/z (rel intensity) 398.3 (100, [M+H]$^+$).

Steps e and f:

Preparation of (S)-5-(diisobutylamino)-N-((R)-1-(naphthalen-1-yl)ethyl)-2-(5,6,7,8-tetrahydroquinolin-8-ylamino)pentanamide trihydrochloride (AY). To a solution of (S)-2-amino-5-(diisobutylamino)-N-((S)-1-(naphthalen-1-yl)ethyl)-pentanamide, 26, (0.60 g, 1.51 mmol) in ethanol (4 mL) was added 6,7-dihydroquinolin-8(5H)-one (0.21 g, 1.43 mmol). The mixture was heated in microwave reactor at 150° C. for 10 min. After cooling the reaction to room temp., NaBH$_4$ (0.11 g, 2.86 mmol) was added to the mixture. The reaction mixture was stirred at room temp for 1 h. The mixture was diluted with aqueous saturated NaHCO$_3$, extracted with ethyl acetate. The organic phase was dried (MgSO$_4$), filtered and concentrated in vacuo. The crude residue was purified by silica gel chromatography (0% to 5% methanol/CH$_2$Cl$_2$) to afford the desired product: $^1$H NMR (d6-DMSO) δ 8.34 (d, J=4.8 Hz, 1H), 8.30-8.25 (m, 1H), 8.11-8.05 (m, 1H), 7.92-7.87 (m, 1H), 7.80-7.76 (m, 1H), 7.52-7.38 (m, 5H), 7.17-7.11 (m, 1H), 5.74-5.67 (m, 1H), 4.50 (d, J=4.0 Hz, 1H), 2.71-2.55 (m, 4H), 2.95 (m, 1H), 2.05-1.80 (m, 6H), 1.58-1.40 (m, 11H), 0.76 (d, J=6.4 Hz, 12H); ESI$^+$ MS: m/z (rel intensity) 529.3 (100, [M+H]$^+$).

SCHEME 16

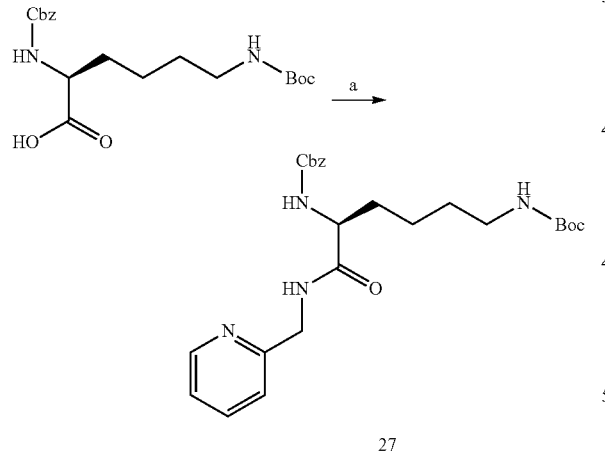

27

Reagents and Conditions:
(a) BOP or hydroxybenzotriazole-hydrate/EDAC, 2-aminomethylpyridine, triethylamine, dimethylformamide

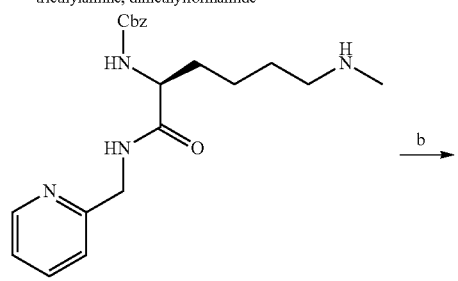

27

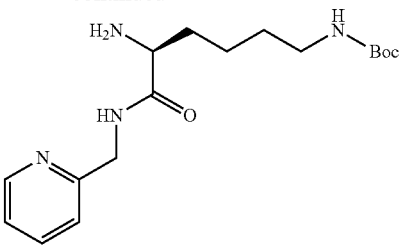

28

Reagents and Conditions:
(b) hydrogen, Pd/C, methanol

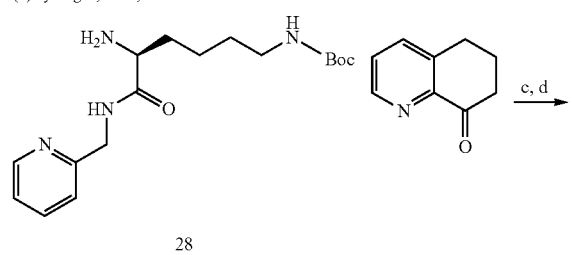

28

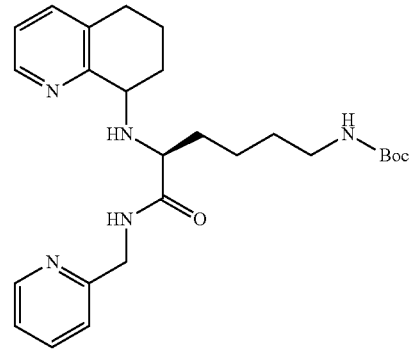

29

Reagents and Conditions:
(c) methanol, microwave, 150° C., 15 min;
(d) NaBH$_4$, methanol, room temp.

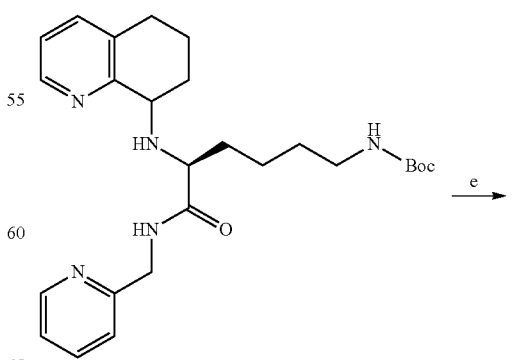

29

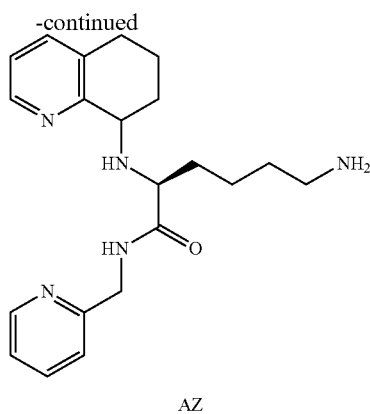

AZ

Reagents and Conditions:
(e) HCl, methanol

Example 21

Preparation of (2S)-6-amino-N-(pyridin-2-ylmethyl)-2-(5,6,7,8-tetrahydroquinolin-8-ylamino)hexanamide tetrahydrochloride (AZ)

Step a:
Preparation of (S)-benzyl 6-((tert-butoxycarbonyl)-amino)-1-oxo-1-(pyridin-2-ylmethylamino)hexan-2-ylcarbamate (27). To a cold (0° C.) solution of Boc-Lys(Z)—OH (Bachem, 10.0 g, 26.3 mmol) in dimethylformamide (80 mL) was added hydroxybenzotriazole-hydrate (4.3 g, 31.6 mmol), triethylamine (7.3 mL, 52.6 mmol) and EDAC (6.1 g, 31.6 mmol). After stirring at 0° C. for 1 h, 2-aminomethylpyridine (3.0 mL, 28.9 mmol) was added to the mixture. The mixture was warmed to room temperature and stirred for an additional 17 h. The mixture was diluted with aqueous saturated NaHCO₃ and extracted with ethyl acetate. The organic phase was dried (MgSO₄), filtered and concentrated in vacuo. The crude residue was purified by silica gel chromatography (0% to 5% methanol/CHCl₃) to afford the desired product 27: $^1$H NMR (d6-DMSO) δ 8.43 (d, J=4.0 Hz, 1H), 8.39 (t, J=5.6 Hz, 1H), 7.68 (t, J=7.6 Hz, 1H), 7.34-7.19 (m, 8H), 6.94 (d, J=7.6 Hz, 1H), 4.96 (s, 2H), 4.31 (d, J=5.6 Hz, 2H), 3.90-3.83 (m, 1H), 2.95-2.90 (m, 2H), 1.60-1.25 (m, 6H), 1.35 (s, 9H); ESI⁺ MS: m/z (rel intensity) 471.2 (100, [M+H]⁺).

Step b:
Preparation of (S)-tert-butyl 5-amino-6-oxo-6-(pyridin-2-ylmethyl-amino)hexylcarbamate (28). To a solution of (S)-benzyl 6-((tert-butoxycarbonyl)-amino)-1-oxo-1-(pyridin-2-ylmethylamino)hexan-2-ylcarbamate, 27, (3.8 g, 8.2 mmol) in methanol (80 mL) was added palladium (10 wt % on carbon, 0.5 g). The mixture was stirred under a hydrogen atmosphere for 2 h. The mixture was filtered through Celite and washed with methanol. The resulting filtrate was concentrated in vacuo. The crude residue was used without further purification: ESI⁺ MS: m/z (rel intensity) 337.2 (100, [M+H]⁺).

Steps c and d:
Preparation of tert-butyl (S)-6-oxo-6-(pyridin-2-ylmethylamino)-5-(5,6,7,8-tetrahydroquinolin-8-ylamino)hexylcarbamate (29). To a solution of (S)-tert-butyl 5-amino-6-oxo-6-(pyridin-2-ylmethyl-amino)hexylcarbamate, 28, (2.16 g, 6.43 mmol) in ethanol (14 mL) was added 6,7-dihydroquinolin-8(5H)-one (0.90 g, 6.12 mmol). The mixture was heated in microwave reactor at 150° C. for 13 min. After cooling the reaction to room temp., NaBH₄ (0.46 g, 12.24 mmol) was added to the mixture. The reaction mixture was stirred at room temp for 1 h. The mixture was diluted with aqueous saturated NaHCO₃, extracted twice with ethyl acetate. The organic phase was dried (MgSO₄), filtered and concentrated in vacuo. The crude residue was purified by silica gel chromatography (5% to 25% methanol/CH₂Cl₂) to afford the desired product 29: $^1$H NMR (d6-DMSO) δ 8.44 (d, J=4.4 Hz, 1H), 8.40 (m, 1H), 8.32-8.31 (m, 1H), 7.66 (t, J=7.2 Hz, 1H), 7.45 (d, J=7.6 Hz, 1H), 7.24 (d, J=8.0 Hz, 1H), 7.20 (t, J=4.8 Hz, 1H), 7.13 (dd, J=8.0, 4.2 Hz, 1H), 6.94 (d, J=7.6 Hz, 1H), 4.32 (d, J=5.6 Hz, 2H), 3.95-3.89 (m, 1H), 3.62-3.57 (m, 1H), 2.69 (d, J=4.8 Hz, 2H), 2.61-2.56 (m, 2H), 1.99-1.95 (m, 1H), 1.89-1.83 (m, 1H), 1.63-1.28 (m, 8H), 1.35 (s, 9H); ESI⁺ MS: m/z (rel intensity) 468.3 (100, [M+H]⁺).

Step e:
Preparation of (2S)-6-amino-N-(pyridin-2-ylmethyl)-2-(5,6,7,8-tetrahydro-quinolin-8-ylamino)hexanamide tetrahydrochloride (AZ). To a solution of tert-butyl (S)-6-oxo-6-(pyridin-2-ylmethylamino)-5-(5,6,7,8-tetrahydroquinolin-8-ylamino)-hexylcarbamate, 29, (1.07 g, 2.29 mmol) in methanol (50 mL) was bubbled HCl gas (generated from H₂SO₄ and NaCl). The reaction mixture was stirred at room temp. for 20 minutes. The mixture was concentrated in vacuo to afford the desired product. The tetrahydrochloride salt was used without further purification: ESI⁺ MS: m/z (rel intensity) 368.2 (100, [M+H]⁺).

Example 22

Preparation of Compound BI, of a Compound of Formula (ID)

Compounds of Formula (ID), such as compound BI, are prepared using the procedure of Scheme 17. The skilled artisan will recognize that various modifications of such compounds are possible by providing modified intermediates. For example, different heterocyclyls corresponding to group Y can be incorporated into the structure by the selection of heterocyclyl in the starting material in step 1 of Scheme 8, different alkylene groups corresponding to L₁ can be provided by the choice of diamine (or diamine synthon) using in step 1 of Scheme 7, etc.

SCHEME 17

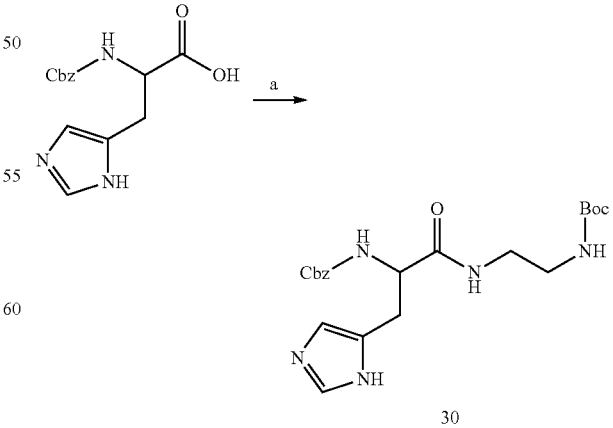

Reagents and Conditions: (a) BOP, tert-butyl 2-aminoethylcarbamate, triethylamine, dimethylformamide

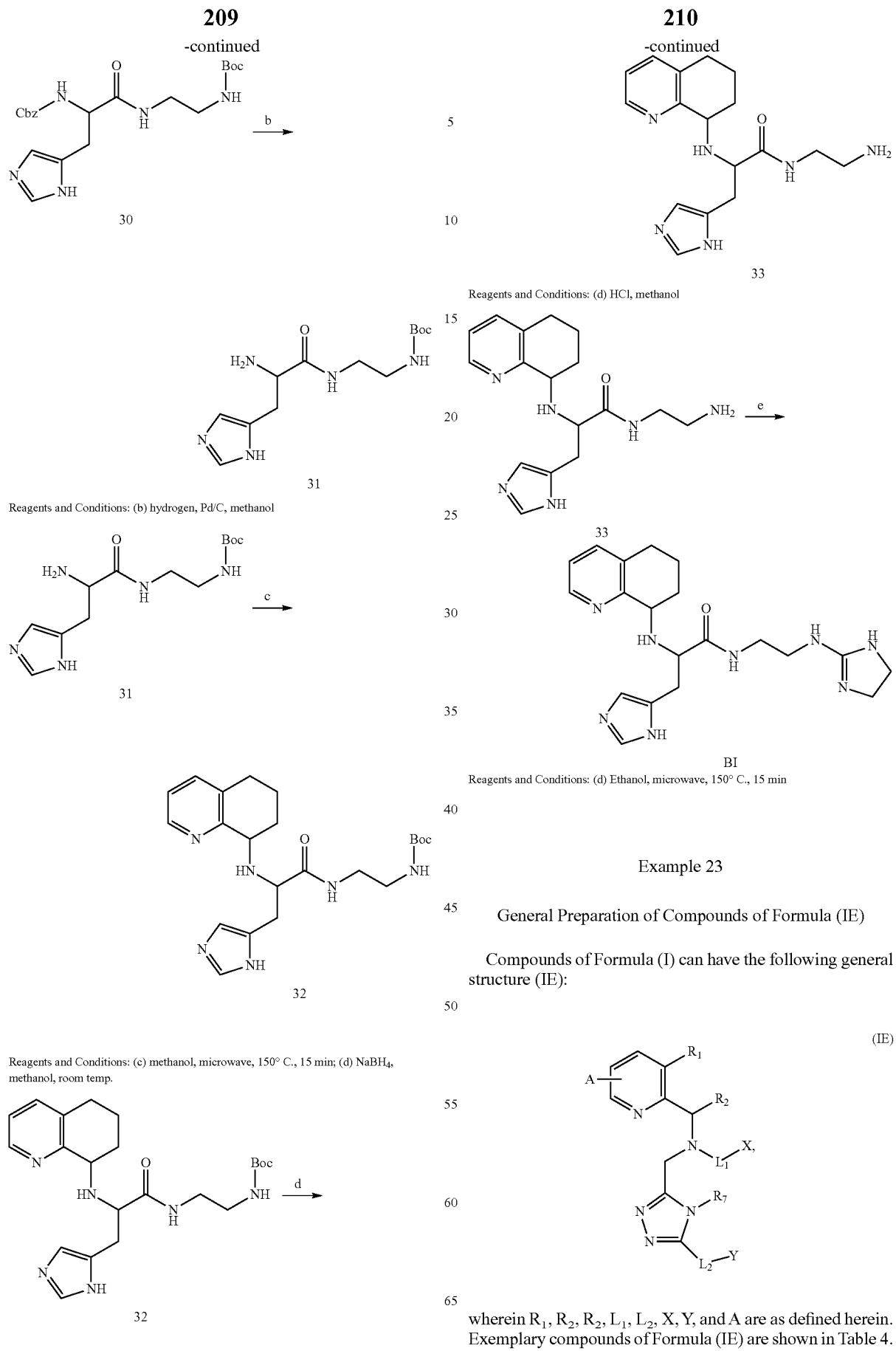
Example 23
General Preparation of Compounds of Formula (IE)
Compounds of Formula (I) can have the following general structure (IE):
wherein $R_1$, $R_2$, $R_2$, $L_1$, $L_2$, X, Y, and A are as defined herein. Exemplary compounds of Formula (IE) are shown in Table 4.

TABLE 4
| Compd. | —R7 | —L1—X | —L2—Y | 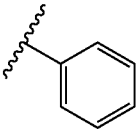 [SMILES: *c1ccccc1] |
|---|---|---|---|---|
| BP | CH3 | CH3 | 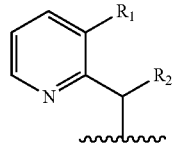 | 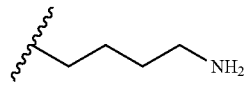 [SMILES: *CCCCN] |
| BQ | CH3 | 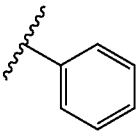 [SMILES: *c1ccccc1] | 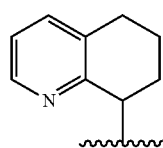 [SMILES: *C1CCCc2cccnc21] | 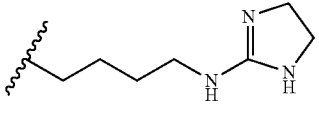 [SMILES: *CCCCNC1=NCCN1] |
| BR | CH3 | 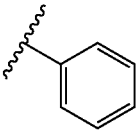 [SMILES: *c1ccccc1] | 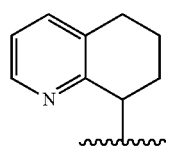 [SMILES: *C1CCCc2cccnc21] | 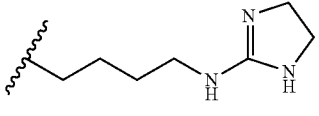 [SMILES: *CCCCNC1=NCCN1] |
| BS | CH3 | 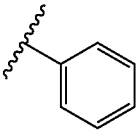 [SMILES: *c1ccccc1] | 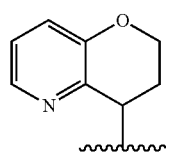 | 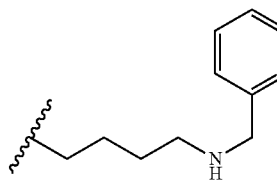 |
| BT | CH3 | 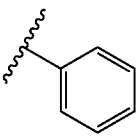 [SMILES: *c1ccccc1] | 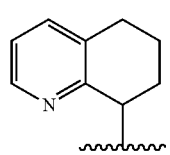 [SMILES: *C1CCCc2cccnc21] | 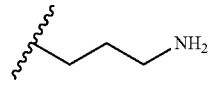 |
| BU | 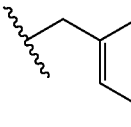 | CH3 | 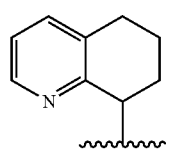 [SMILES: *C1CCCc2cccnc21] | 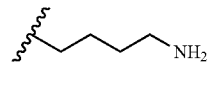 |
| BV | 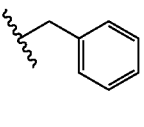 [SMILES: *Cc1ccccc1] | CH3 | 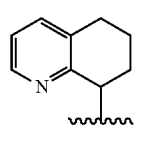 | 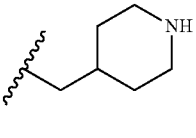 |
| BW | CH3 | CH3 | 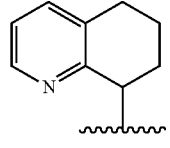 | 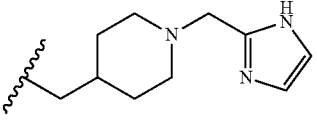 [SMILES: *CC1CCN(Cc2ncc[nH]2)CC1] |
| BX | CH3 | CH3 | 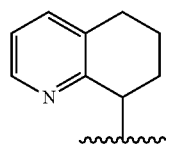 |  |

TABLE 4-continued

| Compd. | —R7 | —L1—X | —L2—Y | |
|---|---|---|---|---|
| BY | CH3 | CH3 | piperidine-CH2-pyridine | 5,6,7,8-tetrahydroquinoline |
| BZ | CH3 | CH3 | piperidine-isobutyl | 5,6,7,8-tetrahydroquinoline |
| CA | CH3 | CH3 | piperidine-imidazoline | 5,6,7,8-tetrahydroquinoline |

SCHEME 18

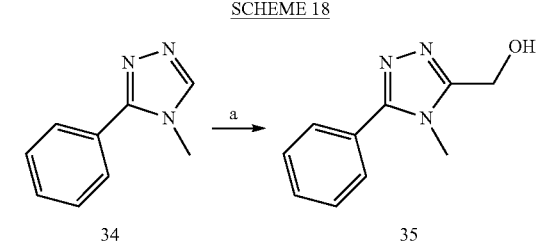

Reagents and Conditions:
(a) (CH2O)n, o-xylene, 125° C., 3 h.

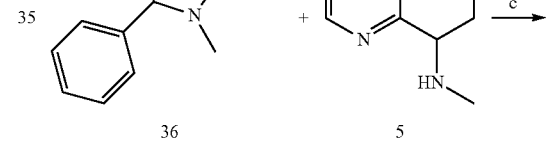

Reagents and Conditions:
(b) MnO2, tetrahydrofuran, room temp., 2 h.

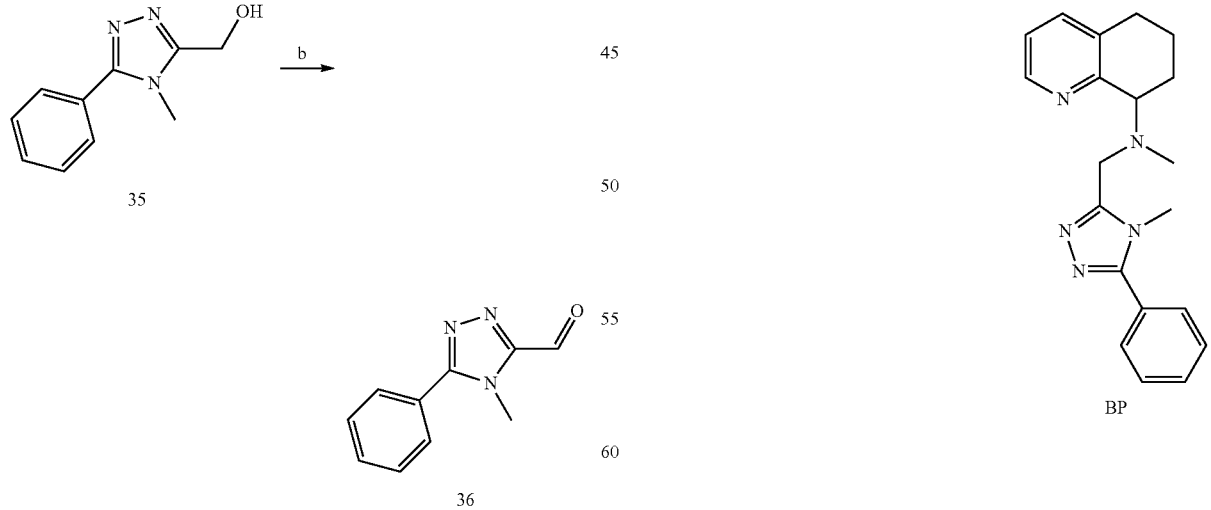

Reagents and Conditions:
(c) Na(OAc)3BH, cat. acetic acid, dichloroethane, 65° C., 18 h.

Example 24

Preparation of N-methyl-N-((4-methyl-5-phenyl-4H-1,2,4-triazol-3-yl)methyl)-5,6,7,8-tetrahydroquinolin-8-amine (BP)

Step a:
Preparation of (4-methyl-5-phenyl-4H-1,2,4-triazol-3-yl) methanol (35). To a o-xylene (20 mL) solution of 4-methyl-3-phenyl-4H-1,2,4-triazole, 34, (Ivanova, N. V.; Sviridov, S. I.; Shorshnev, S. V.; Stepanov, A. E. *Synthesis*, 2006, 1, 156; herein incorporated by reference in its entirety for all purposes) (3.0 g, 18.8 mmol) was added p-formaldehyde (2.8 g, 94.2 mmol). The reaction mixture was heated to 120° C. for 3 h. The reaction mixture was then cooled to room temperature and was diluted into chloroform (40 mL) and was washed with water (30 mL). The organics were dried over MgSO$_4$, filtered, and concentrated in vacuo. The crude material was purified by silica gel chromatography (0-5% methanol/dichloromethane) yielding 1.3 g (37%) of 35: $^1$H NMR (400 MHz, CDCl$_3$) δ 7.56-7.52 (m, 2H), 7.48-7.40 (m, 3H), 5.40 (bs, 1H), 4.83 (s, 2H), 3.74 (s, 3H); ESI$^+$ MS: m/z (rel intensity) 190 (100, M+H).

Step b:
Preparation of 4-methyl-5-phenyl-4H-1,2,4-triazole-3-carbaldehyde (36). To a solution of (4-methyl-5-phenyl-4H-1,2,4-triazol-3-yl)methanol, 35, (1.3 g, 6.9 mmol) in THF (20 mL) was added MnO$_2$ (6.0 g, 68.7 mmol). The reaction stirred at room temperature for 2 h. The reaction mixture was then filtered through a plug of Celite® and concentrated in vacuo. The crude material was purified via silica gel chromatography (0-5% methanol/dichloromethane) yielding 820 mg (64%) of 36: $^1$H NMR (400 MHz, CDCl$_3$) δ 10.14, (s, 1H), 7.68-7.60 (m, 2H), 7.59-7.45, (m, 3H), 3.98 (s, 3H); ESI$^+$ MS: m/z (rel intensity) 188 (100, M+H).

Step c:
Preparation of N-methyl-N-((4-methyl-5-phenyl-4H-1,2,4-triazol-3-yl)methyl)-5,6,7,8-tetrahydroquinolin-8-amine (BP). To a solution of N-methyl-5,6,7,8-tetrahydroquinolin-8-amine, 5, (0.39 g, 2.40 mmol) in 1,2-dichloroethane (4 mL) was added 4-methyl-5-phenyl-4H-1,2,4-triazole-3-carbaldehyde, 36, (0.41 g, 2.20 mmol), sodium triacetoxyborohydride (0.84 g, 3.90 mmol), and AcOH (1 drop). The reaction mixture was heated to 65° C. and stirred for 18 h. The reaction mixture was cooled to room temperature, poured into saturated aqueous NaHCO$_3$ (10 mL) and extracted with ethyl acetate (2×10 mL). The combined organic phases were washed with brine then dried over MgSO$_4$, filtered, and concentrated in vacuo. The crude material was purified via chromatography on basic alumina (0-5% methanol/dichloromethane) yielding BP: $^1$H NMR (400 MHz, CDCl$_3$) δ 8.39, (d, J=4.8 Hz, 1H), 7.58-7.53 (m, 2H), 7.46-7.39, (m, 3H), 7.32, (d, J=8.4 Hz, 1H), 7.01, (dd, J=7.2, 4.4 Hz, 1H), 4.04-3.92, (m, 2H), 3.78, (d, J=14.0 Hz, 1H), 2.85-2.74, (m, 1H), 2.71-2.62 (m, 1H), 3.33, (s, 3H), 2.12-1.94 (m, 3H), 1.74-1.62 (m, 1H); ESI$^+$ MS: m/z (rel intensity) 334 (100, M+H).

SCHEME 19

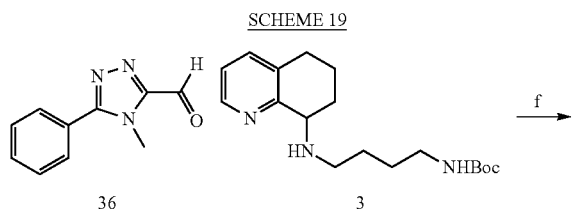

36    3

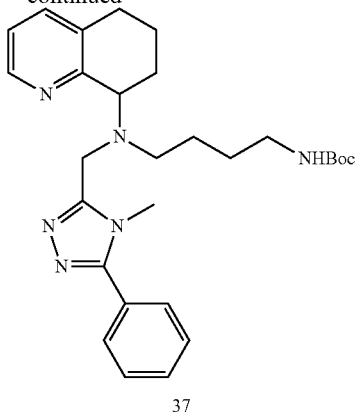

37

Reagents and Conditions:
(f) Na(OAc)$_3$BH, cat. acetic acid, dichloroethane, 65° C.

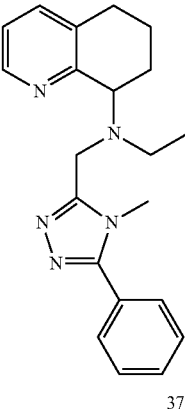

37

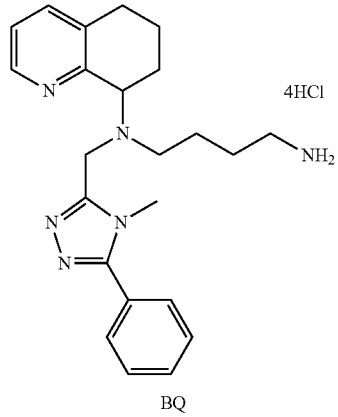

BQ

Reagents and Conditions:
(g) HCl$_{(g)}$, methanol, room temp.

Example 25

Preparation of tert-butyl 4-(((4-methyl-5-phenyl-4H-1,2,4-triazol-3-yl)methyl)(5,6,7,8-tetrahydroquinolin-8-yl)amino)butylcarbamate (37)

Step f:
To a solution of 4-methyl-5-phenyl-4H-1,2,4-triazole-3-carbaldehyde, 36, (0.41 g, 2.20 mmol) in 1,2-dichloroethane (4 mL) was added tert-butyl 4-(5,6,7,8-tetrahydroquinolin-8-ylamino)butylcarbamate, 3, (0.76 g, 2.40 mmol), sodium triacetoxyborohydride (0.84 g, 3.95 mmol), and AcOH (10 drops). The reaction mixture was heated to 65° C. and stirred for 18 h. The reaction mixture was cooled to room temperature and poured into saturated aqueous NaHCO$_3$ (15 mL) and extracted with ethyl acetate (2×10 mL). The combined organic phases were washed with brine then dried over MgSO$_4$, filtered, and concentrated in vacuo. The crude material was purified by silica gel chromatography (0-5% methanol/dichloromethane) to yield 37: $^1$H NMR (400 MHz, CDCl$_3$) δ 8.40, (d, J=5.2 Hz, 1H), 7.60-7.57 (m, 2H), 7.48-7.44, (m, 3H), 7.31, (d, J=7.2 Hz, 1H), 7.0, (dd, J=8.0, 5.2 Hz, 1H), 5.01, (bs, 1H), 4.20-3.92, (m, 3H), 3.20-2.60, (m, 6H), 2.20-1.85, (m, 4H), 1.75-1.30 (m, 13H); ESI$^+$ MS: m/z (rel intensity) 491 (100, M+H).

Step g:

Preparation of N-(4-aminobutyl)-N-(((4-methyl-5-phenyl-4H-1,2,4-triazol-3-yl)methyl)-5,6,7,8-tetrahydroquinolin-8-amine tetrahydrochloride (BQ). Through a methanol (2 mL) solution of 37 (0.16 g, 0.32 mmol) was bubbled HCl$_{(g)}$ generated by the addition of sulfuric acid to dry NaCl. Upon total conversion of the reaction as monitored by LC-MS, the reaction mixture was concentrated in vacuo to yield BQ: ESI$^+$ MS: m/z (rel intensity) 391 (100, M+H).

The skilled practitioner will recognize that the remaining compounds of Table 4 can be prepared using similar methods using the appropriately substituted starting materials and reagents. Alternatively, substituted amine derivatives can be prepared by appropriate derivatization of the unsubstituted amine (e.g., BR-BT can be prepared from BQ, etc.).

Example 26

General Preparation of Compounds of Formula (IF)

Compounds of Formula (I) can have the following general structure (IF):

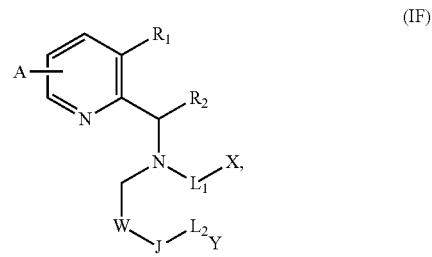

wherein R$_1$, R$_2$, L$_1$, L$_2$, X, Y, W, J, and A are as defined herein. Specific embodiments of the compounds of Formula (IF) are shown below in Table 5.

TABLE 5

TABLE 5-continued

| Compound | —W— | —J— | —L₁—X | —L₂—Y | (pyridine-R₁,R₂ group) |
|---|---|---|---|---|---|
| CG | pyridine | — | CH₃ | ~NH-C(=N)-NH- cyclic guanidine chain | tetrahydroquinoline |
| CH | pyridine | — | CH₃ | ~NH-CH₂-pyridine chain | tetrahydroquinoline |
| CI | dimethylaminopyrimidine | NH | CH₃ | ~NH₂ chain | tetrahydroquinoline |
| CJ | dimethylaminopyrimidine | NH | CH₃ | ~NH₂ shorter chain | tetrahydroquinoline |
| CK | dimethylaminopyrimidine | NH | CH₃ | ~NH₂ chain | tetrahydroquinoline |
| CL | dimethylaminopyrimidine | NH | CH₃ | ~NH-imidazoline | tetrahydroquinoline |
| CM | methoxypyrimidine | NH | CH₃ | ~NH-imidazoline | tetrahydroquinoline |

TABLE 5-continued

| Compound | —W— | —J— | —L₁—X | —L₂—Y | (pyridine-R₁,R₂ group) |
|---|---|---|---|---|---|
| CN | (5-methoxypyrimidin-4,5-diyl) | NH | CH₃ | propyl-NH-CH₂-(2-pyridyl) | 5,6,7,8-tetrahydroquinolin-8-yl |
| CO | (piperazin-2-yl, N-linked) | CO | CH₃ | propyl-NH₂ | 5,6,7,8-tetrahydroquinolin-8-yl |
| CP | (piperazin-2-yl, N-linked) | CO | CH₃ | butyl-NH₂ | 5,6,7,8-tetrahydroquinolin-8-yl |
| CQ | (piperazin-2-yl, N-linked) | CO | CH₃ | butyl-NH-(imidazolin-2-yl) | 5,6,7,8-tetrahydroquinolin-8-yl |
| CR | (piperazin-2-yl, N-linked) | CO | CH₃ | butyl-NH-CH₂-(2-pyridyl) | 5,6,7,8-tetrahydroquinolin-8-yl |
| CS | (piperazin-2-yl, N-linked) | CO | CH₃ | propyl-NH-(imidazolin-2-yl) | 5,6,7,8-tetrahydroquinolin-8-yl |
| CT | (piperazin-2-yl, N-linked) | CONH | CH₃ | propyl-NH₂ | 5,6,7,8-tetrahydroquinolin-8-yl |

TABLE 5-continued

| Compound | —W— | —J— | —L₁—X | —L₂—Y | (pyridine with $R_1$, $R_2$) |
|---|---|---|---|---|---|
| CU | (piperazine) | CONH | CH₃ | (butylamine) | (tetrahydroquinoline) |
| CV | (piperazine) | CONH | CH₃ | (N,N-diethylpropylamine) | (tetrahydroquinoline) |
| CW | (piperazine) | CO | CH₃ | (piperidine-NH) | (tetrahydroquinoline) |
| CX | (piperazine) | CO | CH₃ | (piperidine-CH₂-pyridine) | (tetrahydroquinoline) |
| CY | (piperazine) | CO | CH₃ | (piperidine-imidazoline) | (tetrahydroquinoline) |

The compounds of Formula (IF) generally can be prepared by the procedures of Schemes 20 and 21, below.

SCHEME 20

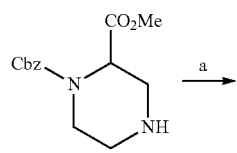

a →

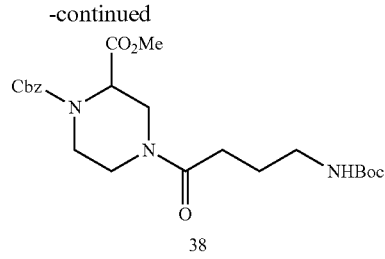

38

Reagents and Conditions: (a) BOP, 4-tert-butoxycarbonylaminobutyric acid, triethylamine, dimethylformamide 225
-continued
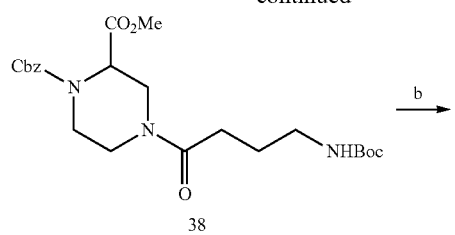
38
b →
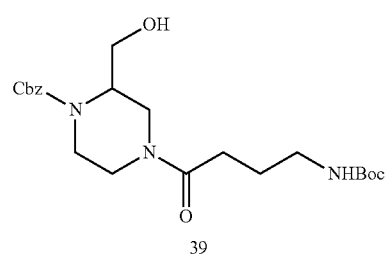
39
Reagents and Conditions: (b) NaBH₄, methanol
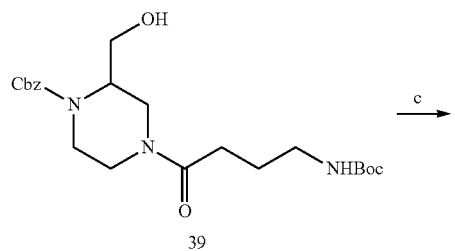
39
c →
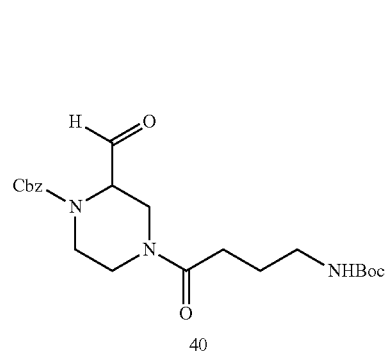
40
Reagents and Conditions: (c) Dess-Martin periodinane, pyridine, CH₂Cl₂
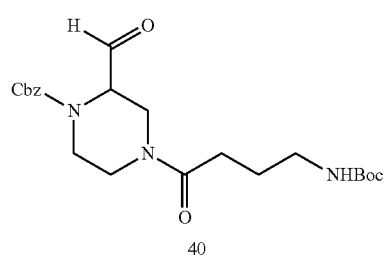
40
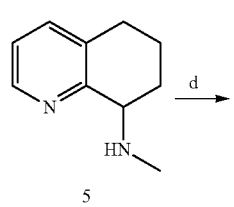
5
d →
226
-continued
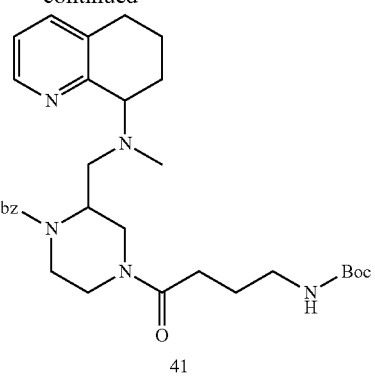
41
Reagents and Conditions: (d) Na(OAc)₃BH, cat. acetic acid, dichloroethane, 65° C., 18 h.
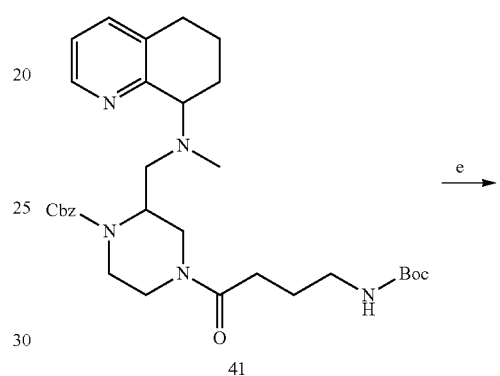
41
e →
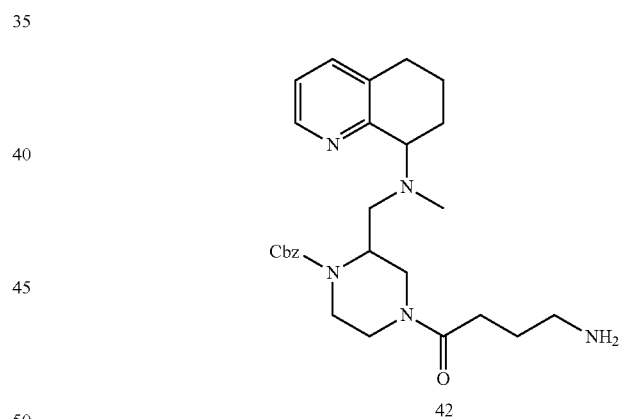
42
Reagents and Conditions: (e) HCl, methanol
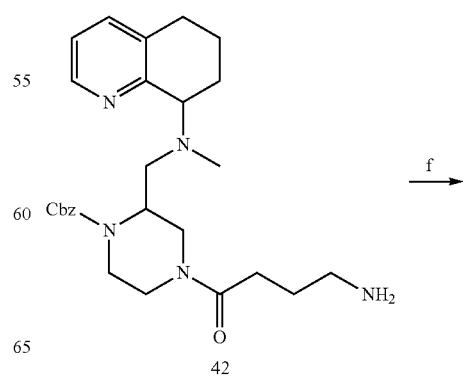
42
f →

227
-continued
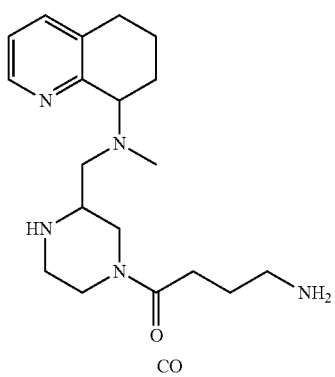
Reagents and Conditions: (f) hydrogen, Pd/C, methanol
SCHEME 21
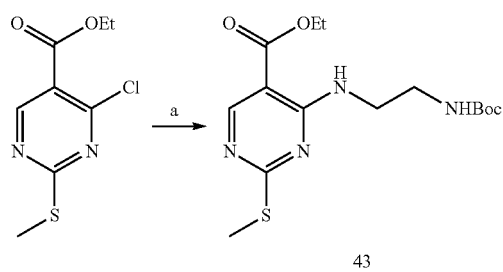
43
Reagents and Conditions: (a) 2-tert-butoxycarbonylaminoethylamine, triethylamine, tetrahydrofuran
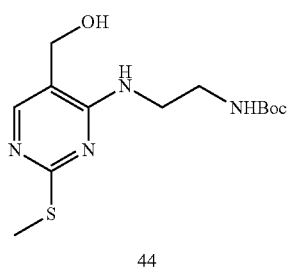
43
Reagents and Conditions: (b) LiAlH$_4$, tetrahydrofuran
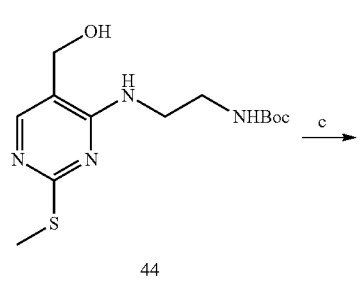
44
228
-continued
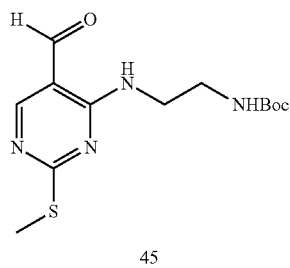
45
Reagents and Conditions: (c) MnO$_2$, CHCl$_3$
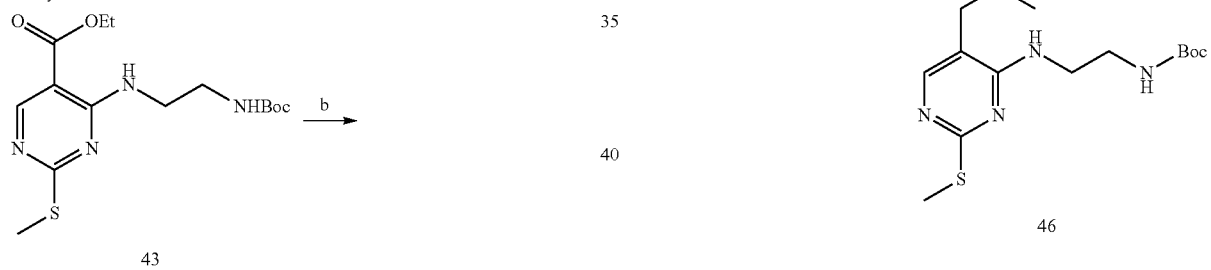
45
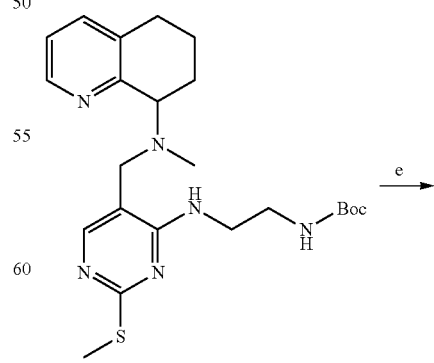
46
Reagents and Conditions: (d) Na(OAc)$_3$BH, cat. acetic acid, dichloroethane, 65° C., 18 h.
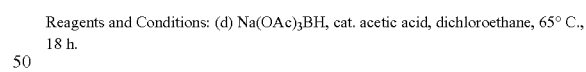
46

229
-continued

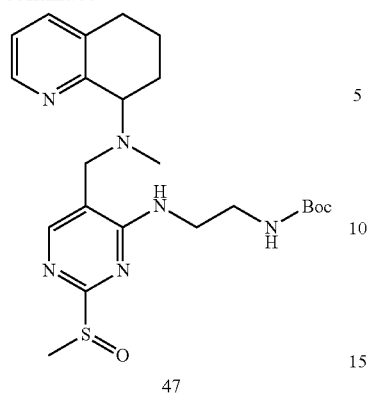
47

Reagents and Conditions: (e) 3-phenyl-2-(phenylsulfonyl)-1,2-oxaziridine, methanol/CH₂Cl₂

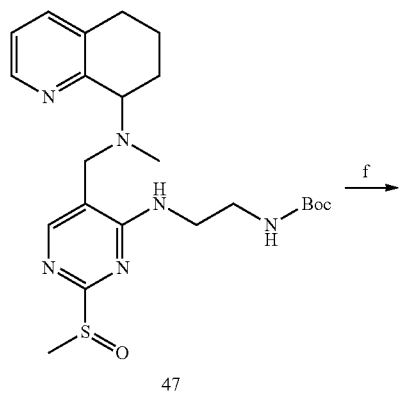
47

Reagents and Conditions: (f) dimethylamine, dimethylformamide

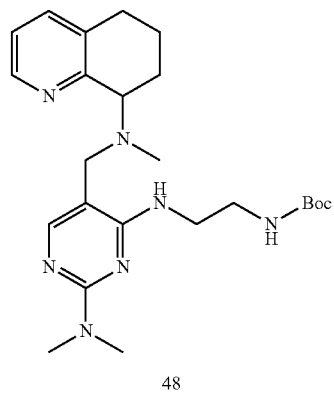
48

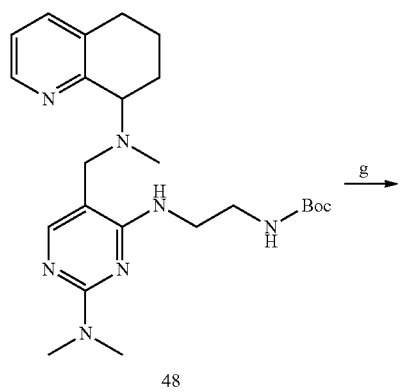
48

230
-continued

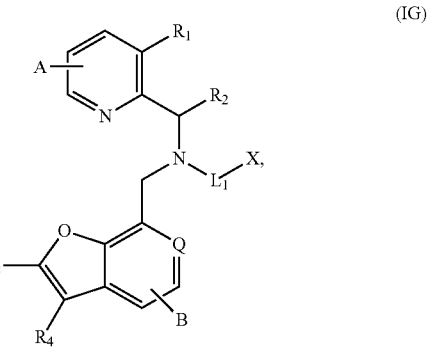
CJ

Reagents and Conditions: (g) HCl, methanol

The skilled practitioner will recognize that the various embodiments of the compounds of Formula (IF) disclosed in Table 5 can be prepared by analogous methods using appropriately substituted starting materials, or by appropriate modification e.g. of an amino-functional compound (e.g., compound CD can be prepared by di-alkylation of compound CC).

Example 27

General Preparation of Compounds of Formula (IG)

Compounds of Formula (I), can have the following general Formula (IG):

(IG)

wherein $R_1$, $R_2$, $R_3$, $R_4$, $L_1$, X, Q, A, and B are as defined herein. Specific embodiments of the compounds of Formula (IG) are shown in Table 6, below.

TABLE 6
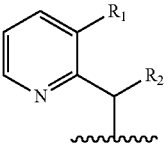
| Compound | —R₃ | —R₄ | Q | —L₁—X | |
|---|---|---|---|---|---|
| CZ | 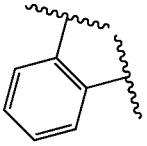 [SMILES: *c1ccccc1*] | | N | 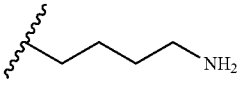 [SMILES: *CCCCN] | 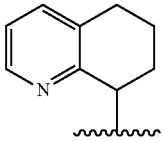 [SMILES: *C1CCCc2cccnc21] |
| DA | H | H | CH | 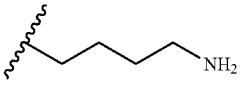 [SMILES: *CCCCN] | 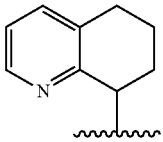 |
| DB | H | H | CH | CH₃ | 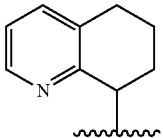 [SMILES: *C1CCCc2cccnc21] |
| DC | 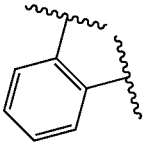 [SMILES: *c1ccccc1*] | | N | 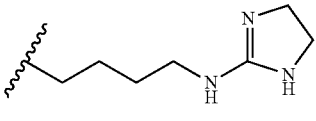 [SMILES: *CCCCNC1=NCCN1] | 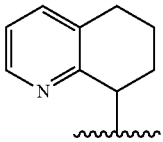 [SMILES: *C1CCCc2cccnc21] |
| DD | 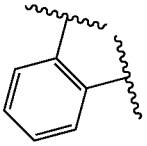 [SMILES: *c1ccccc1*] | | N | 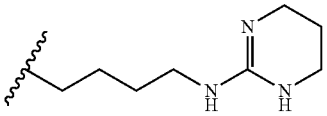 [SMILES: *CCCCNC1=NCCCN1] | 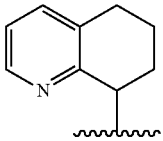 [SMILES: *C1CCCc2cccnc21] |
| DE | 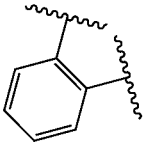 [SMILES: *c1ccccc1*] | | N | 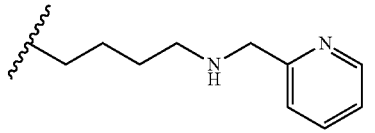 [SMILES: *CCCCNCc1ccccn1] | 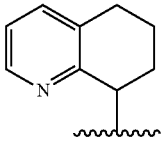 [SMILES: *C1CCCc2cccnc21] |
| DF | 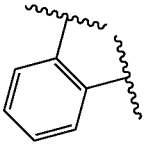 [SMILES: *c1ccccc1*] | | N | 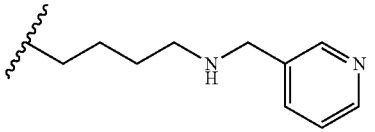 [SMILES: *CCCCNCc1cccnc1] | 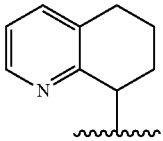 [SMILES: *C1CCCc2cccnc21] |
| DG | 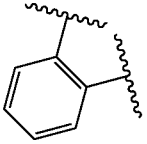 [SMILES: *c1ccccc1*] | | N | 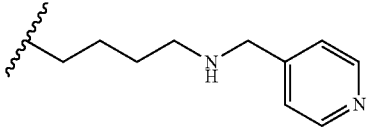 [SMILES: *CCCCNCc1ccncc1] | 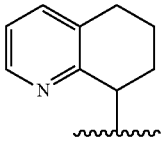 [SMILES: *C1CCCc2cccnc21] |
| DH | 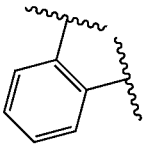 [SMILES: *c1ccccc1*] | | N | 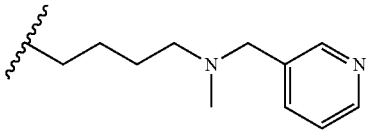 [SMILES: *CCCCN(C)Cc1cccnc1] | 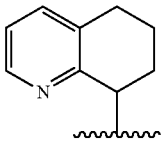 |

TABLE 6-continued
| Compound | —R3 | —R4 | Q | —L1—X | (pyridine-R1/R2 group) |
|---|---|---|---|---|---|
| DI | 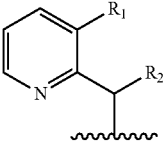 | | N | 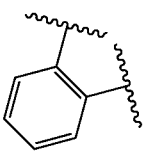 [SMILES: *c1ccccc1*] | 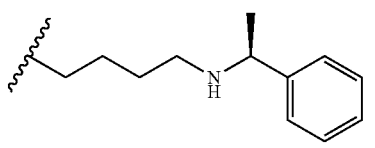 [SMILES: *CCCCN[C@@H](C)c1ccccc1] |
| DJ | 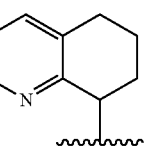 | | N | 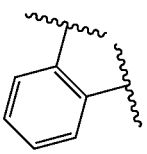 [SMILES: *c1ccccc1*] | 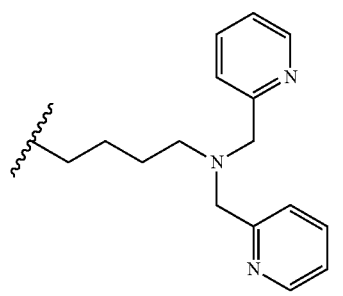 [SMILES: *CCCCN(Cc1ccccn1)Cc1ccccn1] |
| DK | 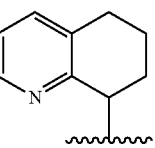 | | N | 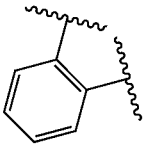 [SMILES: *c1ccccc1*] | 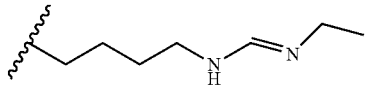 [SMILES: *CCCCN/C=N/CC] |
| DL | 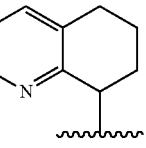 | | N | 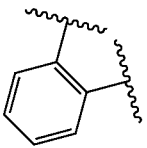 [SMILES: *c1ccccc1*] | 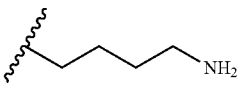 [SMILES: *CCCCN] |
| DM | 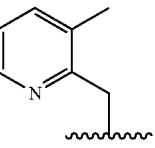 | | N | 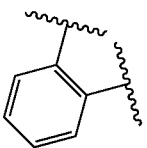 [SMILES: *c1ccccc1*] | 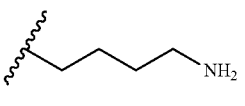 |
| DN | 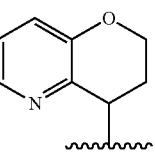 | | N | 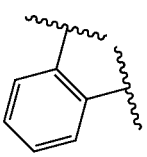 [SMILES: *c1ccccc1*] | 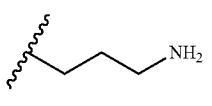 |
| DO | 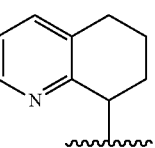 | | N | 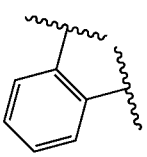 [SMILES: *c1ccccc1*] | 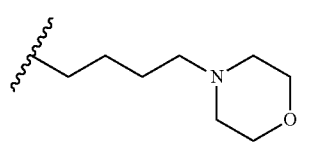 [SMILES: *CCCCN1CCOCC1] |
| DP | 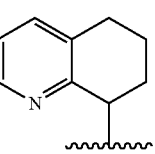 | | N | 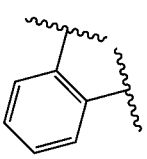 [SMILES: *c1ccccc1*] | 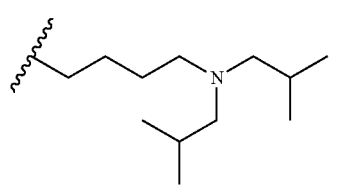 [SMILES: *CCCCN(CC(C)C)CC(C)C] |

TABLE 6-continued

| Compound | —R₃ | —R₄ | Q | —L₁—X | (structure with R₁, R₂) |
|---|---|---|---|---|---|
| DQ | (o-phenylene) | | N | CH₃ | 5,6,7,8-tetrahydroquinolin-8-yl |
| DR | (o-phenylene) | | N | CH₃ | 5,6,7,8-tetrahydroquinolin-8-yl |
| DS | (o-phenylene) | | N | CH₃ | 5,6,7,8-tetrahydroquinolin-8-yl |
| DT | (o-phenylene) | | N | CH₃ | 5,6,7,8-tetrahydroquinolin-8-yl |
| DU | (o-phenylene) | | N | CH₃ | 5,6,7,8-tetrahydroquinolin-8-yl |
| DV | (o-phenylene) | | N | —(CH₂)₄—NH₂ | 1-(pyridin-2-yl)ethyl |

The compounds of Formula (IG) could be prepared as described below.

SCHEME 22

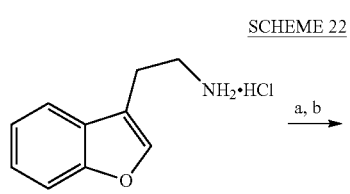

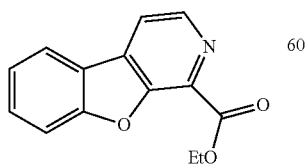

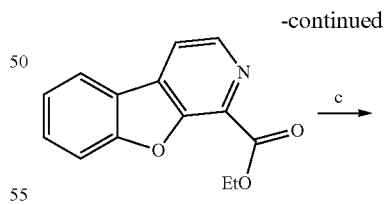

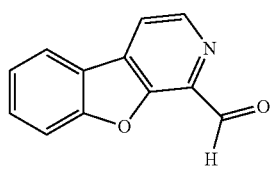

Reagents and Conditions: (a) ethyl glyoxalate, ethanol, toluene, 0° C. to room temp., 17 h; (b) Pd/C, xylene, 140° C.

Reagents and Conditions: (c) DIBAL—H, CH₂Cl₂, -50° C., 10 min.

-continued

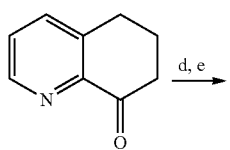

d, e

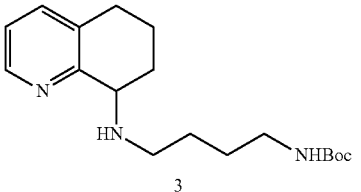

3

Reagents and Conditions: (d) tert-butyl 4-aminobutylcarbamate, 3Å molecular sieves, ethanol, microwave, 150° C., 10 min. (e) NaBH₄, ethanol

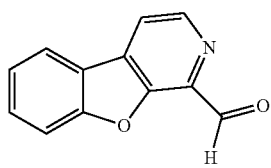

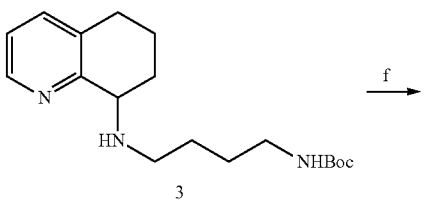

3 f

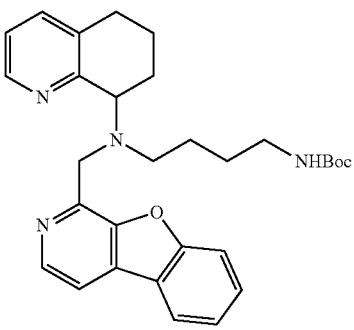

Reagents and Conditions: (f) Na(OAc)₃BH, acetic acid, 4Å molecular sieves, 1,2-dichloroethane, microwave, 100° C., 10 min

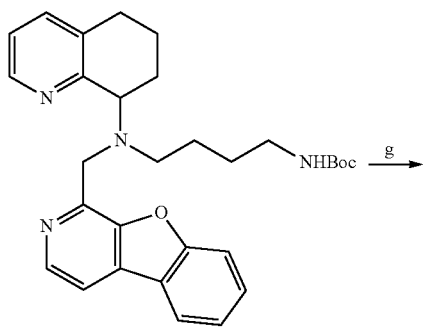

g

-continued

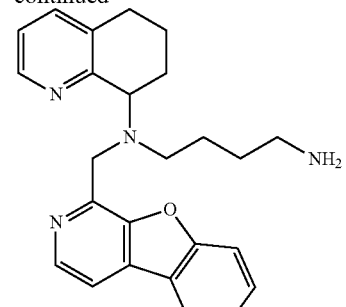

Reagents and Conditions: (g) thionyl chloride, methanol, room temp., 2 h

The skilled practitioner will recognize that the various embodiments of the compounds of Formula (IG) disclosed in Table 6 could be prepared by analogous methods using appropriately substituted starting materials, or by appropriate modification e.g. of an amino-functional compound (e.g., compound DP could be prepared by di-alkylation of compound CZ).

Assay Examples

Small molecule chemokine receptor modulation, agonism or antagonism, can be mediated by direct binding to the receptor affecting the signaling and chemotatic effects of the natural ligand for its receptor. In addition modulation can be obtained by interaction of the small molecule with effectors of the particular chemokine receptor pathway. Small molecules can also affect CXCR4 homodimerization (Rodriguez-Frade, et al., J. Cell. Biol. 1999; Mellado et al., Annual Review of Immunology 2001; Toth et al., J. Pharm. and Exp. Ther. 2004; Wang et al., Mol. Cancer. Ther. 2006), heterodimerization with CCR2 (Percherancier, et al. JBC 2005, Sohy et al. JBC 2007) or CCR5 (Babcock, et al., JBC 2003) or CXCR7 (Sierro et al., PNAS 2007), delta opioid receptor (DOR) (Pello et al European J of 1 mm. 2008, Hereld and Jin European J. of 1 mm. 2008) or a T cell receptor (Kumar et al., Immunity 2006). Modulation of the SDF-1/CXCR4 pathway can also be accomplished by targeting the GPR54/KISS receptor (Navenot et al., Cancer Res. 2005), cannabanoid receptor 2 (CB2R) (Coopman et al., International Immunopharmacology 2007), ZAP-70 tyrosine kinase (Ottoson et al, J Immunology 2001) or sphingosine 1-phosphate receptors (Yopp et al., J. Immunology 2005).

Example 28

Screening by Functional Calcium Mobilization Assay

Functional modulation of CXCR4 was determined by calcium mobilization assay using leukemic lymphoid CEM cells, which naturally express high levels of CXCR4. Generally, the assay is carried out as follows: Cells are grown in vitro to confluency. On the day of the assay, cells are removed from the incubator, culture medium removed and replaced with a calcium sensitive dye (Calcium3 assay kit; Molecular Devices, Sunnyvale, Calif.). The cells are allowed to dye load for 45-60 min at 37° C. in the cell culture incubator and then allowed to equilibrate to room temperature for no more than 15 min before assay.

Compound plates were generated containing up to 3% dimethyl sulfoxide in media kept at room temperature. Test compounds were added to the cells at a 1:3 dilution, and calcium mobilization was measured using a Flex Station fluorescence imager (Molecular Devices). This first read was used to determine direct agonist activation of the CXCR4 receptor by the test compounds. Approximately 45 min after the test compound was added, cells were challenged with SDF-1α at $EC_{80}$-$EC_{90}$ concentration and calcium mobilization measured using a Flex Station fluorescence imager. Full dose response curves were generated daily for SDF-1a to calculate $IC_{50}$ concentrations. The $IC_{50}$ values are reported. In cases, where one was not determined, a percent inhibition at the 1 μM concentration was extrapolated.

The compounds of the invention generally have an $IC_{50}$ value below 100 micromolar for inhibition of calcium mobilization induced by SDF-1a. Results for specified compounds are shown in the Table 7.

TABLE 7

| Compound | Ca Flux $IC_{50}$ (nM) or % inhibition at 1 μM |
|---|---|
| 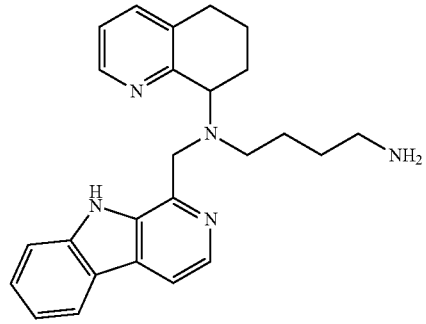 [SMILES: NCCCCN(Cc1nccc2c1[nH]c1ccccc12)C1CCCc2cccnc21] | 142 nM |
| 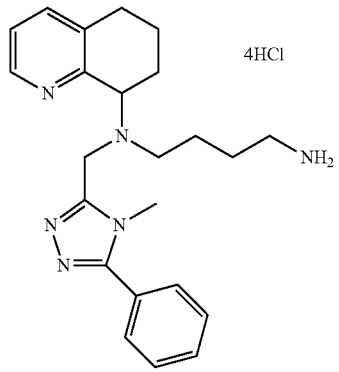 [SMILES: Cn1c(CN(CCCCN)C2CCCc3cccnc32)nnc1-c1ccccc1] 4HCl | 3,200 nM |
| 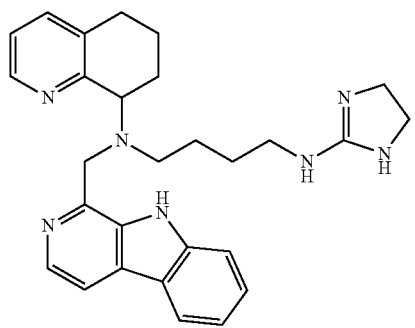 [SMILES: c1cnc2c(c1)CCCC2N(CCCCNC1=NCCN1)Cc1nccc2c1[nH]c1ccccc12] | 1,666 nM |
| 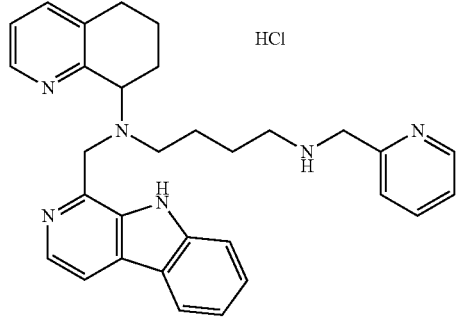 [SMILES: c1ccc(CNCCCCN(Cc2nccc3c2[nH]c2ccccc23)C2CCCc3cccnc32)nc1 ; Cl] HCl | 5,100 nM |

TABLE 7-continued
| Compound | Ca Flux IC$_{50}$ (nM) or % inhibition at 1 μM |
|---|---|
| 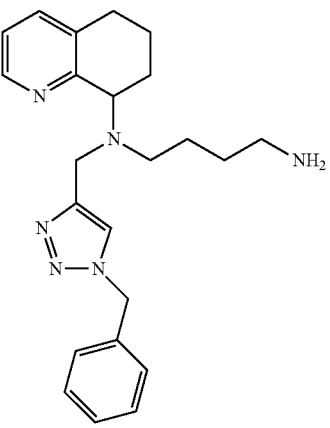 [SMILES: NCCCCN(Cc1cn(Cc2ccccc2)nn1)C1CCCc2cccnc21] | 45% |
| 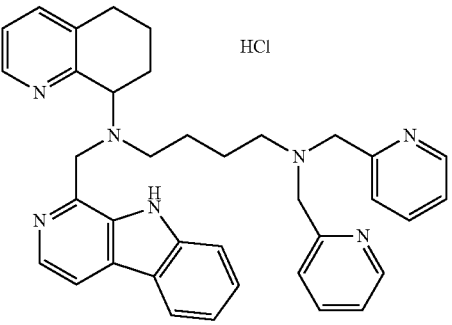 [SMILES: c1ccc(CN(CCCCN(Cc2nccc3c2[nH]c2ccccc23)C2CCCc3cccnc32)Cc2ccccn2)nc1 ; Cl] HCl | 27% |
| 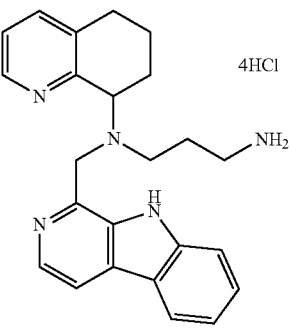 [SMILES: NCCCN(Cc1nccc2c1[nH]c1ccccc12)C1CCCc2cccnc21] 4HCl | 0% |
| 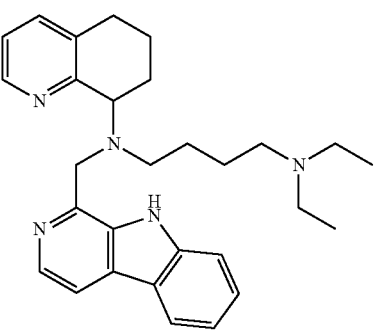 [SMILES: CCN(CC)CCCCN(Cc1nccc2c1[nH]c1ccccc12)C1CCCc2cccnc21] | 4% |

TABLE 7-continued
| Compound | Ca Flux IC$_{50}$ (nM) or % inhibition at 1 μM |
|---|---|
| 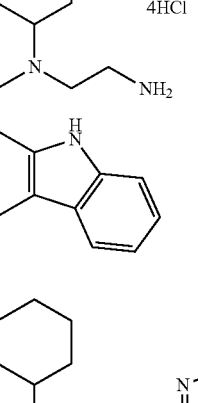 | 0% |
| 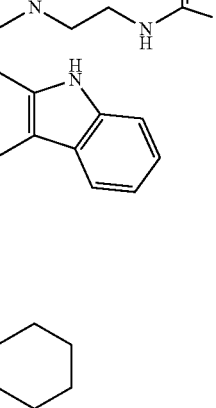 | 0% |
| 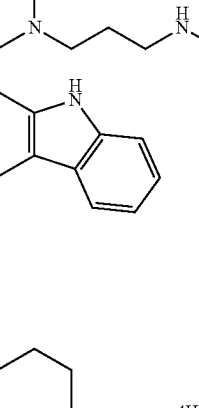 | 6% |
| 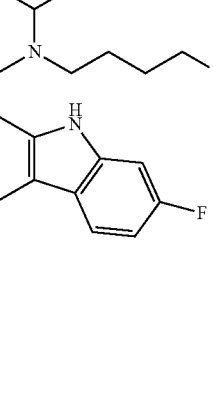 | 565 nM |

TABLE 7-continued

| Compound | Ca Flux IC$_{50}$ (nM) or % inhibition at 1 μM |
|---|---|
| (structure) | 0% |
| (structure) | 729 nM |
| (structure) | 168 nM |
| (structure) | 38 nM |

TABLE 7-continued

| Compound | Ca Flux IC$_{50}$ (nM) or % inhibition at 1 μM |
|---|---|
| [structure] | 1,720 nM |
| [structure] 4HCl | 55% |
| [structure] | 1% |
| [structure] | 20% |

TABLE 7-continued
| Compound | Ca Flux IC$_{50}$ (nM) or % inhibition at 1 μM |
|---|---|
| 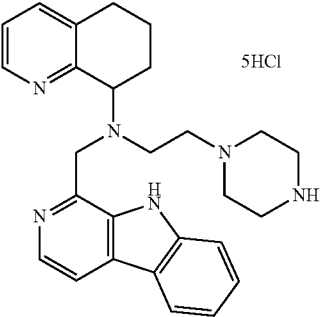 [SMILES: c1cnc2c(c1)CCCC2N(CCN1CCNCC1)Cc1nccc2c1[nH]c1ccccc12] 5HCl | 0% |
| 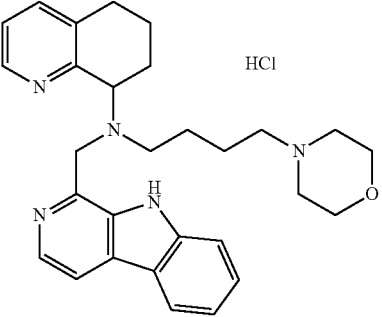 [SMILES: c1cnc2c(c1)CCCC2N(CCCCN1CCOCC1)Cc1nccc2c1[nH]c1ccccc12 ; Cl] HCl | 49% |
| 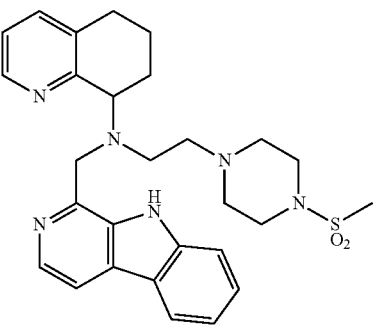 [SMILES: CS(=O)(=O)N1CCN(CCN(Cc2nccc3c2[nH]c2ccccc23)C2CCCc3cccnc32)CC1] | 9,999 nM |
| 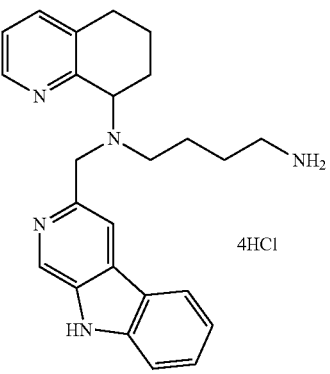 [SMILES: NCCCCN(Cc1cc2c(cn1)[nH]c1ccccc12)C1CCCc2cccnc21] 4HCl | 69 nM |

TABLE 7-continued
| Compound | Ca Flux IC$_{50}$ (nM) or % inhibition at 1 μM |
|---|---|
| 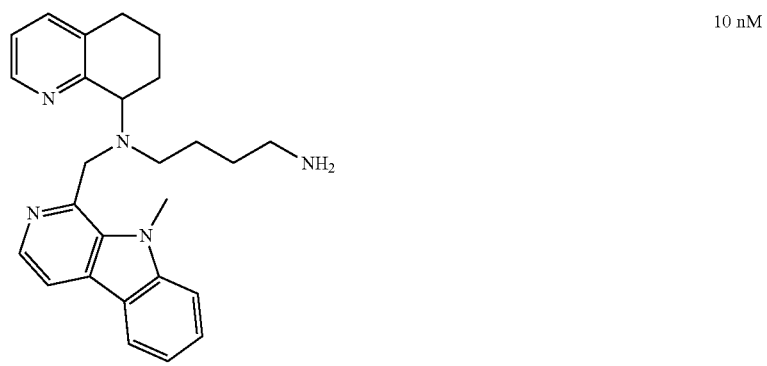 | 10 nM |
| 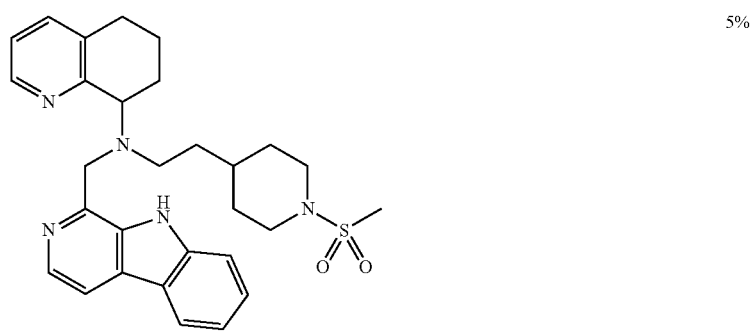 | 5% |
| 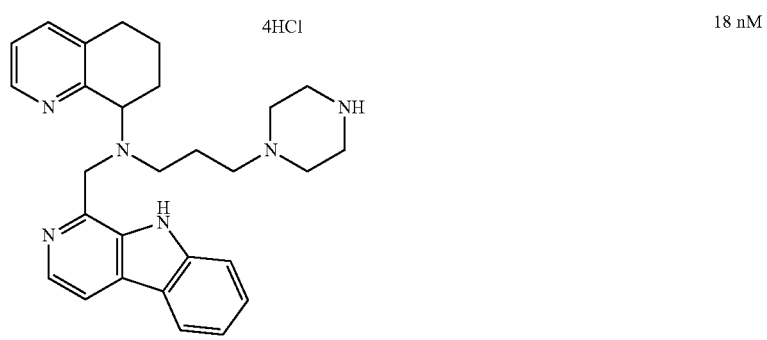 4HCl | 18 nM |
| 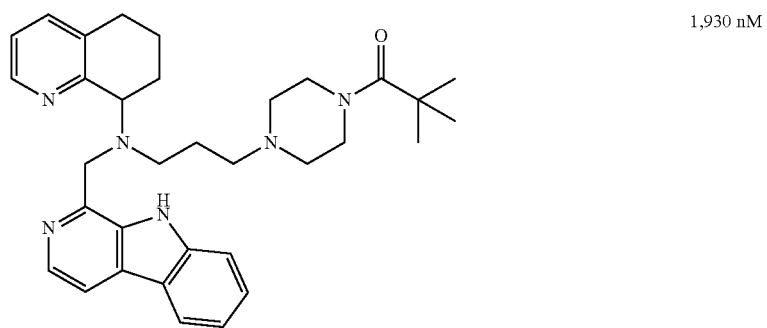 | 1,930 nM |

TABLE 7-continued

| Compound | Ca Flux IC$_{50}$ (nM) or % inhibition at 1 μM |
|---|---|
| (structure) | 27% |
| (structure) 4HCl | 1,955 nM |
| (structure) H H H Cl Cl Cl | 22 nM |
| (structure) | 699 nM |

TABLE 7-continued

| Compound | Ca Flux IC$_{50}$ (nM) or % inhibition at 1 μM |
|---|---|
| (structure) | 39% |
| (structure) | 451 nM |
| (structure) | 19% |
| (structure) | 0% |

TABLE 7-continued
| Compound | Ca Flux IC$_{50}$ (nM) or % inhibition at 1 μM |
|---|---|
| 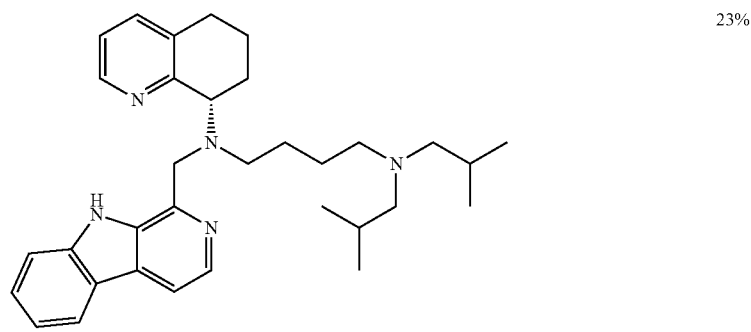 | 23% |
| 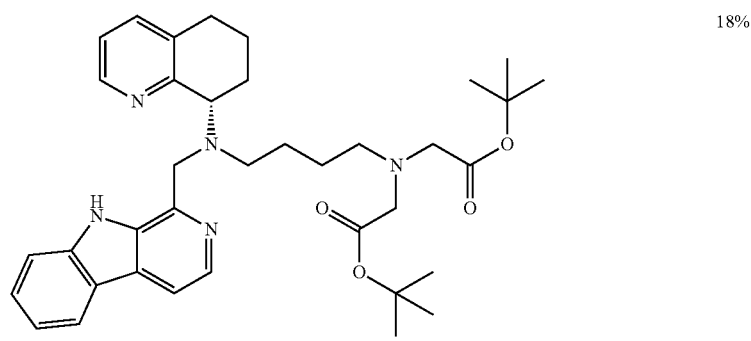 | 18% |
| 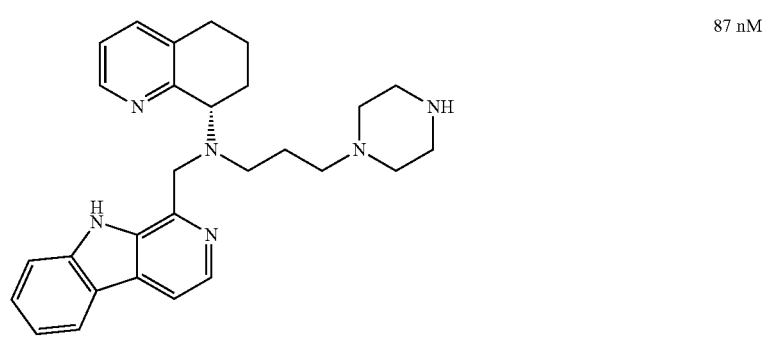 | 87 nM |
| 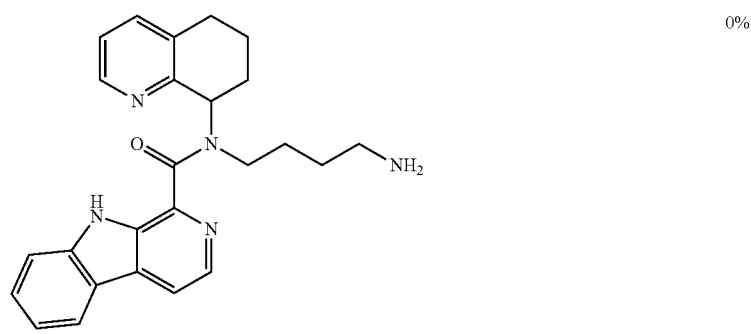 | 0% |

TABLE 7-continued

| Compound | Ca Flux IC$_{50}$ (nM) or % inhibition at 1 μM |
|---|---|
| (5,6,7,8-tetrahydroquinolin-8-yl)aminomethyl-β-carboline derivative | 0% |
| N-(4-aminobutyl)-N-((5,6,7,8-tetrahydroquinolin-8-yl))aminomethyl-β-carboline derivative | 30 nM |
| N-(4-aminobutyl)-N-((5,6,7,8-tetrahydroquinolin-8-yl))aminomethyl-β-carboline derivative (other stereoisomer) | 1,340 nM |
| N-(4-aminobutyl)-N-((5,6,7,8-tetrahydroquinolin-8-yl))aminomethyl-β-carboline derivative (3-substituted) | 1,180 nM |

TABLE 7-continued

| Compound | Ca Flux IC$_{50}$ (nM) or % inhibition at 1 μM |
|---|---|
| [structure] | 100 nM |
| [structure] | 2,810 nM |
| [structure] | 1 nM |
| [structure] | 79 nM |

TABLE 7-continued

| Compound | Ca Flux IC$_{50}$ (nM) or % inhibition at 1 μM |
|---|---|
| (pyridin-2-ylmethyl / 9H-β-carbolin-1-ylmethyl)-N-(4-aminobutyl)amine structure | 1,970 nM |
| (5,6,7,8-tetrahydroquinolin-8-yl / 5-methyl-β-carbolin-3-ylmethyl)-N-(4-aminobutyl)amine structure | 57 nM |
| (5,6,7,8-tetrahydroquinolin-8-yl / 9H-β-carbolin-1-ylmethyl)-N-[4-(pyrimidin-2-ylamino)butyl]amine structure | 0% |
| (5,6,7,8-tetrahydroquinolin-8-yl / 9H-β-carbolin-1-ylmethyl)-N-[4-(N'-phenylhydrazinocarbonyl)benzyl]amine structure | 0% |

TABLE 7-continued

| Compound | Ca Flux IC$_{50}$ (nM) or % inhibition at 1 μM |
|---|---|
| (structure) | 331 nM |
| (structure) | 0% |
| (structure) 4 CF$_3$CO$_2$H | 864 nM |
| (structure) 3 CF$_3$CO$_2$H | 22 nM |

TABLE 7-continued
| Compound | Ca Flux IC$_{50}$ (nM) or % inhibition at 1 μM |
|---|---|
| 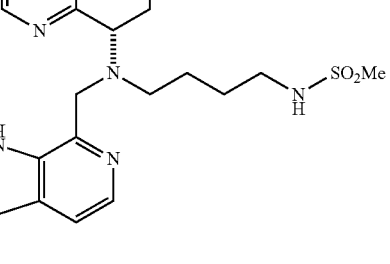 | 0% |
| 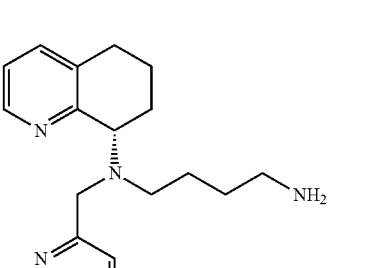 | 949 nM |
| 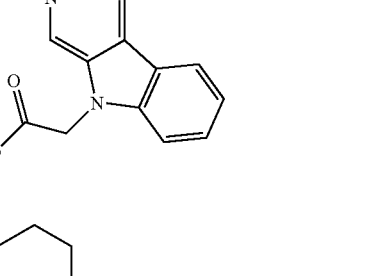 | 0% |
| 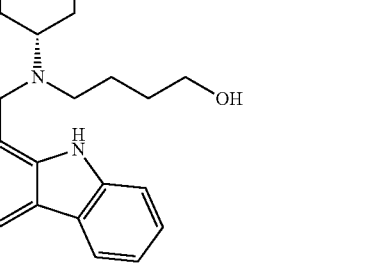 | 6,671 nM |

TABLE 7-continued

| Compound | Ca Flux IC$_{50}$ (nM) or % inhibition at 1 μM |
|---|---|
| [structure] | 0% |
| [structure] | 15 nM |
| [structure] | 0% |
| [structure] | 0% |

TABLE 7-continued

| Compound | Ca Flux IC$_{50}$ (nM) or % inhibition at 1 μM |
|---|---|
| *(structure)* | 663 nM |
| *(structure)* | 110 nM |
| *(structure)* | 20% |
| *(structure)* | 949 nM |

TABLE 7-continued

| Compound | Ca Flux IC$_{50}$ (nM) or % inhibition at 1 μM |
|---|---|
| (structure) | 1,440 nM |
| (structure) | 15 nM |
| (structure) | 32% |
| (structure) | 30 nM |

TABLE 7-continued

| Compound | Ca Flux IC$_{50}$ (nM) or % inhibition at 1 μM |
|---|---|
| | 3,370 nM |
| | 217 nM |
| | 44 nM |
| | 4,390 nM |

TABLE 7-continued

| Compound | Ca Flux IC$_{50}$ (nM) or % inhibition at 1 μM |
|---|---|
| *(phthalimide-ethyl-substituted β-carboline with tetrahydroquinoline-N-methyl group)* | 329 nM |
| *(3-aminopropyl-substituted β-carboline with tetrahydroquinoline-N-methyl group)* | 1,046 nM |
| *(2-aminoethyl-substituted β-carboline with tetrahydroquinoline-N-methyl group)* | 142 nM |
| *(propargyl-substituted β-carboline with tetrahydroquinoline-N-(4-aminobutyl) group)* | 9 nM |

TABLE 7-continued

| Compound | Ca Flux IC$_{50}$ (nM) or % inhibition at 1 μM |
|---|---|
| (structure) | 1,810 nM |
| (structure) | 0% |
| (structure) | 4 nM |
| (structure) | 0% |

TABLE 7-continued

| Compound | Ca Flux IC$_{50}$ (nM) or % inhibition at 1 μM |
|---|---|
| (structure) | 0% |
| (structure) | 8,890 nM |
| (structure) | 11 nM |
| (structure) | 31 nM |

TABLE 7-continued

| Compound | Ca Flux IC$_{50}$ (nM) or % inhibition at 1 μM |
|---|---|
| | 1,640 nM |
| | 59 nM |
| | 123 nM |
| | 0% |

TABLE 7-continued
| Compound | Ca Flux IC$_{50}$ (nM) or % inhibition at 1 µM |
|---|---|
| 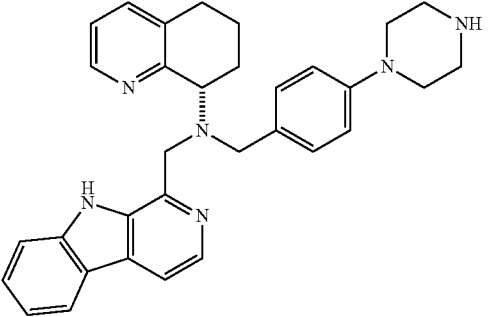 [SMILES: c1cnc2c(c1)CCC[C@@H]2N(Cc1ccc(N2CCNCC2)cc1)Cc1nccc2c1[nH]c1ccccc12] | 0% |
| 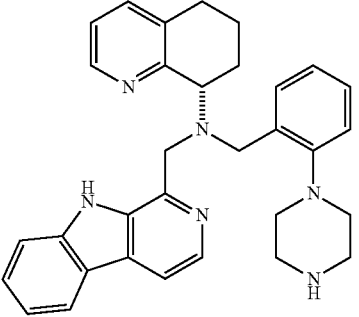 [SMILES: c1ccc(N2CCNCC2)c(CN(Cc2nccc3c2[nH]c2ccccc23)[C@H]2CCCc3cccnc32)c1] | 3,730 nM |
| 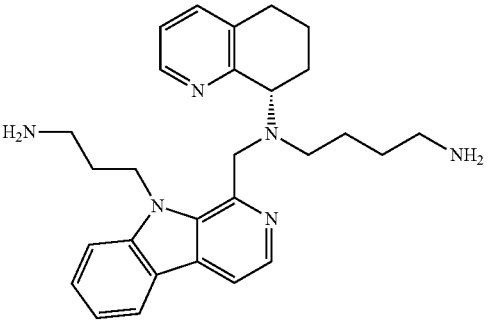 [SMILES: NCCCCN(Cc1nccc2c3ccccc3n(CCCN)c12)[C@H]1CCCc2cccnc21] | 21 nM |
| 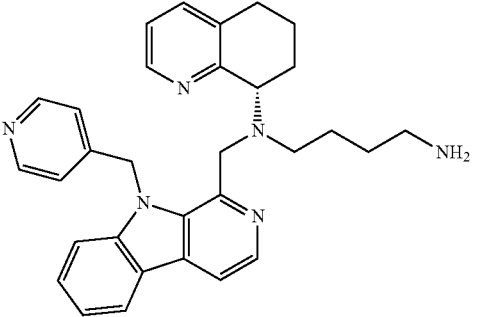 [SMILES: NCCCCN(Cc1nccc2c3ccccc3n(Cc3ccncc3)c12)[C@H]1CCCc2cccnc21] | 120 nM |

TABLE 7-continued
| Compound | Ca Flux IC$_{50}$ (nM) or % inhibition at 1 μM |
|---|---|
| 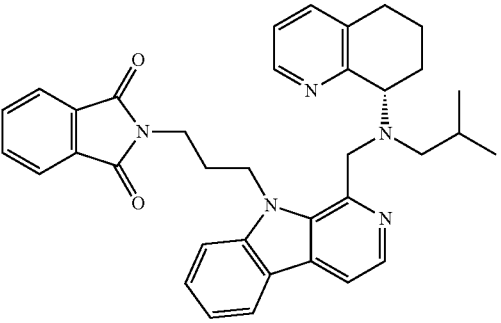 [SMILES: CC(C)CN(Cc1nccc2c3ccccc3n(CCCN3C(=O)c4ccccc4C3=O)c12)[C@H]1CCCc2cccnc21] | 6,650 nM |
| 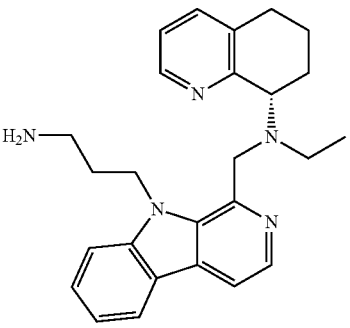 [SMILES: CCN(Cc1nccc2c3ccccc3n(CCCN)c12)[C@H]1CCCc2cccnc21] | 997 nM |
| 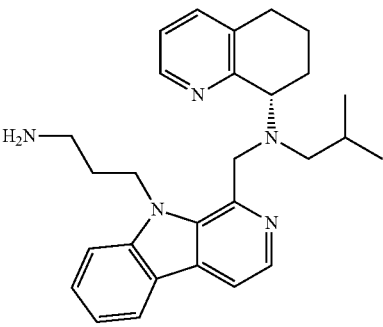 [SMILES: CC(C)CN(Cc1nccc2c3ccccc3n(CCCN)c12)[C@H]1CCCc2cccnc21] | 0% |
| 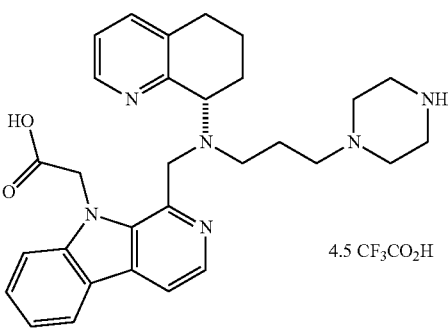 [SMILES: O=C(O)Cn1c2ccccc2c2ccnc(CN(CCCN3CCNCC3)[C@H]3CCCc4cccnc43)c21] 4.5 CF$_3$CO$_2$H | 135 nM |

TABLE 7-continued

| Compound | Ca Flux IC$_{50}$ (nM) or % inhibition at 1 μM |
|---|---|
| | 63 nM |
| | 481 nM |
| | 212 nM |
| | 9,585 nM |

TABLE 7-continued

| Compound | Ca Flux IC$_{50}$ (nM) or % inhibition at 1 μM |
|---|---|
| (structure) | 206 nM |
| (structure) | 24 nM |
| (structure) | 56 nM |
| (structure) | 8,393 nM |

TABLE 7-continued
| Compound | Ca Flux IC$_{50}$ (nM) or % inhibition at 1 µM |
|---|---|
| 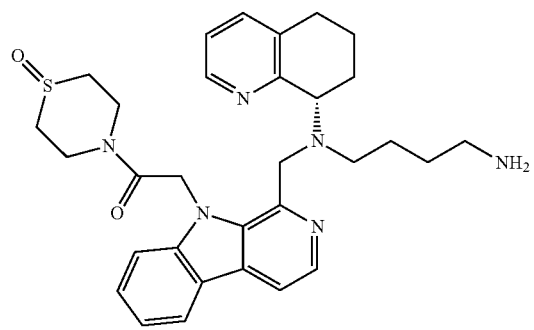 [SMILES: NCCCCN(Cc1nccc2c3ccccc3n(CC(=O)N3CCS(=O)CC3)c12)[C@H]1CCCc2cccnc21] | 61 nM |
| 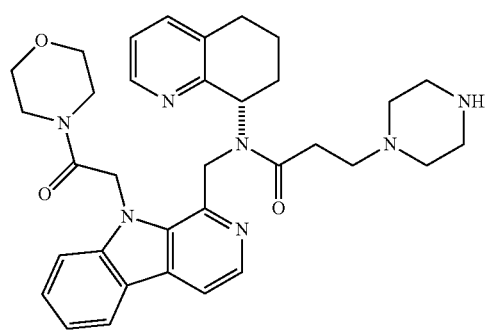 [SMILES: O=C(Cn1c2ccccc2c2ccnc(CN(C(=O)CCN3CCNCC3)[C@H]3CCCc4cccnc43)c21)N1CCOCC1] | 0% |
| 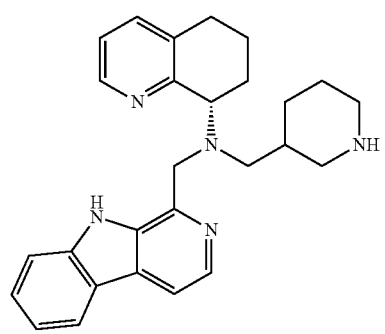 [SMILES: c1cnc2c(c1)CCC[C@@H]2N(Cc1nccc2c1[nH]c1ccccc12)CC1CCCNC1] | 3,597 nM |
| 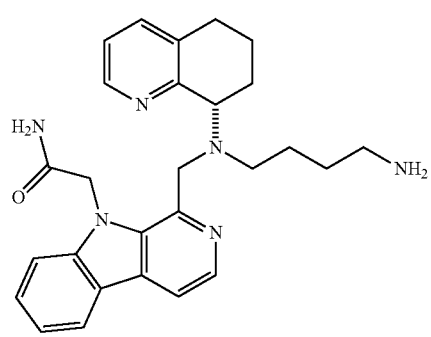 | 17 nM |

TABLE 7-continued

| Compound | Ca Flux IC$_{50}$ (nM) or % inhibition at 1 µM |
|---|---|
| (structure) | 176 nM |
| (structure) | 21 nM |
| (structure) | 8,650 nM |
| (structure) | 628 nM |

TABLE 7-continued
| Compound | Ca Flux IC$_{50}$ (nM) or % inhibition at 1 μM |
|---|---|
| 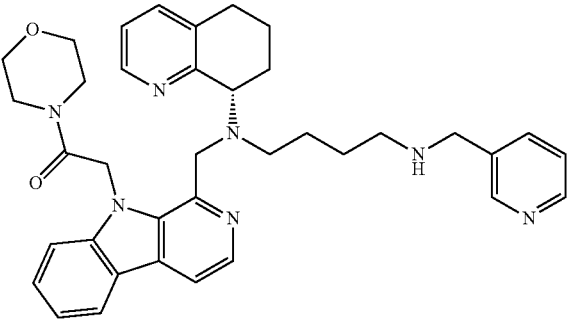 [SMILES: O=C(Cn1c2ccccc2c2ccnc(CN(CCCCNCc3cccnc3)[C@H]3CCCc4cccnc43)c21)N1CCOCC1] | 1,398 nM |
| 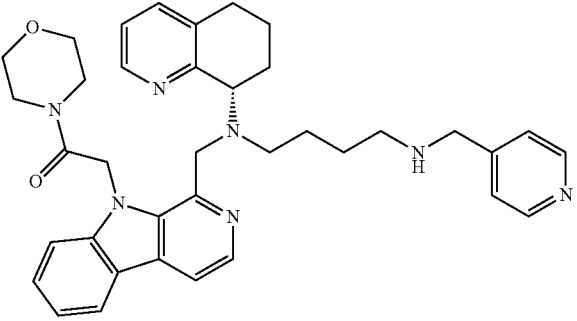 [SMILES: O=C(Cn1c2ccccc2c2ccnc(CN(CCCCNCc3ccncc3)[C@H]3CCCc4cccnc43)c21)N1CCOCC1] | 2,830 nM |
| 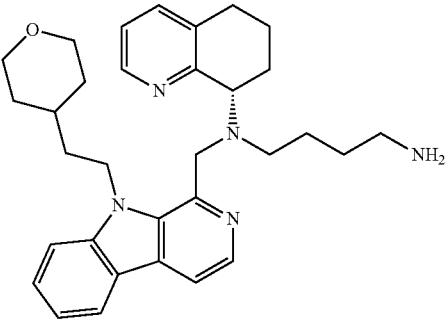 | 13 nM |
| 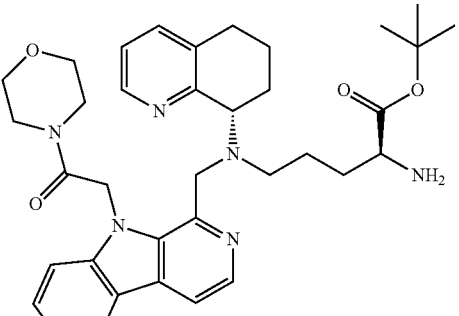 | 0% |

TABLE 7-continued

| Compound | Ca Flux IC$_{50}$ (nM) or % inhibition at 1 μM |
|---|---|
| *(structure)* | 4 nM |
| *(structure)* | 78 nM |
| *(structure)* | 47 nM |
| *(structure)* | 0% |

TABLE 7-continued
| Compound | Ca Flux IC$_{50}$ (nM) or % inhibition at 1 μM |
|---|---|
| 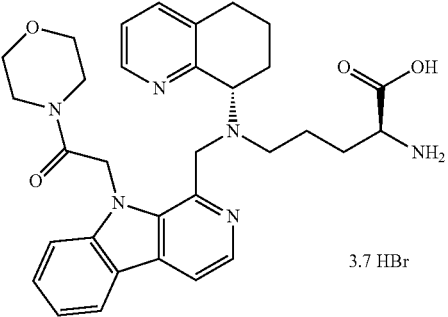 [SMILES: N[C@@H](CCCN(Cc1nccc2c3ccccc3n(CC(=O)N3CCOCC3)c12)[C@H]1CCCc2cccnc21)C(=O)O] 3.7 HBr | 0% |
| 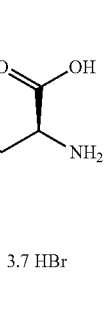 | 8,720 nM |
| 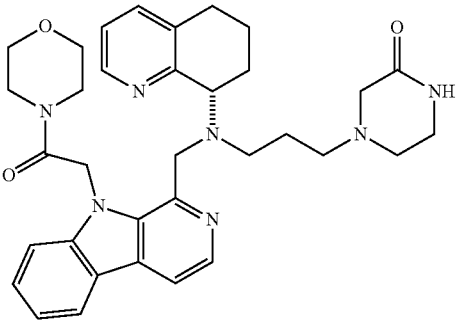 [SMILES: O=C1CN(CCCN(Cc2nccc3c4ccccc4n(CC(=O)N4CCOCC4)c23)[C@H]2CCCc3cccnc32)CCN1] | 26 nM |
| 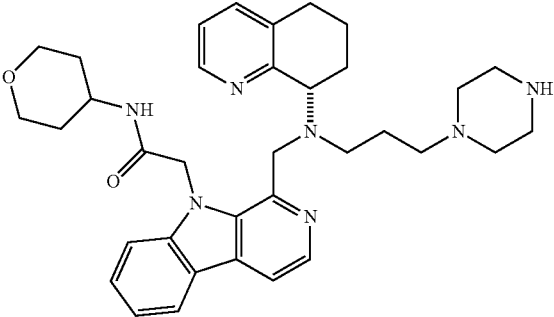 [SMILES: O=C(Cn1c2ccccc2c2ccnc(CN(CCCN3CCNCC3)[C@H]3CCCc4cccnc43)c21)NC1CCOCC1] | 270 nM |

TABLE 7-continued

| Compound | Ca Flux IC$_{50}$ (nM) or % inhibition at 1 µM |
|---|---|
| *[structure]* | 405 nM |
| *[structure]* | 152 nM |
| *[structure]* | 138 nM |
| *[structure]* | 124 nM |

TABLE 7-continued

| Compound | Ca Flux IC$_{50}$ (nM) or % inhibition at 1 μM |
|---|---|
| (structure) | 583 nM |
| (structure) | 44 nM |
| (structure) | 30 nM |
| (structure) | 2,150 nM |

TABLE 7-continued

| Compound | Ca Flux IC$_{50}$ (nM) or % inhibition at 1 μM |
|---|---|
| | 1,260 nM |
| | 20 nM |
| | 44 nM |
| | 9 nM |

TABLE 7-continued

| Compound | Ca Flux IC$_{50}$ (nM) or % inhibition at 1 μM |
|---|---|
| | 5 nM |
| | 0% |
| | 20 nM |
| | 4 nM |

TABLE 7-continued
| Compound | Ca Flux IC$_{50}$ (nM) or % inhibition at 1 μM |
|---|---|
| 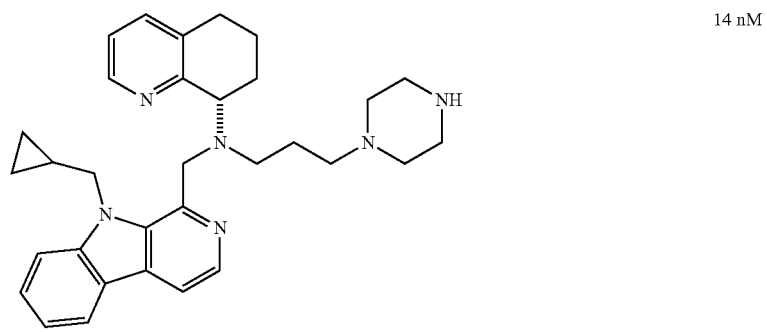 | 14 nM |
| 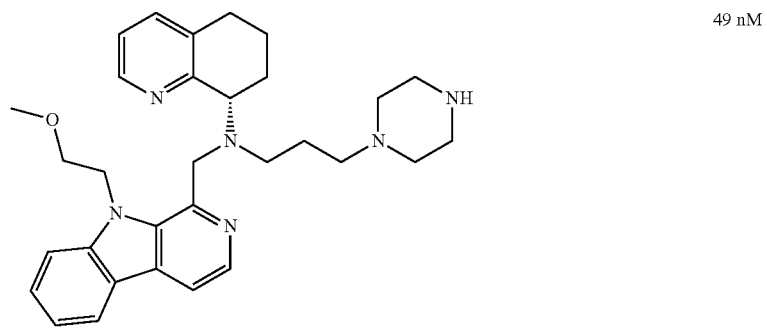 | 49 nM |
| 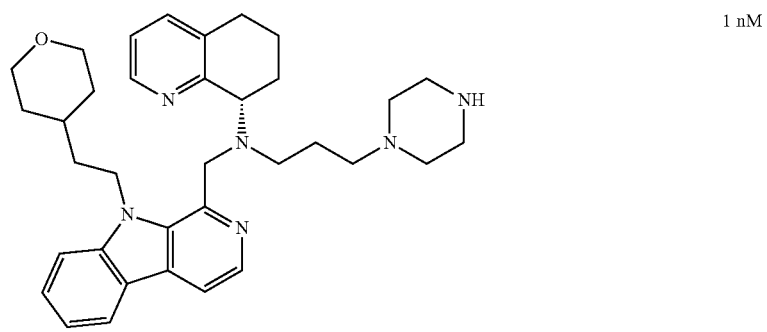 | 1 nM |
| 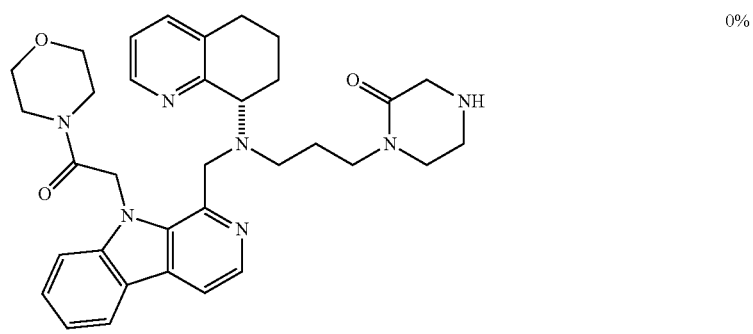 | 0% |

TABLE 7-continued

| Compound | Ca Flux IC$_{50}$ (nM) or % inhibition at 1 μM |
|---|---|
| 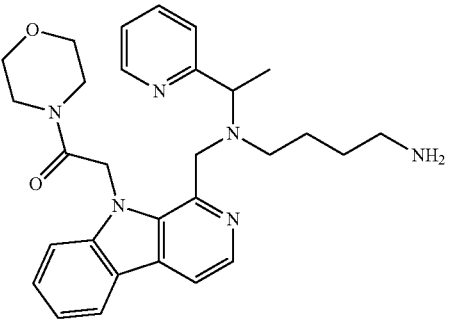 [SMILES: CC(c1ccccn1)N(CCCCN)Cc1nccc2c3ccccc3n(CC(=O)N3CCOCC3)c12] | 423 nM |

Example 29

Testing Inhibition of CXCR4 Pathway by Functional Morphological SDF-1a Induced Changes This assay measures the change in impedance that occurs when cells are stimulated with SDF-1a. Changes in shape and cytoskeleton result in a change of impedance that is dependent on the activation of the CXCR4 receptor. This assay is contracted to MDS Pharma Services and performed as described in http://discovery.mdsps.com/Catalog/Services/Screening/CellKey/AssayDetails.aspx?id=7 (Assay 930070). Briefly, human HeLa cells expressing endogenous CXCR4 are grown in vitro and receptor activation in live cells is measured using cellular dielectric spectroscopy (CDS). EC$_{50}$ is defined as a greater than 50% change in cellular impedance relative to the EC$_{100}$ (10 nM SDF-1a) response. IC$_{50}$ is defined as a greater than 50% inhibition of the cellular impedance change induced by an EC$_{50}$ concentration of SDF-1a incubation at 30 minutes.

The compounds of the invention generally have an IC$_{50}$ value below 100,000 nM the cellular impedance change induced by an EC$_{50}$ concentration of SDF-1α incubation at 30 minutes. Results for specified compounds are shown in the Table 8.

TABLE 8

| Compound | Antagonist IC$_{50}$ (nM) |
|---|---|
| 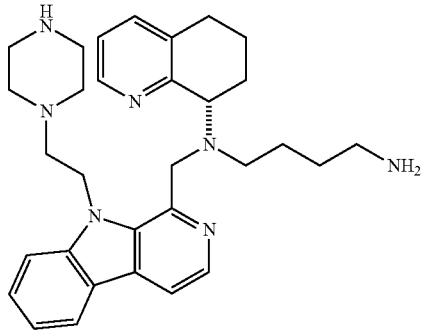 | 5.7 |
| 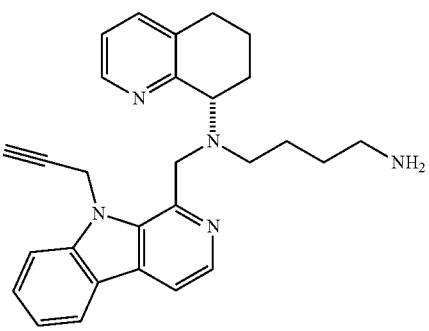 | 5.5 |

TABLE 8-continued

| Compound | Antagonist IC$_{50}$ (nM) |
|---|---|
| | 5.6 |
| | 5.8 |
| | 7.3 |
| | 7.7 |

TABLE 8-continued

| Compound | Antagonist IC$_{50}$ (nM) |
|---|---|
| | 8.1 |
| | 8.3 |
| | 9.3 |
| | 9.9 |

TABLE 8-continued

| Compound | Antagonist IC$_{50}$ (nM) |
|---|---|
| | 11 |
| | 12 |
| | 12 |
| | 12 |

TABLE 8-continued

| Compound | Antagonist IC$_{50}$ (nM) |
|---|---|
| 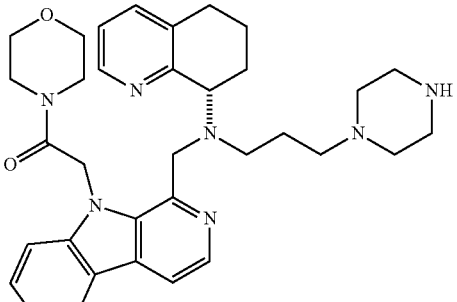 | 15 |
| 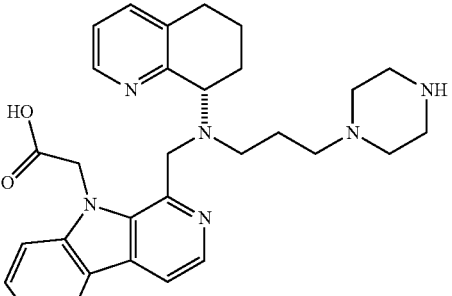 | 26 |

Example 30

Test Compound Activity Against HIV Strains

A selected set of compounds are tested for their ability to inhibit the cellular entry of T-tropic HIV. The assay for this inhibition is carried out on a contractual basis at Monogram Biosciences, Inc. using their well established Phenoscreen™ assay. Briefly, HIV strains of interest are tagged with a luciferase indicator gene to create an appropriate test vector. The test vector is amplified through transfection and the resulting virus is incubated in the presence of target host cells where intracellular florescence activity then becomes a measure of infection. Amplified virus is exposed to target host cells in the presence of a range of test drug concentrations to determine IC$_{50}$ measurements of entry inhibition. A modification of this test is further reapplied as a novel drug assay used in partnership with a number of pharmaceutical companies to test the effectiveness of novel entry inhibitors that target specific chemokines. It can used to detect activity against T-tropic, M-tropic, and dual-tropic viruses and Monogram Biosciences has a large bank of over 10,000 different virus strains to ultimately asses the range of applicability of our chemokine modulators. Certain compounds are tested to establish efficacy in a number of viral strains.

The compounds of the invention generally have an IC$_{50}$ value for viral entry inhibition in the one of the above HIV viral strains of interest of less than or equal to 100 µM. For example, compounds A, B, Z, AB, AY, and BP have IC$_{50}$ values of less than or equal to 10 µm.

In addition, compounds are tested in an HIV replication assay carried out by Southern Research Institute. The primary assay screens compounds in a microtiter assay which measures the ability of selected compounds to inhibit HIV-induced cell killing as well as the toxicity of the test compounds to host cells. Quantitation is performed spectrophotometrically using the tetrazolium dye MTS (Cell Titer; Promega) which is converted to a soluble, colored formazan product by mitochondrial enzymes present in metabolically active cells at six days post-infection. The basic assay involves infection of CEM-SS cells with virus in the presence of the test compound. Data are analyzed using a statistical software program developed at Southern and efficacy and toxicity endpoints are determined, as well as selectivity indices. A follow-up assay is performed using in fresh human peripheral blood lymphocytes and monocyte-macrophages infected with low passage primary virus isolates. Blood is obtained from the American Red Cross (screened for HIV and HBV) and mononuclear cells are isolated by Ficoll-hypaque centrifugation. The following are given as examples (and should not be taken as an exhaustive list) of virus strains tested: 92UG029 (X4), 92UG046 (X4), 93UG065 (X4), CMU02 (X4), 91US005 (R5) and 92UG001 (dual X4/R5), the co-receptor used by each given strain is described in paranthesis.

The compounds of the invention generally have an IC$_{50}$ value for viral entry inhibition in the one of the above HIV viral strains of interest of less than or equal to 100 µM and an antiviral index>10.

Example 31

Screening for CXCR7 Activity

CXCR7 modulation activity was accessed using PathHunter™ β-Arrestin GPCR Assay Pharmacology from DiscoveRx using the protocol recommended by the manufacture for their CXCR7β-Arrestin cell line. The compounds of the invention generally have an IC$_{50}$ value below 100 micromolar for CXCR7 modulation activity using this assay.

Example 32

Screening by Competition Assay Using Radiolabelled SDF-1

For radioligand binding competition test of CXCR4 or CXCR7, the following components are mixed in the wells of a 96 well plate (Master Block, Greiner, 786201) up to 100 μL assay buffer (50 mM HEPES; 5 mM MgCl$_2$; 1 mM CaCl$_2$, 250 mM Sucrose, 100 mM NaCl and 0.5% BSA), compounds to be tested or 200-fold excess of cold ligand for non specific binding determination (SDF1-α R&D, 350-NS), radioligand [$^{125}$I]-SDF-1α (PKI NEX346, 2200 Ci/mmol, diluted in assay buffer to give 0.03 nM) and 1 μg membrane extracts. The plate is incubated during 30 min at 37° C. in a water bath, filtered over GF/B filters (presoaked in 0.5% PEI for 1 h at room temperature) with a Filtermate Harvester (Perkin Elmer), and washed 6 times with 0.5 mL of ice cold filtration buffer (50 mM HEPES; 5 mM MgCl$_2$; 1 mM CaCl$_2$, 250 mM Sucrose, 0.5 M NaCl and 0.5% BSA). Following addition of 50 μL of Microscint 20 (Packard), and incubation during 15 min. on an orbital shaker, the plates are counted with a Top-Count™ for 1 min/well.

The compounds of the invention generally have an IC$_{50}$ value below 100 micromolar for competitive binding versus CXCR4 or CXCR7 activity using this assay.

Example 33

Results of Functional Calcium Mobilization Assay, Cytotoxicity and hERG Binding Assessments for Selected Compounds Functional calcium mobilization assay was conducted as described in Example 27.

Cytotoxicity of the compounds was assessed by the following assay. CCRF-CEM cells in media (RPMI 1640, 15% FBS, Pen/Strep., 1% non-essential amino acids) are incubated with various concentrations of test compound for 6 days undisturbed. Cell number relative to no compound controls is determined using either Serotec's "Alamar blue" per manufacturers protocol or Promega's "Cell Titer 96 Aqueous One Solution Cell Proliferation Assay" kit per manufacturers protocol. The number cells not surviving after test compound administration is determined for each concentration tested and the EC$_{50}$ (concentration of compound in which 50% of the cells survive) is determined The in vitro effects of the selected compounds on the hERG (human ether-á-go-go-related gene) potassium channel current (a surrogate for IKr, the rapidly activating, delayed rectifier cardiac potassium current) expressed in mammalian cells were evaluated at room temperature using the PatchXpress 7000A (Molecular Devices), an automatic parallel patch clamp system. Each compound was evaluated at varying concentrations in duplicate up to 10 μM, and the duration of exposure to each test article concentration was 5 minutes. For select compounds, the IC$_{50}$ values for compounds were determined if the concentration in which 50% channel block was observed was <10 μM. For <50% channel block at the 10 μM concentration, an % inhibition at 10 μM is listed. All other compounds have an % inhibition and concentration listed.

A summary of the results is shown in Table 9.

TABLE 9

| Compound | Ca Flux IC$_{50}$ | Cytotoxicity EC$_{50}$ | hERG %/IC$_{50}$ |
|---|---|---|---|
| (structure) | 12 nM | 30 μM | 42% at 10 μM |
| (structure) | 22 nM | 30 μM | 2.7 μM |

TABLE 9-continued

| Compound | Ca Flux IC$_{50}$ | Cytotoxicity EC$_{50}$ | hERG %/IC$_{50}$ |
|---|---|---|---|
| | 126 nM | 30 μM | 16% at 10 μM |
| | 16 nM | 30 μM | 4.1 μM |
| | 30 nM | 50 μM | 39% at 10 μM |
| | 44 nM | 30 μM | 25% at 10 μM |

TABLE 9-continued

| Compound | Ca Flux IC$_{50}$ | Cytotoxicity EC$_{50}$ | hERG %/IC$_{50}$ |
| --- | --- | --- | --- |
| | 37 nM | 0.6 μM | 26% at 1 μM |
| | 123 nM | 5.3 μM | 18% at 1 μM |
| | 7 nM | 6.4 μM | 46% at 10 μM |
| | 113 nM | >10 μM | 20% at 10 μM |

TABLE 9-continued

| Compound | Ca Flux IC$_{50}$ | Cytotoxicity EC$_{50}$ | hERG %/IC$_{50}$ |
|---|---|---|---|
| | 55 nM | >10 μM | 45% at 10 μM |
| | 24 nM | — | 3.1 μM |
| | 56 nM | — | 2.4 μM |
| | 18 nM | — | 1.8 μM |

Various references have been cited herein, each of which is incorporated herein by reference in its entirety.

We claim:

1. A method of treatment of a disorder associated with chemokine receptor activation in a patient in need of such treatment, comprising administering to the patient an effective amount of at least one compound elected from compounds of Formula I:

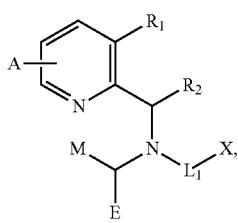
(I)

wherein

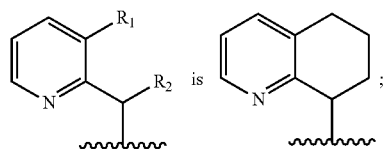

E is

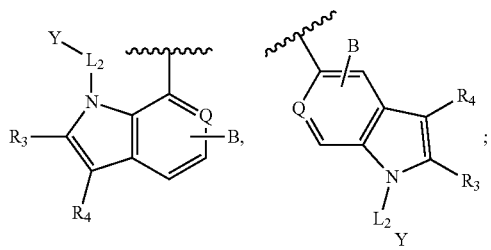

M is H or -G-L$_3$-Z;

L$_1$, and L$_2$, are each independently selected from the group consisting of a covalent bond, substituted or unsubstituted alkylene, substituted or unsubstituted alkenyl, substituted or unsubstituted alkynyl, substituted or unsubstituted carbocycyl, and substituted or unsubstituted heterocyclyl;

X, Y and Z are independently H, NR$_a$R$_b$, —OR$_c$, halogen, CF$_3$, optionally substituted alkyl, optionally substituted alkenyl, optionally substituted alkynyl, acyl, carboxy, optionally substituted alkoxycarbonyl, optionally substituted aminocarbonyl, optionally substituted alkyl- or dialkylaminocarbonyl, cyano, optionally substituted heterocyclylacyl, optionally substituted carbocyclylacyl, substituted or unsubstituted carbocyclyl, substituted or unsubstituted heterocyclyl;

R$_a$ and R$_b$ are each independently selected from the group consisting of H, substituted or unsubstituted alkyl, aldiminyl, substituted or unsubstituted carbocyclyl, substituted or unsubstituted carbocyclylalkyl, substituted or unsubstituted heterocyclylalkyl, and substituted or unsubstituted heterocyclyl; or R$_a$ and R$_b$, together with the nitrogen atom to which they are shown attached form a substituted or unsubstituted heterocyclyl;

R$_c$ is selected from the group consisting of H, substituted or unsubstituted alkyl, substituted or unsubstituted heteroalkyl, substituted or unsubstituted carbocyclyl, substituted or unsubstituted heterocyclyl, substituted or unsubstituted carbocyclylalkyl, substituted or unsubstituted heterocyclylalkyl, Q is N;

G is selected from the group consisting of a covalent bond, alkylene, —C(O)—, —C(O)—O—, and —C(O)—NR$_d$—;

R$_d$ is selected from the group consisting of H, alkyl, and substituted or substituted arylalkyl;

R3 and R4, taken together with the carbon atoms to which they are shown attached, form a substituted or unsubstituted carbocyclyl or a substituted or unsubstituted heterocyclyl; and A and B are each independently one or more substituents selected from the group consisting of H, alkyl, halo, substituted or unsubstituted amino, cyano, nitro, haloalkyl, hydroxyl, and alkoxyl;

with the proviso that only one of M and L$_1$X is H, and wherein the patient is in need of stem cell mobilization and selected from the group of patients defective in white blood cell count, immunosuppressed patients and patients in need of regeneration of cardiac tissue.

2. The method of claim 1, wherein the patient is defective in white blood cell count.

3. The method of claim 1, further comprising administering at least one additional pharmaceutically active compound in combination or alternation to the patient.

4. The method of claim 1, wherein the compound is of Formula IA-1 or IA-3:

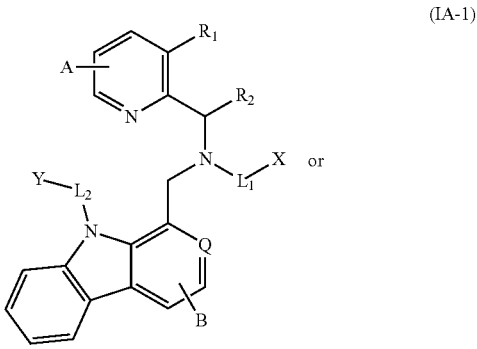
(IA-1)

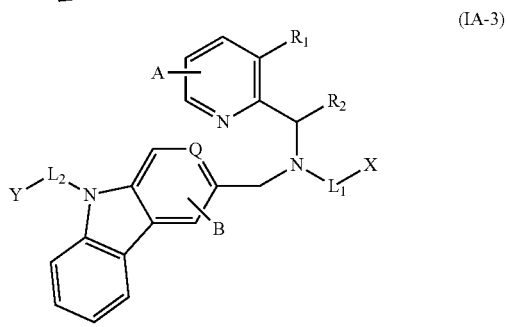
(IA-3)

or a pharmaceutically acceptable salt, solvate, tautomer, stereoisomer, and/or ester thereof.

5. The method of claim 4, wherein the compound has the Formula IA-2S:

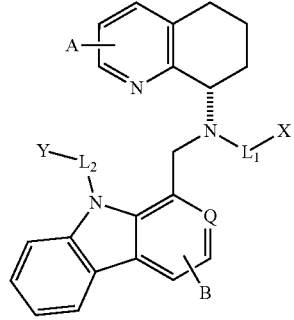

wherein,

L$_1$ and L$_2$ are independently a bond or alkylene; Y is H, NR$_a$R$_b$, —OR$_c$, carbocyclyl, heterocyclyl, triazolyl, tetrazolyl, acyl, alkoxycarbonyl, aminocarbonyl, alkyl- or dialkylaminocarbonyl, heterocyclylacyl, cyano, halogen or CF$_3$; and X is optionally substituted carbocyclyl, optionally substituted heterocyclyl, or NR$_a$R$_b$; or L$_1$-X is

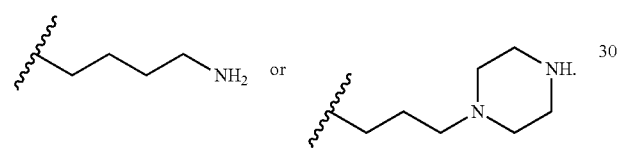

6. The method of claim 5, wherein:

Q is nitrogen;

L$_2$ is a bond or alkylene;

Y is H, NR$_a$R$_b$, —OR$_c$, carbocyclyl, heterocyclyl, tetrazolyl, alkoxycarbonyl, aminocarbonyl, alkyl- or dialkylaminocarbonyl, cyano, halogen or CF$_3$; and L$_1$-X is

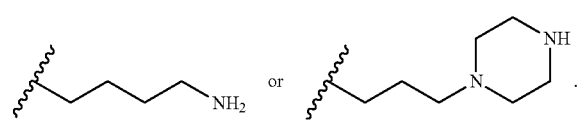 [SMILES: *CCCCN ; *CCCN1CCNCC1]

7. The method of claim 1, wherein:

L$_1$-X is

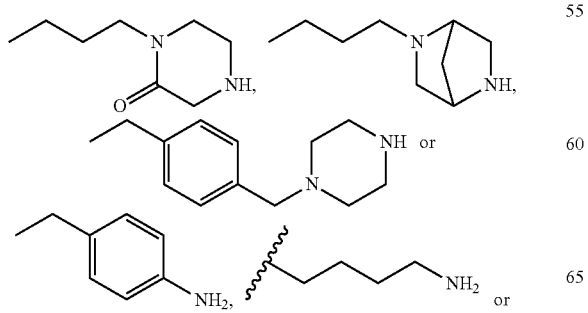

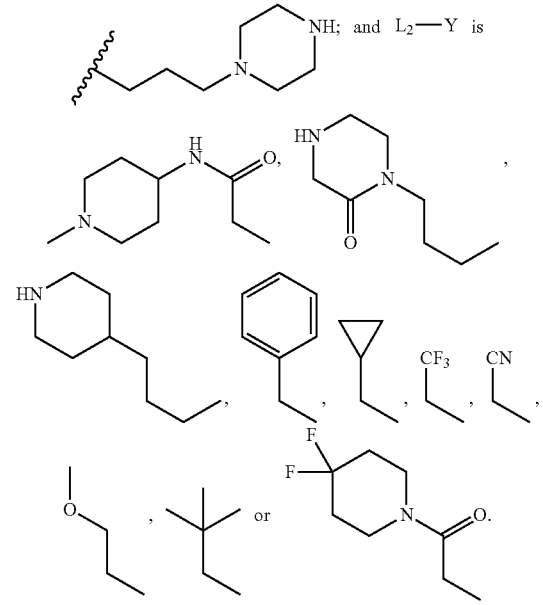

8. The method of claim 1, wherein the compound is selected from:

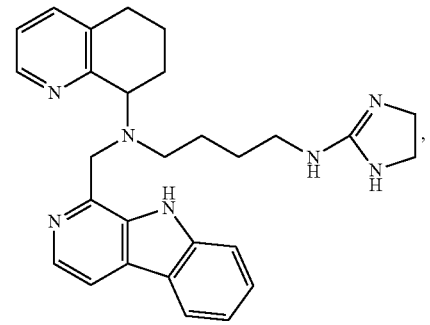

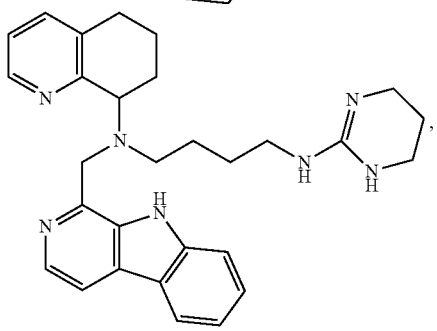

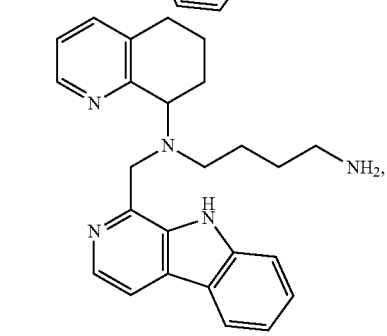

335
-continued
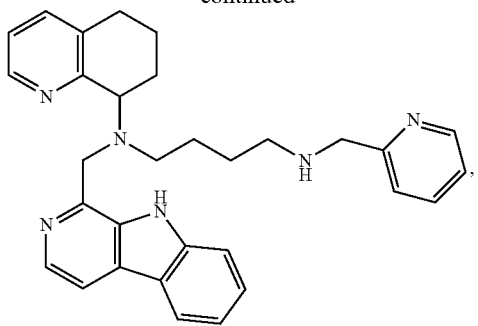
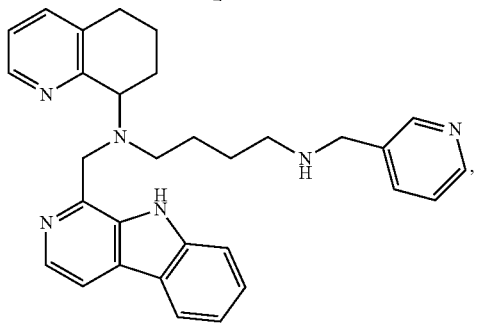
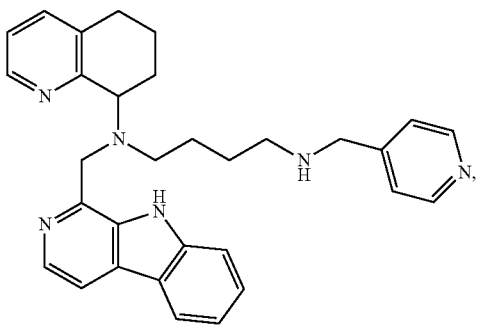
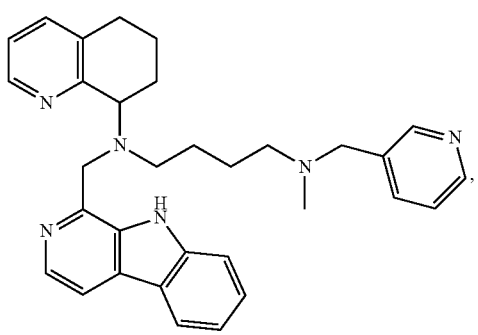
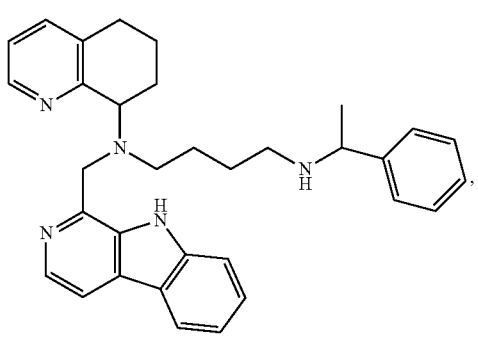
336
-continued
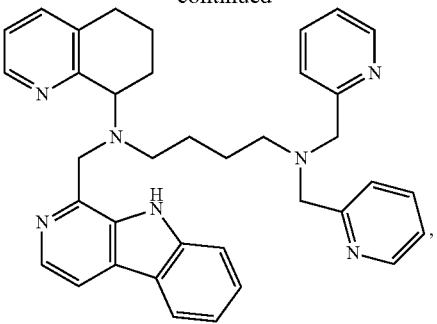
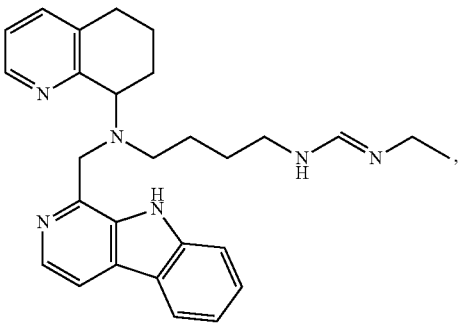
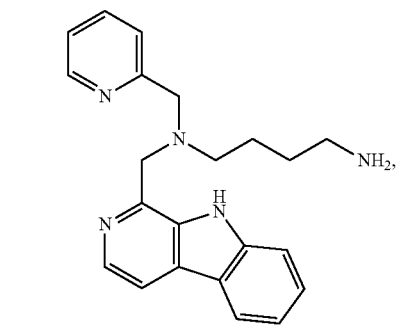
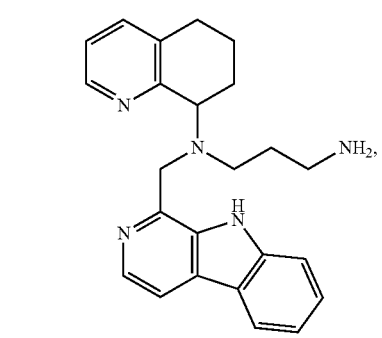
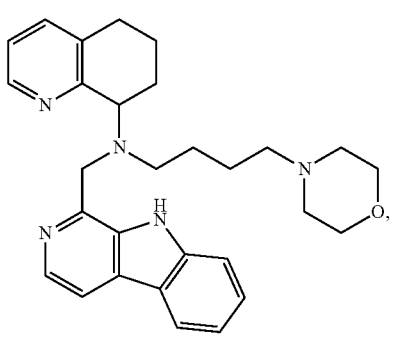

337
-continued
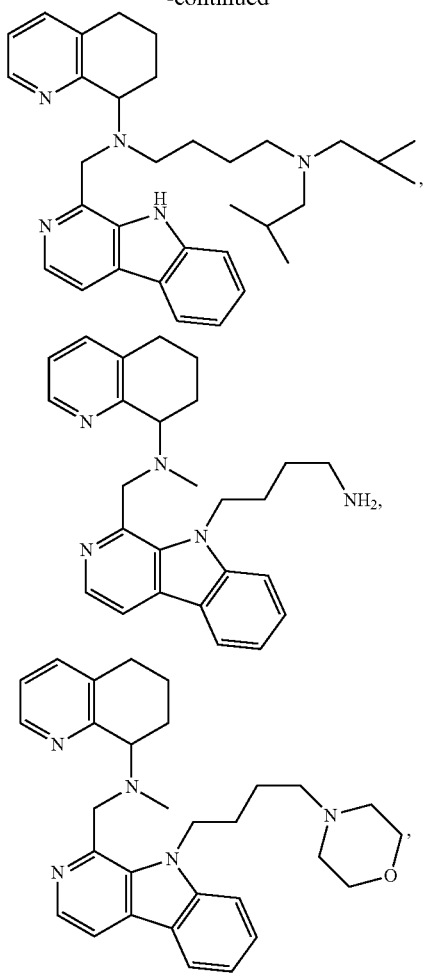
338
-continued
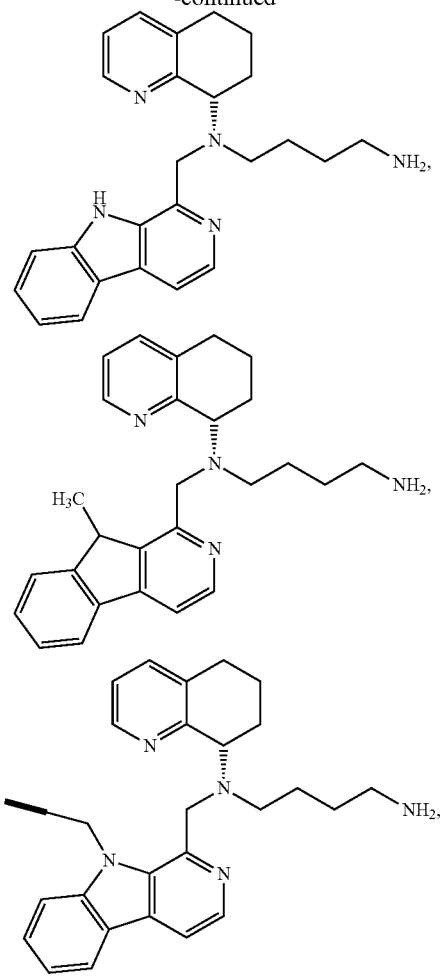

339
-continued
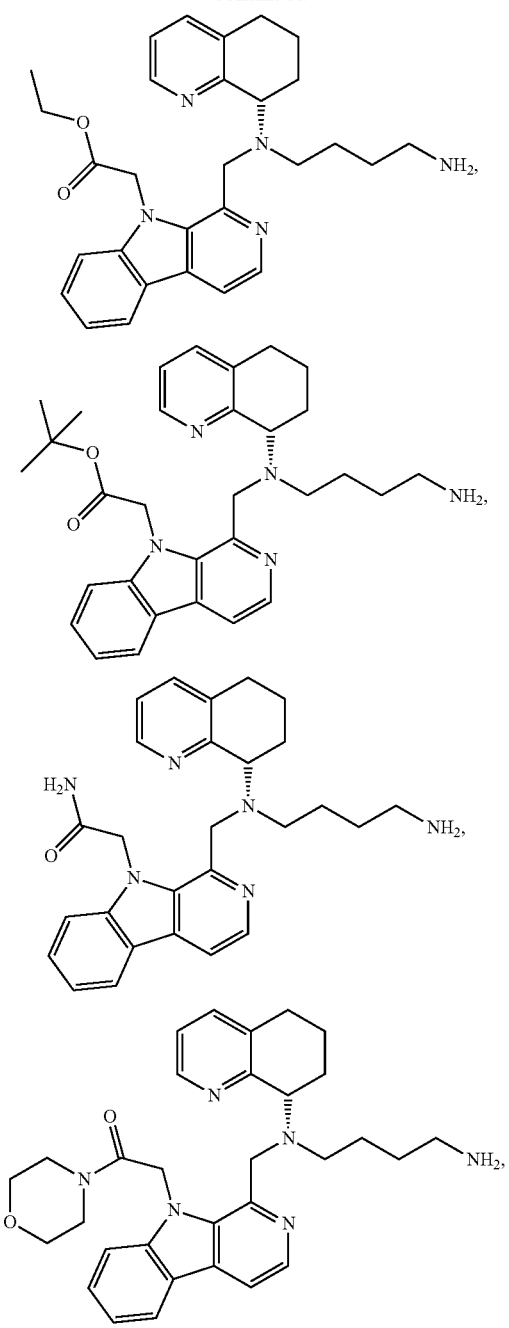
340
-continued
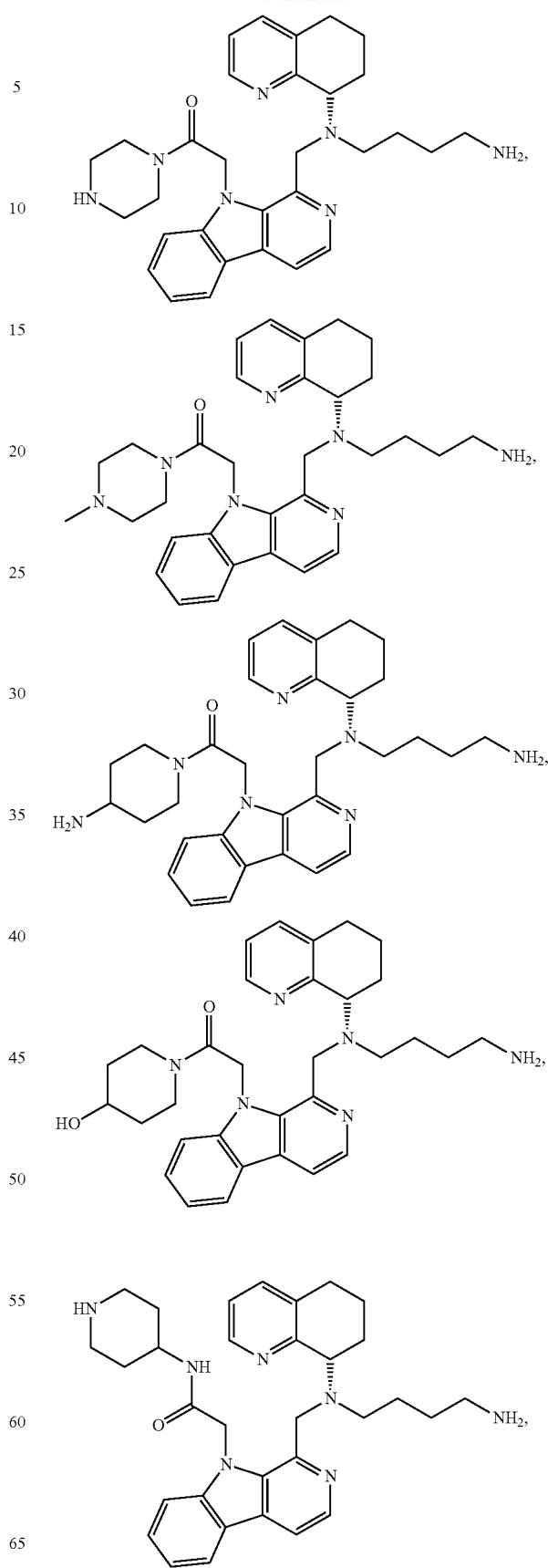

341
-continued
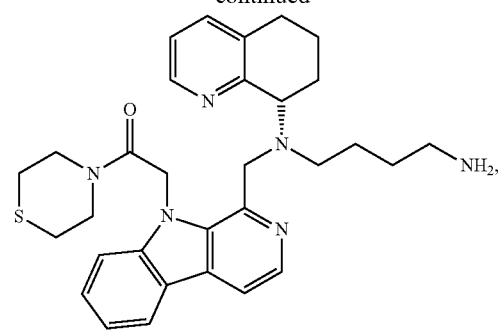
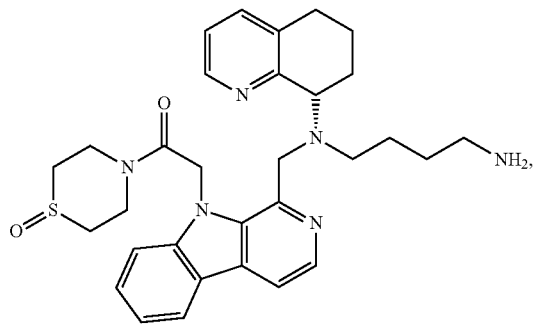
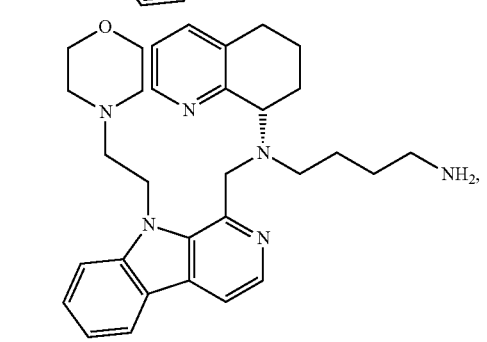
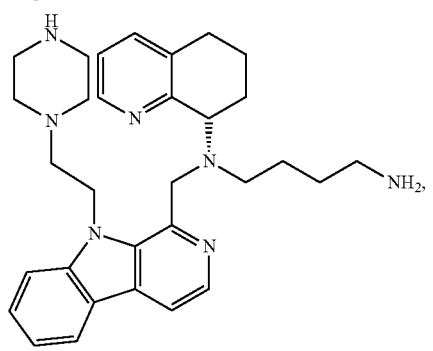
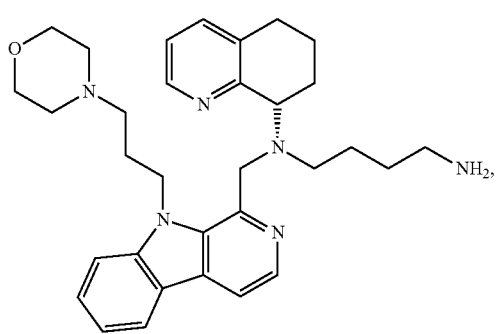
342
-continued
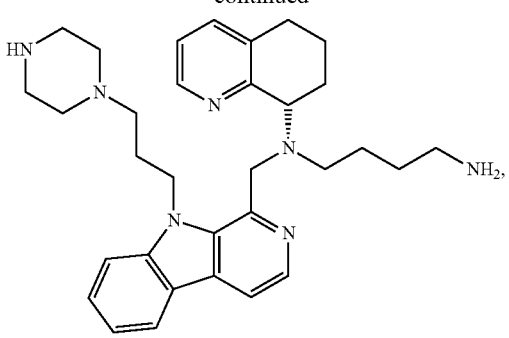
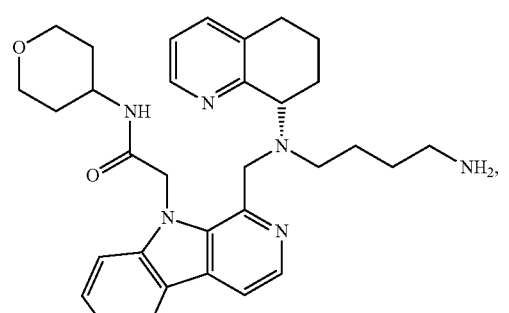
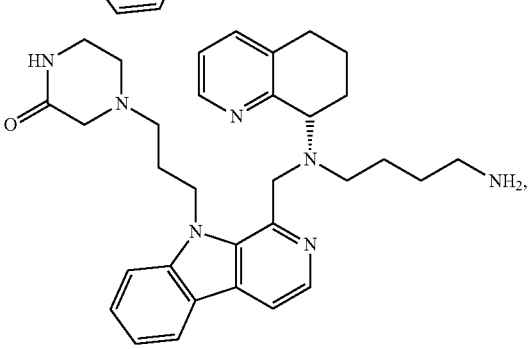
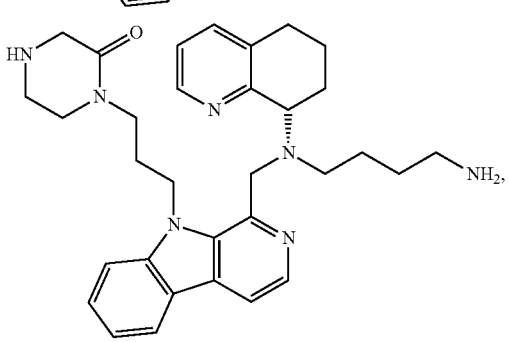
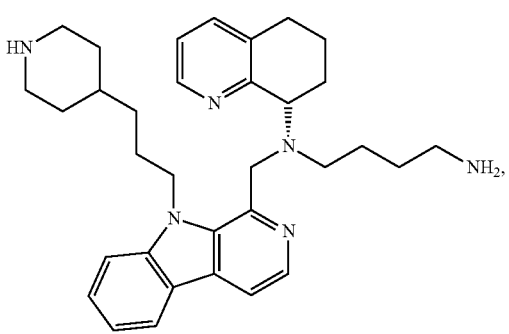

343
-continued
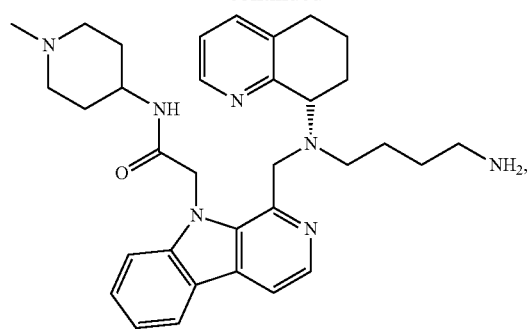
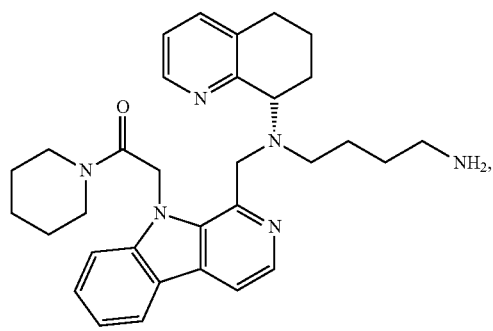
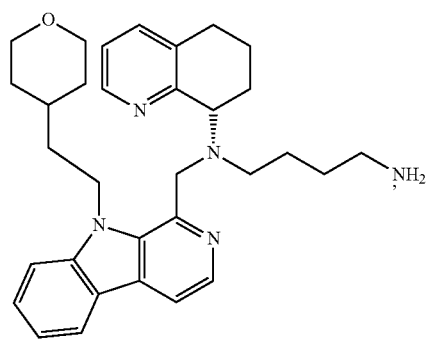
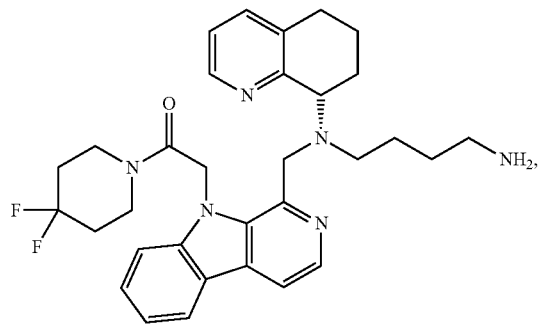
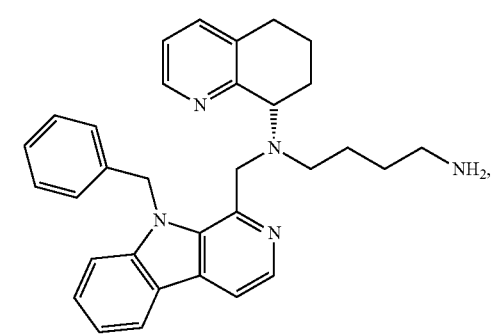
344
-continued
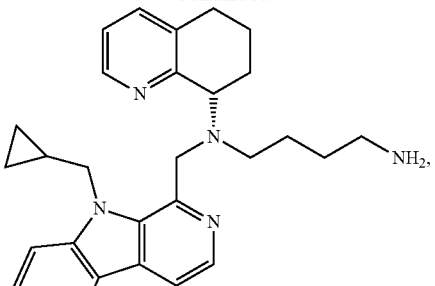
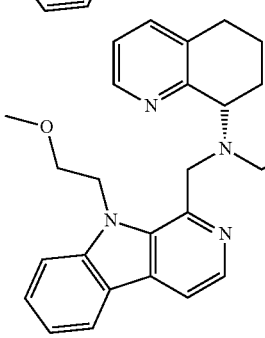
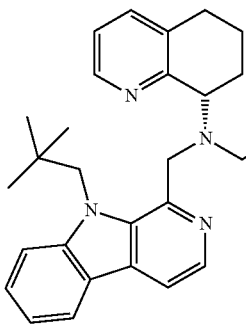
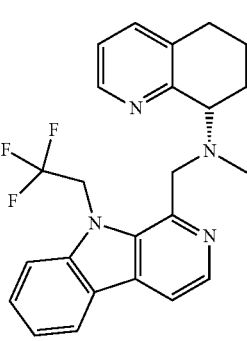
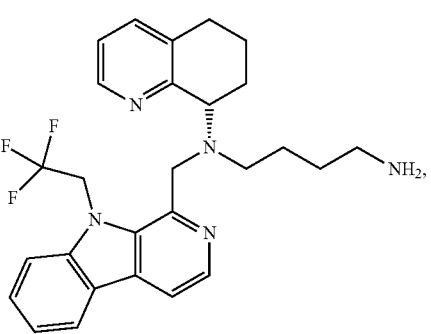

345
-continued
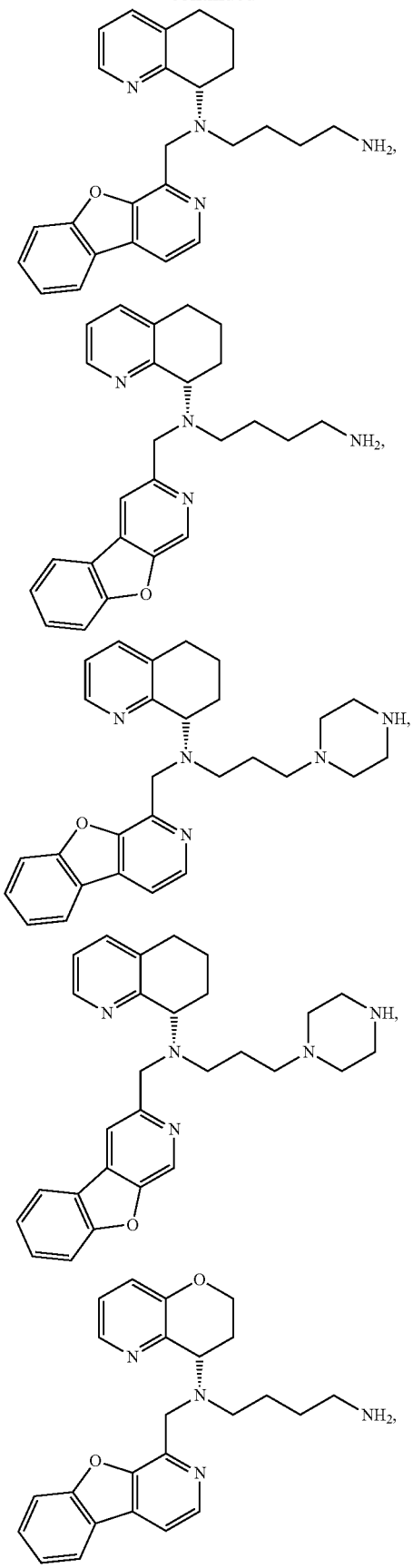
346
-continued
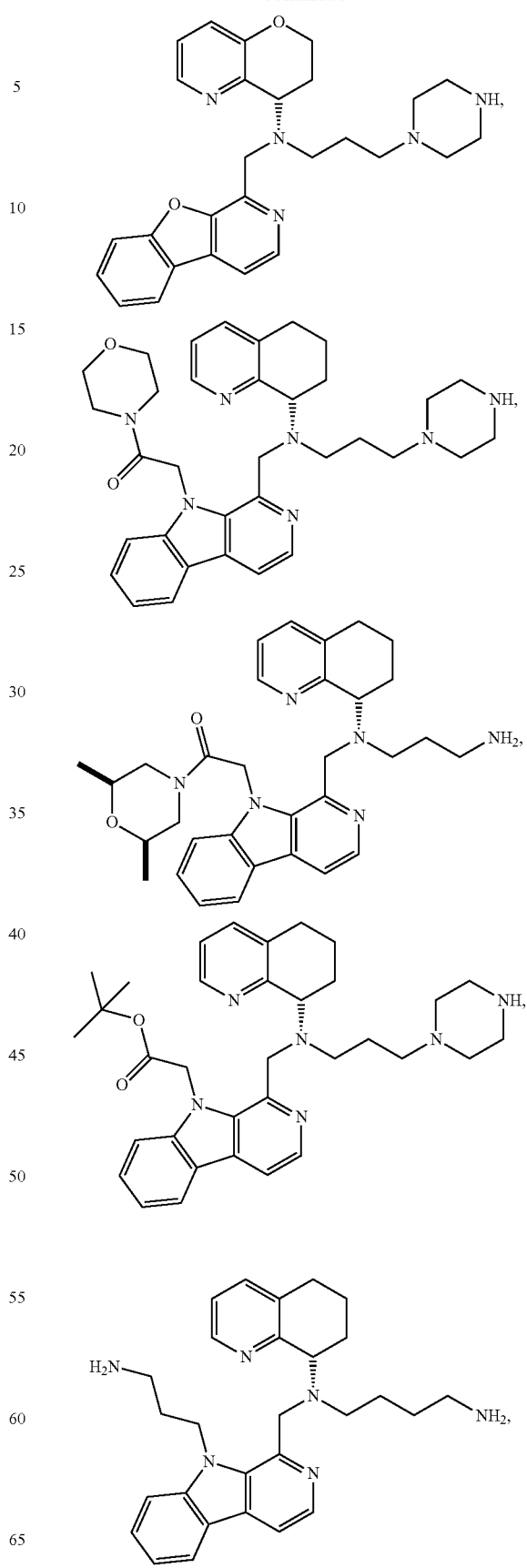

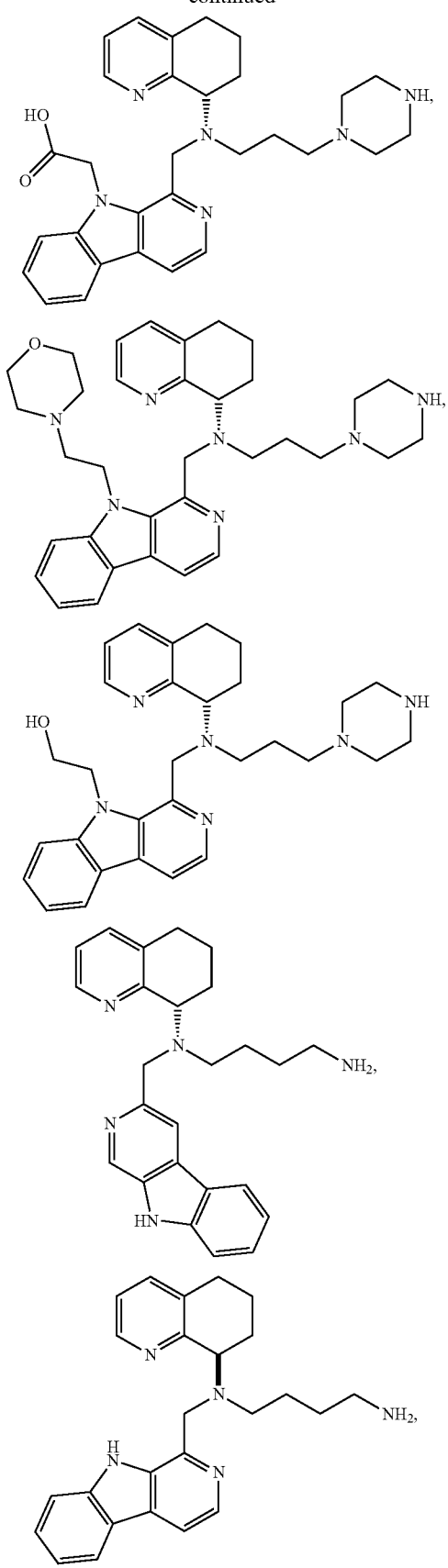
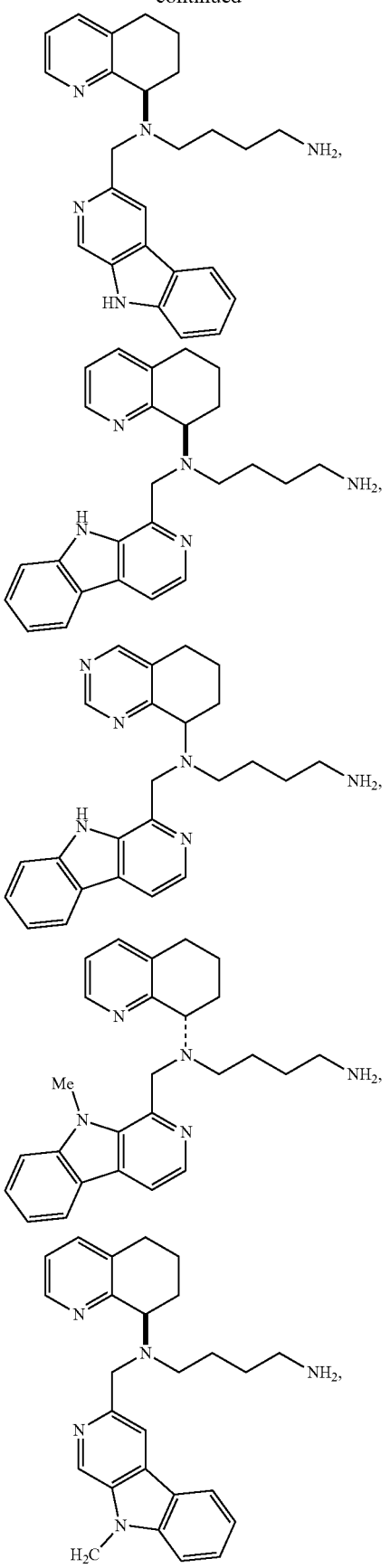

349
-continued
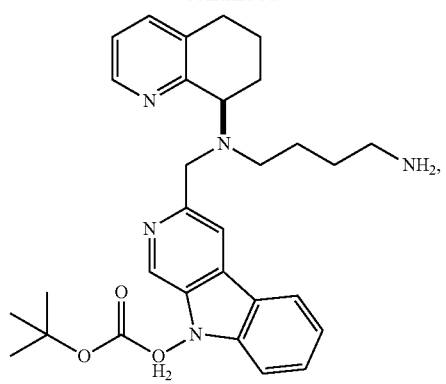
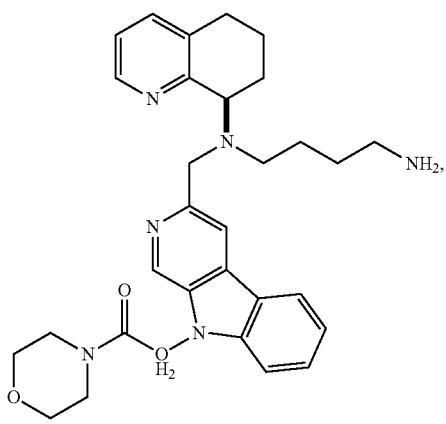
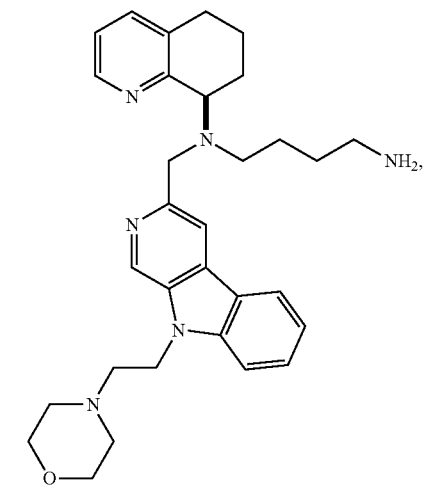
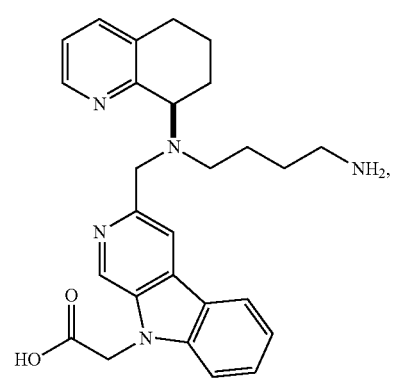
350
-continued
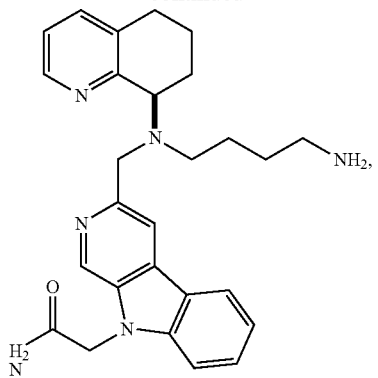
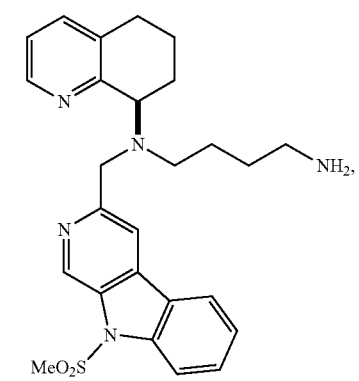
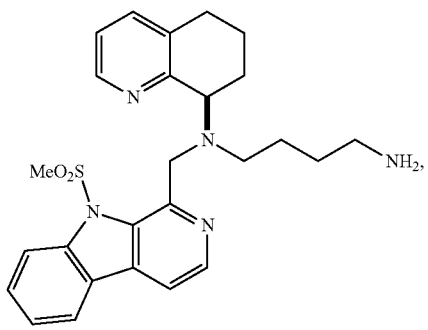
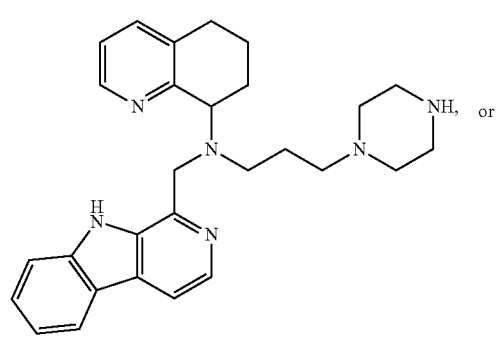

-continued
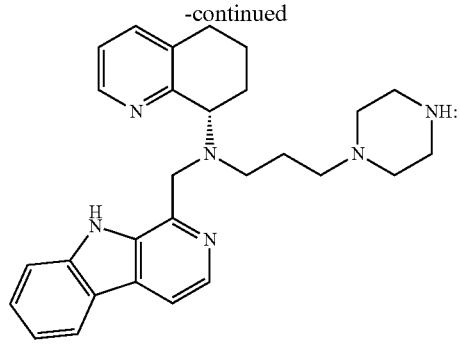
or a pharmaceutically acceptable salt, solvate, tautomer, stereoisomer, and/or ester thereof.
* * * * *